(12) United States Patent
Chien et al.

(10) Patent No.: US 7,319,016 B1
(45) Date of Patent: Jan. 15, 2008

(54) CRYSTALLIZATION OF CATHEPSIN S

(75) Inventors: Ellen Chien, La Jolla, CA (US);
Douglas R. Dougan, Calgary (CA);
Mark W. Knuth, El Cajon, CA (US);
Duncan E. McRee, San Diego, CA (US); Bi Ching Sang, San Diego, CA (US); Robert J. Skene, San Diego, CA (US); Ronald V. Swanson, Del Mar, CA (US); Leslie W. Tari, San Diego, CA (US); Robert A. Wijnands, City Vista, CA (US)

(73) Assignee: Takeda San Diego, Inc., San Diego, CA (US)

( * ) Notice: Subject to any disclaimer, the term of this patent is extended or adjusted under 35 U.S.C. 154(b) by 332 days.

(21) Appl. No.: 10/646,470

(22) Filed: Aug. 22, 2003

Related U.S. Application Data

(60) Provisional application No. 60/405,423, filed on Aug. 23, 2002.

(51) Int. Cl.
*C12Q 1/37* (2006.01)
*C12N 9/50* (2006.01)
*G06F 19/00* (2006.01)

(52) U.S. Cl. .................. 435/23; 435/219; 435/226; 702/27

(58) Field of Classification Search .................. None
See application file for complete search history.

(56) References Cited

U.S. PATENT DOCUMENTS

| 5,856,116 A | 1/1999 | Wilson et al. |
| 2003/0143714 A1* | 7/2003 | Lamers et al. .............. 435/226 |

FOREIGN PATENT DOCUMENTS

| WO | WO 9740066 | 10/1997 |
| WO | WO 99/63115 | * 12/1999 |

OTHER PUBLICATIONS

McGrath et al. Crystal structure of human cathepsin S. Protein Science 1998, 7, 1294-1302.*
Wiencek et al. New strategies for protein crystal growth. Ann. Rev. Biomed. Eng. 1999, 1, 505-534.*
Gilliland et al. Crystallization of biological molecules for X-ray diffraction studies. Current Opinion in Structure Biology 1996, 6, 595-603.*
Ke et al. Crystallization of RNA and RNA-protein complexes. Methods 34, 2004, 408-414.*

* cited by examiner

*Primary Examiner*—Nashaat T. Nashed
(74) *Attorney, Agent, or Firm*—David J. Weitz

(57) ABSTRACT

Provided are crystals relating to Cathepsin S and its various uses.

14 Claims, 86 Drawing Sheets

FIGURE 1

Amino acid sequence for full-length human wild type Cathepsin S [SEQ. ID No. 1]
Residues comprising the catalytic domain (114-331) are underlined

```
MKRLVCVLLV CSSAVAQLHK DPTLDHHWHL WKKTYGKQYK EKNEEAVRRL IWEKNLKFVM    60
LHNLEHSMGM HSYDLGMNHL GDMTSEEVMS LMSSLRVPSQ WQRNITYKSN PNRILPDSVD   120
WREKGCVTEV KYQGSCGACW AFSAVGALEA QLKLKTGKLV SLSAQNLVDC STEKYGNKGC   180
NGGFMTTAFQ YIIDNKGIDS DASYPYKAMD LKCQYDSKYR AATCSKYTEL PYGREDVLKE   240
AVANKGPVSV GVDARHPSFF LYRSGVYYEP SCTQNVNHGV LVVGYGDLNG KEYWLVKNSW   300
GHNFGEEGYI RMARNKGNHC GIASFPSYPE I                                  331
``` cDNA sequence for residues 141-331 of SEQ. ID No. 1 [SEQ. ID No. 2]

```
ATGAAACGGC TGGTTTGTGT GCTCTTGGTG TGCTCCTCTG CAGTGGCACA GTTGCATAAA    60
GATCCTACCC TGGATCACCA CTGGCATCTC TGGAAGAAAA CCTATGGCAA ACAATACAAG   120
GAAAAGAATG AAGAAGCAGT ACGACGTCTC ATCTGGGAAA AGAATCTAAA GTTTGTGATG   180
CTTCACAACC TGGAGCATTC AATGGGAATG CACTCATACG ATCTGGGCAT GAACCACCTG   240
GGAGACATGA CCAGTGAAGA AGTGATGTCT TTGATGAGTT CCCTGAGAGT TCCCAGCCAG   300
TGGCAGAGAA ATATCACATA TAAGTCAAAC CCTAATCGGA TATTGCCTGA TTCTGTGGAC   360
TGGAGAGAGA AAGGGTGTGT TACTGAAGTG AAATATCAAG GTTCTTGTGG TGCTTGCTGG   420
GCTTTCAGTG CTGTGGGGGC CCTGGAAGCA CAGCTGAAGC TGAAAACAGG AAAGCTGGTG   480
TCTCTCAGTG CCCAGAACCT GGTGGATTGC TCAACTGAAA AATATGGAAA CAAAGGCTGC   540
AATGGTGGCT TCATGACAAC GGCTTTCCAG TACATCATTG ATAACAAGGG CATCGACTCA   600
GACGCTTCCT ATCCCTACAA AGCCATGGAT CTGAAATGTC AATATGACTC AAAATATCGT   660
GCTGCCACAT GTTCAAAGTA CACTGAACTT CCTTATGGCA GAGAAGATGT CCTGAAAGAA   720
GCTGTGGCCA ATAAAGGCCC AGTGTCTGTT GGTGTAGATG CGCGTCATCC TTCTTTCTTC   780
CTCTACAGAA GTGGTGTCTA CTATGAACCA TCCTGTACTC AGAATGTGAA TCATGGTGTA   840
CTTGTGGTTG GCTATGGTGA TCTTAATGGG AAAGAATACT GGCTTGTGAA AAACAGCTGG   900
GGCCACAACT TTGGTGAAGA AGGATATATT CGGATGGCAA GAAATAAGG AAATCATTGT   960
GGGATTGCTA GCTTTCCCTC TTACCCAGAA ATCTAG                             996
```

FIGURE 1 (Cont.)

Amino acid sequence for residues 114-331 of Cathepsin S with the addition of a C-terminal
Glycine - 6x-histidine tag [SEQ. ID No. 3]

(Glycine - 6x-histidine tag underlined)

```
ILPDSVDWRE KGCVTEVKYQ GSCGACWAFS AVGALEAQLK LKTGKLVSLS AQNLVDCSTE    60
KYGNKGCNGG FMTTAFQYII DNKGIDSDAS YPYKAMDQKC QYDSKYRAAT CSKYTELPYG   120
REDVLKEAVA NKGPVSVGVD ARHPSFFLYR SGVYYEPSCT QNVNHGVLVV GYGDLNGKEY   180
WLVKNSWGHN FGEEGYIRMA RNKGNHCGIA SFPSYPEIGH HHHHH                   225
```

Amino acid sequence for residues 1-331 of Cathepsin S with the addition of a
N-terminal Methionine-Proline and a C-terminal Glycine - 6x-histidine tag
[SEQ. ID. No. 4] (6x-histidine tag and methionine-proline are underlined)

```
MPMKRLVCVL LVCSSAVAQL HKDPTLDHHW HLWKKTYGKQ YKEKNEEAVR RLIWEKNLKF    60
VMLHNLEHSM GMHSYDLGMN HLGDMTSEEV MSLMSSLRVP SQWQRNITYK SNPNRILPDS   120
VDWREKGCVT EVKYQGSCGA CWAFSAVGAL EAQLKLKTGK LVSLSAQNLV DCSTEKYGNK   180
GCNGGFMTTA FQYIIDNKGI DSDASYPYKA MDQKCQYDSK YRAATCSKYT ELPYGREDVL   240
KEAVANKGPV SVGVDARHPS FFLYRSGVYY EPSCTQNVNH GVLVVGYGDL NGKEYWLVKN   300
SWGHNFGEEG YIRMARNKGN HCGIASFPSY PEIGHHHHHH                         340
```

FIGURE 3

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'

| A | B | C | D | E | F | G | H | I | J |
|---|---|---|---|---|---|---|---|---|---|
| 1 | N | ILE | A | 1 | 82.257 | 8.041 | 57.927 | 1.00 | 26.34 |
| 3 | CA | ILE | A | 1 | 82.504 | 8.282 | 59.377 | 1.00 | 25.81 |
| 5 | CB | ILE | A | 1 | 83.574 | 7.303 | 59.879 | 1.00 | 26.29 |
| 7 | CG1 | ILE | A | 1 | 82.988 | 5.880 | 59.789 | 1.00 | 26.70 |
| 10 | CD1 | ILE | A | 1 | 83.604 | 4.861 | 60.736 | 1.00 | 27.27 |
| 14 | CG2 | ILE | A | 1 | 83.987 | 7.615 | 61.297 | 1.00 | 26.81 |
| 18 | C | ILE | A | 1 | 82.828 | 9.757 | 59.616 | 1.00 | 24.58 |
| 19 | O | ILE | A | 1 | 83.919 | 10.241 | 59.292 | 1.00 | 26.19 |
| 23 | N | LEU | A | 2 | 81.813 | 10.485 | 60.080 | 1.00 | 22.05 |
| 25 | CA | LEU | A | 2 | 81.954 | 11.891 | 60.442 | 1.00 | 20.00 |
| 27 | CB | LEU | A | 2 | 80.605 | 12.453 | 60.868 | 1.00 | 19.56 |
| 30 | CG | LEU | A | 2 | 79.501 | 12.355 | 59.825 | 1.00 | 20.01 |
| 32 | CD1 | LEU | A | 2 | 78.222 | 12.934 | 60.367 | 1.00 | 21.60 |
| 36 | CD2 | LEU | A | 2 | 79.905 | 13.043 | 58.524 | 1.00 | 19.14 |
| 40 | C | LEU | A | 2 | 82.941 | 12.101 | 61.574 | 1.00 | 18.72 |
| 41 | O | LEU | A | 2 | 83.100 | 11.254 | 62.440 | 1.00 | 18.37 |
| 42 | N | PRO | A | 3 | 83.604 | 13.243 | 61.569 | 1.00 | 17.60 |
| 43 | CA | PRO | A | 3 | 84.507 | 13.570 | 62.672 | 1.00 | 16.62 |
| 45 | CB | PRO | A | 3 | 85.045 | 14.949 | 62.305 | 1.00 | 17.14 |
| 48 | CG | PRO | A | 3 | 84.686 | 15.200 | 60.909 | 1.00 | 18.97 |
| 51 | CD | PRO | A | 3 | 83.548 | 14.300 | 60.560 | 1.00 | 17.68 |
| 54 | C | PRO | A | 3 | 83.723 | 13.654 | 63.967 | 1.00 | 15.96 |
| 55 | O | PRO | A | 3 | 82.565 | 14.052 | 63.934 | 1.00 | 15.78 |
| 56 | N | ASP | A | 4 | 84.338 | 13.302 | 65.087 | 1.00 | 15.34 |
| 58 | CA | ASP | A | 4 | 83.677 | 13.369 | 66.383 | 1.00 | 15.46 |
| 60 | CB | ASP | A | 4 | 84.503 | 12.677 | 67.469 | 1.00 | 16.27 |
| 63 | CG | ASP | A | 4 | 84.314 | 11.162 | 67.480 | 1.00 | 20.81 |
| 64 | OD1 | ASP | A | 4 | 83.374 | 10.648 | 66.823 | 1.00 | 22.78 |
| 65 | OD2 | ASP | A | 4 | 85.068 | 10.405 | 68.142 | 1.00 | 24.08 |
| 66 | C | ASP | A | 4 | 83.471 | 14.813 | 66.780 | 1.00 | 14.04 |
| 67 | O | ASP | A | 4 | 82.593 | 15.116 | 67.564 | 1.00 | 14.43 |
| 68 | N | SER | A | 5 | 84.298 | 15.690 | 66.241 | 1.00 | 13.06 |
| 70 | CA | SER | A | 5 | 84.165 | 17.107 | 66.525 | 1.00 | 13.20 |
| 72 | CB | SER | A | 5 | 84.951 | 17.460 | 67.785 | 1.00 | 13.87 |
| 75 | OG | SER | A | 5 | 86.328 | 17.434 | 67.527 | 1.00 | 15.53 |
| 77 | C | SER | A | 5 | 84.589 | 17.965 | 65.344 | 1.00 | 12.32 |
| 78 | O | SER | A | 5 | 85.435 | 17.579 | 64.535 | 1.00 | 12.78 |
| 79 | N | VAL | A | 6 | 83.964 | 19.130 | 65.229 | 1.00 | 11.07 |
| 81 | CA | VAL | A | 6 | 84.253 | 20.077 | 64.179 | 1.00 | 11.25 |
| 83 | CB | VAL | A | 6 | 83.156 | 20.009 | 63.094 | 1.00 | 11.71 |
| 85 | CG1 | VAL | A | 6 | 83.239 | 21.160 | 62.144 | 1.00 | 12.21 |
| 89 | CG2 | VAL | A | 6 | 83.218 | 18.674 | 62.379 | 1.00 | 12.06 |

FIGURE 3 (Cont.)

| A | B | C | D | E | F | G | H | I | J |
|---|---|---|---|---|---|---|---|---|---|
| 93 | C | VAL | A | 6 | 84.244 | 21.476 | 64.765 | 1.00 | 10.82 |
| 94 | O | VAL | A | 6 | 83.468 | 21.747 | 65.667 | 1.00 | 10.70 |
| 95 | N | ASP | A | 7 | 85.092 | 22.360 | 64.250 | 1.00 | 11.43 |
| 97 | CA | ASP | A | 7 | 85.069 | 23.775 | 64.647 | 1.00 | 11.57 |
| 99 | CB | ASP | A | 7 | 85.927 | 24.038 | 65.878 | 1.00 | 11.62 |
| 102 | CG | ASP | A | 7 | 85.834 | 25.469 | 66.382 | 1.00 | 14.15 |
| 103 | OD1 | ASP | A | 7 | 85.435 | 26.374 | 65.617 | 1.00 | 12.41 |
| 104 | OD2 | ASP | A | 7 | 86.154 | 25.766 | 67.577 | 1.00 | 15.00 |
| 105 | C | ASP | A | 7 | 85.549 | 24.564 | 63.457 | 1.00 | 11.35 |
| 106 | O | ASP | A | 7 | 86.731 | 24.639 | 63.171 | 1.00 | 11.67 |
| 107 | N | TRP | A | 8 | 84.613 | 25.145 | 62.709 | 1.00 | 10.50 |
| 109 | CA | TRP | A | 8 | 84.938 | 25.857 | 61.503 | 1.00 | 10.47 |
| 111 | CB | TRP | A | 8 | 83.641 | 26.205 | 60.743 | 1.00 | 10.56 |
| 114 | CG | TRP | A | 8 | 83.120 | 25.010 | 59.975 | 1.00 | 10.28 |
| 115 | CD1 | TRP | A | 8 | 82.073 | 24.218 | 60.294 | 1.00 | 10.49 |
| 117 | NE1 | TRP | A | 8 | 81.956 | 23.200 | 59.372 | 1.00 | 9.78 |
| 119 | CE2 | TRP | A | 8 | 82.932 | 23.340 | 58.429 | 1.00 | 10.67 |
| 120 | CD2 | TRP | A | 8 | 83.696 | 24.459 | 58.788 | 1.00 | 11.28 |
| 121 | CE3 | TRP | A | 8 | 84.759 | 24.830 | 57.964 | 1.00 | 13.13 |
| 123 | CZ3 | TRP | A | 8 | 85.050 | 24.042 | 56.844 | 1.00 | 13.88 |
| 125 | CH2 | TRP | A | 8 | 84.283 | 22.941 | 56.529 | 1.00 | 14.28 |
| 127 | CZ2 | TRP | A | 8 | 83.215 | 22.571 | 57.301 | 1.00 | 14.21 |
| 129 | C | TRP | A | 8 | 85.809 | 27.075 | 61.704 | 1.00 | 10.85 |
| 130 | O | TRP | A | 8 | 86.371 | 27.596 | 60.745 | 1.00 | 11.66 |
| 131 | N | ARG | A | 9 | 85.899 | 27.550 | 62.949 | 1.00 | 11.57 |
| 133 | CA | ARG | A | 9 | 86.787 | 28.663 | 63.251 | 1.00 | 13.62 |
| 135 | CB | ARG | A | 9 | 86.643 | 29.102 | 64.687 | 1.00 | 13.51 |
| 138 | CG | ARG | A | 9 | 85.293 | 29.655 | 65.033 | 1.00 | 13.24 |
| 141 | CD | ARG | A | 9 | 85.175 | 30.056 | 66.498 | 1.00 | 13.68 |
| 144 | NE | ARG | A | 9 | 85.318 | 28.897 | 67.360 | 1.00 | 13.08 |
| 146 | CZ | ARG | A | 9 | 85.231 | 28.912 | 68.670 | 1.00 | 13.37 |
| 147 | NH1 | ARG | A | 9 | 85.011 | 30.041 | 69.314 | 1.00 | 15.01 |
| 150 | NH2 | ARG | A | 9 | 85.385 | 27.792 | 69.342 | 1.00 | 14.86 |
| 153 | C | ARG | A | 9 | 88.213 | 28.246 | 63.012 | 1.00 | 14.93 |
| 154 | O | ARG | A | 9 | 89.034 | 29.059 | 62.580 | 1.00 | 16.62 |
| 155 | N | GLU | A | 10 | 88.502 | 26.968 | 63.234 | 1.00 | 15.84 |
| 157 | CA | GLU | A | 10 | 89.850 | 26.418 | 63.048 | 1.00 | 17.63 |
| 159 | CB | GLU | A | 10 | 89.923 | 25.022 | 63.663 | 1.00 | 18.54 |
| 162 | CG | GLU | A | 10 | 89.627 | 25.009 | 65.152 | 1.00 | 22.00 |
| 165 | CD | GLU | A | 10 | 89.773 | 23.625 | 65.771 | 1.00 | 25.95 |
| 166 | OE1 | GLU | A | 10 | 89.739 | 22.619 | 65.021 | 1.00 | 28.16 |
| 167 | OE2 | GLU | A | 10 | 89.899 | 23.555 | 67.013 | 1.00 | 29.66 |
| 168 | C | GLU | A | 10 | 90.271 | 26.371 | 61.576 | 1.00 | 17.42 |
| 169 | O | GLU | A | 10 | 91.457 | 26.221 | 61.266 | 1.00 | 19.10 |
| 170 | N | LYS | A | 11 | 89.341 | 26.675 | 60.680 | 1.00 | 17.42 |
| 172 | CA | LYS | A | 11 | 89.519 | 26.539 | 59.243 | 1.00 | 17.25 |
| 174 | CB | LYS | A | 11 | 88.484 | 25.622 | 58.578 | 1.00 | 18.47 |
| 177 | CG | LYS | A | 11 | 88.472 | 24.203 | 59.091 | 1.00 | 21.87 |
| 180 | CD | LYS | A | 11 | 89.629 | 23.388 | 58.551 | 1.00 | 25.43 |
| 183 | CE | LYS | A | 11 | 90.038 | 22.289 | 59.530 | 1.00 | 27.42 |
| 186 | NZ | LYS | A | 11 | 91.186 | 21.494 | 59.043 | 1.00 | 29.82 |

FIGURE 3 (Cont.)

| A | B | C | D | E | F | G | H | I | J |
|---|---|---|---|---|---|---|---|---|---|
| 190 | C | LYS | A | 11 | 89.436 | 27.953 | 58.666 | 1.00 | 16.53 |
| 191 | O | LYS | A | 11 | 89.478 | 28.143 | 57.461 | 1.00 | 16.98 |
| 192 | N | GLY | A | 12 | 89.295 | 28.949 | 59.537 | 1.00 | 15.66 |
| 194 | CA | GLY | A | 12 | 89.219 | 30.327 | 59.127 | 1.00 | 15.31 |
| 197 | C | GLY | A | 12 | 87.980 | 30.655 | 58.319 | 1.00 | 14.80 |
| 198 | O | GLY | A | 12 | 88.021 | 31.534 | 57.457 | 1.00 | 15.59 |
| 199 | N | CYS | A | 13 | 86.876 | 29.975 | 58.626 | 1.00 | 13.63 |
| 201 | CA | CYS | A | 13 | 85.658 | 30.135 | 57.830 | 1.00 | 12.55 |
| 203 | CB | CYS | A | 13 | 85.092 | 28.769 | 57.471 | 1.00 | 13.05 |
| 206 | SG | CYS | A | 13 | 86.053 | 27.854 | 56.234 | 1.00 | 15.75 |
| 207 | C | CYS | A | 13 | 84.592 | 30.927 | 58.568 | 1.00 | 12.31 |
| 208 | O | CYS | A | 13 | 83.460 | 31.041 | 58.086 | 1.00 | 11.54 |
| 209 | N | VAL | A | 13 | 84.954 | 31.478 | 59.721 | 1.00 | 10.44 |
| 211 | CA | VAL | A | 14 | 84.022 | 32.223 | 60.562 | 1.00 | 9.80 |
| 213 | CB | VAL | A | 14 | 83.761 | 31.473 | 61.864 | 1.00 | 9.69 |
| 215 | CG1 | VAL | A | 14 | 82.724 | 32.200 | 62.693 | 1.00 | 10.02 |
| 219 | CG2 | VAL | A | 14 | 83.311 | 30.024 | 61.590 | 1.00 | 11.13 |
| 223 | C | VAL | A | 14 | 84.535 | 33.629 | 60.871 | 1.00 | 9.61 |
| 224 | O | VAL | A | 14 | 85.649 | 33.799 | 61.374 | 1.00 | 11.18 |
| 225 | N | THR | A | 15 | 83.720 | 34.635 | 60.596 | 1.00 | 9.79 |
| 227 | CA | THR | A | 15 | 84.104 | 36.013 | 60.862 | 1.00 | 10.47 |
| 229 | CB | THR | A | 15 | 83.296 | 36.995 | 60.013 | 1.00 | 11.70 |
| 231 | OG1 | THR | A | 15 | 81.906 | 36.874 | 60.346 | 1.00 | 12.19 |
| 233 | CG2 | THR | A | 15 | 83.410 | 36.669 | 58.567 | 1.00 | 11.82 |
| 237 | C | THR | A | 15 | 83.929 | 36.357 | 62.324 | 1.00 | 11.20 |
| 238 | O | THR | A | 15 | 83.417 | 35.566 | 63.109 | 1.00 | 10.87 |
| 239 | N | ALA | A | 16 | 84.208 | 37.610 | 62.637 | 1.00 | 12.52 |
| 241 | CA | ALA | A | 16 | 84.188 | 38.078 | 64.011 | 1.00 | 12.09 |
| 243 | CB | ALA | A | 16 | 84.730 | 39.470 | 64.105 | 1.00 | 13.84 |
| 247 | C | ALA | A | 16 | 82.733 | 38.075 | 64.423 | 1.00 | 11.36 |
| 248 | O | ALA | A | 16 | 81.842 | 38.261 | 63.598 | 1.00 | 10.77 |
| 249 | N | VAL | A | 17 | 82.502 | 37.860 | 65.706 | 1.00 | 10.58 |
| 251 | CA | VAL | A | 17 | 81.177 | 37.921 | 66.268 | 1.00 | 10.11 |
| 253 | CB | VAL | A | 17 | 81.222 | 37.468 | 67.730 | 1.00 | 10.38 |
| 255 | CG1 | VAL | A | 17 | 79.950 | 37.835 | 68.464 | 1.00 | 11.56 |
| 259 | CG2 | VAL | A | 17 | 81.488 | 35.989 | 67.780 | 1.00 | 11.48 |
| 263 | C | VAL | A | 17 | 80.680 | 39.347 | 66.131 | 1.00 | 10.10 |
| 264 | O | VAL | A | 17 | 81.414 | 40.297 | 66.382 | 1.00 | 11.71 |
| 265 | N | LYS | A | 18 | 79.421 | 39.489 | 65.747 | 1.00 | 8.56 |
| 267 | CA | LYS | A | 18 | 78.792 | 40.761 | 65.539 | 1.00 | 9.55 |
| 269 | CB | LYS | A | 18 | 77.986 | 40.755 | 64.237 | 1.00 | 10.39 |
| 272 | CG | LYS | A | 18 | 78.766 | 40.394 | 62.990 | 1.00 | 10.71 |
| 275 | CD | LYS | A | 18 | 80.056 | 41.159 | 62.846 | 1.00 | 10.83 |
| 278 | CE | LYS | A | 18 | 80.725 | 40.971 | 61.474 | 1.00 | 12.15 |
| 281 | NZ | LYS | A | 18 | 81.129 | 39.568 | 61.143 | 1.00 | 12.51 |
| 285 | C | LYS | A | 18 | 77.842 | 41.082 | 66.692 | 1.00 | 9.43 |
| 286 | O | LYS | A | 18 | 77.494 | 40.224 | 67.484 | 1.00 | 9.72 |
| 287 | N | TYR | A | 19 | 77.424 | 42.346 | 66.754 | 1.00 | 10.36 |
| 289 | CA | TYR | A | 19 | 76.531 | 42.802 | 67.812 | 1.00 | 10.98 |
| 291 | CB | TYR | A | 19 | 77.250 | 43.834 | 68.694 | 1.00 | 11.20 |
| 294 | CG | TYR | A | 19 | 76.391 | 44.406 | 69.803 | 1.00 | 13.29 |

FIGURE 3 (Cont.)

| A | B | C | D | E | F | G | H | I | J |
|---|---|---|---|---|---|---|---|---|---|
| 295 | CD1 | TYR | A | 19 | 75.859 | 45.676 | 69.695 | 1.00 | 16.23 |
| 297 | CE1 | TYR | A | 19 | 75.087 | 46.210 | 70.700 | 1.00 | 16.53 |
| 299 | CZ | TYR | A | 19 | 74.821 | 45.481 | 71.814 | 1.00 | 19.68 |
| 301 | CE2 | TYR | A | 19 | 75.338 | 44.222 | 71.958 | 1.00 | 19.55 |
| 303 | CD2 | TYR | A | 19 | 76.124 | 43.683 | 70.945 | 1.00 | 16.47 |
| 305 | C | TYR | A | 19 | 75.308 | 43.407 | 67.155 | 1.00 | 10.43 |
| 306 | O | TYR | A | 19 | 75.395 | 44.464 | 66.506 | 1.00 | 11.82 |
| 307 | N | GLN | A | 20 | 74.166 | 42.761 | 67.336 | 1.00 | 9.89 |
| 309 | CA | GLN | A | 20 | 72.943 | 43.194 | 66.646 | 1.00 | 10.10 |
| 311 | CB | GLN | A | 20 | 71.945 | 42.044 | 66.498 | 1.00 | 10.63 |
| 314 | CG | GLN | A | 20 | 71.296 | 41.576 | 67.730 | 1.00 | 11.13 |
| 317 | CD | GLN | A | 20 | 70.402 | 40.388 | 67.480 | 1.00 | 12.73 |
| 318 | OE1 | GLN | A | 20 | 70.875 | 39.244 | 67.381 | 1.00 | 12.94 |
| 319 | NE2 | GLN | A | 20 | 69.109 | 40.633 | 67.395 | 1.00 | 13.57 |
| 322 | C | GLN | A | 20 | 72.280 | 44.376 | 67.310 | 1.00 | 11.11 |
| 323 | O | GLN | A | 20 | 71.514 | 45.087 | 66.684 | 1.00 | 11.05 |
| 324 | N | GLY | A | 21 | 72.605 | 44.624 | 68.563 | 1.00 | 11.36 |
| 326 | CA | GLY | A | 21 | 71.950 | 45.707 | 69.287 | 1.00 | 12.15 |
| 329 | C | GLY | A | 21 | 70.454 | 45.508 | 69.458 | 1.00 | 12.43 |
| 330 | O | GLY | A | 21 | 69.955 | 44.383 | 69.498 | 1.00 | 12.85 |
| 331 | N | SER | A | 22 | 69.688 | 46.606 | 69.468 | 1.00 | 13.09 |
| 333 | CA | SER | A | 22 | 68.251 | 46.505 | 69.693 | 1.00 | 14.69 |
| 335 | CB | SER | A | 22 | 67.754 | 47.740 | 70.441 | 1.00 | 14.53 |
| 338 | OG | SER | A | 22 | 68.301 | 47.790 | 71.722 | 1.00 | 16.94 |
| 340 | C | SER | A | 22 | 67.463 | 46.374 | 68.410 | 1.00 | 15.57 |
| 341 | O | SER | A | 22 | 66.468 | 47.041 | 68.222 | 1.00 | 19.41 |
| 342 | N | CYS | A | 23 | 67.963 | 45.589 | 67.480 | 1.00 | 15.80 |
| 344 | CA | CYS | A | 23 | 67.330 | 45.386 | 66.197 | 1.00 | 15.60 |
| 346 | CB | CYS | A | 23 | 68.238 | 45.961 | 65.104 | 1.00 | 15.66 |
| 349 | SG | CYS | A | 23 | 67.819 | 45.633 | 63.382 | 1.00 | 17.03 |
| 350 | C | CYS | A | 24 | 67.229 | 43.875 | 66.055 | 1.00 | 15.55 |
| 351 | O | CYS | A | 24 | 68.251 | 43.209 | 66.183 | 1.00 | 17.33 |
| 352 | N | GLY | A | 24 | 66.042 | 43.352 | 65.754 | 1.00 | 14.59 |
| 354 | CA | GLY | A | 24 | 65.822 | 41.914 | 65.616 | 1.00 | 14.25 |
| 357 | C | GLY | A | 24 | 66.312 | 41.400 | 64.277 | 1.00 | 13.64 |
| 358 | O | GLY | A | 24 | 65.538 | 40.922 | 63.446 | 1.00 | 14.90 |
| 359 | N | ALA | A | 25 | 67.609 | 41.536 | 64.056 | 1.00 | 12.48 |
| 361 | CA | ALA | A | 25 | 68.219 | 41.150 | 62.789 | 1.00 | 12.26 |
| 363 | CB | ALA | A | 25 | 69.141 | 42.264 | 62.322 | 1.00 | 12.36 |
| 367 | C | ALA | A | 25 | 69.008 | 39.855 | 62.876 | 1.00 | 12.16 |
| 368 | O | ALA | A | 25 | 69.858 | 39.580 | 62.038 | 1.00 | 11.56 |
| 369 | N | CYS | A | 26 | 68.722 | 39.059 | 63.902 | 1.00 | 12.16 |
| 371 | CA | CYS | A | 26 | 69.397 | 37.778 | 64.097 | 1.00 | 12.81 |
| 373 | CB | CYS | A | 26 | 68.784 | 37.016 | 65.280 | 1.00 | 13.57 |
| 376 | SG | CYS | A | 26 | 67.082 | 36.526 | 65.019 | 1.00 | 16.39 |
| 377 | C | CYS | A | 26 | 69.366 | 36.937 | 62.821 | 1.00 | 10.60 |
| 378 | O | CYS | A | 26 | 70.360 | 36.311 | 62.475 | 1.00 | 10.27 |
| 379 | N | TRP | A | 26 | 68.236 | 36.942 | 62.141 | 1.00 | 9.62 |
| 381 | CA | TRP | A | 27 | 68.044 | 36.178 | 60.924 | 1.00 | 9.30 |
| 383 | CB | TRP | A | 27 | 66.628 | 36.374 | 60.377 | 1.00 | 9.21 |
| 386 | CG | TRP | A | 27 | 66.280 | 37.802 | 60.086 | 1.00 | 9.70 |

FIGURE 3 (Cont.)

| A | B | C | D | E | F | G | H | I | J |
|---|---|---|---|---|---|---|---|---|---|
| 387 | CD1 | TRP | A | 27 | 65.877 | 38.728 | 60.989 | 1.00 | 10.89 |
| 389 | NE1 | TRP | A | 27 | 65.640 | 39.931 | 60.374 | 1.00 | 9.72 |
| 391 | CE2 | TRP | A | 27 | 65.898 | 39.795 | 59.037 | 1.00 | 8.87 |
| 392 | CD2 | TRP | A | 27 | 66.315 | 38.457 | 58.832 | 1.00 | 8.08 |
| 393 | CE3 | TRP | A | 27 | 66.641 | 38.054 | 57.534 | 1.00 | 8.37 |
| 395 | CZ3 | TRP | A | 27 | 66.517 | 38.963 | 56.511 | 1.00 | 9.65 |
| 397 | CH2 | TRP | A | 27 | 66.129 | 40.292 | 56.759 | 1.00 | 9.26 |
| 399 | CZ2 | TRP | A | 27 | 65.813 | 40.717 | 58.012 | 1.00 | 10.67 |
| 401 | C | TRP | A | 27 | 69.071 | 36.588 | 59.880 | 1.00 | 8.89 |
| 402 | O | TRP | A | 27 | 69.601 | 35.740 | 59.140 | 1.00 | 8.97 |
| 403 | N | ALA | A | 28 | 69.370 | 37.878 | 59.822 | 1.00 | 7.92 |
| 405 | CA | ALA | A | 28 | 70.296 | 38.408 | 58.825 | 1.00 | 7.88 |
| 407 | CB | ALA | A | 28 | 70.158 | 39.926 | 58.661 | 1.00 | 8.39 |
| 411 | C | ALA | A | 28 | 71.715 | 38.023 | 59.179 | 1.00 | 8.24 |
| 412 | O | ALA | A | 28 | 72.492 | 37.658 | 58.320 | 1.00 | 8.11 |
| 413 | N | PHE | A | 29 | 72.067 | 38.103 | 60.457 | 1.00 | 8.15 |
| 415 | CA | PHE | A | 29 | 73.381 | 37.681 | 60.872 | 1.00 | 7.56 |
| 417 | CB | PHE | A | 29 | 73.631 | 38.067 | 62.339 | 1.00 | 8.09 |
| 420 | CG | PHE | A | 29 | 73.899 | 39.523 | 62.518 | 1.00 | 8.52 |
| 421 | CD1 | PHE | A | 29 | 72.937 | 40.367 | 63.030 | 1.00 | 10.35 |
| 423 | CE1 | PHE | A | 29 | 73.180 | 41.738 | 63.140 | 1.00 | 11.21 |
| 425 | CZ | PHE | A | 29 | 74.371 | 42.246 | 62.710 | 1.00 | 9.28 |
| 427 | CE2 | PHE | A | 29 | 75.306 | 41.431 | 62.157 | 1.00 | 10.01 |
| 429 | CD2 | PHE | A | 29 | 75.080 | 40.063 | 62.073 | 1.00 | 9.08 |
| 431 | C | PHE | A | 29 | 73.593 | 36.210 | 60.653 | 1.00 | 7.36 |
| 432 | O | PHE | A | 29 | 74.683 | 35.803 | 60.279 | 1.00 | 8.40 |
| 433 | N | SER | A | 30 | 72.580 | 35.420 | 60.943 | 1.00 | 7.43 |
| 435 | CA | SER | A | 30 | 72.669 | 33.984 | 60.763 | 1.00 | 7.87 |
| 437 | CB | SER | A | 30 | 71.398 | 33.332 | 61.233 | 1.00 | 8.44 |
| 440 | OG | SER | A | 30 | 71.436 | 31.948 | 60.941 | 1.00 | 8.69 |
| 442 | C | SER | A | 30 | 72.912 | 33.665 | 59.298 | 1.00 | 7.91 |
| 443 | O | SER | A | 30 | 73.800 | 32.889 | 58.957 | 1.00 | 8.20 |
| 444 | N | ALA | A | 31 | 72.146 | 34.329 | 58.451 | 1.00 | 7.85 |
| 446 | CA | ALA | A | 31 | 72.237 | 34.117 | 57.019 | 1.00 | 8.22 |
| 448 | CB | ALA | A | 31 | 71.085 | 34.839 | 56.311 | 1.00 | 8.26 |
| 452 | C | ALA | A | 31 | 73.589 | 34.575 | 56.463 | 1.00 | 8.69 |
| 453 | O | ALA | A | 32 | 74.192 | 33.862 | 55.671 | 1.00 | 9.42 |
| 454 | N | VAL | A | 32 | 74.076 | 35.733 | 56.872 | 1.00 | 8.72 |
| 456 | CA | VAL | A | 32 | 75.353 | 36.156 | 56.337 | 1.00 | 9.28 |
| 458 | CB | VAL | A | 32 | 75.675 | 37.659 | 56.586 | 1.00 | 10.50 |
| 460 | CG1 | VAL | A | 32 | 74.561 | 38.564 | 56.090 | 1.00 | 12.29 |
| 464 | CG2 | VAL | A | 32 | 75.949 | 37.927 | 57.999 | 1.00 | 11.66 |
| 468 | C | VAL | A | 32 | 76.495 | 35.265 | 56.851 | 1.00 | 8.52 |
| 469 | O | VAL | A | 32 | 77.453 | 35.022 | 56.130 | 1.00 | 8.68 |
| 470 | N | GLY | A | 33 | 76.392 | 34.776 | 58.081 | 1.00 | 7.85 |
| 472 | CA | GLY | A | 33 | 77.411 | 33.915 | 58.637 | 1.00 | 8.13 |
| 475 | C | GLY | A | 33 | 77.594 | 32.664 | 57.842 | 1.00 | 7.86 |
| 476 | O | GLY | A | 33 | 78.710 | 32.184 | 57.563 | 1.00 | 8.58 |
| 477 | N | ALA | A | 34 | 76.459 | 32.052 | 57.473 | 1.00 | 8.26 |
| 479 | CA | ALA | A | 34 | 76.472 | 30.838 | 56.676 | 1.00 | 7.48 |
| 481 | CB | ALA | A | 34 | 75.083 | 30.353 | 56.481 | 1.00 | 8.24 |

FIGURE 3 (Cont.)

| A | B | C | D | E | F | G | H | I | J |
|---|---|---|---|---|---|---|---|---|---|
| 485 | C | ALA | A | 34 | 77.140 | 31.109 | 55.327 | 1.00 | 7.77 |
| 486 | O | ALA | A | 34 | 77.918 | 30.301 | 54.834 | 1.00 | 8.24 |
| 487 | N | LEU | A | 35 | 76.760 | 32.199 | 54.691 | 1.00 | 8.26 |
| 489 | CA | LEU | A | 35 | 77.293 | 32.512 | 53.368 | 1.00 | 8.98 |
| 491 | CB | LEU | A | 35 | 76.477 | 33.606 | 52.715 | 1.00 | 8.91 |
| 494 | CG | LEU | A | 35 | 76.747 | 33.828 | 51.232 | 1.00 | 9.66 |
| 496 | CD1 | LEU | A | 35 | 76.569 | 32.534 | 50.402 | 1.00 | 11.47 |
| 500 | CD2 | LEU | A | 35 | 75.805 | 34.866 | 50.766 | 1.00 | 10.37 |
| 504 | C | LEU | A | 35 | 78.775 | 32.854 | 53.399 | 1.00 | 9.66 |
| 505 | O | LEU | A | 35 | 79.520 | 32.473 | 52.508 | 1.00 | 9.96 |
| 506 | N | GLU | A | 36 | 79.196 | 33.541 | 54.449 | 1.00 | 10.00 |
| 508 | CA | GLU | A | 36 | 80.610 | 33.894 | 54.609 | 1.00 | 9.89 |
| 510 | CB | GLU | A | 36 | 80.819 | 34.665 | 55.932 | 1.00 | 11.60 |
| 513 | CG | GLU | A | 36 | 80.206 | 36.067 | 55.965 | 1.00 | 12.79 |
| 516 | CD | GLU | A | 36 | 79.998 | 36.642 | 57.364 | 1.00 | 13.45 |
| 517 | OE1 | GLU | A | 36 | 80.230 | 35.978 | 58.420 | 1.00 | 12.49 |
| 518 | OE2 | GLU | A | 36 | 79.582 | 37.809 | 57.412 | 1.00 | 12.98 |
| 519 | C | GLU | A | 36 | 81.480 | 32.656 | 54.596 | 1.00 | 9.61 |
| 520 | O | GLU | A | 36 | 82.558 | 32.670 | 54.017 | 1.00 | 9.71 |
| 521 | N | ALA | A | 37 | 81.038 | 31.587 | 55.244 | 1.00 | 8.84 |
| 523 | CA | ALA | A | 37 | 81.845 | 30.370 | 55.281 | 1.00 | 9.23 |
| 525 | CB | ALA | A | 37 | 81.211 | 29.352 | 56.209 | 1.00 | 10.31 |
| 529 | C | ALA | A | 37 | 81.983 | 29.793 | 53.867 | 1.00 | 9.85 |
| 530 | O | ALA | A | 37 | 83.065 | 29.383 | 53.428 | 1.00 | 9.44 |
| 531 | N | GLN | A | 38 | 80.873 | 29.755 | 53.157 | 1.00 | 9.66 |
| 533 | CA | GLN | A | 38 | 80.890 | 29.248 | 51.782 | 1.00 | 9.39 |
| 535 | CB | GLN | A | 38 | 79.470 | 29.164 | 51.208 | 1.00 | 9.32 |
| 538 | CG | GLN | A | 38 | 78.580 | 28.228 | 51.991 | 1.00 | 9.58 |
| 541 | CD | GLN | A | 38 | 79.117 | 26.831 | 52.046 | 1.00 | 11.36 |
| 542 | OE1 | GLN | A | 38 | 79.515 | 26.281 | 51.017 | 1.00 | 12.35 |
| 543 | NE2 | GLN | A | 38 | 79.139 | 26.241 | 53.236 | 1.00 | 10.20 |
| 546 | C | GLN | A | 38 | 81.771 | 30.106 | 50.894 | 1.00 | 9.59 |
| 547 | O | GLN | A | 38 | 82.479 | 29.590 | 50.042 | 1.00 | 11.42 |
| 548 | N | LEU | A | 39 | 81.775 | 31.419 | 51.119 | 1.00 | 9.82 |
| 550 | CA | LEU | A | 39 | 82.615 | 32.322 | 50.339 | 1.00 | 9.67 |
| 552 | CB | LEU | A | 39 | 82.276 | 33.763 | 50.674 | 1.00 | 10.76 |
| 555 | CG | LEU | A | 39 | 83.111 | 34.826 | 49.966 | 1.00 | 11.15 |
| 557 | CD1 | LEU | A | 39 | 82.834 | 34.877 | 48.468 | 1.00 | 11.91 |
| 561 | CD2 | LEU | A | 39 | 82.855 | 36.147 | 50.574 | 1.00 | 11.50 |
| 565 | C | LEU | A | 39 | 84.100 | 32.040 | 50.561 | 1.00 | 11.18 |
| 566 | O | LEU | A | 39 | 84.885 | 31.977 | 49.625 | 1.00 | 11.71 |
| 567 | N | LYS | A | 40 | 84.441 | 31.605 | 51.746 | 1.00 | 11.49 |
| 569 | CA | LYS | A | 40 | 85.829 | 31.444 | 52.132 | 1.00 | 13.02 |
| 571 | CB | LYS | A | 40 | 86.033 | 31.581 | 53.645 | 1.00 | 12.61 |
| 574 | CG | LYS | A | 40 | 87.223 | 30.839 | 54.231 | 1.00 | 16.62 |
| 577 | CD | LYS | A | 40 | 88.538 | 31.446 | 53.870 | 1.00 | 20.40 |
| 580 | CE | LYS | A | 40 | 89.690 | 30.651 | 54.503 | 1.00 | 21.72 |
| 583 | NZ | LYS | A | 40 | 89.233 | 29.337 | 55.032 | 1.00 | 28.53 |
| 587 | C | LYS | A | 40 | 86.212 | 30.075 | 51.551 | 1.00 | 13.24 |
| 588 | O | LYS | A | 40 | 87.289 | 29.917 | 50.943 | 1.00 | 13.01 |
| 589 | N | LEU | A | 41 | 85.299 | 29.109 | 51.631 | 1.00 | 13.53 |

FIGURE 3 (Cont.)

| A | B | C | D | E | F | G | H | I | J |
|---|---|---|---|---|---|---|---|---|---|
| 591 | CA | LEU | A | 41 | 85.536 | 27.782 | 51.067 | 1.00 | 14.77 |
| 593 | CB | LEU | A | 41 | 84.395 | 26.815 | 51.416 | 1.00 | 14.64 |
| 596 | CG | LEU | A | 41 | 84.314 | 26.365 | 52.866 | 1.00 | 15.86 |
| 598 | CD1 | LEU | A | 41 | 82.988 | 25.629 | 53.172 | 1.00 | 16.87 |
| 602 | CD2 | LEU | A | 41 | 85.491 | 25.488 | 53.224 | 1.00 | 17.83 |
| 606 | C | LEU | A | 41 | 85.735 | 27.863 | 49.545 | 1.00 | 15.17 |
| 607 | O | LEU | A | 41 | 86.608 | 27.188 | 48.979 | 1.00 | 15.80 |
| 608 | N | ALA | A | 42 | 85.046 | 28.787 | 48.903 | 1.00 | 15.49 |
| 610 | CA | ALA | A | 42 | 85.019 | 28.884 | 47.458 | 1.00 | 16.60 |
| 612 | CB | ALA | A | 42 | 83.687 | 29.459 | 46.969 | 1.00 | 17.33 |
| 616 | C | ALA | A | 42 | 86.175 | 29.755 | 46.972 | 1.00 | 17.55 |
| 617 | O | ALA | A | 42 | 86.818 | 29.432 | 45.963 | 1.00 | 18.46 |
| 618 | N | THR | A | 43 | 86.453 | 30.857 | 47.662 | 1.00 | 16.62 |
| 620 | CA | THR | A | 43 | 87.441 | 31.818 | 47.169 | 1.00 | 16.41 |
| 622 | CB | THR | A | 43 | 86.828 | 33.206 | 47.115 | 1.00 | 16.85 |
| 624 | OG1 | THR | A | 43 | 86.616 | 33.713 | 48.449 | 1.00 | 15.15 |
| 626 | CG2 | THR | A | 43 | 85.483 | 33.160 | 46.458 | 1.00 | 17.28 |
| 630 | C | THR | A | 43 | 88.706 | 31.932 | 47.972 | 1.00 | 16.79 |
| 631 | O | THR | A | 43 | 89.679 | 32.553 | 47.515 | 1.00 | 16.90 |
| 632 | N | GLY | A | 44 | 88.691 | 31.393 | 49.180 | 1.00 | 15.71 |
| 634 | CA | GLY | A | 44 | 89.829 | 31.470 | 50.071 | 1.00 | 15.97 |
| 637 | C | GLY | A | 44 | 89.844 | 32.748 | 50.891 | 1.00 | 15.78 |
| 638 | O | GLY | A | 44 | 90.720 | 32.925 | 51.750 | 1.00 | 18.08 |
| 639 | N | LYS | A | 45 | 88.888 | 33.641 | 50.638 | 1.00 | 14.70 |
| 641 | CA | LYS | A | 45 | 88.828 | 34.921 | 51.327 | 1.00 | 14.35 |
| 643 | CB | LYS | A | 45 | 88.524 | 36.037 | 50.348 | 1.00 | 14.89 |
| 646 | CG | LYS | A | 45 | 89.588 | 36.220 | 49.276 | 1.00 | 16.99 |
| 649 | CD | LYS | A | 45 | 89.353 | 37.471 | 48.497 | 1.00 | 19.33 |
| 652 | CE | LYS | A | 45 | 90.447 | 37.641 | 47.446 | 1.00 | 22.13 |
| 655 | NZ | LYS | A | 45 | 90.294 | 38.951 | 46.812 | 1.00 | 22.04 |
| 659 | C | LYS | A | 45 | 87.745 | 34.931 | 52.384 | 1.00 | 13.26 |
| 660 | O | LYS | A | 45 | 86.606 | 34.562 | 52.100 | 1.00 | 13.74 |
| 661 | N | LEU | A | 46 | 88.102 | 35.362 | 53.587 | 1.00 | 11.64 |
| 663 | CA | LEU | A | 46 | 87.154 | 35.533 | 54.676 | 1.00 | 11.56 |
| 665 | CB | LEU | A | 46 | 87.771 | 35.156 | 56.019 | 1.00 | 11.55 |
| 668 | CG | LEU | A | 46 | 86.766 | 35.211 | 57.164 | 1.00 | 13.05 |
| 670 | CD1 | LEU | A | 46 | 85.653 | 34.215 | 56.915 | 1.00 | 12.63 |
| 674 | CD2 | LEU | A | 46 | 87.433 | 34.929 | 58.475 | 1.00 | 14.82 |
| 678 | C | LEU | A | 46 | 86.733 | 37.001 | 54.691 | 1.00 | 11.68 |
| 679 | O | LEU | A | 46 | 87.519 | 37.888 | 55.018 | 1.00 | 12.55 |
| 680 | N | VAL | A | 47 | 85.456 | 37.244 | 54.400 | 1.00 | 11.66 |
| 682 | CA | VAL | A | 47 | 84.917 | 38.581 | 54.298 | 1.00 | 11.70 |
| 684 | CB | VAL | A | 47 | 84.663 | 38.947 | 52.801 | 1.00 | 12.60 |
| 686 | CG1 | VAL | A | 47 | 84.118 | 40.336 | 52.678 | 1.00 | 14.24 |
| 690 | CG2 | VAL | A | 47 | 85.935 | 38.776 | 51.975 | 1.00 | 14.03 |
| 694 | C | VAL | A | 47 | 83.574 | 38.659 | 55.015 | 1.00 | 11.12 |
| 695 | O | VAL | A | 47 | 82.702 | 37.851 | 54.741 | 1.00 | 12.16 |
| 696 | N | SER | A | 48 | 83.388 | 39.618 | 55.907 | 1.00 | 9.97 |
| 698 | CA | SER | A | 48 | 82.093 | 39.805 | 56.538 | 1.00 | 9.81 |
| 700 | CB | SER | A | 48 | 82.204 | 40.749 | 57.712 | 1.00 | 9.87 |
| 703 | OG | SER | A | 48 | 82.806 | 40.089 | 58.826 | 1.00 | 11.68 |

FIGURE 3 (Cont.)

| A | B | C | D | E | F | G | H | I | J |
|---|---|---|---|---|---|---|---|---|---|
| 705 | C | SER | A | 48 | 81.147 | 40.402 | 55.517 | 1.00 | 9.76 |
| 706 | O | SER | A | 48 | 81.479 | 41.378 | 54.837 | 1.00 | 10.20 |
| 707 | N | LEU | A | 49 | 79.972 | 39.800 | 55.414 | 1.00 | 9.28 |
| 709 | CA | LEU | A | 49 | 78.947 | 40.236 | 54.473 | 1.00 | 8.88 |
| 711 | CB | LEU | A | 49 | 78.297 | 39.049 | 53.793 | 1.00 | 9.29 |
| 714 | CG | LEU | A | 49 | 79.318 | 38.188 | 53.066 | 1.00 | 9.50 |
| 716 | CD1 | LEU | A | 49 | 78.677 | 36.909 | 52.544 | 1.00 | 9.17 |
| 720 | CD2 | LEU | A | 49 | 79.989 | 38.963 | 51.949 | 1.00 | 10.72 |
| 724 | C | LEU | A | 49 | 77.931 | 41.100 | 55.204 | 1.00 | 9.30 |
| 725 | O | LEU | A | 49 | 77.824 | 41.062 | 56.426 | 1.00 | 9.63 |
| 726 | N | SER | A | 50 | 77.166 | 41.855 | 54.443 | 1.00 | 8.22 |
| 728 | CA | SER | A | 50 | 76.319 | 42.877 | 55.009 | 1.00 | 8.41 |
| 730 | CB | SER | A | 50 | 76.102 | 43.979 | 53.981 | 1.00 | 7.71 |
| 733 | OG | SER | A | 50 | 75.262 | 44.969 | 54.515 | 1.00 | 8.95 |
| 735 | C | SER | A | 50 | 74.948 | 42.411 | 55.513 | 1.00 | 8.25 |
| 736 | O | SER | A | 50 | 74.035 | 42.196 | 54.732 | 1.00 | 7.24 |
| 737 | N | ALA | A | 51 | 74.807 | 42.244 | 56.822 | 1.00 | 8.23 |
| 739 | CA | ALA | A | 51 | 73.530 | 41.981 | 57.437 | 1.00 | 8.22 |
| 741 | CB | ALA | A | 51 | 73.686 | 41.778 | 58.914 | 1.00 | 9.58 |
| 745 | C | ALA | A | 51 | 72.585 | 43.155 | 57.170 | 1.00 | 8.52 |
| 746 | O | ALA | A | 51 | 71.398 | 42.973 | 57.015 | 1.00 | 8.76 |
| 747 | N | GLN | A | 52 | 73.122 | 44.364 | 57.108 | 1.00 | 8.59 |
| 749 | CA | GLN | A | 52 | 72.297 | 45.543 | 56.887 | 1.00 | 8.33 |
| 751 | CB | GLN | A | 52 | 73.113 | 46.841 | 57.004 | 1.00 | 8.51 |
| 754 | CG | GLN | A | 52 | 72.217 | 48.056 | 57.014 | 1.00 | 9.63 |
| 757 | CD | GLN | A | 52 | 71.387 | 48.139 | 58.270 | 1.00 | 11.05 |
| 758 | OE1 | GLN | A | 52 | 71.911 | 48.022 | 59.376 | 1.00 | 11.76 |
| 759 | NE2 | GLN | A | 52 | 70.064 | 48.317 | 58.105 | 1.00 | 11.59 |
| 762 | C | GLN | A | 52 | 71.624 | 45.462 | 55.513 | 1.00 | 7.46 |
| 763 | O | GLN | A | 52 | 70.463 | 45.835 | 55.360 | 1.00 | 9.03 |
| 764 | N | ASN | A | 53 | 72.368 | 44.973 | 54.524 | 1.00 | 7.94 |
| 766 | CA | ASN | A | 53 | 71.877 | 44.775 | 53.154 | 1.00 | 8.17 |
| 768 | CB | ASN | A | 53 | 73.010 | 44.117 | 52.361 | 1.00 | 8.71 |
| 771 | CG | ASN | A | 53 | 72.764 | 43.987 | 50.864 | 1.00 | 9.78 |
| 772 | OD1 | ASN | A | 53 | 73.715 | 43.784 | 50.139 | 1.00 | 9.29 |
| 773 | ND2 | ASN | A | 53 | 71.520 | 44.062 | 50.400 | 1.00 | 10.22 |
| 776 | C | ASN | A | 53 | 70.630 | 43.903 | 53.228 | 1.00 | 8.45 |
| 777 | O | ASN | A | 53 | 69.614 | 44.184 | 52.575 | 1.00 | 9.39 |
| 778 | N | LEU | A | 54 | 70.671 | 42.836 | 54.004 | 1.00 | 8.18 |
| 780 | CA | LEU | A | 54 | 69.500 | 41.992 | 54.159 | 1.00 | 8.18 |
| 782 | CB | LEU | A | 54 | 69.880 | 40.772 | 54.949 | 1.00 | 7.76 |
| 785 | CG | LEU | A | 54 | 70.186 | 39.458 | 54.243 | 1.00 | 13.79 |
| 787 | CD1 | LEU | A | 54 | 70.262 | 39.403 | 52.719 | 1.00 | 8.45 |
| 791 | CD2 | LEU | A | 54 | 71.181 | 38.560 | 54.955 | 1.00 | 10.18 |
| 795 | C | LEU | A | 54 | 68.366 | 42.737 | 54.865 | 1.00 | 8.34 |
| 796 | O | LEU | A | 54 | 67.212 | 42.739 | 54.420 | 1.00 | 8.16 |
| 797 | N | VAL | A | 55 | 68.673 | 43.399 | 55.967 | 1.00 | 8.48 |
| 799 | CA | VAL | A | 55 | 67.643 | 44.115 | 56.709 | 1.00 | 9.52 |
| 801 | CB | VAL | A | 55 | 68.235 | 44.839 | 57.920 | 1.00 | 9.28 |
| 803 | CG1 | VAL | A | 55 | 67.256 | 45.856 | 58.503 | 1.00 | 10.40 |
| 807 | CG2 | VAL | A | 55 | 68.648 | 43.819 | 58.958 | 1.00 | 10.57 |

FIGURE 3 (Cont.)

| A | B | C | D | E | F | G | H | I | J |
|---|---|---|---|---|---|---|---|---|---|
| 811 | C | VAL | A | 55 | 66.863 | 45.098 | 55.848 | 1.00 | 10.23 |
| 812 | O | VAL | A | 55 | 65.645 | 45.216 | 55.955 | 1.00 | 10.25 |
| 813 | N | ASP | A | 56 | 67.611 | 45.834 | 55.019 | 1.00 | 9.86 |
| 815 | CA | ASP | A | 56 | 67.059 | 46.911 | 54.217 | 1.00 | 10.61 |
| 817 | CB | ASP | A | 56 | 68.138 | 47.920 | 53.816 | 1.00 | 10.86 |
| 820 | CG | ASP | A | 56 | 68.782 | 48.643 | 54.966 | 1.00 | 11.97 |
| 821 | OD1 | ASP | A | 56 | 68.248 | 48.677 | 56.097 | 1.00 | 11.58 |
| 822 | OD2 | ASP | A | 56 | 69.829 | 49.316 | 54.755 | 1.00 | 13.77 |
| 823 | C | ASP | A | 56 | 66.464 | 46.460 | 52.904 | 1.00 | 11.01 |
| 824 | O | ASP | A | 56 | 65.590 | 47.143 | 52.369 | 1.00 | 11.28 |
| 825 | N | CYS | A | 57 | 66.967 | 45.356 | 52.369 | 1.00 | 10.95 |
| 827 | CA | CYS | A | 57 | 66.615 | 44.945 | 51.016 | 1.00 | 11.42 |
| 829 | CB | CYS | A | 57 | 67.872 | 44.800 | 50.159 | 1.00 | 12.43 |
| 832 | SG | CYS | A | 57 | 68.897 | 46.285 | 50.192 | 1.00 | 13.92 |
| 833 | C | CYS | A | 57 | 65.812 | 43.681 | 50.895 | 1.00 | 11.72 |
| 834 | O | CYS | A | 57 | 65.031 | 43.551 | 49.946 | 1.00 | 12.21 |
| 835 | N | SER | A | 58 | 66.016 | 42.725 | 51.787 | 1.00 | 10.84 |
| 837 | CA | SER | A | 58 | 65.268 | 41.472 | 51.753 | 1.00 | 10.61 |
| 839 | CB | SER | A | 58 | 66.126 | 40.323 | 52.295 | 1.00 | 10.76 |
| 842 | OG | SER | A | 58 | 65.428 | 39.103 | 52.285 | 1.00 | 11.12 |
| 844 | C | SER | A | 58 | 64.091 | 41.714 | 52.656 | 1.00 | 10.65 |
| 845 | O | SER | A | 58 | 64.104 | 41.339 | 53.815 | 1.00 | 10.18 |
| 846 | N | THR | A | 59 | 63.069 | 42.372 | 52.119 | 1.00 | 10.99 |
| 848 | CA | THR | A | 59 | 61.995 | 42.873 | 52.964 | 1.00 | 11.26 |
| 850 | CB | THR | A | 59 | 61.860 | 44.394 | 52.821 | 1.00 | 11.69 |
| 852 | OG1 | THR | A | 59 | 61.811 | 44.753 | 51.444 | 1.00 | 14.33 |
| 854 | CG2 | THR | A | 59 | 63.110 | 45.104 | 53.357 | 1.00 | 12.46 |
| 858 | C | THR | A | 59 | 60.683 | 42.161 | 52.703 | 1.00 | 11.35 |
| 859 | O | THR | A | 59 | 60.650 | 40.953 | 52.702 | 1.00 | 9.51 |
| 860 | N | GLU | A | 60 | 59.609 | 42.903 | 52.512 | 1.00 | 12.57 |
| 862 | CA | GLU | A | 60 | 58.291 | 42.289 | 52.443 | 1.00 | 13.36 |
| 864 | CB | GLU | A | 60 | 57.237 | 43.375 | 52.248 | 1.00 | 15.43 |
| 867 | CG | GLU | A | 60 | 57.314 | 44.112 | 50.949 | 1.00 | 19.60 |
| 870 | CD | GLU | A | 60 | 58.226 | 45.341 | 50.986 | 1.00 | 24.88 |
| 871 | OE1 | GLU | A | 60 | 58.376 | 45.966 | 49.904 | 1.00 | 33.16 |
| 872 | OE2 | GLU | A | 60 | 58.785 | 45.678 | 52.075 | 1.00 | 22.39 |
| 873 | C | GLU | A | 60 | 58.103 | 41.182 | 51.409 | 1.00 | 12.79 |
| 874 | O | GLU | A | 60 | 57.394 | 40.200 | 51.668 | 1.00 | 12.73 |
| 875 | N | LYS | A | 61 | 58.755 | 41.300 | 50.264 | 1.00 | 12.42 |
| 877 | CA | LYS | A | 61 | 58.598 | 40.289 | 49.238 | 1.00 | 12.20 |
| 879 | CB | LYS | A | 61 | 59.282 | 40.704 | 47.954 | 1.00 | 13.66 |
| 882 | CG | LYS | A | 61 | 58.587 | 41.891 | 47.308 | 1.00 | 19.06 |
| 885 | CD | LYS | A | 61 | 59.032 | 42.058 | 45.877 | 1.00 | 24.18 |
| 888 | CE | LYS | A | 61 | 57.994 | 42.804 | 45.067 | 1.00 | 28.09 |
| 891 | NZ | LYS | A | 61 | 56.687 | 42.062 | 45.085 | 1.00 | 31.37 |
| 895 | C | LYS | A | 61 | 59.165 | 38.958 | 49.695 | 1.00 | 11.07 |
| 896 | O | LYS | A | 61 | 58.833 | 37.916 | 49.146 | 1.00 | 11.28 |
| 897 | N | TYR | A | 62 | 60.043 | 39.012 | 50.696 | 1.00 | 8.88 |
| 899 | CA | TYR | A | 62 | 60.706 | 37.841 | 51.240 | 1.00 | 8.58 |
| 901 | CB | TYR | A | 62 | 62.220 | 38.087 | 51.317 | 1.00 | 8.55 |
| 904 | CG | TYR | A | 62 | 62.769 | 38.216 | 49.942 | 1.00 | 8.17 |

FIGURE 3 (Cont.)

| A | B | C | D | E | F | G | H | I | J |
|---|---|---|---|---|---|---|---|---|---|
| 905 | CD1 | TYR | A | 62 | 62.915 | 39.453 | 49.335 | 1.00 | 8.94 |
| 907 | CE1 | TYR | A | 62 | 63.372 | 39.548 | 48.053 | 1.00 | 9.49 |
| 909 | CZ | TYR | A | 62 | 63.682 | 38.421 | 47.354 | 1.00 | 10.13 |
| 910 | OH | TYR | A | 62 | 64.131 | 38.536 | 46.068 | 1.00 | 12.74 |
| 912 | CE2 | TYR | A | 62 | 63.519 | 37.185 | 47.913 | 1.00 | 9.66 |
| 914 | CD2 | TYR | A | 62 | 63.083 | 37.091 | 49.219 | 1.00 | 8.09 |
| 916 | C | TYR | A | 62 | 60.139 | 37.438 | 52.591 | 1.00 | 9.11 |
| 917 | O | TYR | A | 62 | 60.641 | 36.532 | 53.255 | 1.00 | 9.78 |
| 918 | N | GLY | A | 63 | 59.065 | 38.106 | 52.996 | 1.00 | 9.58 |
| 920 | CA | GLY | A | 63 | 58.426 | 37.782 | 54.258 | 1.00 | 10.70 |
| 923 | C | GLY | A | 63 | 59.202 | 38.249 | 55.485 | 1.00 | 10.96 |
| 924 | O | GLY | A | 63 | 58.839 | 37.883 | 56.596 | 1.00 | 12.09 |
| 925 | N | ASN | A | 64 | 60.260 | 39.030 | 55.287 | 1.00 | 10.88 |
| 927 | CA | ASN | A | 64 | 61.064 | 39.585 | 56.390 | 1.00 | 10.67 |
| 929 | CB | ASN | A | 64 | 62.533 | 39.520 | 56.039 | 1.00 | 10.44 |
| 932 | CG | ASN | A | 64 | 62.948 | 38.144 | 55.666 | 1.00 | 9.70 |
| 933 | OD1 | ASN | A | 64 | 62.551 | 37.163 | 56.268 | 1.00 | 11.46 |
| 934 | ND2 | ASN | A | 64 | 63.803 | 38.089 | 54.658 | 1.00 | 10.82 |
| 937 | C | ASN | A | 64 | 60.619 | 41.004 | 56.713 | 1.00 | 11.80 |
| 938 | O | ASN | A | 64 | 60.106 | 41.699 | 55.842 | 1.00 | 14.10 |
| 939 | N | ALA | A | 65 | 60.837 | 41.425 | 57.963 | 1.00 | 11.58 |
| 941 | CA | ALA | A | 65 | 60.453 | 42.744 | 58.450 | 1.00 | 12.22 |
| 943 | CB | ALA | A | 65 | 59.288 | 42.643 | 59.391 | 1.00 | 13.20 |
| 947 | C | ALA | A | 65 | 61.620 | 43.459 | 59.121 | 1.00 | 12.25 |
| 948 | O | ALA | A | 65 | 61.447 | 44.109 | 60.143 | 1.00 | 12.30 |
| 949 | N | GLY | A | 66 | 62.809 | 43.296 | 58.560 | 1.00 | 11.56 |
| 951 | CA | GLY | A | 66 | 63.974 | 44.032 | 58.999 | 1.00 | 11.65 |
| 954 | C | GLY | A | 66 | 64.277 | 43.859 | 60.459 | 1.00 | 12.26 |
| 955 | O | GLY | A | 66 | 64.526 | 42.755 | 60.911 | 1.00 | 11.35 |
| 956 | N | CYS | A | 67 | 64.235 | 44.960 | 61.203 | 1.00 | 12.76 |
| 958 | CA | CYS | A | 67 | 64.512 | 44.908 | 62.633 | 1.00 | 13.87 |
| 960 | CB | CYS | A | 67 | 64.765 | 46.310 | 63.185 | 1.00 | 14.98 |
| 963 | SG | CYS | A | 67 | 66.367 | 46.936 | 62.633 | 1.00 | 20.83 |
| 964 | C | CYS | A | 67 | 63.432 | 44.209 | 63.444 | 1.00 | 13.60 |
| 965 | O | CYS | A | 67 | 63.589 | 44.029 | 64.638 | 1.00 | 13.97 |
| 966 | N | ASN | A | 68 | 62.344 | 43.804 | 62.795 | 1.00 | 12.40 |
| 968 | CA | ASN | A | 68 | 61.276 | 43.111 | 63.478 | 1.00 | 13.63 |
| 970 | CB | ASN | A | 68 | 59.954 | 43.843 | 63.288 | 1.00 | 13.48 |
| 973 | CG | ASN | A | 68 | 59.831 | 45.020 | 64.227 | 1.00 | 16.37 |
| 974 | OD1 | ASN | A | 68 | 59.655 | 44.838 | 65.425 | 1.00 | 19.66 |
| 975 | ND2 | ASN | A | 68 | 59.992 | 46.216 | 63.702 | 1.00 | 17.62 |
| 978 | C | ASN | A | 68 | 61.188 | 41.651 | 63.052 | 1.00 | 13.20 |
| 979 | O | ASN | A | 68 | 60.159 | 41.002 | 63.211 | 1.00 | 15.60 |
| 980 | N | GLY | A | 69 | 62.284 | 41.126 | 62.506 | 1.00 | 12.13 |
| 982 | CA | GLY | A | 69 | 62.370 | 39.705 | 62.246 | 1.00 | 10.81 |
| 985 | C | GLY | A | 69 | 62.347 | 39.303 | 60.795 | 1.00 | 10.90 |
| 986 | O | GLY | A | 69 | 61.908 | 40.051 | 59.924 | 1.00 | 11.79 |
| 987 | N | GLY | A | 70 | 62.832 | 38.102 | 60.546 | 1.00 | 9.81 |
| 989 | CA | GLY | A | 70 | 62.887 | 37.573 | 59.207 | 1.00 | 9.19 |
| 992 | C | GLY | A | 70 | 63.291 | 36.117 | 59.210 | 1.00 | 9.71 |
| 993 | O | GLY | A | 70 | 63.359 | 35.487 | 60.251 | 1.00 | 9.76 |

FIGURE 3 (Cont.)

| A | B | C | D | E | F | G | H | I | J |
|---|---|---|---|---|---|---|---|---|---|
| 994 | N | PHE | A | 71 | 63.593 | 35.600 | 58.028 | 1.00 | 8.93 |
| 996 | CA | PHE | A | 71 | 63.939 | 34.214 | 57.837 | 1.00 | 9.61 |
| 998 | CB | PHE | A | 71 | 62.906 | 33.562 | 56.921 | 1.00 | 9.47 |
| 1001 | CG | PHE | A | 71 | 61.503 | 33.587 | 57.458 | 1.00 | 12.32 |
| 1002 | CD1 | PHE | A | 71 | 60.577 | 34.511 | 57.007 | 1.00 | 15.23 |
| 1004 | CE1 | PHE | A | 71 | 59.270 | 34.515 | 57.508 | 1.00 | 16.98 |
| 1006 | CZ | PHE | A | 71 | 58.903 | 33.601 | 58.461 | 1.00 | 17.37 |
| 1008 | CE2 | PHE | A | 71 | 59.810 | 32.696 | 58.918 | 1.00 | 18.52 |
| 1010 | CD2 | PHE | A | 71 | 61.110 | 32.675 | 58.405 | 1.00 | 16.82 |
| 1012 | C | PHE | A | 71 | 65.279 | 34.080 | 57.169 | 1.00 | 9.78 |
| 1013 | O | PHE | A | 71 | 65.573 | 34.842 | 56.269 | 1.00 | 9.49 |
| 1014 | N | MET | A | 72 | 66.092 | 33.103 | 57.571 | 1.00 | 8.77 |
| 1016 | CA | MET | A | 72 | 67.366 | 32.893 | 56.923 | 1.00 | 8.42 |
| 1018 | CB | MET | A | 72 | 68.253 | 31.937 | 57.707 | 1.00 | 8.41 |
| 1021 | CG | MET | A | 72 | 68.778 | 32.526 | 59.001 | 1.00 | 8.98 |
| 1024 | SD | MET | A | 72 | 67.633 | 32.408 | 60.355 | 1.00 | 10.95 |
| 1025 | CE | MET | A | 72 | 67.802 | 30.753 | 60.771 | 1.00 | 11.40 |
| 1029 | C | MET | A | 72 | 67.190 | 32.397 | 55.496 | 1.00 | 8.50 |
| 1030 | O | MET | A | 72 | 67.876 | 32.845 | 54.605 | 1.00 | 9.24 |
| 1031 | N | THR | A | 73 | 66.248 | 31.469 | 55.277 | 1.00 | 8.71 |
| 1033 | CA | THR | A | 73 | 66.041 | 30.918 | 53.935 | 1.00 | 9.14 |
| 1035 | CB | THR | A | 73 | 65.010 | 29.798 | 53.940 | 1.00 | 10.51 |
| 1037 | OG1 | THR | A | 73 | 63.814 | 30.236 | 54.589 | 1.00 | 12.31 |
| 1039 | CG2 | THR | A | 73 | 65.483 | 28.642 | 54.742 | 1.00 | 10.43 |
| 1043 | C | THR | A | 73 | 65.607 | 31.981 | 52.959 | 1.00 | 8.69 |
| 1044 | O | THR | A | 73 | 66.053 | 31.980 | 51.808 | 1.00 | 7.94 |
| 1045 | N | THR | A | 74 | 64.710 | 32.874 | 53.366 | 1.00 | 7.74 |
| 1047 | CA | THR | A | 74 | 64.255 | 33.872 | 52.395 | 1.00 | 8.53 |
| 1049 | CB | THR | A | 74 | 62.935 | 34.503 | 52.747 | 1.00 | 9.08 |
| 1051 | OG1 | THR | A | 74 | 63.112 | 35.358 | 53.873 | 1.00 | 9.41 |
| 1053 | CG2 | THR | A | 74 | 61.937 | 33.471 | 53.152 | 1.00 | 10.41 |
| 1057 | C | THR | A | 74 | 65.338 | 34.891 | 52.158 | 1.00 | 7.89 |
| 1058 | O | THR | A | 74 | 65.416 | 35.472 | 51.081 | 1.00 | 9.88 |
| 1059 | N | ALA | A | 75 | 66.188 | 35.113 | 53.159 | 1.00 | 8.72 |
| 1061 | CA | ALA | A | 75 | 67.349 | 35.954 | 52.956 | 1.00 | 8.46 |
| 1063 | CB | ALA | A | 75 | 68.126 | 36.104 | 54.247 | 1.00 | 8.87 |
| 1067 | C | ALA | A | 75 | 68.254 | 35.352 | 51.869 | 1.00 | 8.67 |
| 1068 | O | ALA | A | 75 | 68.756 | 36.062 | 50.997 | 1.00 | 7.71 |
| 1069 | N | PHE | A | 76 | 68.483 | 34.046 | 51.929 | 1.00 | 8.62 |
| 1071 | CA | PHE | A | 76 | 69.280 | 33.387 | 50.907 | 1.00 | 7.80 |
| 1073 | CB | PHE | A | 76 | 69.467 | 31.880 | 51.165 | 1.00 | 7.93 |
| 1076 | CG | PHE | A | 76 | 70.188 | 31.552 | 52.444 | 1.00 | 8.07 |
| 1077 | CD1 | PHE | A | 76 | 69.801 | 30.479 | 53.206 | 1.00 | 8.11 |
| 1079 | CE1 | PHE | A | 76 | 70.497 | 30.162 | 54.367 | 1.00 | 8.27 |
| 1081 | CZ | PHE | A | 76 | 71.576 | 30.919 | 54.732 | 1.00 | 9.23 |
| 1083 | CE2 | PHE | A | 76 | 71.984 | 31.948 | 53.951 | 1.00 | 8.76 |
| 1085 | CD2 | PHE | A | 76 | 71.300 | 32.269 | 52.825 | 1.00 | 8.16 |
| 1087 | C | PHE | A | 76 | 68.615 | 33.605 | 49.550 | 1.00 | 8.47 |
| 1088 | O | PHE | A | 76 | 69.283 | 33.895 | 48.558 | 1.00 | 7.71 |
| 1089 | N | GLN | A | 77 | 67.297 | 33.462 | 49.496 | 1.00 | 7.96 |
| 1091 | CA | GLN | A | 77 | 66.626 | 33.605 | 48.206 | 1.00 | 8.60 |

FIGURE 3 (Cont.)

| A | B | C | D | E | F | G | H | I | J |
|---|---|---|---|---|---|---|---|---|---|
| 1093 | CB | GLN | A | 77 | 65.163 | 33.204 | 48.298 | 1.00 | 8.91 |
| 1096 | CG | GLN | A | 77 | 64.494 | 33.127 | 46.917 | 1.00 | 9.75 |
| 1099 | CD | GLN | A | 77 | 65.106 | 32.047 | 46.007 | 1.00 | 9.93 |
| 1100 | OE1 | GLN | A | 77 | 65.336 | 30.917 | 46.434 | 1.00 | 12.13 |
| 1101 | NE2 | GLN | A | 77 | 65.348 | 32.402 | 44.733 | 1.00 | 11.34 |
| 1104 | C | GLN | A | 77 | 66.796 | 35.002 | 47.677 | 1.00 | 8.48 |
| 1105 | O | GLN | A | 77 | 66.975 | 35.186 | 46.484 | 1.00 | 8.43 |
| 1106 | N | TYR | A | 78 | 66.727 | 36.001 | 48.547 | 1.00 | 8.18 |
| 1108 | CA | TYR | A | 78 | 66.993 | 37.373 | 48.147 | 1.00 | 7.66 |
| 1110 | CB | TYR | A | 78 | 66.808 | 38.371 | 49.315 | 1.00 | 7.86 |
| 1113 | CG | TYR | A | 78 | 67.545 | 39.675 | 49.051 | 1.00 | 7.75 |
| 1114 | CD1 | TYR | A | 78 | 66.972 | 40.685 | 48.312 | 1.00 | 8.74 |
| 1116 | CE1 | TYR | A | 78 | 67.658 | 41.846 | 48.030 | 1.00 | 8.07 |
| 1118 | CZ | TYR | A | 78 | 68.967 | 42.017 | 48.500 | 1.00 | 9.19 |
| 1119 | OH | TYR | A | 78 | 69.658 | 43.178 | 48.214 | 1.00 | 10.00 |
| 1121 | CE2 | TYR | A | 78 | 69.557 | 41.014 | 49.242 | 1.00 | 8.23 |
| 1123 | CD2 | TYR | A | 78 | 68.861 | 39.851 | 49.488 | 1.00 | 8.01 |
| 1125 | C | TYR | A | 78 | 68.383 | 37.497 | 47.519 | 1.00 | 8.03 |
| 1126 | O | TYR | A | 78 | 68.564 | 38.088 | 46.467 | 1.00 | 8.18 |
| 1127 | N | ILE | A | 79 | 69.385 | 36.911 | 48.144 | 1.00 | 7.87 |
| 1129 | CA | ILE | A | 79 | 70.718 | 37.024 | 47.593 | 1.00 | 8.22 |
| 1131 | CB | ILE | A | 79 | 71.743 | 36.393 | 48.551 | 1.00 | 8.27 |
| 1133 | CG1 | ILE | A | 79 | 71.696 | 37.098 | 49.889 | 1.00 | 8.93 |
| 1136 | CD1 | ILE | A | 79 | 72.532 | 36.457 | 50.938 | 1.00 | 9.31 |
| 1140 | CG2 | ILE | A | 79 | 73.143 | 36.514 | 47.986 | 1.00 | 8.27 |
| 1144 | C | ILE | A | 79 | 70.788 | 36.384 | 46.205 | 1.00 | 8.54 |
| 1145 | O | ILE | A | 79 | 71.428 | 36.933 | 45.286 | 1.00 | 9.65 |
| 1146 | N | ILE | A | 80 | 70.097 | 35.266 | 46.042 | 1.00 | 8.96 |
| 1148 | CA | ILE | A | 80 | 70.020 | 34.598 | 44.745 | 1.00 | 9.08 |
| 1150 | CB | ILE | A | 80 | 69.271 | 33.268 | 44.851 | 1.00 | 9.18 |
| 1152 | CG1 | ILE | A | 80 | 70.065 | 32.285 | 45.717 | 1.00 | 9.39 |
| 1155 | CD1 | ILE | A | 80 | 69.265 | 31.099 | 46.122 | 1.00 | 11.40 |
| 1159 | CG2 | ILE | A | 80 | 68.998 | 32.713 | 43.470 | 1.00 | 11.43 |
| 1163 | C | ILE | A | 80 | 69.346 | 35.509 | 43.744 | 1.00 | 9.68 |
| 1164 | O | ILE | A | 80 | 69.898 | 35.795 | 42.669 | 1.00 | 10.88 |
| 1165 | N | ASP | A | 81 | 68.159 | 35.973 | 44.087 | 1.00 | 10.14 |
| 1167 | CA | ASP | A | 81 | 67.378 | 36.837 | 43.194 | 1.00 | 10.72 |
| 1169 | CB | ASP | A | 81 | 66.058 | 37.201 | 43.848 | 1.00 | 11.65 |
| 1172 | CG | ASP | A | 81 | 65.145 | 36.010 | 44.013 | 1.00 | 12.53 |
| 1173 | OD1 | ASP | A | 81 | 64.158 | 36.131 | 44.773 | 1.00 | 14.38 |
| 1174 | OD2 | ASP | A | 81 | 65.334 | 34.930 | 43.424 | 1.00 | 13.77 |
| 1175 | C | ASP | A | 81 | 68.095 | 38.117 | 42.847 | 1.00 | 11.90 |
| 1176 | O | ASP | A | 81 | 68.035 | 38.590 | 41.706 | 1.00 | 12.57 |
| 1177 | N | ASN | A | 82 | 68.783 | 38.678 | 43.831 | 1.00 | 10.91 |
| 1179 | CA | ASN | A | 82 | 69.470 | 39.966 | 43.692 | 1.00 | 11.60 |
| 1181 | CB | ASN | A | 82 | 69.710 | 40.570 | 45.085 | 1.00 | 11.41 |
| 1184 | CG | ASN | A | 82 | 70.127 | 42.002 | 45.031 | 1.00 | 12.60 |
| 1185 | OD1 | ASN | A | 82 | 69.430 | 42.837 | 44.477 | 1.00 | 12.65 |
| 1186 | ND2 | ASN | A | 82 | 71.277 | 42.309 | 45.620 | 1.00 | 11.59 |
| 1189 | C | ASN | A | 82 | 70.805 | 39.855 | 42.970 | 1.00 | 11.62 |
| 1190 | O | ASN | A | 82 | 71.409 | 40.875 | 42.613 | 1.00 | 12.76 |

FIGURE 3 (Cont.)

| A | B | C | D | E | F | G | H | I | J |
|---|---|---|---|---|---|---|---|---|---|
| 1191 | N | LYS | A | 83 | 71.269 | 38.628 | 42.833 | 1.00 | 11.17 |
| 1193 | CA | LYS | A | 83 | 72.534 | 38.317 | 42.179 | 1.00 | 11.77 |
| 1195 | CB | LYS | A | 83 | 72.534 | 38.799 | 40.723 | 1.00 | 13.02 |
| 1198 | CG | LYS | A | 83 | 71.424 | 38.104 | 39.923 | 1.00 | 16.14 |
| 1201 | CD | LYS | A | 83 | 71.668 | 38.199 | 38.438 | 1.00 | 21.01 |
| 1204 | CE | LYS | A | 83 | 70.429 | 37.943 | 37.594 | 1.00 | 24.55 |
| 1207 | NZ | LYS | A | 83 | 69.794 | 36.626 | 37.843 | 1.00 | 27.58 |
| 1211 | C | LYS | A | 83 | 73.701 | 38.860 | 42.986 | 1.00 | 11.66 |
| 1212 | O | LYS | A | 83 | 74.748 | 39.187 | 42.441 | 1.00 | 12.84 |
| 1213 | N | GLY | A | 84 | 73.517 | 38.947 | 44.307 | 1.00 | 10.77 |
| 1215 | CA | GLY | A | 84 | 74.605 | 39.370 | 45.155 | 1.00 | 10.74 |
| 1218 | C | GLY | A | 84 | 74.222 | 39.972 | 46.482 | 1.00 | 10.21 |
| 1219 | O | GLY | A | 84 | 73.079 | 40.320 | 46.761 | 1.00 | 9.37 |
| 1220 | N | ILE | A | 85 | 75.239 | 40.121 | 47.324 | 1.00 | 8.79 |
| 1222 | CA | ILE | A | 85 | 75.114 | 40.813 | 48.598 | 1.00 | 8.78 |
| 1224 | CB | ILE | A | 85 | 74.882 | 39.805 | 49.758 | 1.00 | 8.92 |
| 1226 | CG1 | ILE | A | 85 | 74.678 | 40.543 | 51.074 | 1.00 | 8.01 |
| 1229 | CD1 | ILE | A | 85 | 74.298 | 39.603 | 52.203 | 1.00 | 9.78 |
| 1233 | CG2 | ILE | A | 85 | 76.016 | 38.796 | 49.885 | 1.00 | 8.34 |
| 1237 | C | ILE | A | 85 | 76.402 | 41.604 | 48.786 | 1.00 | 8.57 |
| 1238 | O | ILE | A | 85 | 77.471 | 41.130 | 48.424 | 1.00 | 9.25 |
| 1239 | N | ASP | A | 86 | 76.290 | 42.792 | 49.348 | 1.00 | 8.93 |
| 1241 | CA | ASP | A | 86 | 77.439 | 43.665 | 49.582 | 1.00 | 8.56 |
| 1243 | CB | ASP | A | 86 | 76.967 | 45.086 | 49.777 | 1.00 | 9.03 |
| 1246 | CG | ASP | A | 86 | 76.495 | 45.712 | 48.507 | 1.00 | 8.05 |
| 1247 | OD1 | ASP | A | 86 | 76.974 | 45.278 | 47.420 | 1.00 | 10.46 |
| 1248 | OD2 | ASP | A | 86 | 75.731 | 46.685 | 48.534 | 1.00 | 9.08 |
| 1249 | C | ASP | A | 86 | 78.240 | 43.210 | 50.803 | 1.00 | 8.72 |
| 1250 | O | ASP | A | 86 | 77.765 | 42.468 | 51.658 | 1.00 | 8.71 |
| 1251 | N | SER | A | 87 | 79.469 | 43.661 | 50.873 | 1.00 | 9.41 |
| 1253 | CA | SER | A | 87 | 80.273 | 43.400 | 52.056 | 1.00 | 9.29 |
| 1255 | CB | SER | A | 87 | 81.734 | 43.744 | 51.771 | 1.00 | 9.72 |
| 1258 | OG | SER | A | 87 | 81.871 | 45.137 | 51.637 | 1.00 | 10.12 |
| 1260 | C | SER | A | 87 | 79.774 | 44.258 | 53.207 | 1.00 | 9.23 |
| 1261 | O | SER | A | 87 | 79.166 | 45.290 | 53.030 | 1.00 | 8.87 |
| 1262 | N | ASP | A | 88 | 80.058 | 43.819 | 54.423 | 1.00 | 9.52 |
| 1264 | CA | ASP | A | 88 | 79.731 | 44.578 | 55.627 | 1.00 | 11.12 |
| 1266 | CB | ASP | A | 88 | 80.115 | 43.730 | 56.838 | 1.00 | 11.26 |
| 1269 | CG | ASP | A | 88 | 79.774 | 44.375 | 58.137 | 1.00 | 15.89 |
| 1270 | OD1 | ASP | A | 88 | 78.598 | 44.691 | 58.384 | 1.00 | 17.31 |
| 1271 | OD2 | ASP | A | 88 | 80.637 | 44.525 | 59.019 | 1.00 | 22.11 |
| 1272 | C | ASP | A | 88 | 80.471 | 45.943 | 55.623 | 1.00 | 10.71 |
| 1273 | O | ASP | A | 88 | 79.909 | 46.990 | 55.966 | 1.00 | 11.43 |
| 1274 | N | ALA | A | 89 | 81.727 | 45.926 | 55.202 | 1.00 | 11.74 |
| 1276 | CA | ALA | A | 89 | 82.512 | 47.173 | 55.121 | 1.00 | 11.97 |
| 1278 | CB | ALA | A | 89 | 83.919 | 46.899 | 54.601 | 1.00 | 12.13 |
| 1282 | C | ALA | A | 89 | 81.854 | 48.254 | 54.257 | 1.00 | 12.39 |
| 1284 | N | SER | A | 90 | 81.246 | 47.770 | 53.174 | 1.00 | 11.37 |
| 1286 | CA | SER | A | 90 | 80.644 | 48.666 | 52.207 | 1.00 | 12.12 |
| 1288 | CB | SER | A | 90 | 80.601 | 48.009 | 50.829 | 1.00 | 11.86 |
| 1291 | OG | SER | A | 90 | 79.623 | 46.974 | 50.742 | 1.00 | 14.44 |

FIGURE 3 (Cont.)

| A | B | C | D | E | F | G | H | I | J |
|---|---|---|---|---|---|---|---|---|---|
| 1293 | C | SER | A | 90 | 79.250 | 49.099 | 52.585 | 1.00 | 12.03 |
| 1294 | O | SER | A | 90 | 78.796 | 50.165 | 52.176 | 1.00 | 13.24 |
| 1295 | N | TYR | A | 91 | 78.578 | 48.267 | 53.364 | 1.00 | 10.91 |
| 1297 | CA | TYR | A | 91 | 77.171 | 48.462 | 53.699 | 1.00 | 10.77 |
| 1299 | CB | TYR | A | 91 | 76.323 | 47.538 | 52.828 | 1.00 | 10.86 |
| 1302 | CG | TYR | A | 91 | 74.857 | 47.900 | 52.704 | 1.00 | 9.36 |
| 1303 | CD1 | TYR | A | 91 | 74.209 | 48.625 | 53.678 | 1.00 | 10.28 |
| 1305 | CE1 | TYR | A | 91 | 72.896 | 48.949 | 53.575 | 1.00 | 9.06 |
| 1307 | CZ | TYR | A | 91 | 72.169 | 48.538 | 52.476 | 1.00 | 11.94 |
| 1308 | OH | TYR | A | 91 | 70.842 | 48.876 | 52.359 | 1.00 | 12.23 |
| 1311 | CD2 | TYR | A | 91 | 74.114 | 47.440 | 51.635 | 1.00 | 12.15 |
| 1312 | C | TYR | A | 91 | 77.060 | 48.096 | 55.172 | 1.00 | 11.20 |
| 1313 | O | TYR | A | 91 | 76.670 | 47.003 | 55.547 | 1.00 | 10.53 |
| 1314 | N | PRO | A | 92 | 77.503 | 49.019 | 56.018 | 1.00 | 12.04 |
| 1315 | CA | PRO | A | 92 | 77.639 | 48.729 | 57.447 | 1.00 | 12.68 |
| 1317 | CB | PRO | A | 92 | 78.431 | 49.915 | 57.957 | 1.00 | 13.19 |
| 1320 | CG | PRO | A | 92 | 78.872 | 50.585 | 56.760 | 1.00 | 15.61 |
| 1323 | CD | PRO | A | 92 | 77.917 | 50.399 | 55.701 | 1.00 | 13.69 |
| 1326 | C | PRO | A | 92 | 76.356 | 48.619 | 58.203 | 1.00 | 11.86 |
| 1327 | O | PRO | A | 92 | 75.332 | 49.143 | 57.810 | 1.00 | 11.43 |
| 1328 | N | TYR | A | 93 | 76.446 | 47.942 | 59.331 | 1.00 | 11.87 |
| 1330 | CA | TYR | A | 93 | 75.271 | 47.655 | 60.131 | 1.00 | 11.07 |
| 1332 | CB | TYR | A | 93 | 75.540 | 46.400 | 60.941 | 1.00 | 10.94 |
| 1335 | CG | TYR | A | 93 | 74.367 | 45.954 | 61.770 | 1.00 | 10.33 |
| 1336 | CD1 | TYR | A | 93 | 73.225 | 45.444 | 61.177 | 1.00 | 9.36 |
| 1338 | CE1 | TYR | A | 93 | 72.151 | 45.042 | 61.947 | 1.00 | 9.94 |
| 1340 | CZ | TYR | A | 93 | 72.215 | 45.176 | 63.308 | 1.00 | 10.19 |
| 1341 | OH | TYR | A | 93 | 71.148 | 44.778 | 64.060 | 1.00 | 11.44 |
| 1343 | CE2 | TYR | A | 93 | 73.333 | 45.693 | 63.913 | 1.00 | 9.57 |
| 1345 | CD2 | TYR | A | 93 | 74.383 | 46.093 | 63.140 | 1.00 | 10.07 |
| 1347 | C | TYR | A | 93 | 74.943 | 48.808 | 61.050 | 1.00 | 12.05 |
| 1348 | O | TYR | A | 93 | 75.817 | 49.280 | 61.783 | 1.00 | 13.21 |
| 1349 | N | LYS | A | 94 | 73.691 | 49.245 | 61.011 | 1.00 | 12.38 |
| 1351 | CA | LYS | A | 94 | 73.250 | 50.387 | 61.790 | 1.00 | 13.76 |
| 1353 | CB | LYS | A | 94 | 72.690 | 51.432 | 60.845 | 1.00 | 15.11 |
| 1356 | CG | LYS | A | 94 | 73.668 | 51.887 | 59.776 | 1.00 | 17.85 |
| 1359 | CD | LYS | A | 94 | 74.784 | 52.654 | 60.385 | 1.00 | 23.31 |
| 1362 | CE | LYS | A | 94 | 75.753 | 53.161 | 59.342 | 1.00 | 26.53 |
| 1365 | NZ | LYS | A | 94 | 76.764 | 54.033 | 59.984 | 1.00 | 29.62 |
| 1369 | C | LYS | A | 94 | 72.184 | 50.052 | 62.814 | 1.00 | 13.22 |
| 1370 | O | LYS | A | 94 | 71.735 | 50.925 | 63.556 | 1.00 | 13.40 |
| 1371 | N | ALA | A | 95 | 71.763 | 48.798 | 62.851 | 1.00 | 12.76 |
| 1373 | CA | ALA | A | 95 | 70.758 | 48.332 | 63.805 | 1.00 | 12.89 |
| 1375 | CB | ALA | A | 95 | 71.297 | 48.339 | 65.242 | 1.00 | 12.52 |
| 1379 | C | ALA | A | 95 | 69.456 | 49.125 | 63.699 | 1.00 | 13.54 |
| 1380 | O | ALA | A | 95 | 68.818 | 49.449 | 64.715 | 1.00 | 13.99 |
| 1381 | N | MET | A | 96 | 69.091 | 49.453 | 62.472 | 1.00 | 13.83 |
| 1383 | CA | MET | A | 96 | 67.842 | 50.135 | 62.181 | 1.00 | 14.33 |
| 1385 | CB | MET | A | 96 | 68.016 | 51.646 | 62.301 | 1.00 | 16.16 |
| 1389 | SD | MET | A | 96 | 69.058 | 54.164 | 62.344 | 1.00 | 38.83 |
| 1390 | CE | MET | A | 96 | 68.589 | 54.315 | 64.043 | 1.00 | 39.15 |

FIGURE 3 (Cont.)

| A | B | C | D | E | F | G | H | I | J |
|---|---|---|---|---|---|---|---|---|---|
| 1391 | C | MET | A | 96 | 67.398 | 49.801 | 60.775 | 1.00 | 14.77 |
| 1392 | O | MET | A | 96 | 68.208 | 49.394 | 59.952 | 1.00 | 15.57 |
| 1393 | N | ASP | A | 97 | 66.113 | 49.992 | 60.504 | 1.00 | 14.90 |
| 1395 | CA | ASP | A | 97 | 65.592 | 49.840 | 59.163 | 1.00 | 15.37 |
| 1397 | CB | ASP | A | 97 | 64.071 | 49.712 | 59.176 | 1.00 | 15.74 |
| 1400 | CG | ASP | A | 97 | 63.602 | 48.461 | 59.858 | 1.00 | 17.13 |
| 1401 | OD1 | ASP | A | 97 | 62.674 | 48.534 | 60.694 | 1.00 | 21.38 |
| 1402 | OD2 | ASP | A | 97 | 64.092 | 47.356 | 59.624 | 1.00 | 16.47 |
| 1403 | C | ASP | A | 97 | 65.964 | 51.065 | 58.351 | 1.00 | 15.67 |
| 1404 | O | ASP | A | 97 | 65.831 | 52.208 | 58.813 | 1.00 | 18.09 |
| 1405 | N | GLN | A | 98 | 66.433 | 50.833 | 57.142 | 1.00 | 15.57 |
| 1407 | CA | GLN | A | 98 | 66.751 | 51.927 | 56.250 | 1.00 | 15.92 |
| 1409 | CB | GLN | A | 98 | 68.254 | 52.191 | 56.215 | 1.00 | 16.42 |
| 1412 | CG | GLN | A | 98 | 68.986 | 52.134 | 57.542 | 1.00 | 17.34 |
| 1415 | CD | GLN | A | 98 | 70.513 | 52.159 | 57.348 | 1.00 | 20.16 |
| 1416 | OE1 | GLN | A | 98 | 71.077 | 51.362 | 56.589 | 1.00 | 21.49 |
| 1417 | NE2 | GLN | A | 98 | 71.172 | 53.068 | 58.025 | 1.00 | 20.71 |
| 1420 | C | GLN | A | 98 | 66.315 | 51.566 | 54.851 | 1.00 | 16.04 |
| 1421 | O | GLN | A | 98 | 65.953 | 50.438 | 54.558 | 1.00 | 16.92 |
| 1422 | N | LYS | A | 99 | 66.388 | 52.517 | 53.942 | 1.00 | 17.33 |
| 1424 | CA | LYS | A | 99 | 66.011 | 52.179 | 52.589 | 1.00 | 18.24 |
| 1426 | CB | LYS | A | 99 | 65.812 | 53.423 | 51.755 | 1.00 | 19.45 |
| 1429 | CG | LYS | A | 99 | 66.837 | 54.460 | 51.983 | 1.00 | 24.15 |
| 1432 | CD | LYS | A | 99 | 66.632 | 55.620 | 51.001 | 1.00 | 29.03 |
| 1435 | CE | LYS | A | 99 | 65.247 | 55.569 | 50.340 | 1.00 | 30.82 |
| 1438 | NZ | LYS | A | 99 | 64.089 | 55.683 | 51.292 | 1.00 | 32.46 |
| 1442 | C | LYS | A | 99 | 67.075 | 51.298 | 51.964 | 1.00 | 17.60 |
| 1443 | O | LYS | A | 99 | 68.233 | 51.310 | 52.387 | 1.00 | 17.19 |
| 1444 | N | CYS | A | 100 | 66.668 | 50.530 | 50.968 | 1.00 | 17.89 |
| 1446 | CA | CYS | A | 100 | 67.563 | 49.656 | 50.240 | 1.00 | 18.61 |
| 1448 | CB | CYS | A | 100 | 66.785 | 48.912 | 49.160 | 1.00 | 19.74 |
| 1451 | SG | CYS | A | 100 | 67.861 | 47.885 | 48.131 | 1.00 | 27.28 |
| 1452 | C | CYS | A | 100 | 68.660 | 50.466 | 49.582 | 1.00 | 17.61 |
| 1453 | O | CYS | A | 100 | 68.362 | 51.409 | 48.851 | 1.00 | 17.91 |
| 1454 | N | GLN | A | 101 | 69.919 | 50.123 | 49.846 | 1.00 | 16.17 |
| 1456 | CA | GLN | A | 101 | 71.042 | 50.835 | 49.260 | 1.00 | 16.13 |
| 1458 | CB | GLN | A | 101 | 71.727 | 51.683 | 50.322 | 1.00 | 16.73 |
| 1461 | CG | GLN | A | 101 | 70.791 | 52.712 | 50.947 | 1.00 | 20.43 |
| 1464 | CD | GLN | A | 101 | 71.229 | 53.147 | 52.329 | 1.00 | 23.94 |
| 1465 | OE1 | GLN | A | 101 | 70.466 | 53.012 | 53.301 | 1.00 | 25.49 |
| 1466 | NE2 | GLN | A | 101 | 72.454 | 53.673 | 52.432 | 1.00 | 25.45 |
| 1469 | C | GLN | A | 101 | 72.024 | 49.883 | 48.602 | 1.00 | 14.01 |
| 1470 | O | GLN | A | 101 | 73.195 | 50.197 | 48.424 | 1.00 | 13.51 |
| 1471 | N | TYR | A | 102 | 71.545 | 48.699 | 48.247 | 1.00 | 12.47 |
| 1473 | CA | TYR | A | 102 | 72.383 | 47.723 | 47.595 | 1.00 | 12.18 |
| 1475 | CB | TYR | A | 102 | 71.600 | 46.477 | 47.192 | 1.00 | 11.65 |
| 1478 | CG | TYR | A | 102 | 72.451 | 45.520 | 46.371 | 1.00 | 11.45 |
| 1479 | CD1 | TYR | A | 102 | 73.403 | 44.707 | 46.961 | 1.00 | 10.07 |
| 1481 | CE1 | TYR | A | 102 | 74.173 | 43.863 | 46.246 | 1.00 | 10.60 |
| 1483 | CZ | TYR | A | 102 | 74.082 | 43.836 | 44.874 | 1.00 | 10.34 |
| 1484 | OH | TYR | A | 102 | 74.879 | 42.972 | 44.174 | 1.00 | 12.26 |

FIGURE 3 (Cont.)

| A | B | C | D | E | F | G | H | I | J |
|---|---|---|---|---|---|---|---|---|---|
| 1486 | CE2 | TYR | A | 102 | 73.155 | 44.636 | 44.265 | 1.00 | 9.92 |
| 1488 | CD2 | TYR | A | 102 | 72.372 | 45.474 | 44.994 | 1.00 | 11.91 |
| 1490 | C | TYR | A | 102 | 73.050 | 48.327 | 46.364 | 1.00 | 12.74 |
| 1491 | O | TYR | A | 102 | 72.405 | 49.007 | 45.560 | 1.00 | 12.69 |
| 1492 | N | ASP | A | 103 | 74.332 | 48.039 | 46.211 | 1.00 | 12.98 |
| 1494 | CA | ASP | A | 103 | 75.088 | 48.479 | 45.059 | 1.00 | 13.79 |
| 1496 | CB | ASP | A | 103 | 75.903 | 49.703 | 45.437 | 1.00 | 14.41 |
| 1499 | CG | ASP | A | 103 | 76.537 | 50.373 | 44.243 | 1.00 | 16.28 |
| 1500 | OD1 | ASP | A | 103 | 76.745 | 49.722 | 43.206 | 1.00 | 19.81 |
| 1501 | OD2 | ASP | A | 103 | 76.843 | 51.582 | 44.278 | 1.00 | 24.23 |
| 1502 | C | ASP | A | 103 | 75.980 | 47.346 | 44.596 | 1.00 | 13.61 |
| 1503 | O | ASP | A | 103 | 76.801 | 46.839 | 45.351 | 1.00 | 13.25 |
| 1504 | N | SER | A | 104 | 75.835 | 46.914 | 43.349 | 1.00 | 13.73 |
| 1506 | CA | SER | A | 104 | 76.638 | 45.805 | 42.857 | 1.00 | 14.25 |
| 1508 | CB | SER | A | 104 | 76.175 | 45.382 | 41.481 | 1.00 | 15.37 |
| 1511 | OG | SER | A | 104 | 76.373 | 46.434 | 40.564 | 1.00 | 18.86 |
| 1513 | C | SER | A | 104 | 78.148 | 46.058 | 42.836 | 1.00 | 13.62 |
| 1514 | O | SER | A | 104 | 78.933 | 45.111 | 42.780 | 1.00 | 13.57 |
| 1515 | N | ALA | A | 105 | 78.536 | 47.329 | 42.874 | 1.00 | 14.02 |
| 1517 | CA | ALA | A | 105 | 79.949 | 47.678 | 42.887 | 1.00 | 14.05 |
| 1519 | CB | ALA | A | 105 | 80.114 | 49.188 | 42.778 | 1.00 | 15.04 |
| 1523 | C | ALA | A | 105 | 80.594 | 47.172 | 44.157 | 1.00 | 14.12 |
| 1524 | O | ALA | A | 105 | 81.811 | 46.993 | 44.212 | 1.00 | 14.91 |
| 1525 | N | TYR | A | 106 | 79.774 | 46.987 | 45.189 | 1.00 | 12.65 |
| 1527 | CA | TYR | A | 106 | 80.270 | 46.538 | 46.491 | 1.00 | 12.64 |
| 1529 | CB | TYR | A | 106 | 79.717 | 47.432 | 47.584 | 1.00 | 13.67 |
| 1532 | CG | TYR | A | 106 | 80.068 | 48.883 | 47.414 | 1.00 | 15.56 |
| 1533 | CD1 | TYR | A | 106 | 79.136 | 49.863 | 47.675 | 1.00 | 22.60 |
| 1535 | CE1 | TYR | A | 106 | 79.447 | 51.197 | 47.538 | 1.00 | 24.51 |
| 1537 | CZ | TYR | A | 106 | 80.723 | 51.556 | 47.141 | 1.00 | 25.64 |
| 1538 | OH | TYR | A | 106 | 81.049 | 52.902 | 47.002 | 1.00 | 30.95 |
| 1540 | CE2 | TYR | A | 106 | 81.667 | 50.594 | 46.892 | 1.00 | 23.29 |
| 1542 | CD2 | TYR | A | 106 | 81.338 | 49.260 | 47.042 | 1.00 | 19.28 |
| 1544 | C | TYR | A | 106 | 79.924 | 45.080 | 46.801 | 1.00 | 12.60 |
| 1545 | O | TYR | A | 106 | 80.112 | 44.623 | 47.915 | 1.00 | 12.29 |
| 1546 | N | ARG | A | 107 | 79.675 | 44.286 | 45.780 | 1.00 | 11.59 |
| 1548 | CA | ARG | A | 107 | 79.141 | 42.948 | 45.929 | 1.00 | 12.06 |
| 1550 | CB | ARG | A | 107 | 78.651 | 42.364 | 44.600 | 1.00 | 12.43 |
| 1553 | CG | ARG | A | 107 | 77.642 | 41.239 | 44.760 | 1.00 | 19.10 |
| 1556 | CD | ARG | A | 107 | 77.714 | 40.157 | 43.714 | 1.00 | 21.47 |
| 1559 | NE | ARG | A | 107 | 78.378 | 40.600 | 42.511 | 1.00 | 25.78 |
| 1561 | CZ | ARG | A | 107 | 77.939 | 41.600 | 41.745 | 1.00 | 28.57 |
| 1562 | NH1 | ARG | A | 107 | 78.624 | 41.971 | 40.673 | 1.00 | 30.25 |
| 1565 | NH2 | ARG | A | 107 | 76.827 | 42.249 | 42.063 | 1.00 | 32.84 |
| 1568 | C | ARG | A | 107 | 80.338 | 42.141 | 46.399 | 1.00 | 12.40 |
| 1569 | O | ARG | A | 107 | 81.414 | 42.215 | 45.804 | 1.00 | 12.31 |
| 1570 | N | ALA | A | 108 | 80.167 | 41.352 | 47.445 | 1.00 | 10.86 |
| 1572 | CA | ALA | A | 108 | 81.228 | 40.480 | 47.924 | 1.00 | 11.36 |
| 1574 | CB | ALA | A | 108 | 81.622 | 40.882 | 49.342 | 1.00 | 11.48 |
| 1578 | C | ALA | A | 108 | 80.906 | 38.997 | 47.878 | 1.00 | 11.31 |
| 1579 | O | ALA | A | 108 | 81.790 | 38.167 | 48.063 | 1.00 | 12.89 |

FIGURE 3 (Cont.)

| A | B | C | D | E | F | G | H | I | J |
|---|---|---|---|---|---|---|---|---|---|
| 1580 | N | ALA | A | 109 | 79.657 | 38.650 | 47.601 | 1.00 | 10.73 |
| 1582 | CA | ALA | A | 109 | 79.283 | 37.261 | 47.498 | 1.00 | 10.90 |
| 1584 | CB | ALA | A | 109 | 79.051 | 36.650 | 48.879 | 1.00 | 10.89 |
| 1588 | C | ALA | A | 109 | 78.033 | 37.131 | 46.668 | 1.00 | 10.82 |
| 1589 | O | ALA | A | 109 | 77.316 | 38.101 | 46.463 | 1.00 | 10.40 |
| 1590 | N | THR | A | 110 | 77.816 | 35.902 | 46.234 | 1.00 | 11.20 |
| 1592 | CA | THR | A | 110 | 76.629 | 35.495 | 45.507 | 1.00 | 11.72 |
| 1594 | CB | THR | A | 110 | 76.914 | 35.257 | 44.026 | 1.00 | 12.47 |
| 1596 | OG1 | THR | A | 110 | 77.961 | 34.278 | 43.875 | 1.00 | 14.50 |
| 1598 | CG2 | THR | A | 110 | 77.401 | 36.538 | 43.346 | 1.00 | 14.63 |
| 1602 | C | THR | A | 110 | 76.154 | 34.217 | 46.144 | 1.00 | 11.75 |
| 1603 | O | THR | A | 110 | 76.846 | 33.619 | 46.951 | 1.00 | 12.09 |
| 1604 | N | CYS | A | 111 | 74.962 | 33.782 | 45.773 | 1.00 | 11.68 |
| 1606 | CA | CYS | A | 111 | 74.408 | 32.536 | 46.268 | 1.00 | 11.58 |
| 1608 | CB | CYS | A | 111 | 73.443 | 32.820 | 47.425 | 1.00 | 11.73 |
| 1611 | SG | CYS | A | 111 | 72.680 | 31.361 | 48.109 | 1.00 | 14.24 |
| 1612 | C | CYS | A | 111 | 73.699 | 31.887 | 45.078 | 1.00 | 11.92 |
| 1613 | O | CYS | A | 111 | 73.008 | 32.601 | 44.340 | 1.00 | 12.45 |
| 1614 | N | SER | A | 112 | 73.876 | 30.576 | 44.898 | 1.00 | 12.05 |
| 1616 | CA | SER | A | 112 | 73.225 | 29.857 | 43.785 | 1.00 | 13.72 |
| 1618 | CB | SER | A | 112 | 74.173 | 28.872 | 43.102 | 1.00 | 13.55 |
| 1621 | OG | SER | A | 112 | 74.734 | 27.958 | 44.000 | 1.00 | 17.64 |
| 1623 | C | SER | A | 112 | 71.971 | 29.142 | 44.236 | 1.00 | 14.06 |
| 1624 | O | SER | A | 112 | 71.059 | 28.884 | 43.432 | 1.00 | 15.16 |
| 1625 | N | LYS | A | 113 | 71.946 | 28.777 | 45.506 | 1.00 | 14.21 |
| 1627 | CA | LYS | A | 113 | 70.757 | 28.223 | 46.093 | 1.00 | 14.09 |
| 1629 | CB | LYS | A | 113 | 70.248 | 27.077 | 45.290 | 1.00 | 17.46 |
| 1632 | CG | LYS | A | 113 | 70.764 | 25.827 | 45.665 | 1.00 | 17.84 |
| 1635 | CD | LYS | A | 113 | 72.230 | 25.770 | 45.745 | 1.00 | 20.97 |
| 1638 | CE | LYS | A | 113 | 72.631 | 24.386 | 45.318 | 1.00 | 24.42 |
| 1641 | NZ | LYS | A | 113 | 71.876 | 23.382 | 46.102 | 1.00 | 26.61 |
| 1645 | C | LYS | A | 113 | 70.976 | 27.866 | 47.545 | 1.00 | 12.54 |
| 1646 | O | LYS | A | 113 | 72.023 | 28.182 | 48.099 | 1.00 | 11.47 |
| 1647 | N | TYR | A | 114 | 69.974 | 27.275 | 48.169 | 1.00 | 10.94 |
| 1649 | CA | TYR | A | 114 | 70.096 | 26.913 | 49.575 | 1.00 | 10.67 |
| 1651 | CB | TYR | A | 114 | 69.552 | 28.024 | 50.492 | 1.00 | 9.80 |
| 1654 | CG | TYR | A | 114 | 68.072 | 28.255 | 50.337 | 1.00 | 10.15 |
| 1655 | CD1 | TYR | A | 114 | 67.173 | 27.627 | 51.171 | 1.00 | 9.93 |
| 1657 | CE1 | TYR | A | 114 | 65.816 | 27.808 | 51.048 | 1.00 | 11.07 |
| 1659 | CZ | TYR | A | 114 | 65.357 | 28.635 | 50.063 | 1.00 | 10.47 |
| 1660 | OH | TYR | A | 114 | 63.979 | 28.824 | 49.933 | 1.00 | 13.05 |
| 1662 | CE2 | TYR | A | 114 | 66.216 | 29.291 | 49.237 | 1.00 | 9.92 |
| 1664 | CD2 | TYR | A | 114 | 67.588 | 29.105 | 49.368 | 1.00 | 10.20 |
| 1666 | C | TYR | A | 114 | 69.366 | 25.617 | 49.831 | 1.00 | 10.45 |
| 1667 | O | TYR | A | 114 | 68.549 | 25.174 | 49.023 | 1.00 | 10.52 |
| 1668 | N | THR | A | 115 | 69.672 | 24.999 | 50.956 | 1.00 | 10.04 |
| 1670 | CA | THR | A | 115 | 69.124 | 23.733 | 51.321 | 1.00 | 10.39 |
| 1672 | CB | THR | A | 115 | 70.240 | 22.677 | 51.288 | 1.00 | 11.48 |
| 1674 | OG1 | THR | A | 115 | 70.762 | 22.562 | 49.953 | 1.00 | 13.46 |
| 1676 | CG2 | THR | A | 115 | 69.706 | 21.282 | 51.656 | 1.00 | 12.62 |
| 1680 | C | THR | A | 115 | 68.589 | 23.835 | 52.724 | 1.00 | 10.67 |

FIGURE 3 (Cont.)

| A | B | C | D | E | F | G | H | I | J |
|---|---|---|---|---|---|---|---|---|---|
| 1681 | O | THR | A | 115 | 69.276 | 24.344 | 53.593 | 1.00 | 11.00 |
| 1682 | N | GLU | A | 116 | 67.381 | 23.353 | 52.940 | 1.00 | 10.19 |
| 1684 | CA | GLU | A | 116 | 66.777 | 23.282 | 54.257 | 1.00 | 10.63 |
| 1686 | CB | GLU | A | 116 | 65.316 | 23.747 | 54.241 | 1.00 | 11.21 |
| 1689 | CG | GLU | A | 116 | 64.585 | 23.591 | 55.559 | 1.00 | 16.56 |
| 1692 | CD | GLU | A | 116 | 64.938 | 24.657 | 56.577 | 1.00 | 21.26 |
| 1693 | OE1 | GLU | A | 116 | 64.685 | 24.415 | 57.762 | 1.00 | 19.91 |
| 1694 | OE2 | GLU | A | 116 | 65.429 | 25.737 | 56.194 | 1.00 | 22.35 |
| 1695 | C | GLU | A | 116 | 66.871 | 21.828 | 54.728 | 1.00 | 10.99 |
| 1696 | O | GLU | A | 116 | 66.487 | 20.899 | 53.992 | 1.00 | 11.77 |
| 1697 | N | LEU | A | 117 | 67.357 | 21.619 | 55.942 | 1.00 | 9.54 |
| 1699 | CA | LEU | A | 117 | 67.495 | 20.271 | 56.468 | 1.00 | 10.33 |
| 1701 | CB | LEU | A | 117 | 68.592 | 20.261 | 57.529 | 1.00 | 10.13 |
| 1704 | CG | LEU | A | 117 | 70.007 | 20.490 | 57.017 | 1.00 | 13.64 |
| 1706 | CD1 | LEU | A | 117 | 71.012 | 20.212 | 58.133 | 1.00 | 14.25 |
| 1710 | CD2 | LEU | A | 117 | 70.373 | 19.703 | 55.785 | 1.00 | 16.55 |
| 1714 | C | LEU | A | 117 | 66.195 | 19.784 | 57.046 | 1.00 | 9.94 |
| 1715 | O | LEU | A | 117 | 65.369 | 20.580 | 57.471 | 1.00 | 10.75 |
| 1716 | N | PRO | A | 118 | 66.051 | 18.472 | 57.136 | 1.00 | 10.31 |
| 1717 | CA | PRO | A | 118 | 64.820 | 17.889 | 57.653 | 1.00 | 10.41 |
| 1719 | CB | PRO | A | 118 | 65.044 | 16.390 | 57.483 | 1.00 | 11.40 |
| 1722 | CG | PRO | A | 118 | 66.490 | 16.204 | 57.467 | 1.00 | 13.12 |
| 1725 | CD | PRO | A | 118 | 67.055 | 17.432 | 56.877 | 1.00 | 12.37 |
| 1728 | C | PRO | A | 118 | 64.662 | 18.262 | 59.117 | 1.00 | 9.57 |
| 1729 | O | PRO | A | 118 | 65.636 | 18.336 | 59.885 | 1.00 | 10.97 |
| 1730 | N | TYR | A | 119 | 63.426 | 18.480 | 59.503 | 1.00 | 8.92 |
| 1732 | CA | TYR | A | 119 | 63.087 | 18.965 | 60.826 | 1.00 | 8.35 |
| 1734 | CB | TYR | A | 119 | 61.574 | 19.168 | 60.949 | 1.00 | 7.88 |
| 1737 | CG | TYR | A | 119 | 61.190 | 19.665 | 62.313 | 1.00 | 7.93 |
| 1738 | CD1 | TYR | A | 119 | 61.126 | 21.015 | 62.577 | 1.00 | 9.08 |
| 1740 | CE1 | TYR | A | 119 | 60.824 | 21.472 | 63.814 | 1.00 | 9.37 |
| 1742 | CZ | TYR | A | 119 | 60.588 | 20.603 | 64.837 | 1.00 | 9.28 |
| 1743 | OH | TYR | A | 119 | 60.293 | 21.103 | 66.092 | 1.00 | 12.09 |
| 1745 | CE2 | TYR | A | 119 | 60.637 | 19.245 | 64.626 | 1.00 | 9.95 |
| 1747 | CD2 | TYR | A | 119 | 60.933 | 18.785 | 63.349 | 1.00 | 8.02 |
| 1749 | C | TYR | A | 119 | 63.536 | 18.074 | 61.945 | 1.00 | 8.81 |
| 1750 | O | TYR | A | 119 | 63.231 | 16.894 | 61.966 | 1.00 | 9.91 |
| 1751 | N | GLY | A | 120 | 64.299 | 18.649 | 62.876 | 1.00 | 10.11 |
| 1753 | CA | GLY | A | 120 | 64.647 | 17.981 | 64.108 | 1.00 | 10.48 |
| 1756 | C | GLY | A | 120 | 65.723 | 16.924 | 64.048 | 1.00 | 10.39 |
| 1757 | O | GLY | A | 120 | 65.980 | 16.279 | 65.061 | 1.00 | 12.29 |
| 1758 | N | ARG | A | 121 | 66.340 | 16.719 | 62.891 | 1.00 | 10.56 |
| 1760 | CA | ARG | A | 121 | 67.264 | 15.597 | 62.726 | 1.00 | 11.08 |
| 1762 | CB | ARG | A | 121 | 67.163 | 15.021 | 61.318 | 1.00 | 11.64 |
| 1765 | CG | ARG | A | 121 | 65.805 | 14.331 | 61.037 | 1.00 | 13.97 |
| 1768 | CD | ARG | A | 121 | 65.701 | 12.938 | 61.675 | 1.00 | 18.88 |
| 1771 | NE | ARG | A | 121 | 66.804 | 12.039 | 61.273 | 1.00 | 23.70 |
| 1773 | CZ | ARG | A | 121 | 67.071 | 11.576 | 60.047 | 1.00 | 26.61 |
| 1774 | NH1 | ARG | A | 121 | 66.336 | 11.876 | 58.978 | 1.00 | 29.00 |
| 1777 | NH2 | ARG | A | 121 | 68.110 | 10.767 | 59.879 | 1.00 | 27.92 |
| 1780 | C | ARG | A | 121 | 68.691 | 16.051 | 63.070 | 1.00 | 10.81 |

FIGURE 3 (Cont.)

| A | B | C | D | E | F | G | H | I | J |
|---|---|---|---|---|---|---|---|---|---|
| 1781 | O | ARG | A | 121 | 69.367 | 16.693 | 62.269 | 1.00 | 10.99 |
| 1782 | N | GLU | A | 122 | 69.172 | 15.658 | 64.238 | 1.00 | 10.92 |
| 1784 | CA | GLU | A | 122 | 70.449 | 16.220 | 64.691 | 1.00 | 10.77 |
| 1786 | CB | GLU | A | 122 | 70.620 | 16.312 | 66.201 | 1.00 | 11.30 |
| 1789 | CG | GLU | A | 122 | 69.670 | 17.273 | 66.903 | 1.00 | 11.49 |
| 1792 | CD | GLU | A | 122 | 69.914 | 17.279 | 68.383 | 1.00 | 10.90 |
| 1793 | OE1 | GLU | A | 122 | 70.907 | 17.924 | 68.809 | 1.00 | 12.61 |
| 1794 | OE2 | GLU | A | 122 | 69.158 | 16.617 | 69.113 | 1.00 | 12.77 |
| 1795 | C | GLU | A | 122 | 71.587 | 15.480 | 64.025 | 1.00 | 10.70 |
| 1796 | O | GLU | A | 122 | 72.685 | 16.019 | 63.883 | 1.00 | 10.04 |
| 1797 | N | ASP | A | 123 | 71.319 | 14.245 | 63.611 | 1.00 | 11.23 |
| 1799 | CA | ASP | A | 123 | 72.294 | 13.496 | 62.832 | 1.00 | 11.54 |
| 1801 | CB | ASP | A | 123 | 71.919 | 12.004 | 62.746 | 1.00 | 12.35 |
| 1804 | CG | ASP | A | 123 | 70.522 | 11.758 | 62.259 | 1.00 | 16.29 |
| 1805 | OD1 | ASP | A | 123 | 70.224 | 10.549 | 62.035 | 1.00 | 23.03 |
| 1806 | OD2 | ASP | A | 123 | 69.645 | 12.629 | 62.091 | 1.00 | 17.22 |
| 1807 | C | ASP | A | 123 | 72.546 | 14.105 | 61.444 | 1.00 | 10.74 |
| 1808 | O | ASP | A | 123 | 73.690 | 14.193 | 60.962 | 1.00 | 11.34 |
| 1809 | N | VAL | A | 124 | 71.481 | 14.561 | 60.798 | 1.00 | 10.66 |
| 1811 | CA | VAL | A | 124 | 71.609 | 15.201 | 59.509 | 1.00 | 10.45 |
| 1813 | CB | VAL | A | 124 | 70.233 | 15.362 | 58.831 | 1.00 | 10.68 |
| 1815 | CG1 | VAL | A | 124 | 70.379 | 16.127 | 57.531 | 1.00 | 11.63 |
| 1819 | CG2 | VAL | A | 124 | 69.605 | 13.981 | 58.619 | 1.00 | 12.29 |
| 1823 | C | VAL | A | 124 | 72.314 | 16.552 | 59.671 | 1.00 | 9.04 |
| 1824 | O | VAL | A | 124 | 73.123 | 16.944 | 58.838 | 1.00 | 10.27 |
| 1825 | N | LEU | A | 125 | 71.999 | 17.263 | 60.759 | 1.00 | 9.71 |
| 1827 | CA | LEU | A | 125 | 72.655 | 18.523 | 61.022 | 1.00 | 8.77 |
| 1829 | CB | LEU | A | 125 | 72.002 | 19.215 | 62.216 | 1.00 | 8.25 |
| 1832 | CG | LEU | A | 125 | 72.631 | 20.545 | 62.603 | 1.00 | 8.58 |
| 1834 | CD1 | LEU | A | 125 | 72.640 | 21.547 | 61.459 | 1.00 | 7.65 |
| 1838 | CD2 | LEU | A | 125 | 71.956 | 21.115 | 63.819 | 1.00 | 8.88 |
| 1842 | C | LEU | A | 125 | 74.144 | 18.295 | 61.231 | 1.00 | 8.32 |
| 1843 | O | LEU | A | 125 | 74.958 | 19.040 | 60.720 | 1.00 | 8.40 |
| 1844 | N | LYS | A | 126 | 74.488 | 17.221 | 61.933 | 1.00 | 9.47 |
| 1846 | CA | LYS | A | 126 | 75.884 | 16.902 | 62.181 | 1.00 | 9.80 |
| 1848 | CB | LYS | A | 126 | 75.982 | 15.710 | 63.116 | 1.00 | 10.35 |
| 1851 | CG | LYS | A | 126 | 77.422 | 15.326 | 63.446 | 1.00 | 11.29 |
| 1854 | CD | LYS | A | 126 | 77.496 | 14.014 | 64.157 | 1.00 | 11.93 |
| 1857 | CE | LYS | A | 126 | 78.932 | 13.613 | 64.384 | 1.00 | 14.42 |
| 1860 | NZ | LYS | A | 126 | 79.002 | 12.244 | 65.003 | 1.00 | 14.97 |
| 1864 | C | LYS | A | 126 | 76.632 | 16.645 | 60.878 | 1.00 | 10.19 |
| 1865 | O | LYS | A | 126 | 77.689 | 17.168 | 60.618 | 1.00 | 9.36 |
| 1866 | N | GLU | A | 127 | 75.940 | 16.060 | 59.934 | 1.00 | 10.68 |
| 1868 | CA | GLU | A | 127 | 76.528 | 15.618 | 58.698 | 1.00 | 11.80 |
| 1870 | CB | GLU | A | 127 | 75.581 | 14.703 | 57.924 | 1.00 | 12.26 |
| 1873 | CG | GLU | À | 127 | 76.183 | 14.184 | 56.625 | 1.00 | 17.82 |
| 1876 | CD | GLU | A | 127 | 75.249 | 13.231 | 55.880 | 1.00 | 24.81 |
| 1877 | OE1 | GLU | A | 127 | 75.594 | 12.820 | 54.748 | 1.00 | 30.58 |
| 1878 | OE2 | GLU | A | 127 | 74.169 | 12.878 | 56.415 | 1.00 | 30.81 |
| 1879 | C | GLU | A | 127 | 76.765 | 16.890 | 57.886 | 1.00 | 10.63 |
| 1880 | O | GLU | A | 127 | 77.803 | 17.063 | 57.261 | 1.00 | 10.41 |

FIGURE 3 (Cont.)

| A | B | C | D | E | F | G | H | I | J |
|---|---|---|---|---|---|---|---|---|---|
| 1881 | N | ALA | A | 128 | 75.802 | 17.802 | 57.919 | 1.00 | 9.65 |
| 1883 | CA | ALA | A | 128 | 75.906 | 19.038 | 57.162 | 1.00 | 9.46 |
| 1885 | CB | ALA | A | 128 | 74.572 | 19.791 | 57.174 | 1.00 | 9.65 |
| 1889 | C | ALA | A | 128 | 77.026 | 19.929 | 57.705 | 1.00 | 9.71 |
| 1890 | O | ALA | A | 128 | 77.773 | 20.557 | 56.966 | 1.00 | 8.97 |
| 1891 | N | VAL | A | 129 | 77.104 | 20.009 | 59.024 | 1.00 | 9.81 |
| 1893 | CA | VAL | A | 129 | 78.131 | 20.834 | 59.641 | 1.00 | 10.35 |
| 1895 | CB | VAL | A | 129 | 77.932 | 20.917 | 61.164 | 1.00 | 9.67 |
| 1897 | CG1 | VAL | A | 129 | 79.111 | 21.636 | 61.831 | 1.00 | 10.09 |
| 1901 | CG2 | VAL | A | 129 | 76.657 | 21.658 | 61.498 | 1.00 | 11.58 |
| 1905 | C | VAL | A | 129 | 79.512 | 20.257 | 59.304 | 1.00 | 10.25 |
| 1906 | O | VAL | A | 129 | 80.451 | 21.011 | 58.991 | 1.00 | 11.60 |
| 1907 | N | ALA | A | 130 | 79.635 | 18.931 | 59.303 | 1.00 | 10.33 |
| 1909 | CA | ALA | A | 130 | 80.921 | 18.297 | 58.986 | 1.00 | 10.92 |
| 1911 | CB | ALA | A | 130 | 80.887 | 16.835 | 59.372 | 1.00 | 11.58 |
| 1915 | C | ALA | A | 130 | 81.320 | 18.420 | 57.512 | 1.00 | 11.52 |
| 1916 | O | ALA | A | 130 | 82.473 | 18.681 | 57.169 | 1.00 | 13.47 |
| 1917 | N | ASN | A | 131 | 80.328 | 18.230 | 56.647 | 1.00 | 12.06 |
| 1919 | CA | ASN | A | 131 | 80.564 | 18.098 | 55.216 | 1.00 | 12.89 |
| 1921 | CB | ASN | A | 131 | 79.779 | 16.903 | 54.697 | 1.00 | 13.41 |
| 1924 | CG | ASN | A | 131 | 80.098 | 15.642 | 55.462 | 1.00 | 18.03 |
| 1925 | OD1 | ASN | A | 131 | 81.175 | 15.529 | 56.058 | 1.00 | 23.95 |
| 1926 | ND2 | ASN | A | 131 | 79.162 | 14.685 | 55.468 | 1.00 | 24.96 |
| 1929 | C | ASN | A | 131 | 80.265 | 19.299 | 54.346 | 1.00 | 12.52 |
| 1930 | O | ASN | A | 131 | 80.785 | 19.386 | 53.224 | 1.00 | 14.05 |
| 1931 | N | LYS | A | 132 | 79.447 | 20.219 | 54.828 | 1.00 | 11.98 |
| 1933 | CA | LYS | A | 132 | 79.047 | 21.379 | 54.034 | 1.00 | 11.52 |
| 1935 | CB | LYS | A | 132 | 77.523 | 21.475 | 53.903 | 1.00 | 12.09 |
| 1938 | CG | LYS | A | 132 | 76.879 | 20.234 | 53.333 | 1.00 | 14.86 |
| 1941 | CD | LYS | A | 132 | 77.338 | 19.976 | 51.948 | 1.00 | 18.60 |
| 1944 | CE | LYS | A | 132 | 76.628 | 18.765 | 51.370 | 1.00 | 22.39 |
| 1947 | NZ | LYS | A | 132 | 77.040 | 18.566 | 49.974 | 1.00 | 24.93 |
| 1951 | C | LYS | A | 132 | 79.579 | 22.672 | 54.618 | 1.00 | 10.89 |
| 1952 | O | LYS | A | 132 | 80.044 | 23.511 | 53.890 | 1.00 | 12.16 |
| 1953 | N | GLY | A | 133 | 79.509 | 22.825 | 55.933 | 1.00 | 10.86 |
| 1955 | CA | GLY | A | 133 | 80.018 | 24.022 | 56.574 | 1.00 | 10.39 |
| 1958 | C | GLY | A | 133 | 79.024 | 24.471 | 57.621 | 1.00 | 9.08 |
| 1959 | O | GLY | A | 133 | 78.100 | 23.754 | 57.957 | 1.00 | 9.22 |
| 1960 | N | PRO | A | 134 | 79.237 | 25.667 | 58.151 | 1.00 | 8.54 |
| 1961 | CA | PRO | A | 134 | 78.321 | 26.231 | 59.126 | 1.00 | 8.52 |
| 1963 | CB | PRO | A | 134 | 78.898 | 27.624 | 59.367 | 1.00 | 8.68 |
| 1966 | CG | PRO | A | 134 | 80.386 | 27.413 | 59.170 | 1.00 | 8.71 |
| 1969 | CD | PRO | A | 134 | 80.400 | 26.527 | 57.936 | 1.00 | 8.56 |
| 1972 | C | PRO | A | 134 | 76.890 | 26.293 | 58.605 | 1.00 | 8.18 |
| 1973 | O | PRO | A | 134 | 76.646 | 26.564 | 57.423 | 1.00 | 9.37 |
| 1974 | N | VAL | A | 135 | 75.958 | 26.069 | 59.519 | 1.00 | 7.77 |
| 1976 | CA | VAL | A | 135 | 74.552 | 25.970 | 59.171 | 1.00 | 7.23 |
| 1978 | CB | VAL | A | 135 | 74.013 | 24.564 | 59.455 | 1.00 | 7.86 |
| 1980 | CG1 | VAL | A | 135 | 72.528 | 24.473 | 59.155 | 1.00 | 7.98 |
| 1984 | CG2 | VAL | A | 135 | 74.793 | 23.524 | 58.652 | 1.00 | 9.33 |
| 1988 | C | VAL | A | 135 | 73.724 | 26.964 | 59.948 | 1.00 | 7.50 |

FIGURE 3 (Cont.)

| A | B | C | D | E | F | G | H | I | J |
|---|---|---|---|---|---|---|---|---|---|
| 1989 | O | VAL | A | 135 | 73.855 | 27.053 | 61.166 | 1.00 | 7.45 |
| 1990 | N | SER | A | 136 | 72.879 | 27.701 | 59.261 | 1.00 | 6.93 |
| 1992 | CA | SER | A | 136 | 71.992 | 28.640 | 59.914 | 1.00 | 6.89 |
| 1994 | CB | SER | A | 136 | 71.336 | 29.558 | 58.896 | 1.00 | 7.58 |
| 1997 | OG | SER | A | 136 | 72.280 | 30.389 | 58.274 | 1.00 | 9.26 |
| 1999 | C | SER | A | 136 | 70.904 | 27.873 | 60.625 | 1.00 | 7.76 |
| 2000 | O | SER | A | 136 | 70.312 | 26.979 | 60.050 | 1.00 | 8.27 |
| 2001 | N | VAL | A | 137 | 70.608 | 28.229 | 61.861 | 1.00 | 6.95 |
| 2003 | CA | VAL | A | 137 | 69.553 | 27.579 | 62.604 | 1.00 | 7.33 |
| 2005 | CB | VAL | A | 137 | 70.106 | 26.481 | 63.549 | 1.00 | 7.43 |
| 2007 | CG1 | VAL | A | 137 | 70.796 | 25.365 | 62.779 | 1.00 | 7.54 |
| 2011 | CG2 | VAL | A | 137 | 71.018 | 27.098 | 64.582 | 1.00 | 8.98 |
| 2015 | C | VAL | A | 137 | 68.798 | 28.565 | 63.453 | 1.00 | 7.01 |
| 2016 | O | VAL | A | 137 | 69.272 | 29.670 | 63.673 | 1.00 | 7.91 |
| 2017 | N | GLY | A | 138 | 67.632 | 28.155 | 63.930 | 1.00 | 7.99 |
| 2019 | CA | GLY | A | 138 | 66.915 | 28.927 | 64.927 | 1.00 | 8.21 |
| 2022 | C | GLY | A | 138 | 66.959 | 28.190 | 66.241 | 1.00 | 8.99 |
| 2023 | O | GLY | A | 138 | 66.969 | 26.950 | 66.266 | 1.00 | 10.44 |
| 2024 | N | VAL | A | 139 | 66.994 | 28.945 | 67.335 | 1.00 | 8.90 |
| 2026 | CA | VAL | A | 139 | 66.934 | 28.357 | 68.646 | 1.00 | 8.49 |
| 2028 | CB | VAL | A | 139 | 68.301 | 28.366 | 69.380 | 1.00 | 9.11 |
| 2030 | CG1 | VAL | A | 139 | 69.303 | 27.488 | 68.667 | 1.00 | 10.12 |
| 2034 | CG2 | VAL | A | 139 | 68.809 | 29.787 | 69.552 | 1.00 | 10.01 |
| 2038 | C | VAL | A | 139 | 65.915 | 29.113 | 69.470 | 1.00 | 8.74 |
| 2039 | O | VAL | A | 139 | 65.580 | 30.261 | 69.168 | 1.00 | 9.27 |
| 2040 | N | ASP | A | 140 | 65.439 | 28.453 | 70.515 | 1.00 | 9.41 |
| 2042 | CA | ASP | A | 140 | 64.619 | 29.080 | 71.532 | 1.00 | 9.75 |
| 2044 | CB | ASP | A | 140 | 63.758 | 28.027 | 72.221 | 1.00 | 10.36 |
| 2047 | CG | ASP | A | 140 | 62.973 | 28.567 | 73.382 | 1.00 | 13.95 |
| 2048 | OD1 | ASP | A | 140 | 63.018 | 29.788 | 73.636 | 1.00 | 13.07 |
| 2049 | OD2 | ASP | A | 140 | 62.280 | 27.821 | 74.089 | 1.00 | 12.63 |
| 2050 | C | ASP | A | 140 | 65.582 | 29.742 | 72.509 | 1.00 | 10.48 |
| 2051 | O | ASP | A | 140 | 66.192 | 29.070 | 73.340 | 1.00 | 11.23 |
| 2052 | N | ALA | A | 141 | 65.736 | 31.055 | 72.376 | 1.00 | 9.84 |
| 2054 | CA | ALA | A | 141 | 66.627 | 31.800 | 73.255 | 1.00 | 10.56 |
| 2056 | CB | ALA | A | 141 | 67.563 | 32.644 | 72.403 | 1.00 | 10.21 |
| 2060 | C | ALA | A | 141 | 65.864 | 32.696 | 74.230 | 1.00 | 11.65 |
| 2061 | O | ALA | A | 141 | 66.420 | 33.703 | 74.660 | 1.00 | 13.88 |
| 2062 | N | ALA | A | 142 | 64.618 | 32.340 | 74.559 | 1.00 | 11.62 |
| 2064 | CA | ALA | A | 142 | 63.701 | 33.170 | 75.383 | 1.00 | 12.34 |
| 2066 | CB | ALA | A | 142 | 62.279 | 32.790 | 75.045 | 1.00 | 13.28 |
| 2070 | C | ALA | A | 142 | 63.848 | 33.075 | 76.893 | 1.00 | 12.91 |
| 2071 | O | ALA | A | 142 | 63.299 | 33.897 | 77.640 | 1.00 | 14.20 |
| 2072 | N | HIS | A | 143 | 64.542 | 32.028 | 77.328 | 1.00 | 11.67 |
| 2074 | CA | HIS | A | 143 | 64.734 | 31.745 | 78.736 | 1.00 | 10.65 |
| 2076 | CB | HIS | A | 143 | 64.909 | 30.229 | 78.886 | 1.00 | 11.31 |
| 2079 | CG | HIS | A | 143 | 63.760 | 29.489 | 78.294 | 1.00 | 12.62 |
| 2080 | ND1 | HIS | A | 143 | 62.563 | 29.392 | 78.958 | 1.00 | 15.67 |
| 2082 | CE1 | HIS | A | 143 | 61.677 | 28.789 | 78.187 | 1.00 | 18.84 |
| 2084 | NE2 | HIS | A | 143 | 62.233 | 28.582 | 77.012 | 1.00 | 17.98 |
| 2086 | CD2 | HIS | A | 143 | 63.541 | 28.995 | 77.055 | 1.00 | 16.74 |

FIGURE 3 (Cont.)

| A | B | C | D | E | F | G | H | I | J |
|---|---|---|---|---|---|---|---|---|---|
| 2088 | C | HIS | A | 143 | 65.867 | 32.533 | 79.375 | 1.00 | 10.05 |
| 2089 | O | HIS | A | 143 | 66.957 | 32.677 | 78.813 | 1.00 | 8.85 |
| 2090 | N | PRO | A | 144 | 65.618 | 33.058 | 80.572 | 1.00 | 9.31 |
| 2091 | CA | PRO | A | 144 | 66.619 | 33.858 | 81.263 | 1.00 | 9.10 |
| 2093 | CB | PRO | A | 144 | 65.981 | 34.078 | 82.639 | 1.00 | 9.27 |
| 2096 | CG | PRO | A | 144 | 64.554 | 34.116 | 82.356 | 1.00 | 9.48 |
| 2099 | CD | PRO | A | 144 | 64.356 | 33.003 | 81.328 | 1.00 | 10.45 |
| 2102 | C | PRO | A | 144 | 68.002 | 33.226 | 81.356 | 1.00 | 9.20 |
| 2103 | O | PRO | A | 144 | 69.002 | 33.922 | 81.269 | 1.00 | 9.58 |
| 2104 | N | SER | A | 145 | 68.074 | 31.912 | 81.469 | 1.00 | 8.53 |
| 2106 | CA | SER | A | 145 | 69.355 | 31.241 | 81.507 | 1.00 | 9.24 |
| 2108 | CB | SER | A | 145 | 69.181 | 29.741 | 81.708 | 1.00 | 9.98 |
| 2111 | OG | SER | A | 145 | 68.353 | 29.206 | 80.689 | 1.00 | 10.17 |
| 2113 | C | SER | A | 145 | 70.195 | 31.442 | 80.252 | 1.00 | 9.24 |
| 2114 | O | SER | A | 145 | 71.404 | 31.438 | 80.302 | 1.00 | 10.26 |
| 2115 | N | PHE | A | 146 | 69.550 | 31.622 | 79.120 | 1.00 | 8.12 |
| 2117 | CA | PHE | A | 146 | 70.280 | 31.777 | 77.878 | 1.00 | 8.41 |
| 2119 | CB | PHE | A | 146 | 69.311 | 31.790 | 76.696 | 1.00 | 8.68 |
| 2122 | CG | PHE | A | 146 | 69.989 | 31.730 | 75.353 | 1.00 | 9.31 |
| 2123 | CD1 | PHE | A | 146 | 70.446 | 32.864 | 74.738 | 1.00 | 9.11 |
| 2125 | CE1 | PHE | A | 146 | 71.073 | 32.815 | 73.499 | 1.00 | 10.41 |
| 2127 | CZ | PHE | A | 146 | 71.237 | 31.604 | 72.858 | 1.00 | 8.98 |
| 2129 | CE2 | PHE | A | 146 | 70.784 | 30.463 | 73.447 | 1.00 | 9.09 |
| 2131 | CD2 | PHE | A | 146 | 70.168 | 30.514 | 74.713 | 1.00 | 9.83 |
| 2133 | C | PHE | A | 146 | 71.099 | 33.051 | 77.918 | 1.00 | 8.58 |
| 2134 | O | PHE | A | 146 | 72.256 | 33.075 | 77.535 | 1.00 | 8.66 |
| 2135 | N | PHE | A | 147 | 70.463 | 34.134 | 78.344 | 1.00 | 8.28 |
| 2137 | CA | PHE | A | 147 | 71.145 | 35.416 | 78.385 | 1.00 | 8.90 |
| 2139 | CB | PHE | A | 147 | 70.175 | 36.519 | 78.836 | 1.00 | 8.80 |
| 2142 | CG | PHE | A | 147 | 68.910 | 36.602 | 78.030 | 1.00 | 9.02 |
| 2143 | CD1 | PHE | A | 147 | 68.874 | 37.264 | 76.829 | 1.00 | 10.28 |
| 2145 | CE1 | PHE | A | 147 | 67.695 | 37.367 | 76.112 | 1.00 | 11.17 |
| 2147 | CZ | PHE | A | 147 | 66.559 | 36.771 | 76.579 | 1.00 | 11.26 |
| 2149 | CE2 | PHE | A | 147 | 66.588 | 36.141 | 77.766 | 1.00 | 10.27 |
| 2151 | CD2 | PHE | A | 147 | 67.742 | 36.050 | 78.496 | 1.00 | 11.76 |
| 2153 | C | PHE | A | 147 | 72.332 | 35.409 | 79.336 | 1.00 | 8.96 |
| 2154 | O | PHE | A | 147 | 73.280 | 36.161 | 79.153 | 1.00 | 9.91 |
| 2155 | N | LEU | A | 148 | 72.257 | 34.562 | 80.357 | 1.00 | 8.62 |
| 2157 | CA | LEU | A | 148 | 73.269 | 34.494 | 81.405 | 1.00 | 8.80 |
| 2159 | CB | LEU | A | 148 | 72.587 | 34.268 | 82.750 | 1.00 | 9.36 |
| 2162 | CG | LEU | A | 148 | 71.784 | 35.450 | 83.268 | 1.00 | 11.87 |
| 2164 | CD1 | LEU | A | 148 | 70.837 | 35.007 | 84.357 | 1.00 | 13.02 |
| 2168 | CD2 | LEU | A | 148 | 72.709 | 36.549 | 83.731 | 1.00 | 14.79 |
| 2172 | C | LEU | A | 148 | 74.315 | 33.419 | 81.194 | 1.00 | 8.48 |
| 2173 | O | LEU | A | 148 | 75.194 | 33.203 | 82.040 | 1.00 | 8.85 |
| 2174 | N | TYR | A | 149 | 74.251 | 32.723 | 80.068 | 1.00 | 8.43 |
| 2176 | CA | TYR | A | 149 | 75.216 | 31.682 | 79.795 | 1.00 | 8.84 |
| 2178 | CB | TYR | A | 149 | 74.903 | 31.084 | 78.413 | 1.00 | 9.11 |
| 2181 | CG | TYR | A | 149 | 75.998 | 30.135 | 77.957 | 1.00 | 8.12 |
| 2182 | CD1 | TYR | A | 149 | 77.085 | 30.588 | 77.249 | 1.00 | 10.58 |
| 2184 | CE1 | TYR | A | 149 | 78.093 | 29.724 | 76.861 | 1.00 | 10.61 |

FIGURE 3 (Cont.)

| A | B | C | D | E | F | G | H | I | J |
|---|---|---|---|---|---|---|---|---|---|
| 2186 | CZ | TYR | A | 149 | 78.030 | 28.432 | 77.211 | 1.00 | 10.21 |
| 2187 | OH | TYR | A | 149 | 79.002 | 27.527 | 76.847 | 1.00 | 12.73 |
| 2189 | CE2 | TYR | A | 149 | 76.973 | 27.949 | 77.918 | 1.00 | 8.84 |
| 2191 | CD2 | TYR | A | 149 | 75.974 | 28.812 | 78.316 | 1.00 | 8.14 |
| 2193 | C | TYR | A | 149 | 76.630 | 32.239 | 79.786 | 1.00 | 9.36 |
| 2194 | O | TYR | A | 149 | 76.894 | 33.240 | 79.156 | 1.00 | 9.91 |
| 2195 | N | ARG | A | 150 | 77.562 | 31.475 | 80.337 | 1.00 | 11.00 |
| 2197 | CA | ARG | A | 150 | 78.940 | 31.916 | 80.410 | 1.00 | 13.06 |
| 2199 | CB | ARG | A | 150 | 79.383 | 32.296 | 81.818 | 1.00 | 13.71 |
| 2202 | CG | ARG | A | 150 | 78.785 | 33.579 | 82.319 | 1.00 | 17.64 |
| 2205 | CD | ARG | A | 150 | 79.526 | 34.139 | 83.521 | 1.00 | 22.44 |
| 2208 | NE | ARG | A | 150 | 80.525 | 35.139 | 83.150 | 1.00 | 28.55 |
| 2210 | CZ | ARG | A | 150 | 81.330 | 35.754 | 84.011 | 1.00 | 29.06 |
| 2211 | NH1 | ARG | A | 150 | 81.275 | 35.466 | 85.315 | 1.00 | 32.76 |
| 2214 | NH2 | ARG | A | 150 | 82.212 | 36.646 | 83.566 | 1.00 | 32.91 |
| 2217 | C | ARG | A | 150 | 79.847 | 30.859 | 79.853 | 1.00 | 14.38 |
| 2218 | O | ARG | A | 150 | 80.711 | 31.177 | 79.051 | 1.00 | 16.28 |
| 2219 | N | SER | A | 151 | 79.635 | 29.623 | 80.254 | 1.00 | 14.09 |
| 2221 | CA | SER | A | 151 | 80.498 | 28.530 | 79.838 | 1.00 | 15.27 |
| 2223 | CB | SER | A | 151 | 81.763 | 28.574 | 80.702 | 1.00 | 16.19 |
| 2226 | OG | SER | A | 151 | 81.422 | 28.217 | 82.023 | 1.00 | 20.80 |
| 2228 | C | SER | A | 151 | 79.841 | 27.175 | 80.004 | 1.00 | 13.74 |
| 2229 | O | SER | A | 151 | 78.766 | 27.039 | 80.535 | 1.00 | 14.33 |
| 2230 | N | GLY | A | 152 | 80.513 | 26.140 | 79.519 | 1.00 | 14.22 |
| 2232 | CA | GLY | A | 152 | 79.983 | 24.808 | 79.634 | 1.00 | 13.52 |
| 2235 | C | GLY | A | 152 | 78.998 | 24.506 | 78.519 | 1.00 | 12.08 |
| 2236 | O | GLY | A | 152 | 78.956 | 25.171 | 77.499 | 1.00 | 13.44 |
| 2237 | N | VAL | A | 153 | 78.205 | 23.482 | 78.735 | 1.00 | 10.92 |
| 2239 | CA | VAL | A | 153 | 77.216 | 23.103 | 77.735 | 1.00 | 10.45 |
| 2241 | CB | VAL | A | 153 | 77.243 | 21.614 | 77.462 | 1.00 | 9.54 |
| 2243 | CG1 | VAL | A | 153 | 76.052 | 21.211 | 76.602 | 1.00 | 12.64 |
| 2247 | CG2 | VAL | A | 153 | 78.545 | 21.268 | 76.795 | 1.00 | 10.69 |
| 2251 | C | VAL | A | 153 | 75.857 | 23.493 | 78.243 | 1.00 | 10.27 |
| 2252 | O | VAL | A | 153 | 75.387 | 23.015 | 79.278 | 1.00 | 12.04 |
| 2253 | N | TYR | A | 154 | 75.198 | 24.361 | 77.495 | 1.00 | 9.96 |
| 2255 | CA | TYR | A | 154 | 73.890 | 24.856 | 77.873 | 1.00 | 9.51 |
| 2257 | CB | TYR | A | 154 | 73.513 | 26.043 | 77.003 | 1.00 | 9.63 |
| 2260 | CG | TYR | A | 154 | 72.192 | 26.721 | 77.327 | 1.00 | 7.69 |
| 2261 | CD1 | TYR | A | 154 | 72.065 | 27.565 | 78.410 | 1.00 | 9.40 |
| 2263 | CE1 | TYR | A | 154 | 70.891 | 28.185 | 78.667 | 1.00 | 8.73 |
| 2265 | CZ | TYR | A | 154 | 69.809 | 27.993 | 77.857 | 1.00 | 9.00 |
| 2266 | OH | TYR | A | 154 | 68.624 | 28.620 | 78.089 | 1.00 | 9.78 |
| 2268 | CE2 | TYR | A | 154 | 69.894 | 27.172 | 76.783 | 1.00 | 10.21 |
| 2270 | CD2 | TYR | A | 154 | 71.083 | 26.549 | 76.511 | 1.00 | 9.56 |
| 2272 | C | TYR | A | 154 | 72.798 | 23.809 | 77.749 | 1.00 | 10.46 |
| 2273 | O | TYR | A | 154 | 72.546 | 23.248 | 76.683 | 1.00 | 10.19 |
| 2274 | N | TYR | A | 155 | 72.137 | 23.545 | 78.858 | 1.00 | 11.08 |
| 2276 | CA | TYR | A | 155 | 70.962 | 22.703 | 78.890 | 1.00 | 11.49 |
| 2278 | CB | TYR | A | 155 | 71.261 | 21.291 | 79.366 | 1.00 | 11.90 |
| 2281 | CG | TYR | A | 155 | 70.029 | 20.416 | 79.355 | 1.00 | 13.97 |
| 2282 | CD1 | TYR | A | 155 | 69.609 | 19.792 | 78.188 | 1.00 | 16.03 |

FIGURE 3 (Cont.)

| A | B | C | D | E | F | G | H | I | J |
|---|---|---|---|---|---|---|---|---|---|
| 2284 | CE1 | TYR | A | 155 | 68.479 | 19.018 | 78.160 | 1.00 | 17.16 |
| 2286 | CZ | TYR | A | 155 | 67.755 | 18.855 | 79.317 | 1.00 | 19.32 |
| 2287 | OH | TYR | A | 155 | 66.627 | 18.085 | 79.327 | 1.00 | 21.76 |
| 2289 | CE2 | TYR | A | 155 | 68.148 | 19.459 | 80.480 | 1.00 | 18.42 |
| 2291 | CD2 | TYR | A | 155 | 69.270 | 20.239 | 80.497 | 1.00 | 16.68 |
| 2293 | C | TYR | A | 155 | 69.948 | 23.378 | 79.803 | 1.00 | 12.53 |
| 2294 | O | TYR | A | 155 | 70.248 | 23.643 | 80.971 | 1.00 | 12.82 |
| 2295 | N | GLU | A | 156 | 68.775 | 23.664 | 79.264 | 1.00 | 11.20 |
| 2297 | CA | GLU | A | 156 | 67.724 | 24.357 | 79.989 | 1.00 | 12.03 |
| 2299 | CB | GLU | A | 156 | 67.501 | 25.714 | 79.326 | 1.00 | 12.58 |
| 2302 | CG | GLU | A | 156 | 66.272 | 26.509 | 79.780 | 1.00 | 13.48 |
| 2305 | CD | GLU | A | 156 | 66.192 | 26.623 | 81.281 | 1.00 | 15.11 |
| 2306 | OE1 | GLU | A | 156 | 66.809 | 27.561 | 81.860 | 1.00 | 15.68 |
| 2307 | OE2 | GLU | A | 156 | 65.542 | 25.771 | 81.919 | 1.00 | 15.92 |
| 2308 | C | GLU | A | 156 | 66.473 | 23.486 | 79.900 | 1.00 | 12.76 |
| 2309 | O | GLU | A | 156 | 65.887 | 23.384 | 78.845 | 1.00 | 12.36 |
| 2310 | N | PRO | A | 157 | 66.080 | 22.870 | 81.015 | 1.00 | 13.89 |
| 2311 | CA | PRO | A | 157 | 64.876 | 22.036 | 81.084 | 1.00 | 15.01 |
| 2313 | CB | PRO | A | 157 | 64.714 | 21.783 | 82.585 | 1.00 | 15.26 |
| 2316 | CG | PRO | A | 157 | 66.057 | 21.897 | 83.121 | 1.00 | 15.94 |
| 2319 | CD | PRO | A | 157 | 66.809 | 22.891 | 82.288 | 1.00 | 14.46 |
| 2322 | C | PRO | A | 157 | 63.639 | 22.726 | 80.555 | 1.00 | 15.21 |
| 2323 | O | PRO | A | 157 | 62.798 | 22.051 | 79.979 | 1.00 | 16.52 |
| 2324 | N | SER | A | 158 | 63.534 | 24.037 | 80.704 | 1.00 | 15.00 |
| 2326 | CA | SER | A | 158 | 62.360 | 24.768 | 80.231 | 1.00 | 15.20 |
| 2328 | CB | SER | A | 158 | 62.195 | 26.054 | 81.040 | 1.00 | 15.85 |
| 2331 | OG | SER | A | 158 | 63.200 | 27.009 | 80.694 | 1.00 | 18.36 |
| 2333 | C | SER | A | 158 | 62.395 | 25.112 | 78.739 | 1.00 | 15.01 |
| 2334 | O | SER | A | 158 | 61.444 | 25.698 | 78.195 | 1.00 | 14.99 |
| 2335 | N | CYS | A | 159 | 63.479 | 24.765 | 78.058 | 1.00 | 14.65 |
| 2337 | CA | CYS | A | 159 | 63.576 | 25.121 | 76.659 | 1.00 | 15.32 |
| 2339 | CB | CYS | A | 159 | 64.971 | 24.807 | 76.111 | 1.00 | 15.82 |
| 2342 | SG | CYS | A | 159 | 65.717 | 26.157 | 75.134 | 1.00 | 19.46 |
| 2343 | C | CYS | A | 159 | 62.506 | 24.363 | 75.865 | 1.00 | 15.27 |
| 2344 | O | CYS | A | 159 | 61.992 | 23.325 | 76.303 | 1.00 | 16.56 |
| 2345 | N | THR | A | 160 | 62.196 | 24.894 | 74.691 | 1.00 | 14.37 |
| 2347 | CA | THR | A | 160 | 61.195 | 24.313 | 73.800 | 1.00 | 14.29 |
| 2349 | CB | THR | A | 160 | 59.929 | 25.174 | 73.781 | 1.00 | 15.27 |
| 2351 | OG1 | THR | A | 160 | 60.186 | 26.373 | 73.034 | 1.00 | 15.16 |
| 2353 | CG2 | THR | A | 160 | 59.555 | 25.644 | 75.163 | 1.00 | 15.70 |
| 2357 | C | THR | A | 160 | 61.739 | 24.279 | 72.400 | 1.00 | 13.99 |
| 2358 | O | THR | A | 160 | 62.850 | 24.736 | 72.134 | 1.00 | 13.31 |
| 2359 | N | GLN | A | 161 | 60.916 | 23.758 | 71.490 | 1.00 | 13.08 |
| 2361 | CA | GLN | A | 161 | 61.240 | 23.746 | 70.090 | 1.00 | 13.25 |
| 2363 | CB | GLN | A | 161 | 60.896 | 22.388 | 69.467 | 1.00 | 13.15 |
| 2366 | CG | GLN | A | 161 | 61.858 | 21.270 | 69.856 | 1.00 | 12.98 |
| 2369 | CD | GLN | A | 161 | 61.565 | 20.677 | 71.210 | 1.00 | 13.59 |
| 2370 | OE1 | GLN | A | 161 | 60.429 | 20.644 | 71.657 | 1.00 | 14.17 |
| 2371 | NE2 | GLN | A | 161 | 62.615 | 20.193 | 71.884 | 1.00 | 15.01 |
| 2374 | C | GLN | A | 161 | 60.533 | 24.906 | 69.372 | 1.00 | 13.83 |
| 2375 | O | GLN | A | 161 | 60.429 | 24.913 | 68.152 | 1.00 | 15.62 |

FIGURE 3 (Cont.)

| A | B | C | D | E | F | G | H | I | J |
|---|---|---|---|---|---|---|---|---|---|
| 2376 | N | ASN | A | 162 | 60.080 | 25.897 | 70.127 | 1.00 | 14.74 |
| 2378 | CA | ASN | A | 162 | 59.421 | 27.067 | 69.564 | 1.00 | 15.59 |
| 2380 | CB | ASN | A | 162 | 58.341 | 27.560 | 70.512 | 1.00 | 16.23 |
| 2383 | CG | ASN | A | 162 | 57.219 | 26.544 | 70.671 | 1.00 | 19.55 |
| 2384 | OD1 | ASN | A | 162 | 56.731 | 25.975 | 69.673 | 1.00 | 23.25 |
| 2385 | ND2 | ASN | A | 162 | 56.819 | 26.293 | 71.904 | 1.00 | 24.33 |
| 2388 | C | ASN | A | 162 | 60.465 | 28.140 | 69.298 | 1.00 | 15.36 |
| 2389 | O | ASN | A | 162 | 60.998 | 28.734 | 70.219 | 1.00 | 15.41 |
| 2390 | N | VAL | A | 163 | 61.244 | 28.131 | 68.187 | 1.00 | 10.65 |
| 2392 | CA | VAL | A | 163 | 62.485 | 28.881 | 68.008 | 1.00 | 10.29 |
| 2394 | CB | VAL | A | 163 | 63.377 | 28.307 | 66.901 | 1.00 | 10.87 |
| 2396 | CG1 | VAL | A | 163 | 63.729 | 26.861 | 67.248 | 1.00 | 12.53 |
| 2400 | CG2 | VAL | A | 163 | 62.717 | 28.419 | 65.514 | 1.00 | 12.13 |
| 2404 | C | VAL | A | 163 | 62.164 | 30.342 | 67.757 | 1.00 | 10.71 |
| 2405 | O | VAL | A | 163 | 61.155 | 30.657 | 67.136 | 1.00 | 12.16 |
| 2406 | N | ASN | A | 164 | 63.039 | 31.227 | 68.213 | 1.00 | 9.91 |
| 2408 | CA | ASN | A | 164 | 62.806 | 32.652 | 68.074 | 1.00 | 10.63 |
| 2410 | CB | ASN | A | 164 | 62.208 | 33.229 | 69.355 | 1.00 | 10.42 |
| 2413 | CG | ASN | A | 164 | 63.244 | 33.413 | 70.465 | 1.00 | 13.48 |
| 2414 | OD1 | ASN | A | 164 | 64.071 | 32.579 | 70.671 | 1.00 | 12.41 |
| 2415 | ND2 | ASN | A | 164 | 63.180 | 34.555 | 71.186 | 1.00 | 19.14 |
| 2418 | C | ASN | A | 164 | 64.045 | 33.427 | 67.692 | 1.00 | 9.92 |
| 2419 | O | ASN | A | 164 | 63.965 | 34.638 | 67.463 | 1.00 | 11.88 |
| 2420 | N | HIS | A | 165 | 65.191 | 32.767 | 67.602 | 1.00 | 8.50 |
| 2422 | CA | HIS | A | 165 | 66.438 | 33.483 | 67.417 | 1.00 | 8.73 |
| 2424 | CB | HIS | A | 165 | 67.081 | 33.581 | 68.793 | 1.00 | 8.53 |
| 2427 | CG | HIS | A | 165 | 68.328 | 34.386 | 68.828 | 1.00 | 9.08 |
| 2428 | ND1 | HIS | A | 165 | 68.371 | 35.704 | 68.410 | 1.00 | 14.10 |
| 2430 | CE1 | HIS | A | 165 | 69.597 | 36.171 | 68.592 | 1.00 | 14.09 |
| 2432 | NE2 | HIS | A | 165 | 70.331 | 35.218 | 69.142 | 1.00 | 11.57 |
| 2434 | CD2 | HIS | A | 165 | 69.555 | 34.099 | 69.311 | 1.00 | 11.96 |
| 2436 | C | HIS | A | 165 | 67.370 | 32.780 | 66.434 | 1.00 | 8.56 |
| 2437 | O | HIS | A | 165 | 67.745 | 31.614 | 66.634 | 1.00 | 9.41 |
| 2438 | N | GLY | A | 166 | 67.717 | 33.467 | 65.374 | 1.00 | 7.36 |
| 2440 | CA | GLY | A | 166 | 68.592 | 32.911 | 64.370 | 1.00 | 7.82 |
| 2443 | C | GLY | A | 166 | 70.032 | 32.978 | 64.818 | 1.00 | 7.99 |
| 2444 | O | GLY | A | 166 | 70.501 | 34.036 | 65.242 | 1.00 | 9.99 |
| 2445 | N | VAL | A | 167 | 70.744 | 31.866 | 64.694 | 1.00 | 7.36 |
| 2447 | CA | VAL | A | 167 | 72.145 | 31.790 | 65.058 | 1.00 | 7.23 |
| 2449 | CB | VAL | A | 167 | 72.330 | 31.254 | 66.486 | 1.00 | 7.45 |
| 2451 | CG1 | VAL | A | 167 | 71.776 | 32.242 | 67.496 | 1.00 | 10.34 |
| 2455 | CG2 | VAL | A | 167 | 71.703 | 29.909 | 66.652 | 1.00 | 7.32 |
| 2459 | C | VAL | A | 167 | 72.853 | 30.900 | 64.042 | 1.00 | 7.36 |
| 2460 | O | VAL | A | 167 | 72.233 | 30.459 | 63.065 | 1.00 | 7.38 |
| 2461 | N | LEU | A | 168 | 74.135 | 30.625 | 64.247 | 1.00 | 6.74 |
| 2463 | CA | LEU | A | 168 | 74.915 | 29.864 | 63.302 | 1.00 | 6.96 |
| 2465 | CB | LEU | A | 168 | 75.923 | 30.780 | 62.614 | 1.00 | 7.61 |
| 2468 | CG | LEU | A | 168 | 76.767 | 30.201 | 61.496 | 1.00 | 7.59 |
| 2470 | CD1 | LEU | A | 168 | 75.862 | 29.930 | 60.278 | 1.00 | 8.89 |
| 2474 | CD2 | LEU | A | 168 | 77.897 | 31.107 | 61.118 | 1.00 | 9.51 |
| 2478 | C | LEU | A | 168 | 75.630 | 28.753 | 64.011 | 1.00 | 7.40 |

FIGURE 3 (Cont.)

| A | B | C | D | E | F | G | H | I | J |
|---|---|---|---|---|---|---|---|---|---|
| 2479 | O | LEU | A | 168 | 76.400 | 29.003 | 64.947 | 1.00 | 8.25 |
| 2480 | N | VAL | A | 169 | 75.394 | 27.541 | 63.559 | 1.00 | 6.97 |
| 2482 | CA | VAL | A | 169 | 76.115 | 26.392 | 64.075 | 1.00 | 7.43 |
| 2484 | CB | VAL | A | 169 | 75.348 | 25.099 | 63.926 | 1.00 | 8.17 |
| 2486 | CG1 | VAL | A | 169 | 76.236 | 23.950 | 64.379 | 1.00 | 7.39 |
| 2490 | CG2 | VAL | A | 169 | 74.059 | 25.167 | 64.691 | 1.00 | 8.53 |
| 2494 | C | VAL | A | 169 | 77.425 | 26.302 | 63.324 | 1.00 | 8.18 |
| 2495 | O | VAL | A | 169 | 77.448 | 26.068 | 62.100 | 1.00 | 9.10 |
| 2496 | N | VAL | A | 170 | 78.543 | 26.455 | 64.034 | 1.00 | 8.35 |
| 2498 | CA | VAL | A | 170 | 79.851 | 26.441 | 63.420 | 1.00 | 8.74 |
| 2500 | CB | VAL | A | 170 | 80.664 | 27.719 | 63.735 | 1.00 | 8.05 |
| 2502 | CG1 | VAL | A | 170 | 79.982 | 28.943 | 63.129 | 1.00 | 9.46 |
| 2506 | CG2 | VAL | A | 170 | 80.809 | 27.912 | 65.233 | 1.00 | 10.17 |
| 2510 | C | VAL | A | 170 | 80.662 | 25.216 | 63.815 | 1.00 | 8.49 |
| 2511 | O | VAL | A | 170 | 81.825 | 25.106 | 63.451 | 1.00 | 10.30 |
| 2512 | N | GLY | A | 171 | 80.062 | 24.296 | 64.544 | 1.00 | 7.21 |
| 2514 | CA | GLY | A | 171 | 80.774 | 23.110 | 64.936 | 1.00 | 8.40 |
| 2517 | C | GLY | A | 171 | 79.981 | 22.284 | 65.906 | 1.00 | 8.29 |
| 2518 | O | GLY | A | 171 | 78.808 | 22.542 | 66.190 | 1.00 | 8.22 |
| 2519 | N | TYR | A | 172 | 80.629 | 21.254 | 66.434 | 1.00 | 8.01 |
| 2521 | CA | TYR | A | 172 | 80.011 | 20.367 | 67.390 | 1.00 | 7.80 |
| 2523 | CB | TYR | A | 172 | 79.006 | 19.427 | 66.709 | 1.00 | 8.02 |
| 2526 | CG | TYR | A | 172 | 79.592 | 18.493 | 65.663 | 1.00 | 8.30 |
| 2527 | CD1 | TYR | A | 172 | 80.284 | 17.361 | 66.027 | 1.00 | 8.34 |
| 2529 | CE1 | TYR | A | 172 | 80.815 | 16.518 | 65.075 | 1.00 | 8.68 |
| 2531 | CZ | TYR | A | 172 | 80.618 | 16.792 | 63.747 | 1.00 | 9.96 |
| 2532 | OH | TYR | A | 172 | 81.121 | 15.957 | 62.775 | 1.00 | 11.55 |
| 2534 | CE2 | TYR | A | 172 | 79.912 | 17.876 | 63.360 | 1.00 | 8.86 |
| 2536 | CD2 | TYR | A | 172 | 79.413 | 18.734 | 64.302 | 1.00 | 7.83 |
| 2538 | C | TYR | A | 172 | 81.136 | 19.597 | 68.046 | 1.00 | 8.93 |
| 2539 | O | TYR | A | 172 | 82.249 | 19.563 | 67.543 | 1.00 | 8.28 |
| 2540 | N | GLY | A | 173 | 80.834 | 19.004 | 69.172 | 1.00 | 8.40 |
| 2542 | CA | GLY | A | 173 | 81.820 | 18.201 | 69.876 | 1.00 | 9.34 |
| 2545 | C | GLY | A | 173 | 81.264 | 17.659 | 71.165 | 1.00 | 10.09 |
| 2546 | O | GLY | A | 173 | 80.067 | 17.484 | 71.341 | 1.00 | 9.49 |
| 2547 | N | ASP | A | 174 | 82.175 | 17.379 | 72.104 | 1.00 | 10.45 |
| 2549 | CA | ASP | A | 174 | 81.818 | 16.824 | 73.403 | 1.00 | 12.07 |
| 2551 | CB | ASP | A | 174 | 82.013 | 15.300 | 73.436 | 1.00 | 13.42 |
| 2554 | CG | ASP | A | 174 | 81.284 | 14.610 | 74.585 | 1.00 | 19.33 |
| 2555 | OD1 | ASP | A | 174 | 81.207 | 13.357 | 74.509 | 1.00 | 28.93 |
| 2556 | OD2 | ASP | A | 174 | 80.778 | 15.185 | 75.585 | 1.00 | 27.58 |
| 2557 | C | ASP | A | 174 | 82.709 | 17.469 | 74.437 | 1.00 | 10.98 |
| 2558 | O | ASP | A | 174 | 83.919 | 17.569 | 74.232 | 1.00 | 11.78 |
| 2559 | N | LEU | A | 175 | 82.067 | 17.967 | 75.488 | 1.00 | 10.40 |
| 2561 | CA | LEU | A | 175 | 82.717 | 18.587 | 76.620 | 1.00 | 10.52 |
| 2563 | CB | LEU | A | 175 | 82.469 | 20.086 | 76.644 | 1.00 | 10.62 |
| 2566 | CG | LEU | A | 175 | 83.006 | 20.880 | 77.849 | 1.00 | 12.27 |
| 2568 | CD1 | LEU | A | 175 | 84.506 | 20.809 | 78.011 | 1.00 | 12.13 |
| 2572 | CD2 | LEU | A | 175 | 82.555 | 22.308 | 77.817 | 1.00 | 12.39 |
| 2576 | C | LEU | A | 175 | 82.218 | 17.963 | 77.915 | 1.00 | 10.70 |
| 2578 | N | ASN | A | 176 | 83.244 | 17.305 | 78.488 | 1.00 | 11.40 |

FIGURE 3 (Cont.)

| A | B | C | D | E | F | G | H | I | J |
|---|---|---|---|---|---|---|---|---|---|
| 2580 | CA | ASN | A | 176 | 83.055 | 16.651 | 79.768 | 1.00 | 12.77 |
| 2582 | CB | ASN | A | 176 | 82.958 | 17.689 | 80.875 | 1.00 | 12.71 |
| 2585 | CG | ASN | A | 176 | 84.244 | 18.472 | 81.011 | 1.00 | 12.93 |
| 2586 | OD1 | ASN | A | 176 | 84.246 | 19.699 | 81.145 | 1.00 | 17.26 |
| 2587 | ND2 | ASN | A | 176 | 85.337 | 17.769 | 80.953 | 1.00 | 12.62 |
| 2590 | C | ASN | A | 176 | 81.853 | 15.742 | 79.772 | 1.00 | 13.51 |
| 2591 | O | ASN | A | 176 | 81.044 | 15.776 | 80.695 | 1.00 | 14.67 |
| 2592 | N | GLY | A | 177 | 81.762 | 14.911 | 78.751 | 1.00 | 15.00 |
| 2594 | CA | GLY | A | 177 | 80.671 | 13.965 | 78.665 | 1.00 | 15.11 |
| 2597 | C | GLY | A | 177 | 79.423 | 14.498 | 77.988 | 1.00 | 14.77 |
| 2598 | O | GLY | A | 177 | 78.552 | 13.727 | 77.590 | 1.00 | 17.38 |
| 2599 | N | LYS | A | 178 | 79.339 | 15.813 | 77.811 | 1.00 | 13.42 |
| 2601 | CA | LYS | A | 178 | 78.161 | 16.434 | 77.204 | 1.00 | 12.76 |
| 2603 | CB | LYS | A | 178 | 77.758 | 17.674 | 77.987 | 1.00 | 13.18 |
| 2606 | CG | LYS | A | 178 | 77.487 | 17.411 | 79.472 | 1.00 | 14.98 |
| 2609 | CD | LYS | A | 178 | 76.298 | 16.494 | 79.681 | 1.00 | 18.24 |
| 2612 | CE | LYS | A | 178 | 75.904 | 16.428 | 81.139 | 1.00 | 21.11 |
| 2615 | NZ | LYS | A | 178 | 74.698 | 15.565 | 81.266 | 1.00 | 22.91 |
| 2619 | C | LYS | A | 178 | 78.387 | 16.817 | 75.744 | 1.00 | 11.44 |
| 2620 | O | LYS | A | 178 | 79.223 | 17.660 | 75.441 | 1.00 | 10.83 |
| 2621 | N | GLU | A | 179 | 77.608 | 16.224 | 74.839 | 1.00 | 10.74 |
| 2623 | CA | GLU | A | 179 | 77.712 | 16.577 | 73.444 | 1.00 | 10.50 |
| 2625 | CB | GLU | A | 179 | 76.946 | 15.580 | 72.603 | 1.00 | 11.29 |
| 2628 | CG | GLU | A | 179 | 77.486 | 14.178 | 72.767 | 1.00 | 13.43 |
| 2631 | CD | GLU | A | 179 | 76.904 | 13.219 | 71.758 | 1.00 | 16.91 |
| 2632 | OE1 | GLU | A | 179 | 77.671 | 12.740 | 70.878 | 1.00 | 22.34 |
| 2633 | OE2 | GLU | A | 179 | 75.703 | 12.927 | 71.844 | 1.00 | 21.23 |
| 2634 | C | GLU | A | 179 | 77.146 | 17.964 | 73.246 | 1.00 | 9.11 |
| 2635 | O | GLU | A | 179 | 76.169 | 18.329 | 73.887 | 1.00 | 8.72 |
| 2636 | N | TYR | A | 180 | 77.735 | 18.722 | 72.346 | 1.00 | 7.73 |
| 2638 | CA | TYR | A | 180 | 77.237 | 20.070 | 72.126 | 1.00 | 7.44 |
| 2640 | CB | TYR | A | 180 | 78.063 | 21.093 | 72.962 | 1.00 | 8.20 |
| 2643 | CG | TYR | A | 180 | 79.505 | 21.210 | 72.494 | 1.00 | 7.70 |
| 2644 | CD1 | TYR | A | 180 | 79.860 | 22.025 | 71.428 | 1.00 | 9.52 |
| 2646 | CE1 | TYR | A | 180 | 81.122 | 22.075 | 70.956 | 1.00 | 10.78 |
| 2648 | CZ | TYR | A | 180 | 82.122 | 21.322 | 71.563 | 1.00 | 11.33 |
| 2649 | OH | TYR | A | 180 | 83.392 | 21.365 | 71.077 | 1.00 | 12.64 |
| 2651 | CE2 | TYR | A | 180 | 81.805 | 20.521 | 72.633 | 1.00 | 9.69 |
| 2653 | CD2 | TYR | A | 180 | 80.513 | 20.464 | 73.085 | 1.00 | 9.33 |
| 2655 | C | TYR | A | 180 | 77.302 | 20.456 | 70.658 | 1.00 | 7.90 |
| 2656 | O | TYR | A | 180 | 78.018 | 19.847 | 69.861 | 1.00 | 7.13 |
| 2657 | N | TRP | A | 181 | 76.552 | 21.511 | 70.358 | 1.00 | 7.24 |
| 2659 | CA | TRP | A | 181 | 76.637 | 22.256 | 69.143 | 1.00 | 7.16 |
| 2661 | CB | TRP | A | 181 | 75.238 | 22.605 | 68.635 | 1.00 | 7.34 |
| 2664 | CG | TRP | A | 181 | 74.408 | 21.443 | 68.228 | 1.00 | 6.74 |
| 2665 | CD1 | TRP | A | 181 | 73.331 | 20.944 | 68.863 | 1.00 | 7.18 |
| 2667 | NE1 | TRP | A | 181 | 72.831 | 19.856 | 68.177 | 1.00 | 7.84 |
| 2669 | CE2 | TRP | A | 181 | 73.612 | 19.657 | 67.073 | 1.00 | 7.15 |
| 2670 | CD2 | TRP | A | 181 | 74.605 | 20.643 | 67.063 | 1.00 | 7.46 |
| 2671 | CE3 | TRP | A | 181 | 75.554 | 20.640 | 66.041 | 1.00 | 7.76 |
| 2673 | CZ3 | TRP | A | 181 | 75.472 | 19.667 | 65.052 | 1.00 | 8.31 |

FIGURE 3 (Cont.)

| A | B | C | D | E | F | G | H | I | J |
|---|---|---|---|---|---|---|---|---|---|
| 2675 | CH2 | TRP | A | 181 | 74.457 | 18.711 | 65.088 | 1.00 | 8.20 |
| 2677 | CZ2 | TRP | A | 181 | 73.518 | 18.689 | 66.058 | 1.00 | 7.45 |
| 2679 | C | TRP | A | 181 | 77.351 | 23.555 | 69.471 | 1.00 | 7.52 |
| 2680 | O | TRP | A | 181 | 77.039 | 24.199 | 70.469 | 1.00 | 8.73 |
| 2681 | N | LEU | A | 182 | 78.289 | 23.952 | 68.638 | 1.00 | 7.47 |
| 2683 | CA | LEU | A | 182 | 78.993 | 25.205 | 68.849 | 1.00 | 8.17 |
| 2685 | CB | LEU | A | 182 | 80.425 | 25.114 | 68.377 | 1.00 | 9.09 |
| 2688 | CG | LEU | A | 182 | 81.276 | 26.367 | 68.553 | 1.00 | 10.77 |
| 2690 | CD1 | LEU | A | 182 | 81.449 | 26.692 | 70.017 | 1.00 | 12.41 |
| 2694 | CD2 | LEU | A | 182 | 82.633 | 26.143 | 67.904 | 1.00 | 13.16 |
| 2698 | C | LEU | A | 182 | 78.249 | 26.265 | 68.068 | 1.00 | 8.25 |
| 2699 | O | LEU | A | 182 | 78.206 | 26.205 | 66.829 | 1.00 | 8.17 |
| 2700 | N | VAL | A | 183 | 77.678 | 27.240 | 68.765 | 1.00 | 7.63 |
| 2702 | CA | VAL | A | 183 | 76.808 | 28.220 | 68.146 | 1.00 | 7.97 |
| 2704 | CB | VAL | A | 183 | 75.454 | 28.167 | 68.810 | 1.00 | 8.74 |
| 2706 | CG1 | VAL | A | 183 | 74.544 | 29.283 | 68.332 | 1.00 | 9.15 |
| 2710 | CG2 | VAL | A | 183 | 74.817 | 26.809 | 68.590 | 1.00 | 9.78 |
| 2714 | C | VAL | A | 183 | 77.377 | 29.628 | 68.256 | 1.00 | 8.32 |
| 2715 | O | VAL | A | 183 | 77.752 | 30.084 | 69.352 | 1.00 | 8.39 |
| 2716 | N | LYS | A | 184 | 77.480 | 30.293 | 67.122 | 1.00 | 7.51 |
| 2718 | CA | LYS | A | 184 | 77.860 | 31.689 | 67.039 | 1.00 | 7.53 |
| 2720 | CB | LYS | A | 184 | 78.501 | 31.952 | 65.693 | 1.00 | 7.37 |
| 2723 | CG | LYS | A | 184 | 79.094 | 33.330 | 65.554 | 1.00 | 7.75 |
| 2726 | CD | LYS | A | 184 | 79.435 | 33.681 | 64.102 | 1.00 | 9.08 |
| 2729 | CE | LYS | A | 184 | 80.356 | 34.918 | 63.980 | 1.00 | 10.20 |
| 2732 | NZ | LYS | A | 184 | 80.428 | 35.449 | 62.603 | 1.00 | 10.58 |
| 2736 | C | LYS | A | 184 | 76.635 | 32.535 | 67.168 | 1.00 | 7.84 |
| 2737 | O | LYS | A | 184 | 75.696 | 32.403 | 66.390 | 1.00 | 7.03 |
| 2738 | N | ASN | A | 185 | 76.600 | 33.384 | 68.182 | 1.00 | 7.72 |
| 2740 | CA | ASN | A | 185 | 75.489 | 34.287 | 68.394 | 1.00 | 8.40 |
| 2742 | CB | ASN | A | 185 | 75.172 | 34.300 | 69.892 | 1.00 | 8.73 |
| 2745 | CG | ASN | A | 185 | 73.834 | 34.928 | 70.241 | 1.00 | 8.85 |
| 2746 | OD1 | ASN | A | 185 | 73.010 | 35.241 | 69.374 | 1.00 | 10.62 |
| 2747 | ND2 | ASN | A | 185 | 73.624 | 35.155 | 71.537 | 1.00 | 10.62 |
| 2750 | C | ASN | A | 185 | 75.862 | 35.664 | 67.831 | 1.00 | 8.86 |
| 2751 | O | ASN | A | 185 | 76.995 | 35.865 | 67.386 | 1.00 | 9.97 |
| 2752 | N | SER | A | 186 | 74.924 | 36.608 | 67.856 | 1.00 | 8.64 |
| 2754 | CA | SER | A | 186 | 75.125 | 37.954 | 67.352 | 1.00 | 8.52 |
| 2756 | CB | SER | A | 186 | 74.254 | 38.212 | 66.119 | 1.00 | 8.51 |
| 2759 | OG | SER | A | 186 | 72.928 | 37.811 | 66.345 | 1.00 | 10.18 |
| 2761 | C | SER | A | 186 | 74.824 | 38.989 | 68.442 | 1.00 | 8.57 |
| 2762 | O | SER | A | 186 | 74.280 | 40.047 | 68.168 | 1.00 | 9.56 |
| 2763 | N | TRP | A | 187 | 75.241 | 38.687 | 69.666 | 1.00 | 8.49 |
| 2765 | CA | TRP | A | 187 | 75.092 | 39.629 | 70.783 | 1.00 | 8.55 |
| 2767 | CB | TRP | A | 187 | 74.364 | 39.005 | 71.963 | 1.00 | 8.15 |
| 2770 | CG | TRP | A | 187 | 72.936 | 38.670 | 71.670 | 1.00 | 9.02 |
| 2771 | CD1 | TRP | A | 187 | 72.212 | 39.018 | 70.563 | 1.00 | 9.90 |
| 2773 | NE1 | TRP | A | 187 | 70.939 | 38.506 | 70.654 | 1.00 | 11.51 |
| 2775 | CE2 | TRP | A | 187 | 70.833 | 37.779 | 71.808 | 1.00 | 10.30 |
| 2776 | CD2 | TRP | A | 187 | 72.073 | 37.866 | 72.477 | 1.00 | 9.40 |
| 2777 | CE3 | TRP | A | 187 | 72.223 | 37.205 | 73.696 | 1.00 | 11.10 |

FIGURE 3 (Cont.)

| A | B | C | D | E | F | G | H | I | J |
|---|---|---|---|---|---|---|---|---|---|
| 2779 | CZ3 | TRP | A | 187 | 71.146 | 36.500 | 74.214 | 1.00 | 11.94 |
| 2781 | CH2 | TRP | A | 187 | 69.938 | 36.435 | 73.520 | 1.00 | 12.36 |
| 2783 | CZ2 | TRP | A | 187 | 69.763 | 37.068 | 72.324 | 1.00 | 12.04 |
| 2785 | C | TRP | A | 187 | 76.462 | 40.131 | 71.244 | 1.00 | 9.10 |
| 2786 | O | TRP | A | 187 | 76.651 | 40.493 | 72.414 | 1.00 | 9.20 |
| 2787 | N | GLY | A | 188 | 77.413 | 40.172 | 70.328 | 1.00 | 8.87 |
| 2789 | CA | GLY | A | 188 | 78.747 | 40.633 | 70.656 | 1.00 | 9.53 |
| 2792 | C | GLY | A | 188 | 79.559 | 39.649 | 71.462 | 1.00 | 10.86 |
| 2793 | O | GLY | A | 188 | 79.114 | 38.578 | 71.837 | 1.00 | 10.90 |
| 2794 | N | HIS | A | 189 | 80.785 | 40.048 | 71.763 | 1.00 | 12.56 |
| 2796 | CA | HIS | A | 189 | 81.678 | 39.190 | 72.538 | 1.00 | 15.23 |
| 2798 | CB | HIS | A | 189 | 83.106 | 39.673 | 72.405 | 1.00 | 16.17 |
| 2801 | CG | HIS | A | 189 | 83.577 | 39.734 | 70.999 | 1.00 | 19.95 |
| 2802 | ND1 | HIS | A | 189 | 84.158 | 38.663 | 70.359 | 1.00 | 26.55 |
| 2804 | CE1 | HIS | A | 189 | 84.473 | 39.016 | 69.125 | 1.00 | 26.49 |
| 2806 | NE2 | HIS | A | 189 | 84.100 | 40.270 | 68.939 | 1.00 | 27.65 |
| 2808 | CD2 | HIS | A | 189 | 83.547 | 40.746 | 70.102 | 1.00 | 24.11 |
| 2810 | C | HIS | A | 189 | 81.373 | 39.062 | 74.011 | 1.00 | 14.64 |
| 2811 | O | HIS | A | 189 | 81.915 | 38.156 | 74.642 | 1.00 | 15.50 |
| 2812 | N | ASN | A | 190 | 80.511 | 39.916 | 74.574 | 1.00 | 14.92 |
| 2814 | CA | ASN | A | 190 | 80.164 | 39.837 | 76.006 | 1.00 | 15.35 |
| 2816 | CB | ASN | A | 190 | 79.385 | 41.074 | 76.470 | 1.00 | 16.10 |
| 2819 | CG | ASN | A | 190 | 79.148 | 41.078 | 77.976 | 1.00 | 17.48 |
| 2820 | OD1 | ASN | A | 190 | 80.053 | 41.413 | 78.716 | 1.00 | 20.32 |
| 2821 | ND2 | ASN | A | 190 | 77.959 | 40.651 | 78.435 | 1.00 | 17.49 |
| 2824 | C | ASN | A | 190 | 79.320 | 38.623 | 76.315 | 1.00 | 14.68 |
| 2825 | O | ASN | A | 190 | 79.258 | 38.127 | 77.446 | 1.00 | 16.24 |
| 2826 | N | PHE | A | 191 | 78.651 | 38.152 | 75.289 | 1.00 | 12.73 |
| 2828 | CA | PHE | A | 191 | 77.776 | 37.038 | 75.473 | 1.00 | 11.79 |
| 2830 | CB | PHE | A | 191 | 76.765 | 36.983 | 74.348 | 1.00 | 11.21 |
| 2833 | CG | PHE | A | 191 | 75.981 | 35.719 | 74.356 | 1.00 | 11.11 |
| 2834 | CD1 | PHE | A | 191 | 76.327 | 34.679 | 73.526 | 1.00 | 11.28 |
| 2836 | CE1 | PHE | A | 191 | 75.630 | 33.484 | 73.579 | 1.00 | 10.09 |
| 2838 | CZ | PHE | A | 191 | 74.591 | 33.347 | 74.463 | 1.00 | 13.66 |
| 2840 | CE2 | PHE | A | 191 | 74.253 | 34.371 | 75.285 | 1.00 | 12.49 |
| 2842 | CD2 | PHE | A | 191 | 74.946 | 35.533 | 75.256 | 1.00 | 12.71 |
| 2844 | C | PHE | A | 191 | 78.538 | 35.709 | 75.505 | 1.00 | 11.39 |
| 2845 | O | PHE | A | 191 | 79.409 | 35.476 | 74.662 | 1.00 | 10.84 |
| 2846 | N | GLY | A | 192 | 78.151 | 34.854 | 76.458 | 1.00 | 12.40 |
| 2848 | CA | GLY | A | 192 | 78.728 | 33.532 | 76.624 | 1.00 | 12.52 |
| 2851 | C | GLY | A | 192 | 80.248 | 33.471 | 76.564 | 1.00 | 13.04 |
| 2852 | O | GLY | A | 192 | 80.917 | 34.201 | 77.307 | 1.00 | 13.76 |
| 2853 | N | ALA | A | 192 | 80.771 | 32.661 | 75.631 | 1.00 | 11.69 |
| 2855 | CA | ALA | A | 193 | 82.193 | 32.403 | 75.468 | 1.00 | 12.15 |
| 2857 | CB | ALA | A | 193 | 82.484 | 30.929 | 75.319 | 1.00 | 13.90 |
| 2861 | C | ALA | A | 193 | 82.678 | 33.182 | 74.239 | 1.00 | 12.26 |
| 2862 | O | ALA | A | 193 | 82.768 | 32.656 | 73.133 | 1.00 | 10.86 |
| 2863 | N | GLU | A | 194 | 82.949 | 34.461 | 74.444 | 1.00 | 12.26 |
| 2865 | CA | GLU | A | 194 | 83.389 | 35.354 | 73.385 | 1.00 | 12.28 |
| 2867 | CB | GLU | A | 194 | 84.776 | 35.017 | 72.912 | 1.00 | 13.78 |
| 2870 | CG | GLU | A | 194 | 85.798 | 35.053 | 74.048 | 1.00 | 15.01 |

FIGURE 3 (Cont.)

| A | B | C | D | E | F | G | H | I | J |
|---|---|---|---|---|---|---|---|---|---|
| 2873 | CD | GLU | A | 194 | 86.099 | 36.436 | 74.612 | 1.00 | 19.69 |
| 2874 | OE1 | GLU | A | 194 | 85.781 | 37.478 | 73.964 | 1.00 | 19.31 |
| 2875 | OE2 | GLU | A | 194 | 86.730 | 36.480 | 75.702 | 1.00 | 22.60 |
| 2876 | C | GLU | A | 194 | 82.419 | 35.387 | 72.208 | 1.00 | 10.40 |
| 2877 | O | GLU | A | 194 | 82.829 | 35.504 | 71.054 | 1.00 | 10.53 |
| 2878 | N | GLY | A | 195 | 81.143 | 35.300 | 72.529 | 1.00 | 9.77 |
| 2880 | CA | GLY | A | 195 | 80.109 | 35.433 | 71.531 | 1.00 | 8.91 |
| 2883 | C | GLY | A | 195 | 79.483 | 34.119 | 71.133 | 1.00 | 8.59 |
| 2884 | O | GLY | A | 195 | 78.509 | 34.109 | 70.380 | 1.00 | 9.00 |
| 2885 | N | TYR | A | 196 | 80.028 | 33.024 | 71.650 | 1.00 | 8.38 |
| 2887 | CA | TYR | A | 196 | 79.592 | 31.674 | 71.339 | 1.00 | 8.53 |
| 2889 | CB | TYR | A | 196 | 80.795 | 30.824 | 70.913 | 1.00 | 7.89 |
| 2892 | CG | TYR | A | 196 | 81.383 | 31.261 | 69.602 | 1.00 | 8.55 |
| 2893 | CD1 | TYR | A | 196 | 82.238 | 32.338 | 69.524 | 1.00 | 8.81 |
| 2895 | CE1 | TYR | A | 196 | 82.746 | 32.756 | 68.324 | 1.00 | 10.70 |
| 2897 | CZ | TYR | A | 196 | 82.368 | 32.118 | 67.179 | 1.00 | 11.91 |
| 2898 | OH | TYR | A | 196 | 82.858 | 32.540 | 65.961 | 1.00 | 14.42 |
| 2900 | CE2 | TYR | A | 196 | 81.513 | 31.053 | 67.227 | 1.00 | 11.42 |
| 2902 | CD2 | TYR | A | 196 | 81.016 | 30.626 | 68.421 | 1.00 | 10.79 |
| 2904 | C | TYR | A | 196 | 78.923 | 30.999 | 72.509 | 1.00 | 8.55 |
| 2905 | O | TYR | A | 196 | 79.186 | 31.291 | 73.678 | 1.00 | 8.88 |
| 2906 | N | ILE | A | 197 | 78.061 | 30.050 | 72.196 | 1.00 | 7.00 |
| 2908 | CA | ILE | A | 197 | 77.416 | 29.234 | 73.196 | 1.00 | 7.38 |
| 2910 | CB | ILE | A | 197 | 75.957 | 29.684 | 73.506 | 1.00 | 8.02 |
| 2912 | CG1 | ILE | A | 197 | 75.283 | 28.738 | 74.508 | 1.00 | 8.29 |
| 2915 | CD1 | ILE | A | 197 | 74.007 | 29.325 | 75.074 | 1.00 | 8.75 |
| 2919 | CG2 | ILE | A | 197 | 75.101 | 29.818 | 72.269 | 1.00 | 8.39 |
| 2923 | C | ILE | A | 197 | 77.509 | 27.780 | 72.736 | 1.00 | 8.49 |
| 2924 | O | ILE | A | 197 | 77.294 | 27.461 | 71.578 | 1.00 | 8.35 |
| 2925 | N | ARG | A | 198 | 77.723 | 26.883 | 73.665 | 1.00 | 8.54 |
| 2927 | CA | ARG | A | 198 | 77.814 | 25.466 | 73.377 | 1.00 | 8.93 |
| 2929 | CB | ARG | A | 198 | 78.945 | 24.754 | 74.122 | 1.00 | 8.40 |
| 2932 | CG | ARG | A | 198 | 80.296 | 25.233 | 73.751 | 1.00 | 12.01 |
| 2935 | CD | ARG | A | 198 | 81.362 | 24.260 | 74.180 | 1.00 | 16.18 |
| 2938 | NE | ARG | A | 198 | 82.589 | 24.922 | 74.592 | 1.00 | 20.61 |
| 2940 | CZ | ARG | A | 198 | 83.662 | 24.267 | 74.984 | 1.00 | 28.20 |
| 2941 | NH1 | ARG | A | 198 | 83.678 | 22.935 | 75.011 | 1.00 | 31.60 |
| 2944 | NH2 | ARG | A | 198 | 84.736 | 24.945 | 75.340 | 1.00 | 30.70 |
| 2947 | C | ARG | A | 198 | 76.465 | 24.990 | 73.863 | 1.00 | 8.74 |
| 2948 | O | ARG | A | 198 | 76.145 | 25.140 | 75.044 | 1.00 | 9.35 |
| 2949 | N | MET | A | 199 | 75.626 | 24.488 | 72.955 | 1.00 | 9.08 |
| 2951 | CA | MET | A | 199 | 74.280 | 24.075 | 73.275 | 1.00 | 8.70 |
| 2953 | CB | MET | A | 199 | 73.305 | 24.743 | 72.288 | 1.00 | 9.67 |
| 2956 | CG | MET | A | 199 | 73.354 | 26.254 | 72.393 | 1.00 | 10.15 |
| 2959 | SD | MET | A | 199 | 72.108 | 27.123 | 71.394 | 1.00 | 12.72 |
| 2960 | CE | MET | A | 199 | 70.651 | 26.623 | 72.280 | 1.00 | 13.68 |
| 2964 | C | MET | A | 199 | 74.147 | 22.550 | 73.224 | 1.00 | 8.33 |
| 2965 | O | MET | A | 199 | 74.754 | 21.916 | 72.374 | 1.00 | 9.38 |
| 2966 | N | ALA | A | 200 | 73.345 | 21.982 | 74.109 | 1.00 | 8.62 |
| 2968 | CA | ALA | A | 200 | 73.202 | 20.518 | 74.212 | 1.00 | 8.61 |
| 2970 | CB | ALA | A | 200 | 72.196 | 20.147 | 75.247 | 1.00 | 9.19 |

FIGURE 3 (Cont.)

| A | B | C | D | E | F | G | H | I | J |
|---|---|---|---|---|---|---|---|---|---|
| 2974 | C | ALA | A | 200 | 72.826 | 19.882 | 72.879 | 1.00 | 8.85 |
| 2975 | O | ALA | A | 200 | 71.914 | 20.335 | 72.189 | 1.00 | 9.50 |
| 2976 | N | ARG | A | 201 | 73.566 | 18.837 | 72.537 | 1.00 | 8.05 |
| 2978 | CA | ARG | A | 201 | 73.376 | 18.105 | 71.288 | 1.00 | 8.44 |
| 2980 | CB | ARG | A | 201 | 74.659 | 18.103 | 70.505 | 1.00 | 8.65 |
| 2983 | CG | ARG | A | 201 | 74.695 | 17.217 | 69.263 | 1.00 | 8.03 |
| 2986 | CD | ARG | A | 201 | 75.860 | 17.552 | 68.385 | 1.00 | 8.05 |
| 2989 | NE | ARG | A | 201 | 77.141 | 17.144 | 68.974 | 1.00 | 8.96 |
| 2991 | CZ | ARG | A | 201 | 77.710 | 15.974 | 68.739 | 1.00 | 10.43 |
| 2992 | NH1 | ARG | A | 201 | 77.119 | 15.094 | 67.921 | 1.00 | 11.68 |
| 2995 | NH2 | ARG | A | 201 | 78.862 | 15.663 | 69.317 | 1.00 | 11.45 |
| 2998 | C | ARG | A | 201 | 72.936 | 16.690 | 71.601 | 1.00 | 9.25 |
| 2999 | O | ARG | A | 201 | 73.381 | 16.085 | 72.588 | 1.00 | 10.70 |
| 3000 | N | ASN | A | 202 | 72.068 | 16.161 | 70.751 | 1.00 | 10.22 |
| 3002 | CA | ASN | A | 202 | 71.475 | 14.832 | 70.919 | 1.00 | 12.06 |
| 3004 | CB | ASN | A | 202 | 72.508 | 13.737 | 70.742 | 1.00 | 12.00 |
| 3007 | CG | ASN | A | 202 | 73.074 | 13.694 | 69.349 | 1.00 | 13.75 |
| 3008 | OD1 | ASN | A | 202 | 72.403 | 14.051 | 68.379 | 1.00 | 19.63 |
| 3009 | ND2 | ASN | A | 202 | 74.326 | 13.292 | 69.232 | 1.00 | 16.84 |
| 3012 | C | ASN | A | 202 | 70.723 | 14.694 | 72.244 | 1.00 | 12.14 |
| 3013 | O | ASN | A | 202 | 70.695 | 13.627 | 72.866 | 1.00 | 13.57 |
| 3014 | N | LYS | A | 203 | 70.100 | 15.784 | 72.674 | 1.00 | 12.78 |
| 3016 | CA | LYS | A | 203 | 69.270 | 15.821 | 73.840 | 1.00 | 12.82 |
| 3018 | CB | LYS | A | 203 | 69.814 | 16.817 | 74.858 | 1.00 | 13.07 |
| 3021 | CG | LYS | A | 203 | 71.099 | 16.359 | 75.488 | 1.00 | 15.16 |
| 3024 | CD | LYS | A | 203 | 70.895 | 15.148 | 76.335 | 1.00 | 17.36 |
| 3027 | CE | LYS | A | 203 | 72.119 | 14.878 | 77.168 | 1.00 | 20.65 |
| 3030 | NZ | LYS | A | 203 | 72.037 | 13.539 | 77.804 | 1.00 | 24.01 |
| 3034 | C | LYS | A | 203 | 67.849 | 16.216 | 73.404 | 1.00 | 12.76 |
| 3035 | O | LYS | A | 203 | 67.257 | 17.163 | 73.930 | 1.00 | 13.51 |
| 3036 | N | GLY | A | 204 | 67.322 | 15.491 | 72.424 | 1.00 | 13.21 |
| 3038 | CA | GLY | A | 204 | 65.961 | 15.713 | 71.985 | 1.00 | 12.63 |
| 3041 | C | GLY | A | 204 | 65.728 | 17.037 | 71.270 | 1.00 | 11.61 |
| 3042 | O | GLY | A | 204 | 64.692 | 17.672 | 71.498 | 1.00 | 12.80 |
| 3043 | N | ASN | A | 205 | 66.647 | 17.429 | 70.400 | 1.00 | 10.39 |
| 3045 | CA | ASN | A | 205 | 66.486 | 18.663 | 69.638 | 1.00 | 10.31 |
| 3047 | CB | ASN | A | 205 | 65.294 | 18.601 | 68.694 | 1.00 | 10.00 |
| 3050 | CG | ASN | A | 205 | 65.225 | 19.805 | 67.791 | 1.00 | 9.81 |
| 3051 | OD1 | ASN | A | 205 | 66.220 | 20.472 | 67.595 | 1.00 | 11.31 |
| 3052 | ND2 | ASN | A | 205 | 64.054 | 20.083 | 67.241 | 1.00 | 9.87 |
| 3055 | C | ASN | A | 205 | 66.297 | 19.815 | 70.630 | 1.00 | 9.86 |
| 3056 | O | ASN | A | 205 | 65.355 | 20.603 | 70.580 | 1.00 | 9.58 |
| 3057 | N | HIS | A | 206 | 67.243 | 19.900 | 71.538 | 1.00 | 9.50 |
| 3059 | CA | HIS | A | 206 | 67.184 | 20.879 | 72.602 | 1.00 | 9.83 |
| 3061 | CB | HIS | A | 206 | 68.366 | 20.685 | 73.541 | 1.00 | 10.75 |
| 3064 | CG | HIS | A | 206 | 68.193 | 21.365 | 74.855 | 1.00 | 12.73 |
| 3065 | ND1 | HIS | A | 206 | 69.046 | 22.351 | 75.288 | 1.00 | 18.83 |
| 3067 | CE1 | HIS | A | 206 | 68.673 | 22.748 | 76.491 | 1.00 | 13.41 |
| 3069 | NE2 | HIS | A | 206 | 67.578 | 22.093 | 76.830 | 1.00 | 18.21 |
| 3071 | CD2 | HIS | A | 206 | 67.284 | 21.178 | 75.842 | 1.00 | 16.24 |
| 3073 | C | HIS | A | 206 | 67.151 | 22.312 | 72.059 | 1.00 | 9.05 |

FIGURE 3 (Cont.)

| A | B | C | D | E | F | G | H | I | J |
|---|---|---|---|---|---|---|---|---|---|
| 3074 | O | HIS | A | 206 | 67.970 | 22.705 | 71.217 | 1.00 | 9.40 |
| 3075 | N | CYS | A | 207 | 66.181 | 23.068 | 72.564 | 1.00 | 9.67 |
| 3077 | CA | CYS | A | 207 | 65.987 | 24.462 | 72.183 | 1.00 | 10.09 |
| 3079 | CB | CYS | A | 207 | 67.213 | 25.301 | 72.537 | 1.00 | 11.22 |
| 3082 | SG | CYS | A | 207 | 67.454 | 25.464 | 74.328 | 1.00 | 14.76 |
| 3083 | C | CYS | A | 207 | 65.668 | 24.601 | 70.710 | 1.00 | 8.96 |
| 3084 | O | CYS | A | 207 | 65.742 | 25.695 | 70.181 | 1.00 | 9.52 |
| 3085 | N | GLY | A | 208 | 65.254 | 23.507 | 70.074 | 1.00 | 8.20 |
| 3087 | CA | GLY | A | 208 | 64.903 | 23.559 | 68.666 | 1.00 | 7.73 |
| 3090 | C | GLY | A | 208 | 66.068 | 23.774 | 67.706 | 1.00 | 7.74 |
| 3091 | O | GLY | A | 208 | 65.874 | 24.175 | 66.557 | 1.00 | 8.40 |
| 3092 | N | ILE | A | 209 | 67.290 | 23.502 | 68.157 | 1.00 | 8.32 |
| 3094 | CA | ILE | A | 209 | 68.458 | 23.775 | 67.344 | 1.00 | 8.73 |
| 3096 | CB | ILE | A | 209 | 69.739 | 23.411 | 68.128 | 1.00 | 9.51 |
| 3098 | CG1 | ILE | A | 209 | 70.946 | 23.964 | 67.392 | 1.00 | 13.12 |
| 3101 | CD1 | ILE | A | 209 | 72.002 | 24.462 | 68.282 | 1.00 | 14.36 |
| 3105 | CG2 | ILE | A | 209 | 69.825 | 21.946 | 68.410 | 1.00 | 11.21 |
| 3109 | C | ILE | A | 209 | 68.412 | 23.134 | 65.963 | 1.00 | 8.50 |
| 3110 | O | ILE | A | 209 | 68.844 | 23.767 | 64.984 | 1.00 | 8.73 |
| 3111 | N | ALA | A | 210 | 67.845 | 21.934 | 65.866 | 1.00 | 8.43 |
| 3113 | CA | ALA | A | 210 | 67.805 | 21.244 | 64.584 | 1.00 | 8.37 |
| 3115 | CB | ALA | A | 210 | 68.177 | 19.781 | 64.754 | 1.00 | 8.70 |
| 3119 | C | ALA | A | 210 | 66.451 | 21.360 | 63.933 | 1.00 | 8.52 |
| 3120 | O | ALA | A | 210 | 66.175 | 20.669 | 62.961 | 1.00 | 9.00 |
| 3121 | N | SER | A | 211 | 65.603 | 22.227 | 64.454 | 1.00 | 8.50 |
| 3123 | CA | SER | A | 211 | 64.267 | 22.387 | 63.897 | 1.00 | 8.56 |
| 3125 | CB | SER | A | 211 | 63.423 | 23.278 | 64.785 | 1.00 | 9.59 |
| 3128 | OG | SER | A | 211 | 63.135 | 22.632 | 65.999 | 1.00 | 8.77 |
| 3130 | C | SER | A | 211 | 64.272 | 22.931 | 62.469 | 1.00 | 9.47 |
| 3131 | O | SER | A | 211 | 63.656 | 22.333 | 61.579 | 1.00 | 9.57 |
| 3132 | N | PHE | A | 212 | 64.958 | 24.054 | 62.252 | 1.00 | 8.64 |
| 3134 | CA | PHE | A | 212 | 64.942 | 24.725 | 60.946 | 1.00 | 8.51 |
| 3136 | CB | PHE | A | 212 | 64.040 | 25.940 | 61.020 | 1.00 | 9.02 |
| 3139 | CG | PHE | A | 212 | 62.609 | 25.603 | 61.358 | 1.00 | 10.68 |
| 3140 | CD1 | PHE | A | 212 | 62.108 | 25.848 | 62.629 | 1.00 | 11.62 |
| 3142 | CE1 | PHE | A | 212 | 60.808 | 25.513 | 62.953 | 1.00 | 13.92 |
| 3144 | CZ | PHE | A | 212 | 60.002 | 24.940 | 62.020 | 1.00 | 13.43 |
| 3146 | CE2 | PHE | A | 212 | 60.482 | 24.668 | 60.757 | 1.00 | 13.66 |
| 3148 | CD2 | PHE | A | 212 | 61.794 | 24.990 | 60.425 | 1.00 | 13.75 |
| 3150 | C | PHE | A | 212 | 66.341 | 25.109 | 60.449 | 1.00 | 7.85 |
| 3151 | O | PHE | A | 212 | 66.668 | 26.297 | 60.359 | 1.00 | 7.35 |
| 3152 | N | PRO | A | 213 | 67.171 | 24.132 | 60.137 | 1.00 | 7.87 |
| 3153 | CA | PRO | A | 213 | 68.526 | 24.411 | 59.657 | 1.00 | 7.91 |
| 3155 | CB | PRO | A | 213 | 69.280 | 23.118 | 59.944 | 1.00 | 8.05 |
| 3158 | CG | PRO | A | 213 | 68.326 | 22.271 | 60.751 | 1.00 | 9.03 |
| 3161 | CD | PRO | A | 213 | 66.970 | 22.685 | 60.324 | 1.00 | 8.17 |
| 3164 | C | PRO | A | 213 | 68.569 | 24.645 | 58.168 | 1.00 | 7.81 |
| 3165 | O | PRO | A | 213 | 67.835 | 24.004 | 57.417 | 1.00 | 8.66 |
| 3166 | N | SER | A | 214 | 69.451 | 25.511 | 57.731 | 1.00 | 7.67 |
| 3168 | CA | SER | A | 214 | 69.589 | 25.767 | 56.316 | 1.00 | 8.91 |
| 3170 | CB | SER | A | 214 | 68.585 | 26.823 | 55.843 | 1.00 | 9.92 |

FIGURE 3 (Cont.)

| A | B | C | D | E | F | G | H | I | J |
|---|---|---|---|---|---|---|---|---|---|
| 3173 | OG | SER | A | 214 | 68.686 | 28.029 | 56.549 | 1.00 | 9.41 |
| 3175 | C | SER | A | 214 | 70.990 | 26.242 | 56.018 | 1.00 | 8.74 |
| 3176 | O | SER | A | 214 | 71.644 | 26.890 | 56.854 | 1.00 | 8.41 |
| 3177 | N | TYR | A | 214 | 71.488 | 25.965 | 54.820 | 1.00 | 8.11 |
| 3179 | CA | TYR | A | 215 | 72.770 | 26.496 | 54.419 | 1.00 | 8.57 |
| 3181 | CB | TYR | A | 215 | 73.878 | 25.524 | 54.750 | 1.00 | 8.86 |
| 3184 | CG | TYR | A | 215 | 73.802 | 24.225 | 53.997 | 1.00 | 9.58 |
| 3185 | CD1 | TYR | A | 215 | 73.083 | 23.162 | 54.493 | 1.00 | 10.93 |
| 3187 | CE1 | TYR | A | 215 | 73.014 | 21.984 | 53.824 | 1.00 | 12.85 |
| 3189 | CZ | TYR | A | 215 | 73.660 | 21.840 | 52.629 | 1.00 | 14.08 |
| 3190 | OH | TYR | A | 215 | 73.595 | 20.638 | 51.932 | 1.00 | 17.38 |
| 3192 | CE2 | TYR | A | 215 | 74.387 | 22.870 | 52.098 | 1.00 | 13.57 |
| 3194 | CD2 | TYR | A | 215 | 74.460 | 24.066 | 52.792 | 1.00 | 11.80 |
| 3196 | C | TYR | A | 215 | 72.771 | 26.825 | 52.939 | 1.00 | 8.35 |
| 3197 | O | TYR | A | 215 | 72.071 | 26.171 | 52.148 | 1.00 | 8.32 |
| 3198 | N | PRO | A | 216 | 73.505 | 27.849 | 52.554 | 1.00 | 8.33 |
| 3199 | CA | PRO | A | 216 | 73.558 | 28.279 | 51.164 | 1.00 | 9.32 |
| 3201 | CB | PRO | A | 216 | 73.838 | 29.766 | 51.292 | 1.00 | 9.52 |
| 3204 | CG | PRO | A | 216 | 74.640 | 29.869 | 52.609 | 1.00 | 9.40 |
| 3207 | CD | PRO | A | 216 | 74.338 | 28.694 | 53.428 | 1.00 | 9.08 |
| 3210 | C | PRO | A | 216 | 74.715 | 27.668 | 50.448 | 1.00 | 10.44 |
| 3211 | O | PRO | A | 216 | 75.616 | 27.154 | 51.078 | 1.00 | 10.23 |
| 3212 | N | GLU | A | 217 | 74.693 | 27.738 | 49.130 | 1.00 | 11.74 |
| 3214 | CA | GLU | A | 217 | 75.860 | 27.352 | 48.371 | 1.00 | 14.22 |
| 3216 | CB | GLU | A | 217 | 75.713 | 25.946 | 47.826 | 1.00 | 15.79 |
| 3219 | CG | GLU | A | 217 | 75.928 | 24.888 | 48.913 | 1.00 | 19.53 |
| 3222 | CD | GLU | A | 217 | 75.598 | 23.485 | 48.437 | 1.00 | 23.19 |
| 3223 | OE1 | GLU | A | 217 | 76.533 | 22.762 | 48.014 | 1.00 | 28.75 |
| 3224 | OE2 | GLU | A | 217 | 74.412 | 23.116 | 48.460 | 1.00 | 20.95 |
| 3225 | C | GLU | A | 217 | 76.147 | 28.401 | 47.307 | 1.00 | 15.13 |
| 3226 | O | GLU | A | 217 | 75.261 | 29.132 | 46.859 | 1.00 | 14.99 |
| 3227 | N | ILE | A | 218 | 77.421 | 28.537 | 46.971 | 1.00 | 16.50 |
| 3229 | CA | ILE | A | 218 | 77.837 | 29.462 | 45.940 | 1.00 | 18.88 |
| 3231 | CB | ILE | A | 218 | 79.033 | 30.267 | 46.443 | 1.00 | 18.61 |
| 3233 | CG1 | ILE | A | 218 | 78.692 | 30.969 | 47.755 | 1.00 | 18.17 |
| 3236 | CD1 | ILE | A | 218 | 79.837 | 31.846 | 48.272 | 1.00 | 18.40 |
| 3240 | CG2 | ILE | A | 218 | 79.446 | 31.297 | 45.400 | 1.00 | 18.53 |
| 3244 | C | ILE | A | 218 | 78.212 | 28.569 | 44.771 | 1.00 | 22.02 |
| 3245 | O | ILE | A | 218 | 79.245 | 27.903 | 44.798 | 1.00 | 22.95 |
| 3246 | N | GLY | A | 219 | 77.323 | 28.493 | 43.793 | 1.00 | 25.34 |
| 3248 | CA | GLY | A | 219 | 77.477 | 27.585 | 42.661 | 1.00 | 26.67 |
| 3251 | C | GLY | A | 219 | 78.770 | 26.797 | 42.691 | 1.00 | 28.29 |
| 3252 | O | GLY | A | 219 | 79.804 | 27.285 | 42.206 | 1.00 | 30.46 |
| 3253 | O5 | E64 | A | 220 | 60.443 | 35.689 | 64.169 | 1.00 | 23.18 |
| 3254 | C11 | E64 | A | 220 | 61.269 | 35.440 | 63.307 | 1.00 | 23.53 |
| 3255 | C6 | E64 | A | 220 | 62.709 | 35.061 | 63.604 | 1.00 | 19.61 |
| 3257 | C7 | E64 | A | 220 | 62.844 | 33.610 | 64.019 | 1.00 | 18.27 |
| 3260 | C8 | E64 | A | 220 | 64.294 | 33.135 | 64.052 | 1.00 | 17.47 |
| 3262 | C10 | E64 | A | 220 | 65.114 | 33.414 | 62.804 | 1.00 | 17.99 |
| 3266 | C9 | E64 | A | 220 | 64.309 | 31.638 | 64.321 | 1.00 | 19.43 |
| 3270 | N1 | E64 | A | 220 | 63.254 | 35.884 | 64.676 | 1.00 | 19.19 |

FIGURE 3 (Cont.)

| A | B | C | D | E | F | G | H | I | J |
|---|---|---|---|---|---|---|---|---|---|
| 3272 | C4 | E64 | A | 220 | 63.918 | 37.003 | 64.371 | 1.00 | 21.88 |
| 3273 | O4 | E64 | A | 220 | 64.113 | 37.313 | 63.228 | 1.00 | 20.92 |
| 3274 | C3 | E64 | A | 220 | 64.450 | 37.903 | 65.449 | 1.00 | 24.96 |
| 3276 | O3 | E64 | A | 220 | 63.338 | 38.352 | 66.185 | 1.00 | 27.29 |
| 3278 | C2 | E64 | A | 220 | 65.405 | 37.161 | 66.372 | 1.00 | 25.08 |
| 3281 | C1 | E64 | A | 220 | 66.483 | 38.064 | 66.930 | 1.00 | 26.84 |
| 3282 | O2 | E64 | A | 220 | 67.021 | 39.002 | 66.164 | 1.00 | 23.76 |
| 3284 | O1 | E64 | A | 220 | 66.875 | 37.917 | 68.078 | 1.00 | 25.07 |
| 3285 | N2 | E64 | A | 220 | 61.155 | 35.463 | 61.989 | 1.00 | 24.93 |
| 3287 | C12 | E64 | A | 220 | 60.197 | 35.736 | 60.942 | 1.00 | 29.49 |
| 3290 | C13 | E64 | A | 220 | 59.154 | 36.783 | 61.210 | 1.00 | 30.80 |
| 3293 | C14 | E64 | A | 220 | 58.960 | 37.407 | 59.826 | 1.00 | 32.35 |
| 3296 | C15 | E64 | A | 220 | 58.183 | 38.708 | 59.769 | 1.00 | 32.03 |
| 3299 | N3 | E64 | A | 220 | 57.963 | 39.165 | 61.131 | 1.00 | 33.36 |
| 3301 | C16 | E64 | A | 220 | 57.363 | 40.299 | 61.469 | 1.00 | 35.00 |
| 3302 | N5 | E64 | A | 220 | 57.230 | 40.550 | 62.774 | 1.00 | 34.56 |
| 3305 | N4 | E64 | A | 220 | 56.920 | 41.164 | 60.539 | 1.00 | 35.50 |
| 3308 | N | ILE | B | 1 | 26.179 | 20.401 | 122.831 | 1.00 | 26.31 |
| 3310 | CA | ILE | B | 1 | 27.481 | 21.012 | 123.235 | 1.00 | 25.06 |
| 3312 | CB | ILE | B | 1 | 27.757 | 20.715 | 124.726 | 1.00 | 25.63 |
| 3314 | CG1 | ILE | B | 1 | 26.717 | 21.473 | 125.571 | 1.00 | 26.29 |
| 3317 | CD1 | ILE | B | 1 | 26.963 | 22.985 | 125.666 | 1.00 | 27.69 |
| 3321 | CG2 | ILE | B | 1 | 29.144 | 21.147 | 125.125 | 1.00 | 26.52 |
| 3325 | C | ILE | B | 1 | 28.566 | 20.528 | 122.257 | 1.00 | 23.29 |
| 3326 | O | ILE | B | 1 | 28.642 | 19.347 | 121.941 | 1.00 | 25.95 |
| 3330 | N | LEU | B | 2 | 29.283 | 21.468 | 121.656 | 1.00 | 19.32 |
| 3332 | CA | LEU | B | 2 | 30.356 | 21.120 | 120.729 | 1.00 | 16.44 |
| 3334 | CB | LEU | B | 2 | 30.248 | 22.003 | 119.482 | 1.00 | 15.52 |
| 3337 | CG | LEU | B | 2 | 28.925 | 21.937 | 118.742 | 1.00 | 15.20 |
| 3339 | CD1 | LEU | B | 2 | 28.911 | 22.961 | 117.652 | 1.00 | 16.04 |
| 3343 | CD2 | LEU | B | 2 | 28.681 | 20.533 | 118.197 | 1.00 | 16.50 |
| 3347 | C | LEU | B | 2 | 31.715 | 21.354 | 121.326 | 1.00 | 14.20 |
| 3348 | O | LEU | B | 2 | 31.887 | 22.219 | 122.182 | 1.00 | 13.39 |
| 3349 | N | PRO | B | 3 | 32.720 | 20.634 | 120.831 | 1.00 | 12.67 |
| 3350 | CA | PRO | B | 3 | 34.078 | 20.898 | 121.290 | 1.00 | 12.15 |
| 3352 | CB | PRO | B | 3 | 34.922 | 19.890 | 120.508 | 1.00 | 12.81 |
| 3355 | CG | PRO | B | 3 | 33.997 | 18.845 | 120.014 | 1.00 | 15.27 |
| 3358 | CD | PRO | B | 3 | 32.656 | 19.543 | 119.849 | 1.00 | 13.10 |
| 3361 | C | PRO | B | 3 | 34.521 | 22.320 | 120.970 | 1.00 | 11.96 |
| 3362 | O | PRO | B | 3 | 34.115 | 22.902 | 119.956 | 1.00 | 11.24 |
| 3363 | N | ASP | B | 4 | 35.380 | 22.881 | 121.804 | 1.00 | 11.67 |
| 3365 | CA | ASP | B | 4 | 35.906 | 24.204 | 121.564 | 1.00 | 12.03 |
| 3367 | CB | ASP | B | 4 | 36.663 | 24.692 | 122.793 | 1.00 | 12.55 |
| 3370 | CG | ASP | B | 4 | 35.754 | 25.094 | 123.902 | 1.00 | 16.27 |
| 3371 | OD1 | ASP | B | 4 | 34.550 | 25.364 | 123.641 | 1.00 | 17.55 |
| 3372 | OD2 | ASP | B | 4 | 36.175 | 25.179 | 125.072 | 1.00 | 19.92 |
| 3373 | C | ASP | B | 4 | 36.844 | 24.267 | 120.350 | 1.00 | 11.11 |
| 3374 | O | ASP | B | 4 | 36.999 | 25.309 | 119.726 | 1.00 | 11.94 |
| 3375 | N | SER | B | 5 | 37.503 | 23.159 | 120.069 | 1.00 | 10.88 |
| 3377 | CA | SER | B | 5 | 38.422 | 23.056 | 118.956 | 1.00 | 10.69 |
| 3379 | CB | SER | B | 5 | 39.862 | 23.278 | 119.379 | 1.00 | 12.28 |

FIGURE 3 (Cont.)

| A | B | C | D | E | F | G | H | I | J |
|---|---|---|---|---|---|---|---|---|---|
| 3382 | OG | SER | B | 5 | 40.030 | 24.483 | 120.073 | 1.00 | 13.59 |
| 3384 | C | SER | B | 5 | 38.326 | 21.671 | 118.351 | 1.00 | 10.39 |
| 3385 | O | SER | B | 5 | 38.131 | 20.682 | 119.048 | 1.00 | 10.09 |
| 3386 | N | VAL | B | 6 | 38.490 | 21.608 | 117.042 | 1.00 | 9.75 |
| 3388 | CA | VAL | B | 6 | 38.504 | 20.335 | 116.339 | 1.00 | 10.30 |
| 3390 | CB | VAL | B | 6 | 37.162 | 20.018 | 115.648 | 1.00 | 11.95 |
| 3392 | CG1 | VAL | B | 6 | 37.172 | 18.668 | 114.950 | 1.00 | 14.73 |
| 3396 | CG2 | VAL | B | 6 | 36.039 | 19.995 | 116.635 | 1.00 | 11.35 |
| 3400 | C | VAL | B | 6 | 39.609 | 20.393 | 115.293 | 1.00 | 9.19 |
| 3401 | O | VAL | B | 6 | 39.846 | 21.447 | 114.715 | 1.00 | 8.51 |
| 3402 | N | ASP | B | 7 | 40.291 | 19.276 | 115.069 | 1.00 | 9.75 |
| 3404 | CA | ASP | B | 7 | 41.268 | 19.192 | 113.994 | 1.00 | 9.60 |
| 3406 | CB | ASP | B | 7 | 42.695 | 19.447 | 114.522 | 1.00 | 9.52 |
| 3409 | CG | ASP | B | 7 | 43.746 | 19.537 | 113.411 | 1.00 | 10.94 |
| 3410 | OD1 | ASP | B | 7 | 43.502 | 19.061 | 112.278 | 1.00 | 11.14 |
| 3411 | OD2 | ASP | B | 7 | 44.860 | 20.105 | 113.604 | 1.00 | 13.70 |
| 3412 | C | ASP | B | 7 | 41.201 | 17.790 | 113.401 | 1.00 | 9.72 |
| 3413 | O | ASP | B | 7 | 41.672 | 16.814 | 114.013 | 1.00 | 10.06 |
| 3414 | N | TRP | B | 8 | 40.619 | 17.660 | 112.212 | 1.00 | 8.47 |
| 3416 | CA | TRP | B | 8 | 40.422 | 16.343 | 111.617 | 1.00 | 8.47 |
| 3418 | CB | TRP | B | 8 | 39.438 | 16.421 | 110.438 | 1.00 | 8.76 |
| 3421 | CG | TRP | B | 8 | 38.010 | 16.550 | 110.910 | 1.00 | 9.31 |
| 3422 | CD1 | TRP | B | 8 | 37.268 | 17.706 | 111.021 | 1.00 | 8.05 |
| 3424 | NE1 | TRP | B | 8 | 36.022 | 17.417 | 111.530 | 1.00 | 9.00 |
| 3426 | CE2 | TRP | B | 8 | 35.943 | 16.076 | 111.776 | 1.00 | 13.39 |
| 3427 | CD2 | TRP | B | 8 | 37.173 | 15.499 | 111.400 | 1.00 | 14.09 |
| 3428 | CE3 | TRP | B | 8 | 37.348 | 14.123 | 111.590 | 1.00 | 18.93 |
| 3430 | CZ3 | TRP | B | 8 | 36.306 | 13.389 | 112.125 | 1.00 | 21.96 |
| 3432 | CH2 | TRP | B | 8 | 35.091 | 13.992 | 112.462 | 1.00 | 19.55 |
| 3434 | CZ2 | TRP | B | 8 | 34.888 | 15.325 | 112.297 | 1.00 | 16.30 |
| 3436 | C | TRP | B | 8 | 41.715 | 15.667 | 111.212 | 1.00 | 8.59 |
| 3437 | O | TRP | B | 8 | 41.734 | 14.483 | 110.905 | 1.00 | 9.41 |
| 3438 | N | ARG | B | 9 | 42.798 | 16.418 | 111.194 | 1.00 | 8.31 |
| 3440 | CA | ARG | B | 9 | 44.066 | 15.806 | 110.879 | 1.00 | 9.20 |
| 3442 | CB | ARG | B | 9 | 45.133 | 16.865 | 110.690 | 1.00 | 8.81 |
| 3445 | CG | ARG | B | 9 | 44.866 | 17.793 | 109.504 | 1.00 | 9.65 |
| 3448 | CD | ARG | B | 9 | 45.809 | 18.931 | 109.353 | 1.00 | 8.75 |
| 3451 | NE | ARG | B | 9 | 45.874 | 19.766 | 110.535 | 1.00 | 8.53 |
| 3453 | CZ | ARG | B | 9 | 46.726 | 20.763 | 110.692 | 1.00 | 10.89 |
| 3454 | NH1 | ARG | B | 9 | 47.558 | 21.110 | 109.709 | 1.00 | 9.82 |
| 3457 | NH2 | ARG | B | 9 | 46.745 | 21.416 | 111.831 | 1.00 | 9.81 |
| 3460 | C | ARG | B | 9 | 44.457 | 14.843 | 111.991 | 1.00 | 9.40 |
| 3461 | O | ARG | B | 9 | 45.120 | 13.834 | 111.744 | 1.00 | 9.91 |
| 3462 | N | GLU | B | 10 | 44.032 | 15.169 | 113.206 | 1.00 | 10.75 |
| 3464 | CA | GLU | B | 10 | 44.342 | 14.390 | 114.392 | 1.00 | 12.72 |
| 3466 | CB | GLU | B | 10 | 43.976 | 15.159 | 115.659 | 1.00 | 12.86 |
| 3469 | CG | GLU | B | 10 | 44.908 | 16.267 | 116.030 | 1.00 | 16.15 |
| 3472 | CD | GLU | B | 10 | 44.483 | 16.965 | 117.281 | 1.00 | 18.62 |
| 3473 | OE1 | GLU | B | 10 | 43.648 | 16.384 | 118.010 | 1.00 | 24.05 |
| 3474 | OE2 | GLU | B | 10 | 44.974 | 18.080 | 117.521 | 1.00 | 21.53 |
| 3475 | C | GLU | B | 10 | 43.614 | 13.074 | 114.422 | 1.00 | 14.16 |

FIGURE 3 (Cont.)

| A | B | C | D | E | F | G | H | I | J |
|---|---|---|---|---|---|---|---|---|---|
| 3476 | O | GLU | B | 10 | 43.905 | 12.234 | 115.282 | 1.00 | 15.74 |
| 3477 | N | LYS | B | 11 | 42.609 | 12.943 | 113.537 | 1.00 | 13.88 |
| 3479 | CA | LYS | B | 11 | 41.818 | 11.726 | 113.382 | 1.00 | 15.05 |
| 3481 | CB | LYS | B | 11 | 40.324 | 12.048 | 113.324 | 1.00 | 16.00 |
| 3484 | CG | LYS | B | 11 | 39.480 | 10.931 | 113.942 | 1.00 | 21.01 |
| 3487 | CD | LYS | B | 11 | 38.022 | 11.096 | 113.640 | 1.00 | 24.23 |
| 3490 | CE | LYS | B | 11 | 37.225 | 9.847 | 114.002 | 1.00 | 24.82 |
| 3493 | NZ | LYS | B | 11 | 37.039 | 9.691 | 115.470 | 1.00 | 27.97 |
| 3497 | C | LYS | B | 11 | 42.203 | 10.941 | 112.127 | 1.00 | 14.16 |
| 3498 | O | LYS | B | 11 | 41.555 | 9.961 | 111.764 | 1.00 | 15.76 |
| 3499 | N | GLY | B | 12 | 43.235 | 11.376 | 111.420 | 1.00 | 12.26 |
| 3501 | CA | GLY | B | 12 | 43.717 | 10.637 | 110.283 | 1.00 | 12.43 |
| 3504 | C | GLY | B | 12 | 42.803 | 10.716 | 109.074 | 1.00 | 11.52 |
| 3505 | O | GLY | B | 12 | 42.854 | 9.844 | 108.202 | 1.00 | 11.94 |
| 3506 | N | CYS | B | 13 | 42.016 | 11.791 | 108.988 | 1.00 | 10.65 |
| 3508 | CA | CYS | B | 13 | 41.020 | 11.954 | 107.921 | 1.00 | 10.35 |
| 3510 | CB | CYS | B | 13 | 39.686 | 12.387 | 108.538 | 1.00 | 10.42 |
| 3513 | SG | CYS | B | 13 | 38.895 | 11.060 | 109.450 | 1.00 | 13.71 |
| 3514 | C | CYS | B | 13 | 41.383 | 12.965 | 106.860 | 1.00 | 9.86 |
| 3515 | O | CYS | B | 13 | 40.539 | 13.297 | 106.013 | 1.00 | 10.30 |
| 3516 | N | VAL | B | 14 | 42.621 | 13.432 | 106.862 | 1.00 | 8.32 |
| 3518 | CA | VAL | B | 14 | 43.035 | 14.460 | 105.930 | 1.00 | 7.80 |
| 3520 | CB | VAL | B | 14 | 43.238 | 15.799 | 106.644 | 1.00 | 7.81 |
| 3522 | CG1 | VAL | B | 14 | 43.589 | 16.866 | 105.684 | 1.00 | 9.67 |
| 3526 | CG2 | VAL | B | 14 | 42.006 | 16.211 | 107.388 | 1.00 | 7.81 |
| 3530 | C | VAL | B | 14 | 44.303 | 14.021 | 105.225 | 1.00 | 8.11 |
| 3531 | O | VAL | B | 14 | 45.267 | 13.632 | 105.866 | 1.00 | 8.74 |
| 3532 | N | THR | B | 15 | 44.306 | 14.054 | 103.901 | 1.00 | 8.18 |
| 3534 | CA | THR | B | 15 | 45.465 | 13.638 | 103.154 | 1.00 | 8.66 |
| 3536 | CB | THR | B | 15 | 45.065 | 13.204 | 101.736 | 1.00 | 8.73 |
| 3538 | OG1 | THR | B | 15 | 44.449 | 14.317 | 101.062 | 1.00 | 9.54 |
| 3540 | CG2 | THR | B | 15 | 44.049 | 12.116 | 101.773 | 1.00 | 9.61 |
| 3544 | C | THR | B | 15 | 46.505 | 14.757 | 103.058 | 1.00 | 8.98 |
| 3545 | O | THR | B | 15 | 46.308 | 15.876 | 103.544 | 1.00 | 9.62 |
| 3546 | N | GLU | B | 16 | 47.589 | 14.452 | 102.374 | 1.00 | 10.04 |
| 3548 | CA | GLU | B | 16 | 48.623 | 15.430 | 102.108 | 1.00 | 10.66 |
| 3550 | CB | GLU | B | 16 | 49.744 | 14.786 | 101.282 | 1.00 | 12.98 |
| 3553 | CG | GLU | B | 16 | 50.511 | 13.721 | 102.016 | 1.00 | 18.14 |
| 3556 | CD | GLU | B | 16 | 49.944 | 12.321 | 101.838 | 1.00 | 24.98 |
| 3557 | OE1 | GLU | B | 16 | 48.842 | 12.170 | 101.225 | 1.00 | 28.47 |
| 3558 | OE2 | GLU | B | 16 | 50.597 | 11.363 | 102.341 | 1.00 | 30.56 |
| 3559 | C | GLU | B | 16 | 48.060 | 16.600 | 101.308 | 1.00 | 9.92 |
| 3560 | O | GLU | B | 16 | 47.102 | 16.454 | 100.538 | 1.00 | 9.64 |
| 3561 | N | VAL | B | 17 | 48.621 | 17.773 | 101.540 | 1.00 | 9.32 |
| 3563 | CA | VAL | B | 17 | 48.275 | 18.963 | 100.791 | 1.00 | 9.51 |
| 3565 | CB | VAL | B | 17 | 48.929 | 20.226 | 101.407 | 1.00 | 9.68 |
| 3567 | CG1 | VAL | B | 17 | 48.725 | 21.419 | 100.515 | 1.00 | 10.32 |
| 3571 | CG2 | VAL | B | 17 | 48.346 | 20.472 | 102.794 | 1.00 | 10.05 |
| 3575 | C | VAL | B | 17 | 48.715 | 18.800 | 99.345 | 1.00 | 9.70 |
| 3576 | O | VAL | B | 17 | 49.822 | 18.337 | 99.056 | 1.00 | 11.33 |
| 3577 | N | LYS | B | 18 | 47.812 | 19.164 | 98.452 | 1.00 | 9.14 |

FIGURE 3 (Cont.)

| A | B | C | D | E | F | G | H | I | J |
|---|---|---|---|---|---|---|---|---|---|
| 3579 | CA | LYS | B | 18 | 48.036 | 19.077 | 97.019 | 1.00 | 9.10 |
| 3581 | CB | LYS | B | 18 | 46.792 | 18.510 | 96.317 | 1.00 | 9.82 |
| 3584 | CG | LYS | B | 18 | 46.286 | 17.183 | 96.899 | 1.00 | 9.61 |
| 3587 | CD | LYS | B | 18 | 47.394 | 16.156 | 96.995 | 1.00 | 10.77 |
| 3590 | CE | LYS | B | 18 | 46.863 | 14.765 | 97.356 | 1.00 | 10.68 |
| 3593 | NZ | LYS | B | 18 | 45.971 | 14.681 | 98.574 | 1.00 | 10.54 |
| 3597 | C | LYS | B | 18 | 48.376 | 20.435 | 96.444 | 1.00 | 9.11 |
| 3598 | O | LYS | B | 18 | 48.175 | 21.477 | 97.077 | 1.00 | 8.27 |
| 3599 | N | TYR | B | 18 | 48.913 | 20.392 | 95.237 | 1.00 | 9.99 |
| 3601 | CA | TYR | B | 19 | 49.286 | 21.576 | 94.514 | 1.00 | 11.00 |
| 3603 | CB | TYR | B | 19 | 50.784 | 21.553 | 94.275 | 1.00 | 11.58 |
| 3606 | CG | TYR | B | 19 | 51.312 | 22.759 | 93.574 | 1.00 | 14.54 |
| 3607 | CD1 | TYR | B | 19 | 51.731 | 22.693 | 92.265 | 1.00 | 18.60 |
| 3609 | CE1 | TYR | B | 19 | 52.240 | 23.816 | 91.622 | 1.00 | 19.12 |
| 3611 | CZ | TYR | B | 19 | 52.316 | 25.009 | 92.292 | 1.00 | 19.72 |
| 3612 | OH | TYR | B | 19 | 52.825 | 26.133 | 91.644 | 1.00 | 21.52 |
| 3614 | CE2 | TYR | B | 19 | 51.898 | 25.081 | 93.598 | 1.00 | 20.90 |
| 3616 | CD2 | TYR | B | 19 | 51.411 | 23.959 | 94.227 | 1.00 | 16.93 |
| 3618 | C | TYR | B | 19 | 48.530 | 21.641 | 93.192 | 1.00 | 11.25 |
| 3619 | O | TYR | B | 19 | 48.838 | 20.875 | 92.287 | 1.00 | 12.20 |
| 3620 | N | GLN | B | 20 | 47.551 | 22.548 | 93.085 | 1.00 | 10.99 |
| 3622 | CA | GLN | B | 20 | 46.764 | 22.697 | 91.854 | 1.00 | 11.56 |
| 3624 | CB | GLN | B | 20 | 45.462 | 23.449 | 92.128 | 1.00 | 11.78 |
| 3627 | CG | GLN | B | 20 | 45.634 | 24.886 | 92.479 | 1.00 | 11.89 |
| 3630 | CD | GLN | B | 20 | 44.319 | 25.534 | 92.805 | 1.00 | 14.37 |
| 3631 | OE1 | GLN | B | 20 | 43.874 | 25.500 | 93.946 | 1.00 | 16.74 |
| 3632 | NE2 | GLN | B | 20 | 43.682 | 26.130 | 91.804 | 1.00 | 16.06 |
| 3635 | C | GLN | B | 20 | 47.520 | 23.342 | 90.684 | 1.00 | 13.08 |
| 3636 | O | GLN | B | 20 | 47.154 | 23.148 | 89.532 | 1.00 | 13.49 |
| 3637 | N | GLY | B | 21 | 48.538 | 24.130 | 90.984 | 1.00 | 14.20 |
| 3639 | CA | GLY | B | 21 | 49.291 | 24.796 | 89.928 | 1.00 | 15.55 |
| 3642 | C | GLY | B | 21 | 48.445 | 25.838 | 89.229 | 1.00 | 16.58 |
| 3643 | O | GLY | B | 21 | 47.591 | 26.473 | 89.824 | 1.00 | 17.40 |
| 3644 | N | SER | B | 22 | 48.657 | 26.014 | 87.929 | 1.00 | 18.41 |
| 3646 | CA | SER | B | 22 | 47.926 | 27.050 | 87.216 | 1.00 | 19.92 |
| 3648 | CB | SER | B | 22 | 48.786 | 27.582 | 86.067 | 1.00 | 20.36 |
| 3651 | OG | SER | B | 22 | 49.853 | 28.330 | 86.613 | 1.00 | 26.52 |
| 3653 | C | SER | B | 22 | 46.571 | 26.639 | 86.684 | 1.00 | 19.66 |
| 3654 | O | SER | B | 22 | 46.026 | 27.300 | 85.804 | 1.00 | 22.07 |
| 3655 | N | CYS | B | 23 | 46.014 | 25.567 | 87.227 | 1.00 | 18.12 |
| 3657 | CA | CYS | B | 23 | 44.734 | 25.035 | 86.807 | 1.00 | 17.66 |
| 3659 | CB | CYS | B | 23 | 44.859 | 23.511 | 86.660 | 1.00 | 16.85 |
| 3662 | SG | CYS | B | 23 | 43.329 | 22.596 | 86.359 | 1.00 | 18.12 |
| 3663 | C | CYS | B | 23 | 43.755 | 25.406 | 87.898 | 1.00 | 16.72 |
| 3664 | O | CYS | B | 23 | 44.033 | 25.126 | 89.059 | 1.00 | 17.73 |
| 3665 | N | GLY | B | 24 | 42.641 | 26.041 | 87.529 | 1.00 | 16.59 |
| 3667 | CA | GLY | B | 24 | 41.629 | 26.472 | 88.490 | 1.00 | 15.95 |
| 3670 | C | GLY | B | 24 | 40.765 | 25.313 | 88.940 | 1.00 | 15.26 |
| 3671 | O | GLY | B | 24 | 39.559 | 25.273 | 88.674 | 1.00 | 17.01 |
| 3672 | N | ALA | B | 25 | 41.415 | 24.370 | 89.601 | 1.00 | 14.80 |
| 3674 | CA | ALA | B | 25 | 40.766 | 23.154 | 90.034 | 1.00 | 13.96 |

FIGURE 3 (Cont.)

| A | B | C | D | E | F | G | H | I | J |
|---|---|---|---|---|---|---|---|---|---|
| 3676 | CB | ALA | B | 25 | 41.593 | 21.949 | 89.612 | 1.00 | 14.69 |
| 3680 | C | ALA | B | 25 | 40.569 | 23.131 | 91.533 | 1.00 | 13.78 |
| 3681 | O | ALA | B | 25 | 40.438 | 22.075 | 92.087 | 1.00 | 13.20 |
| 3682 | N | CYS | B | 26 | 40.543 | 24.295 | 92.182 | 1.00 | 13.59 |
| 3684 | CA | CYS | B | 26 | 40.310 | 24.347 | 93.632 | 1.00 | 14.47 |
| 3686 | CB | CYS | B | 26 | 40.128 | 25.796 | 94.108 | 1.00 | 15.45 |
| 3689 | SG | CYS | B | 26 | 38.544 | 26.600 | 93.662 | 1.00 | 20.16 |
| 3690 | C | CYS | B | 26 | 39.055 | 23.578 | 94.036 | 1.00 | 12.35 |
| 3691 | O | CYS | B | 26 | 39.034 | 22.876 | 95.046 | 1.00 | 11.94 |
| 3692 | N | TRP | B | 27 | 38.010 | 23.741 | 93.234 | 1.00 | 11.67 |
| 3694 | CA | TRP | B | 27 | 36.712 | 23.125 | 93.479 | 1.00 | 9.93 |
| 3696 | CB | TRP | B | 27 | 35.723 | 23.494 | 92.368 | 1.00 | 10.34 |
| 3699 | CG | TRP | B | 27 | 36.153 | 23.127 | 90.992 | 1.00 | 9.14 |
| 3700 | CD1 | TRP | B | 27 | 37.007 | 23.828 | 90.172 | 1.00 | 12.09 |
| 3702 | NE1 | TRP | B | 27 | 37.140 | 23.177 | 88.973 | 1.00 | 11.76 |
| 3704 | CE2 | TRP | B | 27 | 36.389 | 22.035 | 88.999 | 1.00 | 11.13 |
| 3705 | CD2 | TRP | B | 27 | 35.756 | 21.977 | 90.258 | 1.00 | 10.11 |
| 3706 | CE3 | TRP | B | 27 | 34.888 | 20.909 | 90.520 | 1.00 | 11.37 |
| 3708 | CZ3 | TRP | B | 27 | 34.704 | 19.944 | 89.572 | 1.00 | 11.10 |
| 3710 | CH2 | TRP | B | 27 | 35.369 | 20.015 | 88.322 | 1.00 | 10.07 |
| 3712 | CZ2 | TRP | B | 27 | 36.186 | 21.072 | 88.020 | 1.00 | 10.00 |
| 3714 | C | TRP | B | 27 | 36.863 | 21.608 | 93.553 | 1.00 | 9.89 |
| 3715 | O | TRP | B | 27 | 36.200 | 20.960 | 94.352 | 1.00 | 9.28 |
| 3716 | N | ALA | B | 28 | 37.696 | 21.067 | 92.684 | 1.00 | 8.71 |
| 3718 | CA | ALA | B | 28 | 37.884 | 19.629 | 92.615 | 1.00 | 8.36 |
| 3720 | CB | ALA | B | 28 | 38.634 | 19.247 | 91.352 | 1.00 | 8.25 |
| 3724 | C | ALA | B | 28 | 38.634 | 19.108 | 93.827 | 1.00 | 8.01 |
| 3725 | O | ALA | B | 28 | 38.277 | 18.080 | 94.381 | 1.00 | 9.03 |
| 3726 | N | PHE | B | 29 | 39.649 | 19.855 | 94.247 | 1.00 | 8.26 |
| 3728 | CA | PHE | B | 29 | 40.429 | 19.478 | 95.410 | 1.00 | 7.81 |
| 3730 | CB | PHE | B | 29 | 41.688 | 20.315 | 95.512 | 1.00 | 7.75 |
| 3733 | CG | PHE | B | 29 | 42.746 | 19.895 | 94.552 | 1.00 | 9.37 |
| 3734 | CD1 | PHE | B | 29 | 43.018 | 20.658 | 93.443 | 1.00 | 10.12 |
| 3736 | CE1 | PHE | B | 29 | 43.989 | 20.270 | 92.559 | 1.00 | 10.86 |
| 3738 | CZ | PHE | B | 29 | 44.676 | 19.114 | 92.761 | 1.00 | 10.23 |
| 3740 | CE2 | PHE | B | 29 | 44.409 | 18.338 | 93.866 | 1.00 | 9.99 |
| 3742 | CD2 | PHE | B | 29 | 43.446 | 18.735 | 94.750 | 1.00 | 10.89 |
| 3744 | C | PHE | B | 29 | 39.591 | 19.605 | 96.665 | 1.00 | 7.26 |
| 3745 | O | PHE | B | 29 | 39.651 | 18.759 | 97.551 | 1.00 | 7.71 |
| 3746 | N | SER | B | 30 | 38.809 | 20.666 | 96.733 | 1.00 | 8.11 |
| 3748 | CA | SER | B | 30 | 37.921 | 20.831 | 97.878 | 1.00 | 7.44 |
| 3750 | CB | SER | B | 30 | 37.149 | 22.142 | 97.725 | 1.00 | 8.02 |
| 3753 | OG | SER | B | 30 | 36.189 | 22.268 | 98.747 | 1.00 | 8.99 |
| 3755 | C | SER | B | 30 | 36.968 | 19.650 | 97.990 | 1.00 | 7.35 |
| 3756 | O | SER | B | 30 | 36.779 | 19.077 | 99.052 | 1.00 | 7.73 |
| 3757 | N | ALA | B | 31 | 36.391 | 19.273 | 96.861 | 1.00 | 6.79 |
| 3759 | CA | ALA | B | 31 | 35.434 | 18.193 | 96.852 | 1.00 | 6.88 |
| 3761 | CB | ALA | B | 31 | 34.794 | 18.096 | 95.474 | 1.00 | 6.95 |
| 3765 | C | ALA | B | 31 | 36.093 | 16.873 | 97.239 | 1.00 | 7.15 |
| 3766 | O | ALA | B | 31 | 35.553 | 16.124 | 98.065 | 1.00 | 7.96 |
| 3767 | N | VAL | B | 32 | 37.225 | 16.548 | 96.634 | 1.00 | 7.79 |

FIGURE 3 (Cont.)

| A | B | C | D | E | F | G | H | I | J |
|---|---|---|---|---|---|---|---|---|---|
| 3769 | CA | VAL | B | 32 | 37.829 | 15.264 | 96.939 | 1.00 | 7.28 |
| 3771 | CB | VAL | B | 32 | 38.970 | 14.832 | 95.997 | 1.00 | 8.12 |
| 3773 | CG1 | VAL | B | 32 | 38.462 | 14.661 | 94.577 | 1.00 | 10.03 |
| 3777 | CG2 | VAL | B | 32 | 40.142 | 15.765 | 96.072 | 1.00 | 8.65 |
| 3781 | C | VAL | B | 32 | 38.280 | 15.247 | 98.393 | 1.00 | 7.08 |
| 3782 | O | VAL | B | 32 | 38.207 | 14.198 | 99.030 | 1.00 | 7.98 |
| 3783 | N | GLY | B | 33 | 38.746 | 16.377 | 98.907 | 1.00 | 6.99 |
| 3785 | CA | GLY | B | 33 | 39.178 | 16.423 | 100.302 | 1.00 | 6.98 |
| 3788 | C | GLY | B | 33 | 38.043 | 16.094 | 101.246 | 1.00 | 6.36 |
| 3789 | O | GLY | B | 33 | 38.182 | 15.354 | 102.220 | 1.00 | 6.80 |
| 3790 | N | ALA | B | 34 | 36.864 | 16.626 | 100.960 | 1.00 | 6.18 |
| 3792 | CA | ALA | B | 34 | 35.719 | 16.337 | 101.795 | 1.00 | 6.46 |
| 3794 | CB | ALA | B | 34 | 34.566 | 17.200 | 101.415 | 1.00 | 7.31 |
| 3798 | C | ALA | B | 34 | 35.362 | 14.861 | 101.707 | 1.00 | 6.99 |
| 3799 | O | ALA | B | 34 | 35.052 | 14.220 | 102.711 | 1.00 | 7.66 |
| 3800 | N | LEU | B | 35 | 35.390 | 14.309 | 100.506 | 1.00 | 7.18 |
| 3802 | CA | LEU | B | 35 | 35.040 | 12.909 | 100.345 | 1.00 | 6.98 |
| 3804 | CB | LEU | B | 35 | 34.741 | 12.596 | 98.869 | 1.00 | 6.57 |
| 3807 | CG | LEU | B | 35 | 34.051 | 11.242 | 98.616 | 1.00 | 7.96 |
| 3809 | CD1 | LEU | B | 35 | 32.767 | 11.102 | 99.367 | 1.00 | 9.26 |
| 3813 | CD2 | LEU | B | 35 | 33.818 | 11.071 | 97.119 | 1.00 | 9.94 |
| 3817 | C | LEU | B | 35 | 36.088 | 11.959 | 100.926 | 1.00 | 7.43 |
| 3818 | O | LEU | B | 35 | 35.732 | 10.909 | 101.448 | 1.00 | 9.03 |
| 3819 | N | GLU | B | 36 | 37.354 | 12.357 | 100.875 | 1.00 | 7.66 |
| 3821 | CA | GLU | B | 36 | 38.439 | 11.558 | 101.420 | 1.00 | 8.49 |
| 3823 | CB | GLU | B | 36 | 39.782 | 12.285 | 101.250 | 1.00 | 9.64 |
| 3826 | CG | GLU | B | 36 | 40.304 | 12.231 | 99.839 | 1.00 | 11.94 |
| 3829 | CD | GLU | B | 36 | 41.381 | 13.244 | 99.509 | 1.00 | 12.43 |
| 3830 | OE1 | GLU | B | 36 | 41.796 | 14.075 | 100.341 | 1.00 | 11.97 |
| 3831 | OE2 | GLU | B | 36 | 41.774 | 13.223 | 98.354 | 1.00 | 11.89 |
| 3832 | C | GLU | B | 36 | 38.198 | 11.303 | 102.897 | 1.00 | 8.34 |
| 3833 | O | GLU | B | 36 | 38.397 | 10.201 | 103.381 | 1.00 | 8.33 |
| 3834 | N | ALA | B | 37 | 37.742 | 12.325 | 103.613 | 1.00 | 8.11 |
| 3836 | CA | ALA | B | 37 | 37.459 | 12.195 | 105.029 | 1.00 | 7.96 |
| 3838 | CB | ALA | B | 37 | 37.136 | 13.535 | 105.613 | 1.00 | 8.55 |
| 3842 | C | ALA | B | 37 | 36.335 | 11.207 | 105.274 | 1.00 | 8.61 |
| 3843 | O | ALA | B | 37 | 36.429 | 10.358 | 106.150 | 1.00 | 9.01 |
| 3844 | N | GLN | B | 38 | 35.255 | 11.301 | 104.508 | 1.00 | 7.93 |
| 3846 | CA | GLN | B | 38 | 34.151 | 10.372 | 104.663 | 1.00 | 7.77 |
| 3848 | CB | GLN | B | 38 | 32.990 | 10.781 | 103.759 | 1.00 | 8.68 |
| 3851 | CG | GLN | B | 38 | 32.450 | 12.121 | 104.110 | 1.00 | 8.64 |
| 3854 | CD | GLN | B | 38 | 31.992 | 12.221 | 105.557 | 1.00 | 10.24 |
| 3855 | OE1 | GLN | B | 38 | 31.279 | 11.334 | 106.059 | 1.00 | 11.05 |
| 3856 | NE2 | GLN | B | 38 | 32.367 | 13.308 | 106.227 | 1.00 | 9.62 |
| 3859 | C | GLN | B | 38 | 34.585 | 8.950 | 104.356 | 1.00 | 8.78 |
| 3860 | O | GLN | B | 38 | 34.156 | 8.016 | 105.002 | 1.00 | 10.17 |
| 3861 | N | LEU | B | 39 | 35.445 | 8.786 | 103.372 | 1.00 | 8.57 |
| 3863 | CA | LEU | B | 39 | 35.952 | 7.465 | 103.000 | 1.00 | 9.27 |
| 3865 | CB | LEU | B | 39 | 36.815 | 7.561 | 101.737 | 1.00 | 9.86 |
| 3868 | CG | LEU | B | 39 | 37.406 | 6.251 | 101.236 | 1.00 | 11.50 |
| 3870 | CD1 | LEU | B | 39 | 36.305 | 5.284 | 100.800 | 1.00 | 12.63 |

FIGURE 3 (Cont.)

| A | B | C | D | E | F | G | H | I | J |
|---|---|---|---|---|---|---|---|---|---|
| 3874 | CD2 | LEU | B | 39 | 38.356 | 6.539 | 100.120 | 1.00 | 11.92 |
| 3878 | C | LEU | B | 39 | 36.723 | 6.868 | 104.167 | 1.00 | 10.55 |
| 3879 | O | LEU | B | 39 | 36.556 | 5.717 | 104.487 | 1.00 | 10.17 |
| 3880 | N | LYS | B | 40 | 37.544 | 7.673 | 104.822 | 1.00 | 10.74 |
| 3882 | CA | LYS | B | 40 | 38.277 | 7.203 | 105.991 | 1.00 | 11.40 |
| 3884 | CB | LYS | B | 40 | 39.219 | 8.310 | 106.467 | 1.00 | 11.15 |
| 3887 | CG | LYS | B | 40 | 39.948 | 7.973 | 107.784 | 1.00 | 11.85 |
| 3890 | CD | LYS | B | 40 | 40.917 | 6.857 | 107.629 | 1.00 | 13.27 |
| 3893 | CE | LYS | B | 40 | 41.569 | 6.576 | 108.974 | 1.00 | 15.75 |
| 3896 | NZ | LYS | B | 40 | 42.653 | 5.537 | 108.883 | 1.00 | 19.28 |
| 3900 | C | LYS | B | 40 | 37.328 | 6.810 | 107.118 | 1.00 | 11.94 |
| 3901 | O | LYS | B | 40 | 37.523 | 5.771 | 107.757 | 1.00 | 12.56 |
| 3902 | N | LEU | B | 41 | 36.300 | 7.617 | 107.376 | 1.00 | 12.13 |
| 3904 | CA | LEU | B | 41 | 35.345 | 7.315 | 108.445 | 1.00 | 13.93 |
| 3906 | CB | LEU | B | 41 | 34.377 | 8.467 | 108.634 | 1.00 | 14.19 |
| 3909 | CG | LEU | B | 41 | 34.983 | 9.719 | 109.258 | 1.00 | 14.84 |
| 3911 | CD1 | LEU | B | 41 | 33.985 | 10.840 | 109.184 | 1.00 | 17.12 |
| 3915 | CD2 | LEU | B | 41 | 35.385 | 9.488 | 110.720 | 1.00 | 17.31 |
| 3919 | C | LEU | B | 41 | 34.577 | 6.038 | 108.159 | 1.00 | 15.21 |
| 3920 | O | LEU | B | 41 | 34.275 | 5.253 | 109.088 | 1.00 | 16.21 |
| 3921 | N | ALA | B | 42 | 34.393 | 5.728 | 106.885 | 1.00 | 15.83 |
| 3923 | CA | ALA | B | 42 | 33.529 | 4.628 | 106.516 | 1.00 | 17.19 |
| 3925 | CB | ALA | B | 42 | 32.844 | 4.894 | 105.163 | 1.00 | 17.38 |
| 3929 | C | ALA | B | 42 | 34.347 | 3.349 | 106.466 | 1.00 | 17.70 |
| 3930 | O | ALA | B | 42 | 33.896 | 2.309 | 106.940 | 1.00 | 19.29 |
| 3931 | N | THR | B | 43 | 35.567 | 3.422 | 105.933 | 1.00 | 16.91 |
| 3933 | CA | THR | B | 43 | 36.348 | 2.220 | 105.653 | 1.00 | 16.81 |
| 3935 | CB | THR | B | 43 | 36.749 | 2.177 | 104.162 | 1.00 | 17.11 |
| 3937 | OG1 | THR | B | 43 | 37.729 | 3.202 | 103.880 | 1.00 | 16.89 |
| 3939 | CG2 | THR | B | 43 | 35.572 | 2.466 | 103.279 | 1.00 | 18.75 |
| 3943 | C | THR | B | 43 | 37.615 | 2.052 | 106.433 | 1.00 | 16.88 |
| 3944 | O | THR | B | 43 | 38.232 | 0.967 | 106.399 | 1.00 | 17.65 |
| 3945 | N | GLY | B | 44 | 38.059 | 3.119 | 107.075 | 1.00 | 15.64 |
| 3947 | CA | GLY | B | 44 | 39.303 | 3.112 | 107.806 | 1.00 | 15.52 |
| 3950 | C | GLY | B | 44 | 40.515 | 3.402 | 106.945 | 1.00 | 15.50 |
| 3951 | O | GLY | B | 44 | 41.652 | 3.430 | 107.443 | 1.00 | 17.62 |
| 3952 | N | ALA | B | 45 | 40.301 | 3.684 | 105.664 | 1.00 | 15.17 |
| 3954 | CA | ALA | B | 45 | 41.423 | 3.919 | 104.789 | 1.00 | 14.36 |
| 3956 | CB | ALA | B | 45 | 41.365 | 3.025 | 103.587 | 1.00 | 15.62 |
| 3960 | C | ALA | B | 45 | 41.501 | 5.368 | 104.343 | 1.00 | 13.15 |
| 3961 | O | ALA | B | 45 | 40.498 | 5.953 | 103.964 | 1.00 | 13.53 |
| 3962 | N | LEU | B | 46 | 42.709 | 5.904 | 104.385 | 1.00 | 12.04 |
| 3964 | CA | LEU | B | 46 | 42.968 | 7.265 | 103.947 | 1.00 | 11.39 |
| 3966 | CB | LEU | B | 46 | 43.933 | 7.961 | 104.885 | 1.00 | 10.93 |
| 3969 | CG | LEU | B | 46 | 44.127 | 9.445 | 104.559 | 1.00 | 12.26 |
| 3971 | CD1 | LEU | B | 46 | 42.825 | 10.262 | 104.667 | 1.00 | 12.42 |
| 3975 | CD2 | LEU | B | 46 | 45.194 | 10.024 | 105.486 | 1.00 | 13.92 |
| 3979 | C | LEU | B | 46 | 43.563 | 7.199 | 102.544 | 1.00 | 11.65 |
| 3980 | O | LEU | B | 46 | 44.690 | 6.734 | 102.344 | 1.00 | 12.63 |
| 3981 | N | VAL | B | 47 | 42.794 | 7.665 | 101.568 | 1.00 | 11.14 |
| 3983 | CA | VAL | B | 47 | 43.182 | 7.557 | 100.181 | 1.00 | 11.02 |

FIGURE 3 (Cont.)

| A | B | C | D | E | F | G | H | I | J |
|---|---|---|---|---|---|---|---|---|---|
| 3985 | CB | VAL | B | 47 | 42.297 | 6.511 | 99.450 | 1.00 | 11.66 |
| 3987 | CG1 | VAL | B | 47 | 42.718 | 6.383 | 97.993 | 1.00 | 13.42 |
| 3991 | CG2 | VAL | B | 47 | 42.360 | 5.192 | 100.152 | 1.00 | 14.64 |
| 3995 | C | VAL | B | 47 | 42.942 | 8.867 | 99.477 | 1.00 | 10.49 |
| 3996 | O | VAL | B | 47 | 41.832 | 9.406 | 99.549 | 1.00 | 11.57 |
| 3997 | N | SER | B | 48 | 43.963 | 9.398 | 98.810 | 1.00 | 8.76 |
| 3999 | CA | SER | B | 48 | 43.777 | 10.609 | 98.023 | 1.00 | 8.96 |
| 4001 | CB | SER | B | 48 | 45.091 | 11.208 | 97.561 | 1.00 | 9.94 |
| 4004 | OG | SER | B | 48 | 45.812 | 11.815 | 98.633 | 1.00 | 11.15 |
| 4006 | C | SER | B | 48 | 42.924 | 10.243 | 96.828 | 1.00 | 9.05 |
| 4007 | O | SER | B | 48 | 43.211 | 9.265 | 96.127 | 1.00 | 10.04 |
| 4008 | N | LEU | B | 49 | 41.862 | 11.011 | 96.612 | 1.00 | 8.38 |
| 4010 | CA | LEU | B | 49 | 40.940 | 10.763 | 95.494 | 1.00 | 8.52 |
| 4012 | CB | LEU | B | 49 | 39.500 | 10.938 | 95.941 | 1.00 | 8.60 |
| 4015 | CG | LEU | B | 49 | 39.103 | 9.978 | 97.050 | 1.00 | 7.65 |
| 4017 | CD1 | LEU | B | 49 | 37.729 | 10.289 | 97.575 | 1.00 | 9.76 |
| 4021 | CD2 | LEU | B | 49 | 39.156 | 8.535 | 96.551 | 1.00 | 9.85 |
| 4025 | C | LEU | B | 49 | 41.294 | 11.670 | 94.333 | 1.00 | 8.59 |
| 4026 | O | LEU | B | 49 | 41.989 | 12.669 | 94.477 | 1.00 | 9.68 |
| 4027 | N | SER | B | 50 | 40.858 | 11.287 | 93.151 | 1.00 | 8.31 |
| 4029 | CA | SER | B | 50 | 41.309 | 11.970 | 91.954 | 1.00 | 7.90 |
| 4031 | CB | SER | B | 50 | 41.116 | 11.036 | 90.763 | 1.00 | 8.16 |
| 4034 | OG | SER | B | 50 | 41.601 | 11.623 | 89.572 | 1.00 | 8.36 |
| 4036 | C | SER | B | 50 | 40.623 | 13.286 | 91.629 | 1.00 | 8.57 |
| 4037 | O | SER | B | 50 | 39.533 | 13.303 | 91.074 | 1.00 | 7.68 |
| 4038 | N | ALA | B | 51 | 41.302 | 14.379 | 91.921 | 1.00 | 8.03 |
| 4040 | CA | ALA | B | 51 | 40.818 | 15.679 | 91.509 | 1.00 | 8.81 |
| 4042 | CB | ALA | B | 51 | 41.695 | 16.793 | 92.049 | 1.00 | 8.95 |
| 4046 | C | ALA | B | 51 | 40.810 | 15.730 | 89.979 | 1.00 | 8.49 |
| 4047 | O | ALA | B | 51 | 39.954 | 16.380 | 89.394 | 1.00 | 8.21 |
| 4048 | N | GLN | B | 52 | 41.753 | 15.050 | 89.343 | 1.00 | 8.63 |
| 4050 | CA | GLN | B | 52 | 41.798 | 15.051 | 87.881 | 1.00 | 8.65 |
| 4052 | CB | GLN | B | 52 | 43.040 | 14.349 | 87.368 | 1.00 | 8.99 |
| 4055 | CG | GLN | B | 52 | 43.223 | 14.579 | 85.870 | 1.00 | 9.63 |
| 4058 | CD | GLN | B | 52 | 43.637 | 16.013 | 85.545 | 1.00 | 11.99 |
| 4059 | OE1 | GLN | B | 52 | 44.521 | 16.559 | 86.168 | 1.00 | 12.65 |
| 4060 | NE2 | GLN | B | 52 | 42.975 | 16.621 | 84.563 | 1.00 | 13.24 |
| 4063 | C | GLN | B | 52 | 40.528 | 14.440 | 87.274 | 1.00 | 9.64 |
| 4064 | O | GLN | B | 52 | 39.981 | 14.931 | 86.278 | 1.00 | 9.33 |
| 4065 | N | ASN | B | 53 | 40.041 | 13.362 | 87.860 | 1.00 | 9.11 |
| 4067 | CA | ASN | B | 53 | 38.810 | 12.714 | 87.458 | 1.00 | 9.28 |
| 4069 | CB | ASN | B | 53 | 38.573 | 11.590 | 88.462 | 1.00 | 9.31 |
| 4072 | CG | ASN | B | 53 | 37.448 | 10.649 | 88.137 | 1.00 | 9.37 |
| 4073 | OD1 | ASN | B | 53 | 37.393 | 9.605 | 88.755 | 1.00 | 11.21 |
| 4074 | ND2 | ASN | B | 53 | 36.506 | 11.012 | 87.280 | 1.00 | 10.32 |
| 4077 | C | ASN | B | 53 | 37.664 | 13.729 | 87.460 | 1.00 | 9.51 |
| 4078 | O | ASN | B | 53 | 36.845 | 13.755 | 86.531 | 1.00 | 9.76 |
| 4079 | N | LEU | B | 54 | 37.615 | 14.596 | 88.461 | 1.00 | 8.97 |
| 4081 | CA | LEU | B | 54 | 36.588 | 15.631 | 88.494 | 1.00 | 10.39 |
| 4083 | CB | LEU | B | 54 | 36.584 | 16.350 | 89.818 | 1.00 | 9.70 |
| 4086 | CG | LEU | B | 54 | 35.558 | 15.949 | 90.881 | 1.00 | 16.46 |

FIGURE 3 (Cont.)

| A | B | C | D | E | F | G | H | I | J |
|---|---|---|---|---|---|---|---|---|---|
| 4088 | CD1 | LEU | B | 54 | 34.797 | 14.670 | 90.688 | 1.00 | 12.87 |
| 4092 | CD2 | LEU | B | 54 | 36.061 | 16.166 | 92.304 | 1.00 | 11.64 |
| 4096 | C | LEU | B | 54 | 36.806 | 16.642 | 87.379 | 1.00 | 9.86 |
| 4097 | O | LEU | B | 54 | 35.850 | 16.994 | 86.659 | 1.00 | 10.00 |
| 4098 | N | VAL | B | 55 | 38.031 | 17.123 | 87.235 | 1.00 | 9.33 |
| 4100 | CA | VAL | B | 55 | 38.347 | 18.116 | 86.219 | 1.00 | 9.99 |
| 4102 | CB | VAL | B | 55 | 39.842 | 18.449 | 86.256 | 1.00 | 9.74 |
| 4104 | CG1 | VAL | B | 55 | 40.286 | 19.212 | 85.018 | 1.00 | 11.28 |
| 4108 | CG2 | VAL | B | 55 | 40.143 | 19.252 | 87.456 | 1.00 | 12.01 |
| 4112 | C | VAL | B | 55 | 37.936 | 17.614 | 84.836 | 1.00 | 10.31 |
| 4113 | O | VAL | B | 55 | 37.351 | 18.361 | 84.048 | 1.00 | 11.19 |
| 4114 | N | ASP | B | 56 | 38.246 | 16.360 | 84.549 | 1.00 | 11.19 |
| 4116 | CA | ASP | B | 56 | 38.039 | 15.795 | 83.226 | 1.00 | 11.46 |
| 4118 | CB | ASP | B | 56 | 38.933 | 14.576 | 83.041 | 1.00 | 11.64 |
| 4121 | CG | ASP | B | 56 | 40.405 | 14.890 | 83.055 | 1.00 | 13.05 |
| 4122 | OD1 | ASP | B | 56 | 40.835 | 16.070 | 82.982 | 1.00 | 14.37 |
| 4123 | OD2 | ASP | B | 56 | 41.248 | 13.962 | 83.109 | 1.00 | 14.70 |
| 4124 | C | ASP | B | 56 | 36.641 | 15.305 | 82.957 | 1.00 | 12.09 |
| 4125 | O | ASP | B | 56 | 36.216 | 15.218 | 81.793 | 1.00 | 13.10 |
| 4126 | N | CYS | B | 57 | 35.948 | 14.880 | 84.001 | 1.00 | 12.05 |
| 4128 | CA | CYS | B | 57 | 34.683 | 14.184 | 83.830 | 1.00 | 12.46 |
| 4130 | CB | CYS | B | 57 | 34.747 | 12.788 | 84.452 | 1.00 | 12.56 |
| 4133 | SG | CYS | B | 57 | 36.201 | 11.822 | 83.971 | 1.00 | 15.36 |
| 4134 | C | CYS | B | 57 | 33.459 | 14.897 | 84.348 | 1.00 | 12.46 |
| 4135 | O | CYS | B | 57 | 32.375 | 14.672 | 83.849 | 1.00 | 13.79 |
| 4136 | N | SER | B | 58 | 33.600 | 15.710 | 85.387 | 1.00 | 11.17 |
| 4138 | CA | SER | B | 58 | 32.498 | 16.478 | 85.911 | 1.00 | 11.43 |
| 4140 | CB | SER | B | 58 | 32.632 | 16.649 | 87.416 | 1.00 | 11.27 |
| 4143 | OG | SER | B | 58 | 31.548 | 17.370 | 87.938 | 1.00 | 11.40 |
| 4145 | C | SER | B | 58 | 32.586 | 17.808 | 85.209 | 1.00 | 11.42 |
| 4146 | O | SER | B | 58 | 33.053 | 18.786 | 85.762 | 1.00 | 11.26 |
| 4147 | N | THR | B | 59 | 32.138 | 17.808 | 83.963 | 1.00 | 11.59 |
| 4149 | CA | THR | B | 59 | 32.349 | 18.947 | 83.092 | 1.00 | 12.31 |
| 4151 | CB | THR | B | 59 | 33.063 | 18.484 | 81.838 | 1.00 | 12.81 |
| 4153 | OG1 | THR | B | 59 | 32.391 | 17.341 | 81.284 | 1.00 | 14.54 |
| 4155 | CG2 | THR | B | 59 | 34.500 | 18.021 | 82.177 | 1.00 | 13.07 |
| 4159 | C | THR | B | 59 | 31.061 | 19.698 | 82.764 | 1.00 | 12.11 |
| 4160 | O | THR | B | 59 | 30.321 | 20.052 | 83.650 | 1.00 | 11.59 |
| 4161 | N | GLU | B | 60 | 30.797 | 19.951 | 81.483 | 1.00 | 13.48 |
| 4163 | CA | GLU | B | 60 | 29.624 | 20.748 | 81.078 | 1.00 | 15.01 |
| 4165 | CB | GLU | B | 60 | 29.505 | 20.703 | 79.559 | 1.00 | 15.79 |
| 4168 | CG | GLU | B | 60 | 30.629 | 21.404 | 78.840 | 1.00 | 21.29 |
| 4171 | CD | GLU | B | 60 | 31.731 | 20.461 | 78.374 | 1.00 | 26.19 |
| 4172 | OE1 | GLU | B | 60 | 31.930 | 19.394 | 79.001 | 1.00 | 26.04 |
| 4173 | OE2 | GLU | B | 60 | 32.396 | 20.812 | 77.371 | 1.00 | 31.07 |
| 4174 | C | GLU | B | 60 | 28.254 | 20.394 | 81.660 | 1.00 | 13.56 |
| 4175 | O | GLU | B | 60 | 27.494 | 21.283 | 82.052 | 1.00 | 13.00 |
| 4176 | N | ALA | B | 61 | 28.021 | 19.141 | 81.954 | 1.00 | 13.64 |
| 4178 | CA | ALA | B | 61 | 26.702 | 18.677 | 82.295 | 1.00 | 12.46 |
| 4180 | CB | ALA | B | 61 | 26.481 | 17.195 | 82.026 | 1.00 | 14.54 |
| 4184 | C | ALA | B | 61 | 26.533 | 19.014 | 83.774 | 1.00 | 11.82 |

FIGURE 3 (Cont.)

| A | B | C | D | E | F | G | H | I | J |
|---|---|---|---|---|---|---|---|---|---|
| 4185 | O | ALA | B | 61 | 25.433 | 19.099 | 84.259 | 1.00 | 12.79 |
| 4186 | N | TYR | B | 62 | 27.653 | 19.292 | 84.443 | 1.00 | 10.69 |
| 4188 | CA | TYR | B | 62 | 27.659 | 19.640 | 85.855 | 1.00 | 9.57 |
| 4190 | CB | TYR | B | 62 | 28.670 | 18.742 | 86.595 | 1.00 | 8.42 |
| 4193 | CG | TYR | B | 62 | 28.178 | 17.325 | 86.563 | 1.00 | 9.60 |
| 4194 | CD1 | TYR | B | 62 | 28.565 | 16.441 | 85.581 | 1.00 | 8.86 |
| 4196 | CE1 | TYR | B | 62 | 28.032 | 15.166 | 85.525 | 1.00 | 9.12 |
| 4198 | CZ | TYR | B | 62 | 27.115 | 14.777 | 86.455 | 1.00 | 8.99 |
| 4199 | OH | TYR | B | 62 | 26.549 | 13.529 | 86.458 | 1.00 | 13.09 |
| 4201 | CE2 | TYR | B | 62 | 26.715 | 15.631 | 87.411 | 1.00 | 8.13 |
| 4203 | CD2 | TYR | B | 62 | 27.228 | 16.898 | 87.462 | 1.00 | 9.81 |
| 4205 | C | TYR | B | 62 | 27.956 | 21.109 | 86.075 | 1.00 | 9.66 |
| 4206 | O | TYR | B | 62 | 28.184 | 21.574 | 87.189 | 1.00 | 9.26 |
| 4207 | N | GLY | B | 63 | 27.934 | 21.865 | 84.979 | 1.00 | 9.48 |
| 4209 | CA | GLY | B | 63 | 28.173 | 23.287 | 85.083 | 1.00 | 10.21 |
| 4212 | C | GLY | B | 63 | 29.616 | 23.653 | 85.363 | 1.00 | 10.62 |
| 4213 | O | GLY | B | 63 | 29.908 | 24.813 | 85.655 | 1.00 | 11.37 |
| 4214 | N | ASN | B | 64 | 30.516 | 22.676 | 85.250 | 1.00 | 10.40 |
| 4216 | CA | ASN | B | 64 | 31.931 | 22.890 | 85.523 | 1.00 | 11.35 |
| 4218 | CB | ASN | B | 64 | 32.512 | 21.709 | 86.299 | 1.00 | 10.23 |
| 4221 | CG | ASN | B | 64 | 31.815 | 21.486 | 87.610 | 1.00 | 10.37 |
| 4222 | OD1 | ASN | B | 64 | 31.643 | 20.330 | 88.047 | 1.00 | 12.69 |
| 4223 | ND2 | ASN | B | 64 | 31.355 | 22.552 | 88.218 | 1.00 | 8.16 |
| 4226 | C | ASN | B | 64 | 32.751 | 23.120 | 84.256 | 1.00 | 12.10 |
| 4227 | O | ASN | B | 64 | 32.422 | 22.619 | 83.187 | 1.00 | 13.78 |
| 4228 | N | ALA | B | 65 | 33.859 | 23.829 | 84.423 | 1.00 | 12.86 |
| 4230 | CA | ALA | B | 65 | 34.723 | 24.232 | 83.330 | 1.00 | 13.97 |
| 4232 | CB | ALA | B | 65 | 34.706 | 25.762 | 83.207 | 1.00 | 15.21 |
| 4236 | C | ALA | B | 65 | 36.154 | 23.757 | 83.508 | 1.00 | 14.13 |
| 4237 | O | ALA | B | 65 | 37.073 | 24.366 | 82.982 | 1.00 | 15.28 |
| 4238 | N | GLY | B | 66 | 36.355 | 22.676 | 84.256 | 1.00 | 13.80 |
| 4240 | CA | GLY | B | 66 | 37.675 | 22.113 | 84.411 | 1.00 | 14.33 |
| 4243 | C | GLY | B | 66 | 38.639 | 23.076 | 85.060 | 1.00 | 14.48 |
| 4244 | O | GLY | B | 66 | 38.443 | 23.568 | 86.179 | 1.00 | 14.34 |
| 4245 | N | CYS | B | 67 | 39.715 | 23.369 | 84.349 | 1.00 | 15.50 |
| 4247 | CA | CYS | B | 67 | 40.714 | 24.266 | 84.882 | 1.00 | 16.73 |
| 4249 | CB | CYS | B | 67 | 41.991 | 24.179 | 84.063 | 1.00 | 17.47 |
| 4252 | SG | CYS | B | 67 | 42.870 | 22.637 | 84.376 | 1.00 | 21.35 |
| 4253 | C | CYS | B | 67 | 40.224 | 25.707 | 84.914 | 1.00 | 17.09 |
| 4254 | O | CYS | B | 67 | 40.927 | 26.591 | 85.382 | 1.00 | 17.41 |
| 4255 | N | ASN | B | 68 | 39.022 | 25.932 | 84.415 | 1.00 | 17.06 |
| 4257 | CA | ASN | B | 68 | 38.444 | 27.251 | 84.477 | 1.00 | 18.11 |
| 4259 | CB | ASN | B | 68 | 38.041 | 27.719 | 83.093 | 1.00 | 18.35 |
| 4262 | CG | ASN | B | 68 | 39.231 | 28.143 | 82.298 | 1.00 | 23.44 |
| 4263 | OD1 | ASN | B | 68 | 39.907 | 29.121 | 82.657 | 1.00 | 27.10 |
| 4264 | ND2 | ASN | B | 68 | 39.554 | 27.383 | 81.257 | 1.00 | 26.80 |
| 4267 | C | ASN | B | 68 | 37.306 | 27.361 | 85.469 | 1.00 | 17.92 |
| 4268 | O | ASN | B | 68 | 36.448 | 28.220 | 85.350 | 1.00 | 19.56 |
| 4269 | N | GLY | B | 69 | 37.318 | 26.500 | 86.470 | 1.00 | 15.88 |
| 4271 | CA | GLY | B | 69 | 36.372 | 26.605 | 87.557 | 1.00 | 14.83 |
| 4274 | C | GLY | B | 69 | 35.225 | 25.625 | 87.564 | 1.00 | 13.38 |

FIGURE 3 (Cont.)

| A | B | C | D | E | F | G | H | I | J |
|---|---|---|---|---|---|---|---|---|---|
| 4275 | O | GLY | B | 69 | 34.821 | 25.064 | 86.545 | 1.00 | 13.78 |
| 4276 | N | GLY | B | 70 | 34.679 | 25.435 | 88.750 | 1.00 | 11.45 |
| 4278 | CA | GLY | B | 70 | 33.568 | 24.535 | 88.917 | 1.00 | 10.88 |
| 4281 | C | GLY | B | 70 | 32.988 | 24.660 | 90.302 | 1.00 | 9.57 |
| 4282 | O | GLY | B | 70 | 33.331 | 25.577 | 91.032 | 1.00 | 11.25 |
| 4283 | N | PHE | B | 71 | 32.130 | 23.706 | 90.659 | 1.00 | 8.89 |
| 4285 | CA | PHE | B | 71 | 31.426 | 23.680 | 91.935 | 1.00 | 8.32 |
| 4287 | CB | PHE | B | 71 | 29.913 | 23.772 | 91.698 | 1.00 | 8.55 |
| 4290 | CG | PHE | B | 71 | 29.478 | 24.990 | 90.940 | 1.00 | 10.94 |
| 4291 | CD1 | PHE | B | 71 | 29.187 | 24.916 | 89.605 | 1.00 | 11.01 |
| 4293 | CE1 | PHE | B | 71 | 28.753 | 26.055 | 88.913 | 1.00 | 15.77 |
| 4295 | CZ | PHE | B | 71 | 28.595 | 27.225 | 89.582 | 1.00 | 16.23 |
| 4297 | CE2 | PHE | B | 71 | 28.881 | 27.302 | 90.908 | 1.00 | 16.21 |
| 4299 | CD2 | PHE | B | 71 | 29.309 | 26.173 | 91.590 | 1.00 | 14.41 |
| 4301 | C | PHE | B | 71 | 31.672 | 22.375 | 92.671 | 1.00 | 8.19 |
| 4302 | O | PHE | B | 71 | 31.660 | 21.316 | 92.073 | 1.00 | 8.98 |
| 4303 | N | MET | B | 72 | 31.851 | 22.446 | 93.986 | 1.00 | 7.88 |
| 4305 | CA | MET | B | 72 | 32.012 | 21.256 | 94.792 | 1.00 | 7.85 |
| 4307 | CB | MET | B | 72 | 32.459 | 21.596 | 96.209 | 1.00 | 7.97 |
| 4310 | CG | MET | B | 72 | 33.853 | 22.147 | 96.295 | 1.00 | 9.20 |
| 4313 | SD | MET | B | 72 | 34.004 | 23.905 | 95.949 | 1.00 | 10.32 |
| 4314 | CE | MET | B | 72 | 33.363 | 24.566 | 97.447 | 1.00 | 10.98 |
| 4318 | C | MET | B | 72 | 30.739 | 20.443 | 94.833 | 1.00 | 7.62 |
| 4319 | O | MET | B | 72 | 30.782 | 19.216 | 94.756 | 1.00 | 7.54 |
| 4320 | N | THR | B | 73 | 29.605 | 21.129 | 94.948 | 1.00 | 8.53 |
| 4322 | CA | THR | B | 73 | 28.343 | 20.412 | 95.022 | 1.00 | 8.73 |
| 4324 | CB | THR | B | 73 | 27.185 | 21.343 | 95.266 | 1.00 | 9.57 |
| 4326 | OG1 | THR | B | 73 | 27.275 | 22.421 | 94.342 | 1.00 | 11.50 |
| 4328 | CG2 | THR | B | 73 | 27.253 | 21.976 | 96.650 | 1.00 | 10.28 |
| 4332 | C | THR | B | 73 | 28.085 | 19.597 | 93.758 | 1.00 | 8.32 |
| 4333 | O | THR | B | 73 | 27.636 | 18.450 | 93.862 | 1.00 | 9.16 |
| 4334 | N | THR | B | 74 | 28.329 | 20.190 | 92.577 | 1.00 | 8.20 |
| 4336 | CA | THR | B | 74 | 28.059 | 19.470 | 91.352 | 1.00 | 8.05 |
| 4338 | CB | THR | B | 74 | 27.917 | 20.383 | 90.134 | 1.00 | 8.06 |
| 4340 | OG1 | THR | B | 74 | 29.199 | 20.870 | 89.765 | 1.00 | 8.32 |
| 4342 | CG2 | THR | B | 74 | 27.086 | 21.594 | 90.453 | 1.00 | 8.91 |
| 4346 | C | THR | B | 74 | 29.112 | 18.393 | 91.131 | 1.00 | 8.37 |
| 4347 | O | THR | B | 74 | 28.833 | 17.397 | 90.466 | 1.00 | 9.64 |
| 4348 | N | ALA | B | 75 | 30.321 | 18.591 | 91.665 | 1.00 | 8.05 |
| 4350 | CA | ALA | B | 75 | 31.305 | 17.526 | 91.690 | 1.00 | 8.09 |
| 4352 | CB | ALA | B | 75 | 32.620 | 18.006 | 92.247 | 1.00 | 8.30 |
| 4356 | C | ALA | B | 75 | 30.768 | 16.328 | 92.493 | 1.00 | 8.31 |
| 4357 | O | ALA | B | 75 | 30.873 | 15.192 | 92.027 | 1.00 | 8.21 |
| 4358 | N | PHE | B | 76 | 30.182 | 16.572 | 93.672 | 1.00 | 7.60 |
| 4360 | CA | PHE | B | 76 | 29.592 | 15.506 | 94.501 | 1.00 | 7.71 |
| 4362 | CB | PHE | B | 76 | 29.022 | 16.048 | 95.803 | 1.00 | 7.65 |
| 4365 | CG | PHE | B | 76 | 30.026 | 16.650 | 96.727 | 1.00 | 7.26 |
| 4366 | CD1 | PHE | B | 76 | 31.284 | 16.079 | 96.914 | 1.00 | 8.91 |
| 4368 | CE1 | PHE | B | 76 | 32.178 | 16.659 | 97.774 | 1.00 | 8.41 |
| 4370 | CZ | PHE | B | 76 | 31.823 | 17.768 | 98.493 | 1.00 | 7.23 |
| 4372 | CE2 | PHE | B | 76 | 30.580 | 18.329 | 98.339 | 1.00 | 7.15 |

FIGURE 3 (Cont.)

| A | B | C | D | E | F | G | H | I | J |
|---|---|---|---|---|---|---|---|---|---|
| 4374 | CD2 | PHE | B | 76 | 29.681 | 17.764 | 97.459 | 1.00 | 7.67 |
| 4376 | C | PHE | B | 76 | 28.492 | 14.753 | 93.761 | 1.00 | 8.67 |
| 4377 | O | PHE | B | 76 | 28.404 | 13.523 | 93.859 | 1.00 | 9.55 |
| 4378 | N | GLN | B | 77 | 27.618 | 15.517 | 93.076 | 1.00 | 8.33 |
| 4380 | CA | GLN | B | 77 | 26.566 | 14.931 | 92.235 | 1.00 | 7.96 |
| 4382 | CB | GLN | B | 77 | 25.585 | 15.978 | 91.691 | 1.00 | 8.51 |
| 4385 | CG | GLN | B | 77 | 24.377 | 15.319 | 91.068 | 1.00 | 8.97 |
| 4388 | CD | GLN | B | 77 | 23.543 | 14.582 | 92.087 | 1.00 | 10.92 |
| 4389 | OE1 | GLN | B | 77 | 23.325 | 15.073 | 93.198 | 1.00 | 12.07 |
| 4390 | NE2 | GLN | B | 77 | 23.064 | 13.399 | 91.719 | 1.00 | 11.85 |
| 4393 | C | GLN | B | 77 | 27.131 | 14.080 | 91.094 | 1.00 | 7.30 |
| 4394 | O | GLN | B | 77 | 26.573 | 13.022 | 90.799 | 1.00 | 9.51 |
| 4395 | N | TYR | B | 78 | 28.204 | 14.516 | 90.457 | 1.00 | 8.18 |
| 4397 | CA | TYR | B | 78 | 28.848 | 13.702 | 89.422 | 1.00 | 7.77 |
| 4399 | CB | TYR | B | 78 | 30.048 | 14.398 | 88.781 | 1.00 | 8.35 |
| 4402 | CG | TYR | B | 78 | 30.998 | 13.432 | 88.138 | 1.00 | 8.06 |
| 4403 | CD1 | TYR | B | 78 | 30.792 | 12.958 | 86.849 | 1.00 | 10.38 |
| 4405 | CE1 | TYR | B | 78 | 31.671 | 12.044 | 86.275 | 1.00 | 10.92 |
| 4407 | CZ | TYR | B | 78 | 32.756 | 11.573 | 87.004 | 1.00 | 9.98 |
| 4408 | OH | TYR | B | 78 | 33.639 | 10.675 | 86.424 | 1.00 | 11.11 |
| 4410 | CE2 | TYR | B | 78 | 32.968 | 12.051 | 88.283 | 1.00 | 10.78 |
| 4412 | CD2 | TYR | B | 78 | 32.091 | 12.949 | 88.834 | 1.00 | 9.09 |
| 4414 | C | TYR | B | 78 | 29.277 | 12.368 | 90.020 | 1.00 | 8.25 |
| 4415 | O | TYR | B | 78 | 29.062 | 11.312 | 89.426 | 1.00 | 8.42 |
| 4416 | N | ILE | B | 79 | 29.909 | 12.405 | 91.192 | 1.00 | 8.19 |
| 4418 | CA | ILE | B | 79 | 30.357 | 11.148 | 91.803 | 1.00 | 8.50 |
| 4420 | CB | ILE | B | 79 | 31.114 | 11.408 | 93.136 | 1.00 | 8.00 |
| 4422 | CG1 | ILE | B | 79 | 32.314 | 12.325 | 92.895 | 1.00 | 9.06 |
| 4425 | CD1 | ILE | B | 79 | 33.058 | 12.711 | 94.130 | 1.00 | 8.90 |
| 4429 | CG2 | ILE | B | 79 | 31.602 | 10.109 | 93.745 | 1.00 | 9.03 |
| 4433 | C | ILE | B | 79 | 29.155 | 10.252 | 92.055 | 1.00 | 8.48 |
| 4434 | O | ILE | B | 79 | 29.207 | 9.031 | 91.839 | 1.00 | 9.49 |
| 4435 | N | ILE | B | 80 | 28.074 | 10.830 | 92.552 | 1.00 | 8.13 |
| 4437 | CA | ILE | B | 80 | 26.841 | 10.066 | 92.808 | 1.00 | 9.58 |
| 4439 | CB | ILE | B | 80 | 25.765 | 10.937 | 93.483 | 1.00 | 10.42 |
| 4441 | CG1 | ILE | B | 80 | 26.244 | 11.493 | 94.820 | 1.00 | 10.50 |
| 4444 | CD1 | ILE | B | 80 | 25.401 | 12.643 | 95.340 | 1.00 | 11.47 |
| 4448 | CG2 | ILE | B | 80 | 24.461 | 10.156 | 93.722 | 1.00 | 10.69 |
| 4452 | C | ILE | B | 80 | 26.310 | 9.477 | 91.491 | 1.00 | 10.18 |
| 4453 | O | ILE | B | 80 | 26.091 | 8.267 | 91.383 | 1.00 | 11.75 |
| 4454 | N | ASP | B | 81 | 26.154 | 10.322 | 90.478 | 1.00 | 9.99 |
| 4456 | CA | ASP | B | 81 | 25.629 | 9.879 | 89.177 | 1.00 | 10.47 |
| 4458 | CB | ASP | B | 81 | 25.536 | 11.066 | 88.225 | 1.00 | 10.84 |
| 4461 | CG | ASP | B | 81 | 24.485 | 12.051 | 88.629 | 1.00 | 11.63 |
| 4462 | OD1 | ASP | B | 81 | 24.498 | 13.178 | 88.045 | 1.00 | 14.19 |
| 4463 | OD2 | ASP | B | 81 | 23.626 | 11.789 | 89.489 | 1.00 | 13.10 |
| 4464 | C | ASP | B | 81 | 26.519 | 8.846 | 88.521 | 1.00 | 11.15 |
| 4465 | O | ASP | B | 81 | 26.030 | 7.908 | 87.882 | 1.00 | 12.20 |
| 4466 | N | ASN | B | 82 | 27.825 | 9.026 | 88.666 | 1.00 | 10.79 |
| 4468 | CA | ASN | B | 82 | 28.826 | 8.200 | 88.021 | 1.00 | 10.42 |
| 4470 | CB | ASN | B | 82 | 30.141 | 8.964 | 87.980 | 1.00 | 10.26 |

FIGURE 3 (Cont.)

| A | B | C | D | E | F | G | H | I | J |
|---|---|---|---|---|---|---|---|---|---|
| 4473 | CG | ASN | B | 82 | 31.163 | 8.316 | 87.073 | 1.00 | 11.69 |
| 4474 | OD1 | ASN | B | 82 | 30.895 | 8.082 | 85.874 | 1.00 | 12.68 |
| 4475 | ND2 | ASN | B | 82 | 32.342 | 8.032 | 87.610 | 1.00 | 12.51 |
| 4478 | C | ASN | B | 82 | 29.063 | 6.887 | 88.748 | 1.00 | 10.42 |
| 4479 | O | ASN | B | 82 | 29.714 | 5.992 | 88.196 | 1.00 | 11.10 |
| 4480 | N | LYS | B | 83 | 28.531 | 6.794 | 89.960 | 1.00 | 10.79 |
| 4482 | CA | LYS | B | 83 | 28.691 | 5.655 | 90.855 | 1.00 | 12.12 |
| 4484 | CB | LYS | B | 83 | 28.063 | 4.387 | 90.274 | 1.00 | 13.64 |
| 4487 | CG | LYS | B | 83 | 26.592 | 4.558 | 89.929 | 1.00 | 16.00 |
| 4490 | CD | LYS | B | 83 | 25.923 | 3.218 | 89.692 | 1.00 | 21.87 |
| 4493 | CE | LYS | B | 83 | 24.466 | 3.356 | 89.234 | 1.00 | 24.58 |
| 4496 | NZ | LYS | B | 83 | 23.671 | 4.285 | 90.077 | 1.00 | 28.17 |
| 4500 | C | LYS | B | 83 | 30.147 | 5.427 | 91.228 | 1.00 | 11.97 |
| 4501 | O | LYS | B | 83 | 30.576 | 4.278 | 91.453 | 1.00 | 12.61 |
| 4502 | N | GLY | B | 84 | 30.926 | 6.505 | 91.297 | 1.00 | 10.76 |
| 4504 | CA | GLY | B | 84 | 32.289 | 6.392 | 91.755 | 1.00 | 10.12 |
| 4507 | C | GLY | B | 84 | 33.218 | 7.493 | 91.340 | 1.00 | 9.65 |
| 4508 | O | GLY | B | 84 | 32.926 | 8.297 | 90.461 | 1.00 | 10.02 |
| 4509 | N | ILE | B | 85 | 34.380 | 7.492 | 91.981 | 1.00 | 8.48 |
| 4511 | CA | ILE | B | 85 | 35.482 | 8.338 | 91.631 | 1.00 | 8.25 |
| 4513 | CB | ILE | B | 85 | 35.530 | 9.639 | 92.497 | 1.00 | 6.86 |
| 4515 | CG1 | ILE | B | 85 | 36.682 | 10.516 | 92.049 | 1.00 | 8.42 |
| 4518 | CD1 | ILE | B | 85 | 36.640 | 11.925 | 92.665 | 1.00 | 9.75 |
| 4522 | CG2 | ILE | B | 85 | 35.623 | 9.294 | 93.977 | 1.00 | 8.15 |
| 4526 | C | ILE | B | 85 | 36.761 | 7.499 | 91.822 | 1.00 | 8.41 |
| 4527 | O | ILE | B | 85 | 36.922 | 6.806 | 92.828 | 1.00 | 9.82 |
| 4528 | N | ASP | B | 86 | 37.696 | 7.690 | 90.914 | 1.00 | 8.81 |
| 4530 | CA | ASP | B | 86 | 38.962 | 6.965 | 90.935 | 1.00 | 8.24 |
| 4532 | CB | ASP | B | 86 | 39.609 | 6.993 | 89.560 | 1.00 | 8.96 |
| 4535 | CG | ASP | B | 86 | 38.873 | 6.150 | 88.560 | 1.00 | 8.27 |
| 4536 | OD1 | ASP | B | 86 | 38.150 | 5.188 | 88.950 | 1.00 | 9.46 |
| 4537 | OD2 | ASP | B | 86 | 39.004 | 6.415 | 87.352 | 1.00 | 9.81 |
| 4538 | C | ASP | B | 86 | 39.918 | 7.526 | 91.979 | 1.00 | 9.50 |
| 4539 | O | ASP | B | 86 | 39.775 | 8.658 | 92.430 | 1.00 | 8.14 |
| 4540 | N | SER | B | 87 | 40.856 | 6.699 | 92.430 | 1.00 | 9.34 |
| 4542 | CA | SER | B | 87 | 41.847 | 7.181 | 93.386 | 1.00 | 10.67 |
| 4544 | CB | SER | B | 87 | 42.615 | 6.043 | 94.040 | 1.00 | 11.08 |
| 4547 | OG | SER | B | 87 | 43.430 | 5.536 | 93.057 | 1.00 | 13.75 |
| 4549 | C | SER | B | 87 | 42.812 | 8.114 | 92.635 | 1.00 | 10.27 |
| 4550 | O | SER | B | 87 | 42.974 | 8.046 | 91.370 | 1.00 | 8.88 |
| 4551 | N | ASP | B | 88 | 43.439 | 9.013 | 93.392 | 1.00 | 10.36 |
| 4553 | CA | ASP | B | 88 | 44.504 | 9.875 | 92.869 | 1.00 | 11.49 |
| 4555 | CB | ASP | B | 88 | 45.006 | 10.769 | 94.026 | 1.00 | 11.83 |
| 4558 | CG | ASP | B | 88 | 46.186 | 11.638 | 93.649 | 1.00 | 16.32 |
| 4559 | OD1 | ASP | B | 88 | 45.974 | 12.611 | 92.887 | 1.00 | 20.70 |
| 4560 | OD2 | ASP | B | 88 | 47.327 | 11.483 | 94.116 | 1.00 | 22.95 |
| 4561 | C | ASP | B | 88 | 45.626 | 9.043 | 92.194 | 1.00 | 10.94 |
| 4562 | O | ASP | B | 88 | 46.111 | 9.347 | 91.109 | 1.00 | 11.59 |
| 4563 | N | ALA | B | 89 | 46.027 | 7.965 | 92.842 | 1.00 | 10.32 |
| 4565 | CA | ALA | B | 89 | 47.107 | 7.117 | 92.306 | 1.00 | 10.44 |
| 4567 | CB | ALA | B | 89 | 47.426 | 6.043 | 93.323 | 1.00 | 11.26 |

FIGURE 3 (Cont.)

| A | B | C | D | E | F | G | H | I | J |
|---|---|---|---|---|---|---|---|---|---|
| 4571 | C | ALA | B | 89 | 46.828 | 6.499 | 90.924 | 1.00 | 11.67 |
| 4573 | N | SER | B | 90 | 45.558 | 6.206 | 90.673 | 1.00 | 10.71 |
| 4575 | CA | SER | B | 90 | 45.171 | 5.613 | 89.390 | 1.00 | 11.12 |
| 4577 | CB | SER | B | 90 | 43.904 | 4.782 | 89.559 | 1.00 | 11.37 |
| 4580 | OG | SER | B | 90 | 42.754 | 5.600 | 89.697 | 1.00 | 13.11 |
| 4582 | C | SER | B | 90 | 44.886 | 6.659 | 88.333 | 1.00 | 11.23 |
| 4583 | O | SER | B | 90 | 44.956 | 6.390 | 87.137 | 1.00 | 12.38 |
| 4584 | N | TYR | B | 91 | 44.551 | 7.868 | 88.773 | 1.00 | 11.41 |
| 4586 | CA | TYR | B | 91 | 44.112 | 8.915 | 87.850 | 1.00 | 10.61 |
| 4588 | CB | TYR | B | 91 | 42.584 | 8.980 | 87.870 | 1.00 | 9.85 |
| 4591 | CG | TYR | B | 91 | 41.910 | 9.681 | 86.733 | 1.00 | 10.08 |
| 4592 | CD1 | TYR | B | 91 | 42.566 | 10.649 | 86.019 | 1.00 | 10.98 |
| 4594 | CE1 | TYR | B | 91 | 41.955 | 11.283 | 84.986 | 1.00 | 10.52 |
| 4596 | CZ | TYR | B | 91 | 40.658 | 10.927 | 84.702 | 1.00 | 11.69 |
| 4597 | OH | TYR | B | 91 | 40.058 | 11.605 | 83.638 | 1.00 | 13.78 |
| 4600 | CD2 | TYR | B | 91 | 40.605 | 9.376 | 86.424 | 1.00 | 10.93 |
| 4601 | C | TYR | B | 91 | 44.757 | 10.212 | 88.360 | 1.00 | 10.48 |
| 4602 | O | TYR | B | 91 | 44.107 | 11.049 | 88.957 | 1.00 | 10.15 |
| 4603 | N | PRO | B | 92 | 46.062 | 10.346 | 88.168 | 1.00 | 11.68 |
| 4604 | CA | PRO | B | 92 | 46.838 | 11.446 | 88.741 | 1.00 | 11.88 |
| 4606 | CB | PRO | B | 92 | 48.290 | 11.045 | 88.465 | 1.00 | 12.35 |
| 4609 | CG | PRO | B | 92 | 48.255 | 9.910 | 87.567 | 1.00 | 14.21 |
| 4612 | CD | PRO | B | 92 | 46.888 | 9.436 | 87.364 | 1.00 | 12.70 |
| 4615 | C | PRO | B | 92 | 46.551 | 12.807 | 88.148 | 1.00 | 11.76 |
| 4616 | O | PRO | B | 92 | 46.024 | 12.965 | 87.041 | 1.00 | 10.77 |
| 4617 | N | TYR | B | 93 | 46.898 | 13.810 | 88.931 | 1.00 | 11.47 |
| 4619 | CA | TYR | B | 93 | 46.624 | 15.197 | 88.617 | 1.00 | 11.76 |
| 4621 | CB | TYR | B | 93 | 46.532 | 15.984 | 89.910 | 1.00 | 11.22 |
| 4624 | CG | TYR | B | 93 | 46.198 | 17.436 | 89.691 | 1.00 | 10.65 |
| 4625 | CD1 | TYR | B | 93 | 44.922 | 17.817 | 89.308 | 1.00 | 11.18 |
| 4627 | CE1 | TYR | B | 93 | 44.609 | 19.127 | 89.115 | 1.00 | 11.70 |
| 4629 | CZ | TYR | B | 93 | 45.571 | 20.087 | 89.307 | 1.00 | 9.89 |
| 4630 | OH | TYR | B | 93 | 45.234 | 21.409 | 89.126 | 1.00 | 11.27 |
| 4632 | CE2 | TYR | B | 93 | 46.849 | 19.733 | 89.676 | 1.00 | 10.31 |
| 4634 | CD2 | TYR | B | 93 | 47.147 | 18.409 | 89.863 | 1.00 | 10.28 |
| 4636 | C | TYR | B | 93 | 47.691 | 15.796 | 87.725 | 1.00 | 12.10 |
| 4637 | O | TYR | B | 93 | 48.898 | 15.725 | 88.023 | 1.00 | 13.64 |
| 4638 | N | LYS | B | 94 | 47.228 | 16.397 | 86.637 | 1.00 | 13.23 |
| 4640 | CA | LYS | B | 94 | 48.100 | 16.918 | 85.603 | 1.00 | 14.76 |
| 4642 | CB | LYS | B | 94 | 47.817 | 16.206 | 84.273 | 1.00 | 16.16 |
| 4645 | CG | LYS | B | 94 | 47.968 | 14.679 | 84.325 | 1.00 | 19.21 |
| 4648 | CD | LYS | B | 94 | 49.374 | 14.247 | 84.575 | 1.00 | 23.76 |
| 4651 | CE | LYS | B | 94 | 49.509 | 12.722 | 84.524 | 1.00 | 26.95 |
| 4654 | NZ | LYS | B | 94 | 50.893 | 12.279 | 84.844 | 1.00 | 29.84 |
| 4658 | C | LYS | B | 94 | 47.964 | 18.427 | 85.420 | 1.00 | 15.08 |
| 4659 | O | LYS | B | 94 | 48.675 | 19.016 | 84.627 | 1.00 | 15.38 |
| 4660 | N | ALA | B | 95 | 47.037 | 19.047 | 86.131 | 1.00 | 15.07 |
| 4662 | CA | ALA | B | 95 | 46.877 | 20.507 | 86.071 | 1.00 | 15.34 |
| 4664 | CB | ALA | B | 95 | 48.113 | 21.224 | 86.609 | 1.00 | 15.03 |
| 4668 | C | ALA | B | 95 | 46.552 | 20.988 | 84.664 | 1.00 | 15.73 |
| 4669 | O | ALA | B | 95 | 47.050 | 22.018 | 84.205 | 1.00 | 16.56 |

FIGURE 3 (Cont.)

| A | B | C | D | E | F | G | H | I | J |
|---|---|---|---|---|---|---|---|---|---|
| 4670 | N | MET | B | 96 | 45.670 | 20.257 | 84.015 | 1.00 | 16.35 |
| 4672 | CA | MET | B | 96 | 45.178 | 20.611 | 82.693 | 1.00 | 17.55 |
| 4674 | CB | MET | B | 96 | 46.227 | 20.346 | 81.617 | 1.00 | 18.91 |
| 4677 | CG | MET | B | 96 | 46.512 | 18.893 | 81.356 | 1.00 | 21.90 |
| 4680 | SD | MET | B | 96 | 47.975 | 18.650 | 80.240 | 1.00 | 30.57 |
| 4681 | CE | MET | B | 96 | 48.879 | 20.074 | 80.606 | 1.00 | 27.93 |
| 4685 | C | MET | B | 96 | 43.909 | 19.843 | 82.404 | 1.00 | 17.30 |
| 4686 | O | MET | B | 96 | 43.635 | 18.831 | 83.041 | 1.00 | 17.10 |
| 4687 | N | ASP | B | 97 | 43.109 | 20.344 | 81.469 | 1.00 | 17.36 |
| 4689 | CA | ASP | B | 97 | 41.900 | 19.663 | 81.049 | 1.00 | 17.45 |
| 4691 | CB | ASP | B | 97 | 40.989 | 20.589 | 80.234 | 1.00 | 17.93 |
| 4694 | CG | ASP | B | 97 | 40.430 | 21.737 | 81.041 | 1.00 | 20.60 |
| 4695 | OD1 | ASP | B | 97 | 40.298 | 22.834 | 80.458 | 1.00 | 27.70 |
| 4696 | OD2 | ASP | B | 97 | 40.082 | 21.651 | 82.232 | 1.00 | 22.07 |
| 4697 | C | ASP | B | 97 | 42.291 | 18.490 | 80.177 | 1.00 | 17.57 |
| 4698 | O | ASP | B | 97 | 43.129 | 18.646 | 79.291 | 1.00 | 17.89 |
| 4699 | N | GLN | B | 98 | 41.674 | 17.341 | 80.424 | 1.00 | 17.20 |
| 4701 | CA | GLN | B | 98 | 41.887 | 16.113 | 79.638 | 1.00 | 17.41 |
| 4703 | CB | GLN | B | 98 | 42.715 | 15.094 | 80.430 | 1.00 | 17.50 |
| 4706 | CG | GLN | B | 98 | 43.968 | 15.638 | 81.018 | 1.00 | 18.00 |
| 4709 | CD | GLN | B | 98 | 44.726 | 14.586 | 81.818 | 1.00 | 19.25 |
| 4710 | OE1 | GLN | B | 98 | 44.113 | 13.767 | 82.536 | 1.00 | 21.54 |
| 4711 | NE2 | GLN | B | 98 | 46.047 | 14.603 | 81.713 | 1.00 | 19.05 |
| 4714 | C | GLN | B | 98 | 40.560 | 15.482 | 79.297 | 1.00 | 17.51 |
| 4715 | O | GLN | B | 98 | 39.518 | 15.832 | 79.861 | 1.00 | 17.06 |
| 4716 | N | ALA | B | 99 | 40.624 | 14.407 | 78.518 | 1.00 | 18.52 |
| 4718 | CA | ALA | B | 99 | 39.435 | 13.705 | 78.079 | 1.00 | 18.69 |
| 4720 | CB | ALA | B | 99 | 39.733 | 12.731 | 76.936 | 1.00 | 19.79 |
| 4724 | C | ALA | B | 99 | 39.056 | 12.920 | 79.307 | 1.00 | 17.88 |
| 4725 | O | ALA | B | 99 | 39.937 | 12.539 | 80.083 | 1.00 | 18.71 |
| 4726 | N | CYS | B | 100 | 37.768 | 12.689 | 79.478 | 1.00 | 18.05 |
| 4728 | CA | CYS | B | 100 | 37.291 | 11.862 | 80.555 | 1.00 | 18.44 |
| 4730 | CB | CYS | B | 100 | 35.794 | 11.704 | 80.451 | 1.00 | 18.49 |
| 4733 | SG | CYS | B | 100 | 35.170 | 10.501 | 81.619 | 1.00 | 25.88 |
| 4734 | C | CYS | B | 100 | 37.930 | 10.494 | 80.440 | 1.00 | 16.92 |
| 4735 | O | CYS | B | 100 | 37.794 | 9.843 | 79.411 | 1.00 | 16.03 |
| 4736 | N | GLN | B | 101 | 38.636 | 10.063 | 81.487 | 1.00 | 15.03 |
| 4738 | CA | GLN | B | 101 | 39.259 | 8.736 | 81.508 | 1.00 | 14.98 |
| 4740 | CB | GLN | B | 101 | 40.766 | 8.863 | 81.435 | 1.00 | 15.56 |
| 4743 | CG | GLN | B | 101 | 41.250 | 9.511 | 80.158 | 1.00 | 19.02 |
| 4746 | CD | GLN | B | 101 | 42.597 | 10.174 | 80.326 | 1.00 | 22.86 |
| 4747 | OE1 | GLN | B | 101 | 42.683 | 11.375 | 80.634 | 1.00 | 27.00 |
| 4748 | NE2 | GLN | B | 101 | 43.656 | 9.406 | 80.109 | 1.00 | 25.05 |
| 4751 | C | GLN | B | 101 | 38.851 | 7.921 | 82.731 | 1.00 | 13.31 |
| 4752 | O | GLN | B | 101 | 39.564 | 6.993 | 83.145 | 1.00 | 13.56 |
| 4753 | N | TYR | B | 102 | 37.707 | 8.243 | 83.308 | 1.00 | 12.42 |
| 4755 | CA | TYR | B | 102 | 37.213 | 7.495 | 84.437 | 1.00 | 11.79 |
| 4757 | CB | TYR | B | 102 | 35.847 | 7.976 | 84.888 | 1.00 | 11.62 |
| 4760 | CG | TYR | B | 102 | 35.269 | 7.084 | 85.945 | 1.00 | 10.52 |
| 4761 | CD1 | TYR | B | 102 | 35.694 | 7.177 | 87.263 | 1.00 | 8.99 |
| 4763 | CE1 | TYR | B | 102 | 35.189 | 6.364 | 88.212 | 1.00 | 10.14 |

FIGURE 3 (Cont.)

| A | B | C | D | E | F | G | H | I | J |
|---|---|---|---|---|---|---|---|---|---|
| 4765 | CZ | TYR | B | 102 | 34.237 | 5.430 | 87.894 | 1.00 | 10.37 |
| 4766 | OH | TYR | B | 102 | 33.735 | 4.602 | 88.865 | 1.00 | 11.45 |
| 4768 | CE2 | TYR | B | 102 | 33.803 | 5.304 | 86.568 | 1.00 | 10.21 |
| 4770 | CD2 | TYR | B | 102 | 34.338 | 6.116 | 85.623 | 1.00 | 10.30 |
| 4772 | C | TYR | B | 102 | 37.120 | 6.025 | 84.058 | 1.00 | 12.30 |
| 4773 | O | TYR | B | 102 | 36.644 | 5.675 | 82.971 | 1.00 | 13.41 |
| 4774 | N | ASP | B | 102 | 37.466 | 5.159 | 84.996 | 1.00 | 12.26 |
| 4776 | CA | ASP | B | 103 | 37.343 | 3.726 | 84.799 | 1.00 | 13.19 |
| 4778 | CB | ASP | B | 103 | 38.620 | 3.086 | 84.313 | 1.00 | 13.30 |
| 4781 | CG | ASP | B | 103 | 38.376 | 1.702 | 83.732 | 1.00 | 15.06 |
| 4782 | OD1 | ASP | B | 103 | 37.634 | 0.916 | 84.344 | 1.00 | 14.48 |
| 4783 | OD2 | ASP | B | 103 | 38.862 | 1.357 | 82.636 | 1.00 | 20.41 |
| 4784 | C | ASP | B | 103 | 36.930 | 3.166 | 86.119 | 1.00 | 12.83 |
| 4785 | O | ASP | B | 103 | 37.604 | 3.394 | 87.128 | 1.00 | 12.67 |
| 4786 | N | SER | B | 104 | 35.813 | 2.462 | 86.148 | 1.00 | 12.16 |
| 4788 | CA | SER | B | 104 | 35.313 | 1.899 | 87.394 | 1.00 | 11.91 |
| 4790 | CB | SER | B | 104 | 33.975 | 1.198 | 87.239 | 1.00 | 12.80 |
| 4793 | OG | SER | B | 104 | 34.087 | 0.078 | 86.362 | 1.00 | 15.16 |
| 4795 | C | SER | B | 104 | 36.309 | 0.918 | 88.003 | 1.00 | 10.68 |
| 4796 | O | SER | B | 104 | 36.242 | 0.642 | 89.178 | 1.00 | 11.66 |
| 4797 | N | LYS | B | 105 | 37.200 | 0.352 | 87.199 | 1.00 | 10.52 |
| 4799 | CA | LYS | B | 105 | 38.152 | -0.601 | 87.777 | 1.00 | 9.41 |
| 4801 | CB | LYS | B | 105 | 38.918 | -1.402 | 86.724 | 1.00 | 9.47 |
| 4804 | CG | LYS | B | 105 | 39.975 | -0.658 | 86.000 | 1.00 | 8.88 |
| 4807 | CD | LYS | B | 105 | 40.513 | -1.392 | 84.758 | 1.00 | 9.76 |
| 4810 | CE | LYS | B | 105 | 41.556 | -0.617 | 84.028 | 1.00 | 12.01 |
| 4813 | NZ | LYS | B | 105 | 41.898 | -1.250 | 82.689 | 1.00 | 14.12 |
| 4817 | C | LYS | B | 105 | 39.119 | 0.082 | 88.736 | 1.00 | 9.62 |
| 4818 | O | LYS | B | 105 | 39.802 | -0.579 | 89.507 | 1.00 | 10.38 |
| 4819 | N | TYR | B | 106 | 39.158 | 1.411 | 88.702 | 1.00 | 9.13 |
| 4821 | CA | TYR | B | 106 | 40.022 | 2.175 | 89.606 | 1.00 | 9.12 |
| 4823 | CB | TYR | B | 106 | 40.890 | 3.149 | 88.822 | 1.00 | 9.76 |
| 4826 | CG | TYR | B | 106 | 41.857 | 2.510 | 87.844 | 1.00 | 11.14 |
| 4827 | CD1 | TYR | B | 106 | 42.042 | 3.044 | 86.599 | 1.00 | 13.82 |
| 4829 | CE1 | TYR | B | 106 | 42.950 | 2.497 | 85.715 | 1.00 | 14.78 |
| 4831 | CZ | TYR | B | 106 | 43.669 | 1.378 | 86.083 | 1.00 | 14.11 |
| 4832 | OH | TYR | B | 106 | 44.569 | 0.849 | 85.181 | 1.00 | 15.45 |
| 4834 | CE2 | TYR | B | 106 | 43.514 | 0.840 | 87.331 | 1.00 | 11.85 |
| 4836 | CD2 | TYR | B | 106 | 42.620 | 1.416 | 88.206 | 1.00 | 11.84 |
| 4838 | C | TYR | B | 106 | 39.219 | 2.930 | 90.672 | 1.00 | 8.87 |
| 4839 | O | TYR | B | 106 | 39.768 | 3.794 | 91.367 | 1.00 | 9.98 |
| 4840 | N | ARG | B | 107 | 37.974 | 2.568 | 90.816 | 1.00 | 9.03 |
| 4842 | CA | ARG | B | 107 | 37.108 | 3.209 | 91.798 | 1.00 | 9.75 |
| 4844 | CB | ARG | B | 107 | 35.693 | 2.701 | 91.701 | 1.00 | 9.91 |
| 4847 | CG | ARG | B | 107 | 34.747 | 3.363 | 92.657 | 1.00 | 12.62 |
| 4850 | CD | ARG | B | 107 | 33.522 | 2.547 | 92.909 | 1.00 | 19.23 |
| 4853 | NE | ARG | B | 107 | 32.776 | 2.354 | 91.678 | 1.00 | 24.16 |
| 4855 | CZ | ARG | B | 107 | 32.387 | 1.179 | 91.184 | 1.00 | 27.02 |
| 4856 | NH1 | ARG | B | 107 | 32.672 | 0.042 | 91.812 | 1.00 | 29.58 |
| 4859 | NH2 | ARG | B | 107 | 31.701 | 1.147 | 90.044 | 1.00 | 26.59 |
| 4862 | C | ARG | B | 107 | 37.612 | 3.038 | 93.232 | 1.00 | 10.74 |

FIGURE 3 (Cont.)

| A | B | C | D | E | F | G | H | I | J |
|---|---|---|---|---|---|---|---|---|---|
| 4863 | O | ARG | B | 107 | 37.843 | 1.928 | 93.727 | 1.00 | 11.98 |
| 4864 | N | ALA | B | 108 | 37.640 | 4.189 | 93.913 | 1.00 | 10.07 |
| 4866 | CA | ALA | B | 108 | 38.161 | 4.235 | 95.262 | 1.00 | 9.59 |
| 4868 | CB | ALA | B | 108 | 39.413 | 5.099 | 95.354 | 1.00 | 10.32 |
| 4872 | C | ALA | B | 108 | 37.144 | 4.749 | 96.223 | 1.00 | 10.28 |
| 4873 | O | ALA | B | 108 | 37.313 | 4.577 | 97.422 | 1.00 | 11.26 |
| 4874 | N | ALA | B | 109 | 36.100 | 5.412 | 95.729 | 1.00 | 9.38 |
| 4876 | CA | ALA | B | 109 | 35.076 | 5.936 | 96.605 | 1.00 | 9.81 |
| 4878 | CB | ALA | B | 109 | 35.465 | 7.306 | 97.176 | 1.00 | 9.71 |
| 4882 | C | ALA | B | 109 | 33.789 | 6.086 | 95.842 | 1.00 | 9.71 |
| 4883 | O | ALA | B | 109 | 33.783 | 6.144 | 94.627 | 1.00 | 10.32 |
| 4884 | N | THR | B | 110 | 32.712 | 6.159 | 96.584 | 1.00 | 10.66 |
| 4886 | CA | THR | B | 110 | 31.389 | 6.453 | 96.067 | 1.00 | 10.67 |
| 4888 | CB | THR | B | 110 | 30.460 | 5.222 | 96.148 | 1.00 | 10.94 |
| 4890 | OG1 | THR | B | 110 | 30.335 | 4.782 | 97.511 | 1.00 | 12.67 |
| 4892 | CG2 | THR | B | 110 | 31.034 | 4.065 | 95.373 | 1.00 | 13.43 |
| 4896 | C | THR | B | 110 | 30.824 | 7.563 | 96.935 | 1.00 | 11.09 |
| 4897 | O | THR | B | 110 | 31.383 | 7.921 | 97.967 | 1.00 | 11.60 |
| 4898 | N | CYS | B | 111 | 29.692 | 8.100 | 96.517 | 1.00 | 10.92 |
| 4900 | CA | CYS | B | 111 | 29.008 | 9.135 | 97.252 | 1.00 | 11.36 |
| 4902 | CB | CYS | B | 111 | 29.373 | 10.502 | 96.669 | 1.00 | 11.52 |
| 4905 | SG | CYS | B | 111 | 28.553 | 11.887 | 97.471 | 1.00 | 13.44 |
| 4906 | C | CYS | B | 111 | 27.526 | 8.854 | 97.097 | 1.00 | 11.23 |
| 4907 | O | CYS | B | 111 | 27.074 | 8.525 | 95.999 | 1.00 | 12.59 |
| 4908 | N | SER | B | 112 | 26.786 | 8.984 | 98.176 | 1.00 | 11.62 |
| 4910 | CA | SER | B | 112 | 25.355 | 8.738 | 98.146 | 1.00 | 12.40 |
| 4912 | CB | SER | B | 112 | 24.909 | 7.880 | 99.329 | 1.00 | 13.35 |
| 4915 | OG | SER | B | 112 | 25.244 | 8.454 | 100.556 | 1.00 | 16.39 |
| 4917 | C | SER | B | 112 | 24.533 | 10.000 | 98.102 | 1.00 | 12.99 |
| 4918 | O | SER | B | 112 | 23.396 | 9.979 | 97.620 | 1.00 | 13.14 |
| 4919 | N | LYS | B | 113 | 25.073 | 11.089 | 98.632 | 1.00 | 12.21 |
| 4921 | CA | LYS | B | 113 | 24.354 | 12.339 | 98.727 | 1.00 | 11.85 |
| 4923 | CB | LYS | B | 113 | 23.177 | 12.234 | 99.679 | 1.00 | 14.07 |
| 4926 | CG | LYS | B | 113 | 23.524 | 11.993 | 101.102 | 1.00 | 16.04 |
| 4929 | CD | LYS | B | 113 | 22.268 | 11.758 | 101.936 | 1.00 | 22.21 |
| 4932 | CE | LYS | B | 113 | 22.298 | 12.578 | 103.200 | 1.00 | 25.39 |
| 4935 | NZ | LYS | B | 113 | 21.136 | 12.292 | 104.118 | 1.00 | 28.97 |
| 4939 | C | LYS | B | 113 | 25.318 | 13.400 | 99.200 | 1.00 | 10.85 |
| 4940 | O | LYS | B | 113 | 26.452 | 13.103 | 99.578 | 1.00 | 9.67 |
| 4941 | N | TYR | B | 114 | 24.881 | 14.644 | 99.141 | 1.00 | 9.74 |
| 4943 | CA | TYR | B | 114 | 25.632 | 15.729 | 99.717 | 1.00 | 9.20 |
| 4945 | CB | TYR | B | 114 | 26.498 | 16.460 | 98.688 | 1.00 | 9.03 |
| 4948 | CG | TYR | B | 114 | 25.722 | 17.150 | 97.586 | 1.00 | 9.02 |
| 4949 | CD1 | TYR | B | 114 | 25.374 | 18.469 | 97.703 | 1.00 | 9.78 |
| 4951 | CE1 | TYR | B | 114 | 24.658 | 19.115 | 96.724 | 1.00 | 11.36 |
| 4953 | CZ | TYR | B | 114 | 24.290 | 18.412 | 95.609 | 1.00 | 12.32 |
| 4954 | OH | TYR | B | 114 | 23.582 | 19.066 | 94.611 | 1.00 | 11.27 |
| 4956 | CE2 | TYR | B | 114 | 24.630 | 17.087 | 95.464 | 1.00 | 10.92 |
| 4958 | CD2 | TYR | B | 114 | 25.357 | 16.463 | 96.441 | 1.00 | 10.80 |
| 4960 | C | TYR | B | 114 | 24.631 | 16.673 | 100.355 | 1.00 | 9.78 |
| 4961 | O | TYR | B | 114 | 23.429 | 16.669 | 100.019 | 1.00 | 10.01 |

FIGURE 3 (Cont.)

| A | B | C | D | E | F | G | H | I | J |
|---|---|---|---|---|---|---|---|---|---|
| 4962 | N | THR | B | 115 | 25.137 | 17.493 | 101.263 | 1.00 | 9.47 |
| 4964 | CA | THR | B | 115 | 24.338 | 18.448 | 102.013 | 1.00 | 10.15 |
| 4966 | CB | THR | B | 115 | 24.358 | 18.026 | 103.476 | 1.00 | 11.73 |
| 4968 | OG1 | THR | B | 115 | 23.731 | 16.745 | 103.599 | 1.00 | 13.04 |
| 4970 | CG2 | THR | B | 115 | 23.525 | 18.954 | 104.329 | 1.00 | 12.40 |
| 4974 | C | THR | B | 115 | 24.947 | 19.830 | 101.870 | 1.00 | 10.79 |
| 4975 | O | THR | B | 115 | 26.155 | 20.007 | 102.061 | 1.00 | 10.14 |
| 4976 | N | GLU | B | 116 | 24.113 | 20.798 | 101.525 | 1.00 | 9.82 |
| 4978 | CA | GLU | B | 116 | 24.519 | 22.180 | 101.481 | 1.00 | 10.23 |
| 4980 | CB | GLU | B | 116 | 23.907 | 22.873 | 100.274 | 1.00 | 11.18 |
| 4983 | CG | GLU | B | 116 | 24.367 | 22.294 | 98.971 | 1.00 | 15.71 |
| 4986 | CD | GLU | B | 116 | 23.742 | 22.967 | 97.767 | 1.00 | 22.02 |
| 4987 | OE1 | GLU | B | 116 | 23.888 | 24.203 | 97.601 | 1.00 | 27.03 |
| 4988 | OE2 | GLU | B | 116 | 23.108 | 22.248 | 96.977 | 1.00 | 23.03 |
| 4989 | C | GLU | B | 116 | 24.032 | 22.852 | 102.731 | 1.00 | 10.08 |
| 4990 | O | GLU | B | 116 | 22.843 | 22.805 | 103.059 | 1.00 | 11.84 |
| 4991 | N | LEU | B | 117 | 24.931 | 23.519 | 103.430 | 1.00 | 9.65 |
| 4993 | CA | LEU | B | 117 | 24.555 | 24.196 | 104.650 | 1.00 | 9.76 |
| 4995 | CB | LEU | B | 117 | 25.770 | 24.415 | 105.529 | 1.00 | 10.35 |
| 4998 | CG | LEU | B | 117 | 26.404 | 23.137 | 106.050 | 1.00 | 12.53 |
| 5000 | CD1 | LEU | B | 117 | 27.481 | 23.557 | 107.064 | 1.00 | 13.35 |
| 5004 | CD2 | LEU | B | 117 | 25.441 | 22.136 | 106.633 | 1.00 | 16.89 |
| 5008 | C | LEU | B | 117 | 23.927 | 25.550 | 104.325 | 1.00 | 10.33 |
| 5009 | O | LEU | B | 117 | 24.167 | 26.124 | 103.261 | 1.00 | 10.92 |
| 5010 | N | PRO | B | 118 | 23.147 | 26.085 | 105.254 | 1.00 | 10.89 |
| 5011 | CA | PRO | B | 118 | 22.458 | 27.352 | 105.014 | 1.00 | 11.46 |
| 5013 | CB | PRO | B | 118 | 21.554 | 27.492 | 106.216 | 1.00 | 11.62 |
| 5016 | CG | PRO | B | 118 | 22.188 | 26.672 | 107.286 | 1.00 | 13.14 |
| 5019 | CD | PRO | B | 118 | 22.914 | 25.585 | 106.616 | 1.00 | 12.06 |
| 5022 | C | PRO | B | 118 | 23.438 | 28.504 | 104.909 | 1.00 | 10.68 |
| 5023 | O | PRO | B | 118 | 24.467 | 28.589 | 105.586 | 1.00 | 10.88 |
| 5024 | N | TYR | B | 119 | 23.103 | 29.435 | 104.048 | 1.00 | 10.04 |
| 5026 | CA | TYR | B | 119 | 23.979 | 30.534 | 103.756 | 1.00 | 9.17 |
| 5028 | CB | TYR | B | 119 | 23.325 | 31.469 | 102.737 | 1.00 | 9.53 |
| 5031 | CG | TYR | B | 119 | 24.209 | 32.609 | 102.374 | 1.00 | 7.93 |
| 5032 | CD1 | TYR | B | 119 | 25.113 | 32.514 | 101.332 | 1.00 | 8.54 |
| 5034 | CE1 | TYR | B | 119 | 25.956 | 33.550 | 101.045 | 1.00 | 8.85 |
| 5036 | CZ | TYR | B | 119 | 25.908 | 34.717 | 101.765 | 1.00 | 8.67 |
| 5037 | OH | TYR | B | 119 | 26.797 | 35.740 | 101.450 | 1.00 | 11.29 |
| 5039 | CE2 | TYR | B | 119 | 25.040 | 34.834 | 102.809 | 1.00 | 8.95 |
| 5041 | CD2 | TYR | B | 119 | 24.189 | 33.792 | 103.102 | 1.00 | 8.19 |
| 5043 | C | TYR | B | 119 | 24.386 | 31.373 | 104.975 | 1.00 | 9.00 |
| 5044 | O | TYR | B | 119 | 23.564 | 31.914 | 105.701 | 1.00 | 9.23 |
| 5045 | N | GLY | B | 120 | 25.694 | 31.503 | 105.137 | 1.00 | 9.56 |
| 5047 | CA | GLY | B | 120 | 26.285 | 32.366 | 106.112 | 1.00 | 10.15 |
| 5050 | C | GLY | B | 120 | 26.228 | 31.973 | 107.550 | 1.00 | 11.00 |
| 5051 | O | GLY | B | 120 | 26.550 | 32.826 | 108.366 | 1.00 | 12.83 |
| 5052 | N | ARG | B | 121 | 25.939 | 30.723 | 107.884 | 1.00 | 10.72 |
| 5054 | CA | ARG | B | 121 | 25.665 | 30.371 | 109.273 | 1.00 | 11.15 |
| 5056 | CB | ARG | B | 121 | 24.384 | 29.579 | 109.457 | 1.00 | 12.58 |
| 5059 | CG | ARG | B | 121 | 23.151 | 30.424 | 109.170 | 1.00 | 15.83 |

FIGURE 3 (Cont.)

| A | B | C | D | E | F | G | H | I | J |
|---|---|---|---|---|---|---|---|---|---|
| 5062 | CD | ARG | B | 121 | 22.612 | 31.062 | 110.488 | 1.00 | 20.35 |
| 5065 | NE | ARG | B | 121 | 21.987 | 30.006 | 111.303 | 1.00 | 26.34 |
| 5067 | CZ | ARG | B | 121 | 21.907 | 29.941 | 112.624 | 1.00 | 26.96 |
| 5068 | NH1 | ARG | B | 121 | 22.430 | 30.880 | 113.409 | 1.00 | 30.93 |
| 5071 | NH2 | ARG | B | 121 | 21.280 | 28.901 | 113.164 | 1.00 | 28.58 |
| 5074 | C | ARG | B | 121 | 26.879 | 29.641 | 109.820 | 1.00 | 10.93 |
| 5075 | O | ARG | B | 121 | 27.060 | 28.455 | 109.663 | 1.00 | 11.09 |
| 5076 | N | GLU | B | 122 | 27.645 | 30.376 | 110.596 | 1.00 | 10.69 |
| 5078 | CA | GLU | B | 122 | 28.952 | 29.897 | 111.020 | 1.00 | 10.41 |
| 5080 | CB | GLU | B | 122 | 29.917 | 30.998 | 111.441 | 1.00 | 9.85 |
| 5083 | CG | GLU | B | 122 | 30.465 | 31.810 | 110.294 | 1.00 | 10.85 |
| 5086 | CD | GLU | B | 122 | 31.599 | 32.716 | 110.697 | 1.00 | 11.35 |
| 5087 | OE1 | GLU | B | 122 | 32.768 | 32.278 | 110.775 | 1.00 | 11.61 |
| 5088 | OE2 | GLU | B | 122 | 31.276 | 33.892 | 110.906 | 1.00 | 13.37 |
| 5089 | C | GLU | B | 122 | 28.715 | 28.927 | 112.150 | 1.00 | 10.45 |
| 5090 | O | GLU | B | 122 | 29.513 | 28.017 | 112.323 | 1.00 | 10.51 |
| 5091 | N | ASP | B | 123 | 27.610 | 29.080 | 112.893 | 1.00 | 10.44 |
| 5093 | CA | ASP | B | 123 | 27.278 | 28.115 | 113.952 | 1.00 | 10.75 |
| 5095 | CB | ASP | B | 123 | 26.162 | 28.626 | 114.884 | 1.00 | 11.31 |
| 5098 | CG | ASP | B | 123 | 24.956 | 29.190 | 114.135 | 1.00 | 14.84 |
| 5099 | OD1 | ASP | B | 123 | 23.952 | 29.544 | 114.817 | 1.00 | 20.72 |
| 5100 | OD2 | ASP | B | 123 | 24.882 | 29.336 | 112.882 | 1.00 | 14.73 |
| 5101 | C | ASP | B | 123 | 26.933 | 26.751 | 113.351 | 1.00 | 10.27 |
| 5102 | O | ASP | B | 123 | 27.321 | 25.710 | 113.883 | 1.00 | 10.55 |
| 5103 | N | VAL | B | 124 | 26.208 | 26.752 | 112.232 | 1.00 | 9.28 |
| 5105 | CA | VAL | B | 124 | 25.859 | 25.509 | 111.557 | 1.00 | 9.51 |
| 5107 | CB | VAL | B | 124 | 24.762 | 25.693 | 110.510 | 1.00 | 9.52 |
| 5109 | CG1 | VAL | B | 124 | 24.458 | 24.400 | 109.819 | 1.00 | 10.41 |
| 5113 | CG2 | VAL | B | 124 | 23.510 | 26.282 | 111.175 | 1.00 | 10.94 |
| 5117 | C | VAL | B | 124 | 27.113 | 24.878 | 110.957 | 1.00 | 8.40 |
| 5118 | O | VAL | B | 124 | 27.284 | 23.673 | 110.990 | 1.00 | 9.46 |
| 5119 | N | LEU | B | 125 | 28.010 | 25.707 | 110.453 | 1.00 | 8.87 |
| 5121 | CA | LEU | B | 125 | 29.261 | 25.200 | 109.909 | 1.00 | 8.13 |
| 5123 | CB | LEU | B | 125 | 30.013 | 26.319 | 109.209 | 1.00 | 8.65 |
| 5126 | CG | LEU | B | 125 | 31.356 | 25.908 | 108.620 | 1.00 | 7.69 |
| 5128 | CD1 | LEU | B | 125 | 31.221 | 24.784 | 107.616 | 1.00 | 8.06 |
| 5132 | CD2 | LEU | B | 125 | 32.010 | 27.077 | 107.992 | 1.00 | 8.99 |
| 5136 | C | LEU | B | 125 | 30.112 | 24.551 | 111.008 | 1.00 | 8.15 |
| 5137 | O | LEU | B | 125 | 30.668 | 23.498 | 110.824 | 1.00 | 7.43 |
| 5138 | N | LYS | B | 126 | 29.993 | 25.033 | 112.224 | 1.00 | 9.04 |
| 5140 | CA | LYS | B | 126 | 30.818 | 24.615 | 113.360 | 1.00 | 8.87 |
| 5142 | CB | LYS | B | 126 | 30.698 | 25.573 | 114.545 | 1.00 | 8.48 |
| 5145 | CG | LYS | B | 126 | 31.720 | 25.344 | 115.619 | 1.00 | 9.52 |
| 5148 | CD | LYS | B | 126 | 31.299 | 25.927 | 116.941 | 1.00 | 10.52 |
| 5151 | CE | LYS | B | 126 | 32.310 | 25.640 | 118.040 | 1.00 | 12.18 |
| 5154 | NZ | LYS | B | 126 | 31.891 | 26.221 | 119.337 | 1.00 | 13.54 |
| 5158 | C | LYS | B | 126 | 30.296 | 23.257 | 113.771 | 1.00 | 9.93 |
| 5159 | O | LYS | B | 126 | 31.044 | 22.312 | 113.958 | 1.00 | 8.70 |
| 5160 | N | GLU | B | 127 | 28.999 | 23.069 | 113.637 | 1.00 | 9.98 |
| 5162 | CA | GLU | B | 127 | 28.343 | 21.873 | 114.104 | 1.00 | 10.72 |
| 5164 | CB | GLU | B | 127 | 26.815 | 22.038 | 114.188 | 1.00 | 11.00 |

FIGURE 3 (Cont.)

| A | B | C | D | E | F | G | H | I | J |
|---|---|---|---|---|---|---|---|---|---|
| 5167 | CG | GLU | B | 127 | 26.133 | 20.796 | 114.744 | 1.00 | 14.85 |
| 5170 | CD | GLU | B | 127 | 24.633 | 20.983 | 114.889 | 1.00 | 22.12 |
| 5171 | OE1 | GLU | B | 127 | 23.873 | 20.276 | 114.198 | 1.00 | 30.96 |
| 5172 | OE2 | GLU | B | 127 | 24.216 | 21.834 | 115.698 | 1.00 | 30.51 |
| 5173 | C | GLU | B | 127 | 28.675 | 20.790 | 113.087 | 1.00 | 9.86 |
| 5174 | O | GLU | B | 127 | 28.946 | 19.628 | 113.434 | 1.00 | 9.90 |
| 5175 | N | ALA | B | 128 | 28.676 | 21.150 | 111.803 | 1.00 | 9.24 |
| 5177 | CA | ALA | B | 128 | 29.002 | 20.187 | 110.767 | 1.00 | 8.77 |
| 5179 | CB | ALA | B | 128 | 28.716 | 20.776 | 109.392 | 1.00 | 9.81 |
| 5183 | C | ALA | B | 128 | 30.463 | 19.724 | 110.862 | 1.00 | 8.18 |
| 5184 | O | ALA | B | 128 | 30.778 | 18.546 | 110.695 | 1.00 | 8.99 |
| 5185 | N | VAL | B | 129 | 31.357 | 20.670 | 111.061 | 1.00 | 8.13 |
| 5187 | CA | VAL | B | 129 | 32.752 | 20.307 | 111.207 | 1.00 | 8.78 |
| 5189 | CB | VAL | B | 129 | 33.654 | 21.544 | 111.241 | 1.00 | 8.18 |
| 5191 | CG1 | VAL | B | 129 | 35.086 | 21.141 | 111.491 | 1.00 | 10.14 |
| 5195 | CG2 | VAL | B | 129 | 33.537 | 22.343 | 109.925 | 1.00 | 9.95 |
| 5199 | C | VAL | B | 129 | 32.962 | 19.420 | 112.439 | 1.00 | 9.42 |
| 5200 | O | VAL | B | 129 | 33.706 | 18.455 | 112.382 | 1.00 | 10.59 |
| 5201 | N | ALA | B | 130 | 32.279 | 19.715 | 113.535 | 1.00 | 9.53 |
| 5203 | CA | ALA | B | 130 | 32.446 | 18.941 | 114.773 | 1.00 | 10.31 |
| 5205 | CB | ALA | B | 130 | 31.743 | 19.666 | 115.935 | 1.00 | 10.22 |
| 5209 | C | ALA | B | 130 | 31.884 | 17.520 | 114.660 | 1.00 | 11.48 |
| 5210 | O | ALA | B | 130 | 32.446 | 16.565 | 115.195 | 1.00 | 13.85 |
| 5211 | N | ASN | B | 131 | 30.744 | 17.402 | 113.974 | 1.00 | 11.81 |
| 5213 | CA | ASN | B | 131 | 29.947 | 16.167 | 113.977 | 1.00 | 12.74 |
| 5215 | CB | ASN | B | 131 | 28.507 | 16.459 | 114.379 | 1.00 | 13.40 |
| 5218 | CG | ASN | B | 131 | 28.391 | 16.955 | 115.795 | 1.00 | 14.96 |
| 5219 | OD1 | ASN | B | 131 | 29.236 | 16.647 | 116.619 | 1.00 | 20.90 |
| 5220 | ND2 | ASN | B | 131 | 27.359 | 17.743 | 116.082 | 1.00 | 19.85 |
| 5223 | C | ASN | B | 131 | 29.909 | 15.357 | 112.699 | 1.00 | 13.26 |
| 5224 | O | ASN | B | 131 | 29.599 | 14.158 | 112.741 | 1.00 | 15.74 |
| 5225 | N | LYS | B | 132 | 30.181 | 15.994 | 111.562 | 1.00 | 11.33 |
| 5227 | CA | LYS | B | 132 | 30.092 | 15.320 | 110.272 | 1.00 | 10.96 |
| 5229 | CB | LYS | B | 132 | 29.182 | 16.101 | 109.323 | 1.00 | 11.23 |
| 5232 | CG | LYS | B | 132 | 27.821 | 16.322 | 109.878 | 1.00 | 14.86 |
| 5235 | CD | LYS | B | 132 | 27.083 | 14.999 | 110.018 | 1.00 | 19.95 |
| 5238 | CE | LYS | B | 132 | 25.624 | 15.220 | 110.354 | 1.00 | 22.43 |
| 5241 | NZ | LYS | B | 132 | 24.842 | 13.943 | 110.245 | 1.00 | 25.65 |
| 5245 | C | LYS | B | 132 | 31.455 | 15.063 | 109.645 | 1.00 | 10.68 |
| 5246 | O | LYS | B | 132 | 31.714 | 13.963 | 109.163 | 1.00 | 11.64 |
| 5247 | N | GLY | B | 133 | 32.325 | 16.065 | 109.638 | 1.00 | 9.74 |
| 5249 | CA | GLY | B | 133 | 33.635 | 15.942 | 109.049 | 1.00 | 9.35 |
| 5252 | C | GLY | B | 133 | 34.040 | 17.241 | 108.387 | 1.00 | 8.28 |
| 5253 | O | GLY | B | 133 | 33.356 | 18.245 | 108.521 | 1.00 | 8.75 |
| 5254 | N | PRO | B | 134 | 35.169 | 17.223 | 107.692 | 1.00 | 7.92 |
| 5255 | CA | PRO | B | 134 | 35.584 | 18.380 | 106.903 | 1.00 | 7.00 |
| 5257 | CB | PRO | B | 134 | 36.828 | 17.879 | 106.194 | 1.00 | 7.70 |
| 5260 | CG | PRO | B | 134 | 37.360 | 16.860 | 107.148 | 1.00 | 8.79 |
| 5263 | CD | PRO | B | 134 | 36.160 | 16.151 | 107.625 | 1.00 | 8.19 |
| 5266 | C | PRO | B | 134 | 34.508 | 18.799 | 105.908 | 1.00 | 7.17 |
| 5267 | O | PRO | B | 134 | 33.807 | 17.955 | 105.352 | 1.00 | 8.23 |

FIGURE 3 (Cont.)

| A | B | C | D | E | F | G | H | I | J |
|---|---|---|---|---|---|---|---|---|---|
| 5268 | N | VAL | B | 135 | 34.416 | 20.100 | 105.715 | 1.00 | 6.17 |
| 5270 | CA | VAL | B | 135 | 33.385 | 20.695 | 104.894 | 1.00 | 6.28 |
| 5272 | CB | VAL | B | 135 | 32.455 | 21.573 | 105.771 | 1.00 | 6.46 |
| 5274 | CG1 | VAL | B | 135 | 31.419 | 22.302 | 104.956 | 1.00 | 7.39 |
| 5278 | CG2 | VAL | B | 135 | 31.792 | 20.716 | 106.866 | 1.00 | 6.98 |
| 5282 | C | VAL | B | 135 | 34.005 | 21.518 | 103.777 | 1.00 | 6.20 |
| 5283 | O | VAL | B | 135 | 34.898 | 22.335 | 103.990 | 1.00 | 7.03 |
| 5284 | N | SER | B | 136 | 33.510 | 21.296 | 102.580 | 1.00 | 6.73 |
| 5286 | CA | SER | B | 136 | 33.946 | 22.080 | 101.443 | 1.00 | 6.36 |
| 5288 | CB | SER | B | 136 | 33.485 | 21.421 | 100.151 | 1.00 | 6.23 |
| 5291 | OG | SER | B | 136 | 34.087 | 20.176 | 99.924 | 1.00 | 8.76 |
| 5293 | C | SER | B | 136 | 33.317 | 23.450 | 101.509 | 1.00 | 6.66 |
| 5294 | O | SER | B | 136 | 32.136 | 23.584 | 101.749 | 1.00 | 7.48 |
| 5295 | N | VAL | B | 136 | 34.114 | 24.483 | 101.314 | 1.00 | 6.15 |
| 5297 | CA | VAL | B | 137 | 33.587 | 25.844 | 101.358 | 1.00 | 6.50 |
| 5299 | CB | VAL | B | 137 | 33.878 | 26.552 | 102.725 | 1.00 | 6.83 |
| 5301 | CG1 | VAL | B | 137 | 33.245 | 25.821 | 103.877 | 1.00 | 8.00 |
| 5305 | CG2 | VAL | B | 137 | 35.362 | 26.671 | 102.940 | 1.00 | 8.64 |
| 5309 | C | VAL | B | 137 | 34.273 | 26.650 | 100.275 | 1.00 | 7.02 |
| 5310 | O | VAL | B | 137 | 35.319 | 26.276 | 99.730 | 1.00 | 7.34 |
| 5311 | N | GLY | B | 138 | 33.650 | 27.763 | 99.944 | 1.00 | 7.52 |
| 5313 | CA | GLY | B | 138 | 34.285 | 28.757 | 99.114 | 1.00 | 7.15 |
| 5316 | C | GLY | B | 138 | 34.701 | 29.952 | 99.928 | 1.00 | 9.04 |
| 5317 | O | GLY | B | 138 | 34.040 | 30.318 | 100.896 | 1.00 | 9.03 |
| 5318 | N | VAL | B | 139 | 35.799 | 30.577 | 99.520 | 1.00 | 7.47 |
| 5320 | CA | VAL | B | 139 | 36.242 | 31.787 | 100.162 | 1.00 | 9.05 |
| 5322 | CB | VAL | B | 139 | 37.464 | 31.583 | 101.093 | 1.00 | 9.17 |
| 5324 | CG1 | VAL | B | 139 | 37.077 | 30.671 | 102.220 | 1.00 | 9.47 |
| 5328 | CG2 | VAL | B | 139 | 38.696 | 31.043 | 100.357 | 1.00 | 8.11 |
| 5332 | C | VAL | B | 139 | 36.573 | 32.819 | 99.150 | 1.00 | 8.77 |
| 5333 | O | VAL | B | 139 | 36.881 | 32.499 | 98.004 | 1.00 | 9.48 |
| 5334 | N | ASP | B | 140 | 36.518 | 34.073 | 99.567 | 1.00 | 9.97 |
| 5336 | CA | ASP | B | 140 | 37.026 | 35.178 | 98.760 | 1.00 | 10.54 |
| 5338 | CB | ASP | B | 140 | 36.393 | 36.476 | 99.249 | 1.00 | 10.83 |
| 5341 | CG | ASP | B | 140 | 36.949 | 37.700 | 98.570 | 1.00 | 14.11 |
| 5342 | OD1 | ASP | B | 140 | 37.762 | 37.557 | 97.637 | 1.00 | 13.49 |
| 5343 | OD2 | ASP | B | 140 | 36.600 | 38.846 | 98.903 | 1.00 | 15.62 |
| 5344 | C | ASP | B | 140 | 38.535 | 35.217 | 98.949 | 1.00 | 11.52 |
| 5345 | O | ASP | B | 140 | 39.022 | 35.614 | 100.003 | 1.00 | 11.69 |
| 5346 | N | ALA | B | 141 | 39.264 | 34.747 | 97.939 | 1.00 | 12.09 |
| 5348 | CA | ALA | B | 141 | 40.721 | 34.706 | 97.981 | 1.00 | 12.78 |
| 5350 | CB | ALA | B | 141 | 41.207 | 33.297 | 97.667 | 1.00 | 13.40 |
| 5354 | C | ALA | B | 141 | 41.319 | 35.671 | 96.985 | 1.00 | 13.87 |
| 5355 | O | ALA | B | 141 | 42.426 | 35.467 | 96.505 | 1.00 | 14.51 |
| 5356 | N | LYS | B | 142 | 40.737 | 36.837 | 96.854 | 1.00 | 14.99 |
| 5358 | CA | LYS | B | 142 | 41.063 | 37.713 | 95.713 | 1.00 | 16.31 |
| 5360 | CB | LYS | B | 142 | 39.836 | 38.370 | 95.093 | 1.00 | 17.07 |
| 5363 | CG | LYS | B | 142 | 38.989 | 37.436 | 94.228 | 1.00 | 20.76 |
| 5366 | CD | LYS | B | 142 | 38.135 | 38.210 | 93.228 | 1.00 | 24.19 |
| 5369 | CE | LYS | B | 142 | 36.825 | 38.589 | 93.829 | 1.00 | 26.69 |
| 5372 | NZ | LYS | B | 142 | 35.976 | 37.446 | 94.259 | 1.00 | 26.99 |

FIGURE 3 (Cont.)

| A | B | C | D | E | F | G | H | I | J |
|---|---|---|---|---|---|---|---|---|---|
| 5376 | C | LYS | B | 142 | 42.046 | 38.762 | 96.187 | 1.00 | 16.96 |
| 5377 | O | LYS | B | 142 | 42.658 | 39.480 | 95.379 | 1.00 | 20.53 |
| 5378 | N | HIS | B | 143 | 42.287 | 38.815 | 97.477 | 1.00 | 14.88 |
| 5380 | CA | HIS | B | 143 | 43.092 | 39.890 | 98.036 | 1.00 | 14.46 |
| 5382 | CB | HIS | B | 143 | 42.464 | 40.356 | 99.343 | 1.00 | 15.50 |
| 5385 | CG | HIS | B | 143 | 41.007 | 40.603 | 99.192 | 1.00 | 15.75 |
| 5386 | ND1 | HIS | B | 143 | 40.506 | 41.776 | 98.672 | 1.00 | 18.10 |
| 5388 | CE1 | HIS | B | 143 | 39.192 | 41.686 | 98.584 | 1.00 | 20.19 |
| 5390 | NE2 | HIS | B | 143 | 38.830 | 40.484 | 98.991 | 1.00 | 18.79 |
| 5392 | CD2 | HIS | B | 143 | 39.944 | 39.786 | 99.367 | 1.00 | 18.55 |
| 5394 | C | HIS | B | 143 | 44.539 | 39.455 | 98.175 | 1.00 | 13.69 |
| 5395 | O | HIS | B | 143 | 44.845 | 38.313 | 98.455 | 1.00 | 12.93 |
| 5396 | N | PRO | B | 144 | 45.466 | 40.356 | 97.907 | 1.00 | 13.23 |
| 5397 | CA | PRO | B | 144 | 46.879 | 39.998 | 97.972 | 1.00 | 12.65 |
| 5399 | CB | PRO | B | 144 | 47.582 | 41.344 | 97.740 | 1.00 | 13.88 |
| 5402 | CG | PRO | B | 144 | 46.509 | 42.387 | 97.847 | 1.00 | 15.37 |
| 5405 | CD | PRO | B | 144 | 45.257 | 41.746 | 97.469 | 1.00 | 13.32 |
| 5408 | C | PRO | B | 144 | 47.254 | 39.364 | 99.319 | 1.00 | 11.62 |
| 5409 | O | PRO | B | 144 | 48.103 | 38.501 | 99.347 | 1.00 | 12.09 |
| 5410 | N | SER | B | 145 | 46.608 | 39.785 | 100.402 | 1.00 | 11.24 |
| 5412 | CA | SER | B | 145 | 46.877 | 39.236 | 101.726 | 1.00 | 10.46 |
| 5414 | CB | SER | B | 145 | 45.997 | 39.909 | 102.761 | 1.00 | 11.01 |
| 5417 | OG | SER | B | 145 | 44.640 | 39.765 | 102.420 | 1.00 | 11.77 |
| 5419 | C | SER | B | 145 | 46.692 | 37.713 | 101.784 | 1.00 | 10.39 |
| 5420 | O | SER | B | 145 | 47.364 | 37.050 | 102.541 | 1.00 | 10.75 |
| 5421 | N | PHE | B | 146 | 45.758 | 37.185 | 101.009 | 1.00 | 9.85 |
| 5423 | CA | PHE | B | 146 | 45.532 | 35.754 | 100.990 | 1.00 | 9.97 |
| 5425 | CB | PHE | B | 146 | 44.247 | 35.432 | 100.264 | 1.00 | 9.49 |
| 5428 | CG | PHE | B | 146 | 43.818 | 34.011 | 100.413 | 1.00 | 9.57 |
| 5429 | CD1 | PHE | B | 146 | 44.314 | 33.032 | 99.579 | 1.00 | 10.99 |
| 5431 | CE1 | PHE | B | 146 | 43.923 | 31.728 | 99.749 | 1.00 | 12.44 |
| 5433 | CZ | PHE | B | 146 | 43.027 | 31.413 | 100.721 | 1.00 | 10.41 |
| 5435 | CE2 | PHE | B | 146 | 42.524 | 32.372 | 101.545 | 1.00 | 11.02 |
| 5437 | CD2 | PHE | B | 146 | 42.914 | 33.659 | 101.397 | 1.00 | 12.00 |
| 5439 | C | PHE | B | 146 | 46.742 | 35.055 | 100.370 | 1.00 | 10.60 |
| 5440 | O | PHE | B | 146 | 47.263 | 34.087 | 100.898 | 1.00 | 10.44 |
| 5441 | N | PHE | B | 147 | 47.214 | 35.574 | 99.247 | 1.00 | 11.47 |
| 5443 | CA | PHE | B | 147 | 48.356 | 34.992 | 98.574 | 1.00 | 11.39 |
| 5445 | CB | PHE | B | 147 | 48.621 | 35.696 | 97.249 | 1.00 | 11.64 |
| 5448 | CG | PHE | B | 147 | 47.608 | 35.399 | 96.200 | 1.00 | 10.84 |
| 5449 | CD1 | PHE | B | 147 | 47.849 | 34.451 | 95.228 | 1.00 | 10.86 |
| 5451 | CE1 | PHE | B | 147 | 46.904 | 34.176 | 94.274 | 1.00 | 10.08 |
| 5453 | CZ | PHE | B | 147 | 45.706 | 34.820 | 94.301 | 1.00 | 11.86 |
| 5455 | CE2 | PHE | B | 147 | 45.466 | 35.760 | 95.250 | 1.00 | 12.59 |
| 5457 | CD2 | PHE | B | 147 | 46.387 | 36.033 | 96.201 | 1.00 | 12.51 |
| 5459 | C | PHE | B | 147 | 49.601 | 35.107 | 99.427 | 1.00 | 11.66 |
| 5460 | O | PHE | B | 147 | 50.477 | 34.242 | 99.354 | 1.00 | 13.04 |
| 5461 | N | LEU | B | 148 | 49.688 | 36.178 | 100.195 | 1.00 | 10.78 |
| 5463 | CA | LEU | B | 148 | 50.870 | 36.472 | 100.987 | 1.00 | 11.88 |
| 5465 | CB | LEU | B | 148 | 51.093 | 37.983 | 101.057 | 1.00 | 12.57 |
| 5468 | CG | LEU | B | 148 | 51.343 | 38.603 | 99.700 | 1.00 | 14.42 |

FIGURE 3 (Cont.)

| A | B | C | D | E | F | G | H | I | J |
|---|---|---|---|---|---|---|---|---|---|
| 5470 | CD1 | LEU | B | 148 | 51.317 | 40.125 | 99.797 | 1.00 | 16.61 |
| 5474 | CD2 | LEU | B | 148 | 52.648 | 38.114 | 99.127 | 1.00 | 15.72 |
| 5478 | C | LEU | B | 148 | 50.809 | 35.909 | 102.388 | 1.00 | 11.97 |
| 5479 | O | LEU | B | 148 | 51.755 | 36.043 | 103.150 | 1.00 | 13.07 |
| 5480 | N | TYR | B | 149 | 49.691 | 35.285 | 102.744 | 1.00 | 11.31 |
| 5482 | CA | TYR | B | 149 | 49.543 | 34.719 | 104.080 | 1.00 | 10.51 |
| 5484 | CB | TYR | B | 149 | 48.211 | 34.014 | 104.166 | 1.00 | 9.45 |
| 5487 | CG | TYR | B | 149 | 48.024 | 33.227 | 105.423 | 1.00 | 8.58 |
| 5488 | CD1 | TYR | B | 149 | 48.279 | 31.870 | 105.448 | 1.00 | 7.97 |
| 5490 | CE1 | TYR | B | 149 | 48.125 | 31.145 | 106.592 | 1.00 | 9.23 |
| 5492 | CZ | TYR | B | 149 | 47.666 | 31.746 | 107.738 | 1.00 | 8.37 |
| 5493 | OH | TYR | B | 149 | 47.462 | 30.982 | 108.828 | 1.00 | 9.21 |
| 5495 | CE2 | TYR | B | 149 | 47.377 | 33.094 | 107.741 | 1.00 | 8.94 |
| 5497 | CD2 | TYR | B | 149 | 47.587 | 33.824 | 106.590 | 1.00 | 8.72 |
| 5499 | C | TYR | B | 149 | 50.631 | 33.742 | 104.475 | 1.00 | 11.02 |
| 5500 | O | TYR | B | 149 | 50.974 | 32.838 | 103.710 | 1.00 | 11.67 |
| 5501 | N | ARG | B | 150 | 51.128 | 33.914 | 105.695 | 1.00 | 12.05 |
| 5503 | CA | ARG | B | 150 | 52.128 | 33.018 | 106.229 | 1.00 | 13.10 |
| 5505 | CB | ARG | B | 150 | 53.404 | 33.808 | 106.523 | 1.00 | 13.66 |
| 5508 | CG | ARG | B | 150 | 54.060 | 34.285 | 105.259 | 1.00 | 16.66 |
| 5511 | CD | ARG | B | 150 | 54.488 | 33.128 | 104.369 | 1.00 | 23.21 |
| 5514 | NE | ARG | B | 150 | 55.714 | 32.515 | 104.877 | 1.00 | 27.93 |
| 5516 | CZ | ARG | B | 150 | 56.329 | 31.476 | 104.330 | 1.00 | 34.05 |
| 5517 | NH1 | ARG | B | 150 | 57.473 | 31.030 | 104.846 | 1.00 | 36.85 |
| 5520 | NH2 | ARG | B | 150 | 55.799 | 30.871 | 103.274 | 1.00 | 36.34 |
| 5523 | C | ARG | B | 150 | 51.725 | 32.280 | 107.469 | 1.00 | 13.08 |
| 5524 | O | ARG | B | 150 | 52.000 | 31.086 | 107.595 | 1.00 | 13.40 |
| 5525 | N | SER | B | 151 | 51.115 | 32.975 | 108.416 | 1.00 | 12.69 |
| 5527 | CA | SER | B | 151 | 50.807 | 32.340 | 109.684 | 1.00 | 13.15 |
| 5529 | CB | SER | B | 151 | 52.087 | 32.213 | 110.514 | 1.00 | 14.45 |
| 5532 | OG | SER | B | 151 | 52.525 | 33.494 | 110.887 | 1.00 | 17.66 |
| 5534 | C | SER | B | 151 | 49.794 | 33.132 | 110.463 | 1.00 | 12.22 |
| 5535 | O | SER | B | 151 | 49.538 | 34.307 | 110.166 | 1.00 | 13.35 |
| 5536 | N | GLY | B | 152 | 49.212 | 32.479 | 111.462 | 1.00 | 11.61 |
| 5538 | CA | GLY | B | 152 | 48.263 | 33.130 | 112.342 | 1.00 | 11.64 |
| 5541 | C | GLY | B | 152 | 46.856 | 33.143 | 111.797 | 1.00 | 11.53 |
| 5542 | O | GLY | B | 152 | 46.522 | 32.417 | 110.857 | 1.00 | 12.06 |
| 5543 | N | VAL | B | 153 | 46.021 | 33.989 | 112.380 | 1.00 | 10.63 |
| 5545 | CA | VAL | B | 153 | 44.619 | 34.030 | 111.976 | 1.00 | 10.56 |
| 5547 | CB | VAL | B | 153 | 43.672 | 34.242 | 113.135 | 1.00 | 11.08 |
| 5549 | CG1 | VAL | B | 153 | 42.225 | 34.346 | 112.641 | 1.00 | 10.84 |
| 5553 | CG2 | VAL | B | 153 | 43.822 | 33.132 | 114.163 | 1.00 | 11.34 |
| 5557 | C | VAL | B | 153 | 44.450 | 35.094 | 110.923 | 1.00 | 11.19 |
| 5558 | O | VAL | B | 153 | 44.689 | 36.288 | 111.161 | 1.00 | 13.43 |
| 5559 | N | TYR | B | 154 | 44.037 | 34.663 | 109.747 | 1.00 | 9.55 |
| 5561 | CA | TYR | B | 154 | 43.839 | 35.570 | 108.645 | 1.00 | 9.45 |
| 5563 | CB | TYR | B | 154 | 43.704 | 34.759 | 107.358 | 1.00 | 8.66 |
| 5566 | CG | TYR | B | 154 | 43.493 | 35.564 | 106.104 | 1.00 | 9.70 |
| 5567 | CD1 | TYR | B | 154 | 44.526 | 36.256 | 105.541 | 1.00 | 8.14 |
| 5569 | CE1 | TYR | B | 154 | 44.361 | 36.975 | 104.395 | 1.00 | 8.81 |
| 5571 | CZ | TYR | B | 154 | 43.149 | 36.989 | 103.775 | 1.00 | 8.19 |

FIGURE 3 (Cont.)

| A | B | C | D | E | F | G | H | I | J |
|---|---|---|---|---|---|---|---|---|---|
| 5572 | OH | TYR | B | 154 | 42.961 | 37.724 | 102.626 | 1.00 | 9.19 |
| 5574 | CE2 | TYR | B | 154 | 42.091 | 36.314 | 104.333 | 1.00 | 8.29 |
| 5576 | CD2 | TYR | B | 154 | 42.276 | 35.594 | 105.476 | 1.00 | 8.68 |
| 5578 | C | TYR | B | 154 | 42.595 | 36.397 | 108.795 | 1.00 | 9.48 |
| 5579 | O | TYR | B | 154 | 41.493 | 35.882 | 108.941 | 1.00 | 9.95 |
| 5580 | N | TYR | B | 155 | 42.761 | 37.702 | 108.614 | 1.00 | 10.50 |
| 5582 | CA | TYR | B | 155 | 41.625 | 38.614 | 108.679 | 1.00 | 11.82 |
| 5584 | CB | TYR | B | 155 | 41.266 | 39.027 | 110.118 | 1.00 | 12.51 |
| 5587 | CG | TYR | B | 155 | 40.133 | 40.009 | 110.202 | 1.00 | 14.71 |
| 5588 | CD1 | TYR | B | 155 | 38.830 | 39.598 | 110.413 | 1.00 | 16.28 |
| 5590 | CE1 | TYR | B | 155 | 37.794 | 40.507 | 110.488 | 1.00 | 18.67 |
| 5592 | CZ | TYR | B | 155 | 38.064 | 41.839 | 110.395 | 1.00 | 21.95 |
| 5593 | OH | TYR | B | 155 | 37.008 | 42.742 | 110.468 | 1.00 | 24.21 |
| 5595 | CE2 | TYR | B | 155 | 39.353 | 42.273 | 110.213 | 1.00 | 21.50 |
| 5597 | CD2 | TYR | B | 155 | 40.384 | 41.356 | 110.127 | 1.00 | 19.87 |
| 5599 | C | TYR | B | 155 | 41.940 | 39.761 | 107.719 | 1.00 | 12.04 |
| 5600 | O | TYR | B | 155 | 42.983 | 40.419 | 107.805 | 1.00 | 13.44 |
| 5601 | N | GLU | B | 156 | 41.092 | 39.938 | 106.732 | 1.00 | 11.56 |
| 5603 | CA | GLU | B | 156 | 41.306 | 40.933 | 105.733 | 1.00 | 12.76 |
| 5605 | CB | GLU | B | 156 | 41.418 | 40.198 | 104.405 | 1.00 | 13.09 |
| 5608 | CG | GLU | B | 156 | 41.430 | 41.087 | 103.182 | 1.00 | 14.67 |
| 5611 | CD | GLU | B | 156 | 42.419 | 42.227 | 103.270 | 1.00 | 17.56 |
| 5612 | OE1 | GLU | B | 156 | 41.941 | 43.387 | 103.365 | 1.00 | 18.67 |
| 5613 | OE2 | GLU | B | 156 | 43.663 | 41.996 | 103.238 | 1.00 | 17.06 |
| 5614 | C | GLU | B | 156 | 40.131 | 41.880 | 105.702 | 1.00 | 13.27 |
| 5615 | O | GLU | B | 156 | 39.052 | 41.505 | 105.253 | 1.00 | 12.29 |
| 5616 | N | PRO | B | 157 | 40.323 | 43.106 | 106.169 | 1.00 | 14.16 |
| 5617 | CA | PRO | B | 157 | 39.229 | 44.083 | 106.177 | 1.00 | 15.60 |
| 5619 | CB | PRO | B | 157 | 39.927 | 45.383 | 106.589 | 1.00 | 15.91 |
| 5622 | CG | PRO | B | 157 | 41.119 | 44.942 | 107.424 | 1.00 | 15.73 |
| 5625 | CD | PRO | B | 157 | 41.541 | 43.619 | 106.819 | 1.00 | 15.55 |
| 5628 | C | PRO | B | 157 | 38.506 | 44.269 | 104.833 | 1.00 | 15.84 |
| 5629 | O | PRO | B | 157 | 37.341 | 44.642 | 104.829 | 1.00 | 17.36 |
| 5630 | N | SER | B | 158 | 39.183 | 44.036 | 103.713 | 1.00 | 15.22 |
| 5632 | CA | SER | B | 158 | 38.588 | 44.209 | 102.390 | 1.00 | 16.32 |
| 5634 | CB | SER | B | 158 | 39.673 | 44.606 | 101.389 | 1.00 | 17.36 |
| 5637 | OG | SER | B | 158 | 40.076 | 45.965 | 101.564 | 1.00 | 20.95 |
| 5639 | C | SER | B | 158 | 37.858 | 42.953 | 101.888 | 1.00 | 15.52 |
| 5640 | O | SER | B | 158 | 37.275 | 42.957 | 100.806 | 1.00 | 15.55 |
| 5641 | N | CYS | B | 159 | 37.903 | 41.874 | 102.654 | 1.00 | 15.43 |
| 5643 | CA | CYS | B | 159 | 37.241 | 40.643 | 102.240 | 1.00 | 15.62 |
| 5645 | CB | CYS | B | 159 | 37.495 | 39.505 | 103.227 | 1.00 | 15.41 |
| 5648 | SG | CYS | B | 159 | 38.336 | 38.143 | 102.397 | 1.00 | 20.02 |
| 5649 | C | CYS | B | 159 | 35.747 | 40.829 | 102.095 | 1.00 | 16.39 |
| 5650 | O | CYS | B | 159 | 35.158 | 41.671 | 102.743 | 1.00 | 17.26 |
| 5651 | N | THR | B | 160 | 35.147 | 40.023 | 101.236 | 1.00 | 16.17 |
| 5653 | CA | THR | B | 160 | 33.710 | 40.088 | 101.033 | 1.00 | 16.60 |
| 5655 | CB | THR | B | 160 | 33.390 | 40.690 | 99.679 | 1.00 | 17.48 |
| 5657 | OG1 | THR | B | 160 | 33.791 | 39.783 | 98.630 | 1.00 | 18.28 |
| 5659 | CG2 | THR | B | 160 | 34.203 | 41.973 | 99.470 | 1.00 | 19.79 |
| 5663 | C | THR | B | 160 | 33.153 | 38.704 | 101.090 | 1.00 | 16.64 |

FIGURE 3 (Cont.)

| A | B | C | D | E | F | G | H | I | J |
|---|---|---|---|---|---|---|---|---|---|
| 5664 | O | THR | B | 160 | 33.886 | 37.757 | 101.277 | 1.00 | 14.66 |
| 5665 | N | GLN | B | 161 | 31.841 | 38.556 | 100.937 | 1.00 | 16.68 |
| 5667 | CA | GLN | B | 161 | 31.359 | 37.188 | 100.913 | 1.00 | 18.21 |
| 5669 | CB | GLN | B | 161 | 30.220 | 36.852 | 101.886 | 1.00 | 19.79 |
| 5672 | CG | GLN | B | 161 | 29.445 | 37.876 | 102.466 | 1.00 | 20.69 |
| 5675 | CD | GLN | B | 161 | 30.197 | 38.882 | 103.330 | 1.00 | 17.61 |
| 5676 | OE1 | GLN | B | 161 | 30.912 | 38.573 | 104.303 | 1.00 | 22.35 |
| 5677 | NE2 | GLN | B | 161 | 29.999 | 40.105 | 102.985 | 1.00 | 13.41 |
| 5680 | C | GLN | B | 161 | 31.098 | 36.680 | 99.513 | 1.00 | 18.73 |
| 5681 | O | GLN | B | 161 | 30.415 | 35.662 | 99.355 | 1.00 | 20.53 |
| 5682 | N | ASN | B | 162 | 31.712 | 37.315 | 98.521 | 1.00 | 18.63 |
| 5684 | CA | ASN | B | 162 | 31.624 | 36.834 | 97.142 | 1.00 | 19.19 |
| 5686 | CB | ASN | B | 162 | 31.425 | 37.981 | 96.186 | 1.00 | 20.60 |
| 5689 | CG | ASN | B | 162 | 29.934 | 38.268 | 95.967 | 1.00 | 21.63 |
| 5690 | OD1 | ASN | B | 162 | 29.153 | 37.387 | 95.506 | 1.00 | 26.69 |
| 5691 | ND2 | ASN | B | 162 | 29.521 | 39.442 | 96.343 | 1.00 | 24.94 |
| 5694 | C | ASN | B | 162 | 32.829 | 35.916 | 96.889 | 1.00 | 17.43 |
| 5695 | O | ASN | B | 162 | 33.991 | 36.354 | 96.749 | 1.00 | 19.14 |
| 5696 | N | VAL | B | 163 | 32.529 | 34.628 | 96.932 | 1.00 | 14.34 |
| 5698 | CA | VAL | B | 163 | 33.564 | 33.615 | 96.996 | 1.00 | 12.85 |
| 5700 | CB | VAL | B | 163 | 33.121 | 32.387 | 97.834 | 1.00 | 12.66 |
| 5702 | CG1 | VAL | B | 163 | 32.704 | 32.826 | 99.240 | 1.00 | 13.58 |
| 5706 | CG2 | VAL | B | 163 | 32.015 | 31.638 | 97.180 | 1.00 | 14.06 |
| 5710 | C | VAL | B | 163 | 34.054 | 33.163 | 95.633 | 1.00 | 11.50 |
| 5711 | O | VAL | B | 163 | 33.267 | 33.099 | 94.671 | 1.00 | 12.03 |
| 5712 | N | ASN | B | 164 | 35.344 | 32.854 | 95.537 | 1.00 | 10.09 |
| 5714 | CA | ASN | B | 164 | 35.910 | 32.452 | 94.256 | 1.00 | 10.38 |
| 5716 | CB | ASN | B | 164 | 36.623 | 33.630 | 93.587 | 1.00 | 11.24 |
| 5719 | CG | ASN | B | 164 | 37.948 | 33.936 | 94.216 | 1.00 | 13.93 |
| 5720 | OD1 | ASN | B | 164 | 38.037 | 34.064 | 95.411 | 1.00 | 12.67 |
| 5721 | ND2 | ASN | B | 164 | 39.012 | 33.972 | 93.409 | 1.00 | 18.85 |
| 5724 | C | ASN | B | 164 | 36.883 | 31.330 | 94.347 | 1.00 | 9.44 |
| 5725 | O | ASN | B | 164 | 37.464 | 30.937 | 93.337 | 1.00 | 12.04 |
| 5726 | N | HIS | B | 165 | 37.093 | 30.781 | 95.537 | 1.00 | 8.88 |
| 5728 | CA | HIS | B | 165 | 38.139 | 29.774 | 95.683 | 1.00 | 8.02 |
| 5730 | CB | HIS | B | 165 | 39.384 | 30.461 | 96.240 | 1.00 | 8.65 |
| 5733 | CG | HIS | B | 165 | 40.550 | 29.555 | 96.422 | 1.00 | 10.78 |
| 5734 | ND1 | HIS | B | 165 | 41.083 | 28.824 | 95.382 | 1.00 | 15.76 |
| 5736 | CE1 | HIS | B | 165 | 42.105 | 28.112 | 95.830 | 1.00 | 15.67 |
| 5738 | NE2 | HIS | B | 165 | 42.270 | 28.386 | 97.108 | 1.00 | 12.26 |
| 5740 | CD2 | HIS | B | 165 | 41.302 | 29.275 | 97.507 | 1.00 | 12.81 |
| 5742 | C | HIS | B | 165 | 37.690 | 28.678 | 96.639 | 1.00 | 8.33 |
| 5743 | O | HIS | B | 165 | 37.384 | 28.941 | 97.786 | 1.00 | 9.64 |
| 5744 | N | GLY | B | 166 | 37.634 | 27.468 | 96.148 | 1.00 | 7.46 |
| 5746 | CA | GLY | B | 166 | 37.223 | 26.334 | 96.935 | 1.00 | 7.29 |
| 5749 | C | GLY | B | 166 | 38.328 | 25.793 | 97.794 | 1.00 | 7.51 |
| 5750 | O | GLY | B | 166 | 39.429 | 25.578 | 97.330 | 1.00 | 9.21 |
| 5751 | N | VAL | B | 167 | 38.019 | 25.567 | 99.064 | 1.00 | 7.37 |
| 5753 | CA | VAL | B | 167 | 38.962 | 25.031 | 100.054 | 1.00 | 6.65 |
| 5755 | CB | VAL | B | 167 | 39.612 | 26.132 | 100.887 | 1.00 | 6.93 |
| 5757 | CG1 | VAL | B | 167 | 40.495 | 27.016 | 99.966 | 1.00 | 9.91 |

FIGURE 3 (Cont.)

| A | B | C | D | E | F | G | H | I | J |
|---|---|---|---|---|---|---|---|---|---|
| 5761 | CG2 | VAL | B | 167 | 38.556 | 26.939 | 101.587 | 1.00 | 7.95 |
| 5765 | C | VAL | B | 167 | 38.202 | 24.093 | 100.971 | 1.00 | 6.60 |
| 5766 | O | VAL | B | 167 | 37.018 | 23.823 | 100.786 | 1.00 | 6.50 |
| 5767 | N | LEU | B | 168 | 38.900 | 23.550 | 101.965 | 1.00 | 6.10 |
| 5769 | CA | LEU | B | 168 | 38.294 | 22.550 | 102.832 | 1.00 | 5.61 |
| 5771 | CB | LEU | B | 168 | 38.965 | 21.199 | 102.588 | 1.00 | 6.00 |
| 5774 | CG | LEU | B | 168 | 38.386 | 20.031 | 103.353 | 1.00 | 7.01 |
| 5776 | CD1 | LEU | B | 168 | 37.010 | 19.680 | 102.806 | 1.00 | 6.78 |
| 5780 | CD2 | LEU | B | 168 | 39.311 | 18.834 | 103.260 | 1.00 | 8.35 |
| 5784 | C | LEU | B | 168 | 38.495 | 22.949 | 104.279 | 1.00 | 6.09 |
| 5785 | O | LEU | B | 168 | 39.620 | 23.139 | 104.711 | 1.00 | 6.83 |
| 5786 | N | VAL | B | 169 | 37.405 | 23.045 | 105.029 | 1.00 | 5.80 |
| 5788 | CA | VAL | B | 169 | 37.516 | 23.346 | 106.430 | 1.00 | 6.41 |
| 5790 | CB | VAL | B | 169 | 36.251 | 24.017 | 106.967 | 1.00 | 6.62 |
| 5792 | CG1 | VAL | B | 169 | 36.382 | 24.204 | 108.459 | 1.00 | 6.69 |
| 5796 | CG2 | VAL | B | 169 | 36.030 | 25.347 | 106.282 | 1.00 | 8.01 |
| 5800 | C | VAL | B | 169 | 37.725 | 22.013 | 107.127 | 1.00 | 6.07 |
| 5801 | O | VAL | B | 169 | 36.856 | 21.154 | 107.098 | 1.00 | 7.50 |
| 5802 | N | VAL | B | 170 | 38.866 | 21.868 | 107.798 | 1.00 | 6.18 |
| 5804 | CA | VAL | B | 170 | 39.194 | 20.622 | 108.477 | 1.00 | 6.52 |
| 5806 | CB | VAL | B | 170 | 40.532 | 20.020 | 107.999 | 1.00 | 6.54 |
| 5808 | CG1 | VAL | B | 170 | 40.450 | 19.666 | 106.514 | 1.00 | 7.17 |
| 5812 | CG2 | VAL | B | 170 | 41.680 | 20.954 | 108.264 | 1.00 | 8.62 |
| 5816 | C | VAL | B | 170 | 39.239 | 20.772 | 109.965 | 1.00 | 7.13 |
| 5817 | O | VAL | B | 170 | 39.633 | 19.833 | 110.659 | 1.00 | 8.39 |
| 5818 | N | GLY | B | 171 | 38.838 | 21.919 | 110.474 | 1.00 | 6.69 |
| 5820 | CA | GLY | B | 171 | 38.777 | 22.104 | 111.907 | 1.00 | 7.58 |
| 5823 | C | GLY | B | 171 | 38.482 | 23.530 | 112.268 | 1.00 | 7.72 |
| 5824 | O | GLY | B | 171 | 38.166 | 24.370 | 111.426 | 1.00 | 7.68 |
| 5825 | N | TYR | B | 172 | 38.570 | 23.814 | 113.565 | 1.00 | 7.68 |
| 5827 | CA | TYR | B | 172 | 38.370 | 25.154 | 114.064 | 1.00 | 7.26 |
| 5829 | CB | TYR | B | 172 | 36.888 | 25.512 | 114.111 | 1.00 | 7.75 |
| 5832 | CG | TYR | B | 172 | 36.026 | 24.639 | 114.994 | 1.00 | 7.71 |
| 5833 | CD1 | TYR | B | 172 | 36.006 | 24.803 | 116.371 | 1.00 | 9.26 |
| 5835 | CE1 | TYR | B | 172 | 35.219 | 24.048 | 117.154 | 1.00 | 8.67 |
| 5837 | CZ | TYR | B | 172 | 34.430 | 23.091 | 116.610 | 1.00 | 8.96 |
| 5838 | OH | TYR | B | 172 | 33.602 | 22.308 | 117.380 | 1.00 | 9.71 |
| 5840 | CE2 | TYR | B | 172 | 34.398 | 22.903 | 115.248 | 1.00 | 10.07 |
| 5842 | CD2 | TYR | B | 172 | 35.194 | 23.680 | 114.446 | 1.00 | 7.92 |
| 5844 | C | TYR | B | 172 | 39.018 | 25.224 | 115.451 | 1.00 | 7.92 |
| 5845 | O | TYR | B | 172 | 39.287 | 24.204 | 116.065 | 1.00 | 8.32 |
| 5846 | N | GLY | B | 173 | 39.221 | 26.429 | 115.953 | 1.00 | 9.22 |
| 5848 | CA | GLY | B | 173 | 39.844 | 26.612 | 117.239 | 1.00 | 9.98 |
| 5851 | C | GLY | B | 173 | 39.966 | 28.090 | 117.494 | 1.00 | 11.46 |
| 5852 | O | GLY | B | 173 | 39.221 | 28.906 | 116.938 | 1.00 | 9.65 |
| 5853 | N | ASP | B | 174 | 40.891 | 28.427 | 118.377 | 1.00 | 12.30 |
| 5855 | CA | ASP | B | 174 | 41.140 | 29.786 | 118.778 | 1.00 | 14.56 |
| 5857 | CB | ASP | B | 174 | 40.384 | 30.097 | 120.055 | 1.00 | 14.89 |
| 5860 | CG | ASP | B | 174 | 40.640 | 29.054 | 121.154 | 1.00 | 21.20 |
| 5861 | OD1 | ASP | B | 174 | 41.804 | 28.938 | 121.609 | 1.00 | 33.99 |
| 5862 | OD2 | ASP | B | 174 | 39.759 | 28.307 | 121.633 | 1.00 | 30.54 |

FIGURE 3 (Cont.)

| A | B | C | D | E | F | G | H | I | J |
|---|---|---|---|---|---|---|---|---|---|
| 5863 | C | ASP | B | 174 | 42.635 | 29.920 | 119.011 | 1.00 | 15.12 |
| 5864 | O | ASP | B | 174 | 43.322 | 28.961 | 119.420 | 1.00 | 16.70 |
| 5865 | N | LEU | B | 175 | 43.113 | 31.111 | 118.691 | 1.00 | 15.94 |
| 5867 | CA | LEU | B | 175 | 44.498 | 31.482 | 118.885 | 1.00 | 17.52 |
| 5869 | CB | LEU | B | 175 | 45.238 | 31.552 | 117.541 | 1.00 | 17.42 |
| 5872 | CG | LEU | B | 175 | 46.692 | 32.017 | 117.658 | 1.00 | 19.48 |
| 5874 | CD1 | LEU | B | 175 | 47.503 | 31.068 | 118.496 | 1.00 | 21.56 |
| 5878 | CD2 | LEU | B | 175 | 47.342 | 32.214 | 116.290 | 1.00 | 20.43 |
| 5882 | C | LEU | B | 175 | 44.559 | 32.817 | 119.624 | 1.00 | 19.18 |
| 5883 | O | LEU | B | 175 | 44.303 | 33.876 | 119.048 | 1.00 | 20.27 |
| 5884 | N | ASN | B | 176 | 44.842 | 32.764 | 120.918 | 1.00 | 23.16 |
| 5886 | CA | ASN | B | 176 | 44.989 | 34.008 | 121.695 | 1.00 | 24.79 |
| 5888 | CB | ASN | B | 176 | 46.379 | 34.566 | 121.530 | 1.00 | 25.89 |
| 5891 | CG | ASN | B | 176 | 47.334 | 33.645 | 122.178 | 1.00 | 27.62 |
| 5892 | OD1 | ASN | B | 176 | 46.924 | 32.910 | 123.060 | 1.00 | 32.87 |
| 5893 | ND2 | ASN | B | 176 | 48.497 | 33.536 | 121.755 | 1.00 | 30.87 |
| 5896 | C | ASN | B | 176 | 43.837 | 34.985 | 121.530 | 1.00 | 24.96 |
| 5897 | O | ASN | B | 176 | 43.987 | 36.180 | 121.202 | 1.00 | 26.41 |
| 5898 | N | GLY | B | 177 | 42.676 | 34.405 | 121.806 | 1.00 | 25.21 |
| 5900 | CA | GLY | B | 177 | 41.387 | 35.062 | 121.759 | 1.00 | 23.98 |
| 5903 | C | GLY | B | 177 | 40.844 | 35.281 | 120.355 | 1.00 | 23.03 |
| 5904 | O | GLY | B | 177 | 39.887 | 36.038 | 120.164 | 1.00 | 24.16 |
| 5905 | N | ALA | B | 178 | 41.471 | 34.674 | 119.353 | 1.00 | 19.96 |
| 5907 | CA | ALA | B | 178 | 41.022 | 34.887 | 118.000 | 1.00 | 17.59 |
| 5909 | CB | ALA | B | 178 | 42.127 | 35.443 | 117.148 | 1.00 | 17.70 |
| 5913 | C | ALA | B | 178 | 40.550 | 33.567 | 117.430 | 1.00 | 13.89 |
| 5914 | O | ALA | B | 178 | 41.357 | 32.701 | 117.138 | 1.00 | 12.51 |
| 5915 | N | GLU | B | 179 | 39.238 | 33.448 | 117.242 | 1.00 | 12.04 |
| 5917 | CA | GLU | B | 179 | 38.643 | 32.230 | 116.758 | 1.00 | 10.60 |
| 5919 | CB | GLU | B | 179 | 37.142 | 32.246 | 116.980 | 1.00 | 12.11 |
| 5922 | CG | GLU | B | 179 | 36.786 | 32.332 | 118.460 | 1.00 | 15.19 |
| 5925 | CD | GLU | B | 179 | 35.312 | 32.201 | 118.720 | 1.00 | 19.64 |
| 5926 | OE1 | GLU | B | 179 | 34.924 | 31.215 | 119.384 | 1.00 | 22.49 |
| 5927 | OE2 | GLU | B | 179 | 34.557 | 33.109 | 118.294 | 1.00 | 23.85 |
| 5928 | C | GLU | B | 179 | 38.979 | 32.072 | 115.290 | 1.00 | 9.89 |
| 5929 | O | GLU | B | 179 | 39.051 | 33.055 | 114.529 | 1.00 | 9.14 |
| 5930 | N | TYR | B | 180 | 39.159 | 30.827 | 114.881 | 1.00 | 8.60 |
| 5932 | CA | TYR | B | 180 | 39.541 | 30.563 | 113.504 | 1.00 | 8.61 |
| 5934 | CB | TYR | B | 180 | 41.088 | 30.438 | 113.373 | 1.00 | 9.24 |
| 5937 | CG | TYR | B | 180 | 41.744 | 29.268 | 114.136 | 1.00 | 9.54 |
| 5938 | CD1 | TYR | B | 180 | 41.738 | 27.984 | 113.626 | 1.00 | 8.66 |
| 5940 | CE1 | TYR | B | 180 | 42.332 | 26.893 | 114.330 | 1.00 | 13.71 |
| 5942 | CZ | TYR | B | 180 | 43.027 | 27.102 | 115.546 | 1.00 | 16.98 |
| 5943 | OH | TYR | B | 180 | 43.597 | 26.048 | 116.253 | 1.00 | 22.27 |
| 5945 | CE2 | TYR | B | 180 | 43.014 | 28.369 | 116.092 | 1.00 | 15.79 |
| 5947 | CD2 | TYR | B | 180 | 42.413 | 29.456 | 115.380 | 1.00 | 12.99 |
| 5949 | C | TYR | B | 180 | 38.898 | 29.291 | 112.974 | 1.00 | 7.75 |
| 5950 | O | TYR | B | 180 | 38.476 | 28.430 | 113.724 | 1.00 | 7.96 |
| 5951 | N | TRP | B | 181 | 38.818 | 29.229 | 111.638 | 1.00 | 7.07 |
| 5953 | CA | TRP | B | 181 | 38.552 | 28.027 | 110.878 | 1.00 | 7.09 |
| 5955 | CB | TRP | B | 181 | 37.713 | 28.364 | 109.645 | 1.00 | 6.52 |

FIGURE 3 (Cont.)

| A | B | C | D | E | F | G | H | I | J |
|---|---|---|---|---|---|---|---|---|---|
| 5958 | CG | TRP | B | 181 | 36.353 | 28.817 | 109.990 | 1.00 | 6.60 |
| 5959 | CD1 | TRP | B | 181 | 35.843 | 30.076 | 109.831 | 1.00 | 6.36 |
| 5961 | NE1 | TRP | B | 181 | 34.534 | 30.111 | 110.240 | 1.00 | 7.27 |
| 5963 | CE2 | TRP | B | 181 | 34.174 | 28.874 | 110.690 | 1.00 | 7.07 |
| 5964 | CD2 | TRP | B | 181 | 35.291 | 28.026 | 110.533 | 1.00 | 6.65 |
| 5965 | CE3 | TRP | B | 181 | 35.179 | 26.706 | 110.944 | 1.00 | 8.43 |
| 5967 | CZ3 | TRP | B | 181 | 33.971 | 26.281 | 111.484 | 1.00 | 7.11 |
| 5969 | CH2 | TRP | B | 181 | 32.899 | 27.134 | 111.603 | 1.00 | 8.05 |
| 5971 | CZ2 | TRP | B | 181 | 32.975 | 28.429 | 111.235 | 1.00 | 6.73 |
| 5973 | C | TRP | B | 181 | 39.889 | 27.515 | 110.372 | 1.00 | 6.50 |
| 5974 | O | TRP | B | 181 | 40.695 | 28.286 | 109.884 | 1.00 | 6.99 |
| 5975 | N | LEU | B | 182 | 40.122 | 26.220 | 110.481 | 1.00 | 5.89 |
| 5977 | CA | LEU | B | 182 | 41.347 | 25.596 | 109.970 | 1.00 | 6.62 |
| 5979 | CB | LEU | B | 182 | 41.769 | 24.413 | 110.831 | 1.00 | 7.19 |
| 5982 | CG | LEU | B | 182 | 43.012 | 23.658 | 110.369 | 1.00 | 9.61 |
| 5984 | CD1 | LEU | B | 182 | 44.194 | 24.571 | 110.280 | 1.00 | 10.31 |
| 5988 | CD2 | LEU | B | 182 | 43.274 | 22.508 | 111.308 | 1.00 | 10.51 |
| 5992 | C | LEU | B | 182 | 41.073 | 25.129 | 108.553 | 1.00 | 6.29 |
| 5993 | O | LEU | B | 182 | 40.240 | 24.239 | 108.353 | 1.00 | 6.93 |
| 5994 | N | VAL | B | 183 | 41.755 | 25.745 | 107.587 | 1.00 | 6.45 |
| 5996 | CA | VAL | B | 183 | 41.461 | 25.502 | 106.180 | 1.00 | 7.13 |
| 5998 | CB | VAL | B | 183 | 41.122 | 26.826 | 105.515 | 1.00 | 6.74 |
| 6000 | CG1 | VAL | B | 183 | 40.953 | 26.682 | 104.013 | 1.00 | 9.42 |
| 6004 | CG2 | VAL | B | 183 | 39.868 | 27.455 | 106.177 | 1.00 | 8.63 |
| 6008 | C | VAL | B | 183 | 42.611 | 24.885 | 105.434 | 1.00 | 6.75 |
| 6009 | O | VAL | B | 183 | 43.731 | 25.390 | 105.512 | 1.00 | 7.21 |
| 6010 | N | LYS | B | 184 | 42.320 | 23.791 | 104.743 | 1.00 | 6.74 |
| 6012 | CA | LYS | B | 184 | 43.269 | 23.118 | 103.881 | 1.00 | 6.51 |
| 6014 | CB | LYS | B | 184 | 42.967 | 21.630 | 103.809 | 1.00 | 6.94 |
| 6017 | CG | LYS | B | 184 | 44.015 | 20.831 | 103.053 | 1.00 | 8.30 |
| 6020 | CD | LYS | B | 184 | 43.559 | 19.421 | 102.814 | 1.00 | 9.04 |
| 6023 | CE | LYS | B | 184 | 44.704 | 18.562 | 102.306 | 1.00 | 8.99 |
| 6026 | NZ | LYS | B | 184 | 44.202 | 17.289 | 101.712 | 1.00 | 11.07 |
| 6030 | C | LYS | B | 184 | 43.131 | 23.728 | 102.483 | 1.00 | 7.54 |
| 6031 | O | LYS | B | 184 | 42.067 | 23.700 | 101.914 | 1.00 | 6.69 |
| 6032 | N | ASN | B | 185 | 44.198 | 24.287 | 101.964 | 1.00 | 7.67 |
| 6034 | CA | ASN | B | 185 | 44.210 | 24.840 | 100.617 | 1.00 | 8.28 |
| 6036 | CB | ASN | B | 185 | 44.973 | 26.163 | 100.637 | 1.00 | 8.39 |
| 6039 | CG | ASN | B | 185 | 44.698 | 27.061 | 99.448 | 1.00 | 9.11 |
| 6040 | OD1 | ASN | B | 185 | 43.876 | 26.756 | 98.600 | 1.00 | 11.82 |
| 6041 | ND2 | ASN | B | 185 | 45.441 | 28.163 | 99.367 | 1.00 | 11.45 |
| 6044 | C | ASN | B | 185 | 44.857 | 23.821 | 99.690 | 1.00 | 8.32 |
| 6045 | O | ASN | B | 185 | 45.294 | 22.778 | 100.121 | 1.00 | 9.99 |
| 6046 | N | SER | B | 186 | 44.867 | 24.125 | 98.400 | 1.00 | 7.52 |
| 6048 | CA | SER | B | 186 | 45.478 | 23.269 | 97.397 | 1.00 | 7.63 |
| 6050 | CB | SER | B | 186 | 44.422 | 22.693 | 96.460 | 1.00 | 8.31 |
| 6053 | OG | SER | B | 186 | 43.592 | 23.694 | 95.916 | 1.00 | 10.44 |
| 6055 | C | SER | B | 186 | 46.508 | 24.055 | 96.599 | 1.00 | 8.21 |
| 6056 | O | SER | B | 186 | 46.619 | 23.897 | 95.363 | 1.00 | 9.13 |
| 6057 | N | TRP | B | 187 | 47.271 | 24.882 | 97.308 | 1.00 | 7.49 |
| 6059 | CA | TRP | B | 187 | 48.358 | 25.657 | 96.726 | 1.00 | 8.01 |

FIGURE 3 (Cont.)

| A | B | C | D | E | F | G | H | I | J |
|---|---|---|---|---|---|---|---|---|---|
| 6061 | CB | TRP | B | 187 | 48.211 | 27.120 | 97.145 | 1.00 | 8.80 |
| 6064 | CG | TRP | B | 187 | 47.116 | 27.865 | 96.436 | 1.00 | 8.97 |
| 6065 | CD1 | TRP | B | 187 | 46.265 | 27.392 | 95.470 | 1.00 | 11.08 |
| 6067 | NE1 | TRP | B | 187 | 45.420 | 28.394 | 95.053 | 1.00 | 13.79 |
| 6069 | CE2 | TRP | B | 187 | 45.706 | 29.534 | 95.755 | 1.00 | 13.15 |
| 6070 | CD2 | TRP | B | 187 | 46.767 | 29.234 | 96.631 | 1.00 | 10.02 |
| 6071 | CE3 | TRP | B | 187 | 47.215 | 30.237 | 97.498 | 1.00 | 12.13 |
| 6073 | CZ3 | TRP | B | 187 | 46.639 | 31.477 | 97.415 | 1.00 | 12.53 |
| 6075 | CH2 | TRP | B | 187 | 45.610 | 31.740 | 96.536 | 1.00 | 12.01 |
| 6077 | CZ2 | TRP | B | 187 | 45.115 | 30.783 | 95.705 | 1.00 | 14.46 |
| 6079 | C | TRP | B | 187 | 49.721 | 25.099 | 97.128 | 1.00 | 9.54 |
| 6080 | O | TRP | B | 187 | 50.727 | 25.799 | 97.128 | 1.00 | 10.61 |
| 6081 | N | GLY | B | 188 | 49.744 | 23.825 | 97.486 | 1.00 | 9.77 |
| 6083 | CA | GLY | B | 188 | 50.979 | 23.166 | 97.862 | 1.00 | 10.92 |
| 6086 | C | GLY | B | 188 | 51.372 | 23.383 | 99.292 | 1.00 | 12.23 |
| 6087 | O | GLY | B | 188 | 50.809 | 24.218 | 100.004 | 1.00 | 11.00 |
| 6088 | N | HIS | B | 189 | 52.382 | 22.640 | 99.711 | 1.00 | 14.93 |
| 6090 | CA | HIS | B | 189 | 52.794 | 22.664 | 101.101 | 1.00 | 17.52 |
| 6092 | CB | HIS | B | 189 | 53.572 | 21.393 | 101.459 | 1.00 | 19.26 |
| 6095 | CG | HIS | B | 189 | 54.838 | 21.226 | 100.689 | 1.00 | 23.21 |
| 6096 | ND1 | HIS | B | 189 | 55.016 | 20.221 | 99.766 | 1.00 | 30.10 |
| 6098 | CE1 | HIS | B | 189 | 56.228 | 20.315 | 99.250 | 1.00 | 29.61 |
| 6100 | NE2 | HIS | B | 189 | 56.840 | 21.345 | 99.804 | 1.00 | 30.15 |
| 6102 | CD2 | HIS | B | 189 | 55.991 | 21.931 | 100.710 | 1.00 | 27.77 |
| 6104 | C | HIS | B | 189 | 53.567 | 23.901 | 101.498 | 1.00 | 18.56 |
| 6105 | O | HIS | B | 189 | 53.820 | 24.081 | 102.692 | 1.00 | 20.82 |
| 6106 | N | ASN | B | 190 | 53.961 | 24.742 | 100.544 | 1.00 | 18.78 |
| 6108 | CA | ASN | B | 190 | 54.701 | 25.967 | 100.867 | 1.00 | 19.85 |
| 6110 | CB | ASN | B | 190 | 55.752 | 26.306 | 99.802 | 1.00 | 20.99 |
| 6113 | CG | ASN | B | 190 | 56.821 | 25.234 | 99.679 | 1.00 | 24.70 |
| 6114 | OD1 | ASN | B | 190 | 57.206 | 24.849 | 98.572 | 1.00 | 30.00 |
| 6115 | ND2 | ASN | B | 190 | 57.288 | 24.733 | 100.811 | 1.00 | 26.39 |
| 6118 | C | ASN | B | 190 | 53.799 | 27.161 | 101.116 | 1.00 | 18.84 |
| 6119 | O | ASN | B | 190 | 54.261 | 28.220 | 101.555 | 1.00 | 21.45 |
| 6120 | N | PHE | B | 191 | 52.507 | 27.008 | 100.849 | 1.00 | 15.51 |
| 6122 | CA | PHE | B | 191 | 51.591 | 28.107 | 101.082 | 1.00 | 13.39 |
| 6124 | CB | PHE | B | 191 | 50.313 | 27.926 | 100.282 | 1.00 | 12.97 |
| 6127 | CG | PHE | B | 191 | 49.208 | 28.833 | 100.724 | 1.00 | 11.32 |
| 6128 | CD1 | PHE | B | 191 | 48.234 | 28.374 | 101.569 | 1.00 | 12.24 |
| 6130 | CE1 | PHE | B | 191 | 47.208 | 29.226 | 102.002 | 1.00 | 13.55 |
| 6132 | CZ | PHE | B | 191 | 47.199 | 30.528 | 101.583 | 1.00 | 14.09 |
| 6134 | CE2 | PHE | B | 191 | 48.155 | 31.001 | 100.765 | 1.00 | 15.47 |
| 6136 | CD2 | PHE | B | 191 | 49.182 | 30.170 | 100.333 | 1.00 | 15.53 |
| 6138 | C | PHE | B | 191 | 51.209 | 28.174 | 102.548 | 1.00 | 12.51 |
| 6139 | O | PHE | B | 191 | 50.906 | 27.158 | 103.153 | 1.00 | 11.67 |
| 6140 | N | GLY | B | 192 | 51.198 | 29.373 | 103.116 | 1.00 | 11.05 |
| 6142 | CA | GLY | B | 192 | 50.723 | 29.537 | 104.475 | 1.00 | 10.23 |
| 6145 | C | GLY | B | 192 | 51.400 | 28.648 | 105.478 | 1.00 | 10.04 |
| 6146 | O | GLY | B | 192 | 52.622 | 28.553 | 105.517 | 1.00 | 10.71 |
| 6147 | N | GLU | B | 193 | 50.588 | 28.022 | 106.324 | 1.00 | 9.21 |
| 6149 | CA | GLU | B | 193 | 51.080 | 27.161 | 107.376 | 1.00 | 9.64 |

FIGURE 3 (Cont.)

| A | B | C | D | E | F | G | H | I | J |
|---|---|---|---|---|---|---|---|---|---|
| 6151 | CB | GLU | B | 193 | 50.161 | 27.254 | 108.603 | 1.00 | 9.93 |
| 6154 | CG | GLU | B | 193 | 50.163 | 28.648 | 109.212 | 1.00 | 10.46 |
| 6157 | CD | GLU | B | 193 | 49.321 | 28.814 | 110.460 | 1.00 | 13.61 |
| 6158 | OE1 | GLU | B | 193 | 48.270 | 28.150 | 110.584 | 1.00 | 13.90 |
| 6159 | OE2 | GLU | B | 193 | 49.687 | 29.663 | 111.305 | 1.00 | 13.61 |
| 6160 | C | GLU | B | 193 | 51.185 | 25.756 | 106.827 | 1.00 | 9.07 |
| 6161 | O | GLU | B | 193 | 50.346 | 24.883 | 107.066 | 1.00 | 8.71 |
| 6162 | N | GLU | B | 194 | 52.206 | 25.558 | 106.017 | 1.00 | 9.53 |
| 6164 | CA | GLU | B | 194 | 52.458 | 24.261 | 105.396 | 1.00 | 9.76 |
| 6166 | CB | GLU | B | 194 | 53.031 | 23.286 | 106.397 | 1.00 | 10.77 |
| 6169 | CG | GLU | B | 194 | 54.425 | 23.745 | 106.795 | 1.00 | 13.32 |
| 6172 | CD | GLU | B | 194 | 54.995 | 22.943 | 107.934 | 1.00 | 16.94 |
| 6173 | OE1 | GLU | B | 194 | 55.872 | 22.095 | 107.676 | 1.00 | 20.88 |
| 6174 | OE2 | GLU | B | 194 | 54.556 | 23.160 | 109.083 | 1.00 | 20.48 |
| 6175 | C | GLU | B | 194 | 51.240 | 23.722 | 104.677 | 1.00 | 9.20 |
| 6176 | O | GLU | B | 194 | 50.919 | 22.535 | 104.744 | 1.00 | 10.36 |
| 6177 | N | GLY | B | 195 | 50.587 | 24.614 | 103.954 | 1.00 | 8.73 |
| 6179 | CA | GLY | B | 195 | 49.467 | 24.271 | 103.107 | 1.00 | 8.32 |
| 6182 | C | GLY | B | 195 | 48.120 | 24.678 | 103.638 | 1.00 | 7.58 |
| 6183 | O | GLY | B | 195 | 47.118 | 24.600 | 102.914 | 1.00 | 8.18 |
| 6184 | N | TYR | B | 196 | 48.093 | 25.126 | 104.890 | 1.00 | 7.53 |
| 6186 | CA | TYR | B | 196 | 46.878 | 25.464 | 105.599 | 1.00 | 8.13 |
| 6188 | CB | TYR | B | 196 | 46.843 | 24.700 | 106.932 | 1.00 | 7.32 |
| 6191 | CG | TYR | B | 196 | 46.661 | 23.229 | 106.695 | 1.00 | 7.26 |
| 6192 | CD1 | TYR | B | 196 | 47.734 | 22.424 | 106.339 | 1.00 | 5.84 |
| 6194 | CE1 | TYR | B | 196 | 47.565 | 21.078 | 106.107 | 1.00 | 6.72 |
| 6196 | CZ | TYR | B | 196 | 46.298 | 20.546 | 106.163 | 1.00 | 6.85 |
| 6197 | OH | TYR | B | 196 | 46.093 | 19.210 | 105.922 | 1.00 | 9.01 |
| 6199 | CE2 | TYR | B | 196 | 45.231 | 21.325 | 106.539 | 1.00 | 7.15 |
| 6201 | CD2 | TYR | B | 196 | 45.403 | 22.642 | 106.797 | 1.00 | 8.02 |
| 6203 | C | TYR | B | 196 | 46.811 | 26.930 | 105.881 | 1.00 | 7.40 |
| 6204 | O | TYR | B | 196 | 47.825 | 27.630 | 105.903 | 1.00 | 7.75 |
| 6205 | N | ILE | B | 197 | 45.595 | 27.410 | 106.115 | 1.00 | 6.80 |
| 6207 | CA | ILE | B | 197 | 45.395 | 28.791 | 106.499 | 1.00 | 6.47 |
| 6209 | CB | ILE | B | 197 | 45.033 | 29.727 | 105.303 | 1.00 | 6.64 |
| 6211 | CG1 | ILE | B | 197 | 44.677 | 31.125 | 105.786 | 1.00 | 6.46 |
| 6214 | CD1 | ILE | B | 197 | 44.552 | 32.110 | 104.681 | 1.00 | 9.47 |
| 6218 | CG2 | ILE | B | 197 | 43.888 | 29.162 | 104.494 | 1.00 | 8.38 |
| 6222 | C | ILE | B | 197 | 44.356 | 28.798 | 107.581 | 1.00 | 7.58 |
| 6223 | O | ILE | B | 197 | 43.362 | 28.102 | 107.504 | 1.00 | 8.26 |
| 6224 | N | ARG | B | 198 | 44.599 | 29.549 | 108.639 | 1.00 | 7.17 |
| 6226 | CA | ARG | B | 198 | 43.602 | 29.693 | 109.687 | 1.00 | 7.14 |
| 6228 | CB | ARG | B | 198 | 44.288 | 29.670 | 111.050 | 1.00 | 8.16 |
| 6231 | CG | ARG | B | 198 | 44.727 | 28.302 | 111.416 | 1.00 | 9.63 |
| 6234 | CD | ARG | B | 198 | 45.306 | 28.125 | 112.769 | 1.00 | 11.17 |
| 6237 | NE | ARG | B | 198 | 46.603 | 28.731 | 112.890 | 1.00 | 13.37 |
| 6239 | CZ | ARG | B | 198 | 47.314 | 28.674 | 113.998 | 1.00 | 18.33 |
| 6240 | NH1 | ARG | B | 198 | 46.871 | 27.970 | 115.042 | 1.00 | 22.48 |
| 6243 | NH2 | ARG | B | 198 | 48.514 | 29.260 | 114.043 | 1.00 | 17.78 |
| 6246 | C | ARG | B | 198 | 42.881 | 31.006 | 109.402 | 1.00 | 8.08 |
| 6247 | O | ARG | B | 198 | 43.505 | 32.042 | 109.276 | 1.00 | 9.33 |

FIGURE 3 (Cont.)

| A | B | C | D | E | F | G | H | I | J |
|---|---|---|---|---|---|---|---|---|---|
| 6248 | N | MET | B | 199 | 41.582 | 30.936 | 109.175 | 1.00 | 7.33 |
| 6250 | CA | MET | B | 199 | 40.792 | 32.082 | 108.759 | 1.00 | 7.98 |
| 6252 | CB | MET | B | 199 | 40.034 | 31.726 | 107.487 | 1.00 | 8.23 |
| 6255 | CG | MET | B | 199 | 40.942 | 31.351 | 106.346 | 1.00 | 10.02 |
| 6258 | SD | MET | B | 199 | 40.132 | 31.141 | 104.757 | 1.00 | 11.68 |
| 6259 | CE | MET | B | 199 | 39.516 | 32.850 | 104.490 | 1.00 | 11.24 |
| 6263 | C | MET | B | 199 | 39.818 | 32.505 | 109.821 | 1.00 | 7.71 |
| 6264 | O | MET | B | 199 | 39.229 | 31.676 | 110.508 | 1.00 | 8.46 |
| 6265 | N | ALA | B | 200 | 39.632 | 33.806 | 109.955 | 1.00 | 7.99 |
| 6267 | CA | ALA | B | 200 | 38.822 | 34.326 | 111.041 | 1.00 | 7.95 |
| 6269 | CB | ALA | B | 200 | 38.722 | 35.831 | 110.954 | 1.00 | 8.38 |
| 6273 | C | ALA | B | 200 | 37.438 | 33.726 | 111.098 | 1.00 | 8.08 |
| 6274 | O | ALA | B | 200 | 36.748 | 33.645 | 110.092 | 1.00 | 8.33 |
| 6275 | N | ARG | B | 201 | 37.043 | 33.311 | 112.297 | 1.00 | 7.98 |
| 6277 | CA | ARG | B | 201 | 35.764 | 32.674 | 112.577 | 1.00 | 7.48 |
| 6279 | CB | ARG | B | 201 | 35.990 | 31.306 | 113.221 | 1.00 | 8.59 |
| 6282 | CG | ARG | B | 201 | 34.793 | 30.534 | 113.621 | 1.00 | 7.84 |
| 6285 | CD | ARG | B | 201 | 35.111 | 29.079 | 113.972 | 1.00 | 8.20 |
| 6288 | NE | ARG | B | 201 | 35.940 | 28.882 | 115.149 | 1.00 | 8.24 |
| 6290 | CZ | ARG | B | 201 | 35.476 | 28.700 | 116.372 | 1.00 | 10.90 |
| 6291 | NH1 | ARG | B | 201 | 34.184 | 28.683 | 116.604 | 1.00 | 11.14 |
| 6294 | NH2 | ARG | B | 201 | 36.341 | 28.510 | 117.335 | 1.00 | 9.17 |
| 6297 | C | ARG | B | 201 | 34.945 | 33.577 | 113.493 | 1.00 | 9.02 |
| 6298 | O | ARG | B | 201 | 35.491 | 34.271 | 114.362 | 1.00 | 10.06 |
| 6299 | N | ASN | B | 201 | 33.641 | 33.529 | 113.293 | 1.00 | 9.73 |
| 6301 | CA | ASN | B | 202 | 32.703 | 34.336 | 114.066 | 1.00 | 10.02 |
| 6303 | CB | ASN | B | 202 | 32.626 | 33.888 | 115.554 | 1.00 | 10.89 |
| 6306 | CG | ASN | B | 202 | 32.101 | 32.453 | 115.704 | 1.00 | 14.32 |
| 6307 | OD1 | ASN | B | 202 | 31.303 | 32.014 | 114.895 | 1.00 | 18.88 |
| 6308 | ND2 | ASN | B | 202 | 32.539 | 31.729 | 116.726 | 1.00 | 16.87 |
| 6311 | C | ASN | B | 202 | 32.979 | 35.817 | 113.899 | 1.00 | 10.95 |
| 6312 | O | ASN | B | 202 | 32.809 | 36.594 | 114.843 | 1.00 | 12.12 |
| 6313 | N | LYS | B | 203 | 33.398 | 36.204 | 112.692 | 1.00 | 10.42 |
| 6315 | CA | LYS | B | 203 | 33.651 | 37.587 | 112.334 | 1.00 | 11.19 |
| 6317 | CB | LYS | B | 203 | 35.135 | 37.834 | 112.084 | 1.00 | 12.43 |
| 6320 | CG | LYS | B | 203 | 35.975 | 37.653 | 113.336 | 1.00 | 15.15 |
| 6323 | CD | LYS | B | 203 | 35.945 | 38.858 | 114.265 | 1.00 | 18.00 |
| 6326 | CE | LYS | B | 203 | 36.601 | 38.516 | 115.606 | 1.00 | 21.86 |
| 6329 | NZ | LYS | B | 203 | 36.870 | 39.722 | 116.429 | 1.00 | 24.73 |
| 6333 | C | LYS | B | 203 | 32.793 | 37.985 | 111.120 | 1.00 | 10.43 |
| 6334 | O | LYS | B | 203 | 33.280 | 38.536 | 110.140 | 1.00 | 13.09 |
| 6335 | N | GLY | B | 204 | 31.516 | 37.670 | 111.195 | 1.00 | 10.71 |
| 6337 | CA | GLY | B | 204 | 30.568 | 38.087 | 110.179 | 1.00 | 9.73 |
| 6340 | C | GLY | B | 204 | 30.758 | 37.394 | 108.856 | 1.00 | 9.79 |
| 6341 | O | GLY | B | 204 | 30.698 | 38.048 | 107.805 | 1.00 | 10.48 |
| 6342 | N | ASN | B | 205 | 30.947 | 36.084 | 108.895 | 1.00 | 8.78 |
| 6344 | CA | ASN | B | 205 | 31.118 | 35.306 | 107.663 | 1.00 | 9.14 |
| 6346 | CB | ASN | B | 205 | 29.816 | 35.287 | 106.847 | 1.00 | 8.57 |
| 6349 | CG | ASN | B | 205 | 29.871 | 34.356 | 105.656 | 1.00 | 9.85 |
| 6350 | OD1 | ASN | B | 205 | 30.714 | 33.457 | 105.606 | 1.00 | 10.55 |
| 6351 | ND2 | ASN | B | 205 | 28.993 | 34.588 | 104.678 | 1.00 | 9.83 |

FIGURE 3 (Cont.)

| A | B | C | D | E | F | G | H | I | J |
|---|---|---|---|---|---|---|---|---|---|
| 6354 | C | ASN | B | 205 | 32.257 | 35.907 | 106.863 | 1.00 | 8.79 |
| 6355 | O | ASN | B | 205 | 32.157 | 36.192 | 105.662 | 1.00 | 8.32 |
| 6356 | N | HIS | B | 206 | 33.390 | 36.022 | 107.527 | 1.00 | 8.97 |
| 6358 | CA | HIS | B | 206 | 34.562 | 36.629 | 106.946 | 1.00 | 9.36 |
| 6360 | CB | HIS | B | 206 | 35.685 | 36.706 | 107.987 | 1.00 | 9.58 |
| 6363 | CG | HIS | B | 206 | 36.709 | 37.718 | 107.620 | 1.00 | 12.39 |
| 6364 | ND1 | HIS | B | 206 | 37.991 | 37.377 | 107.263 | 1.00 | 16.98 |
| 6366 | CE1 | HIS | B | 206 | 38.649 | 38.469 | 106.928 | 1.00 | 11.60 |
| 6368 | NE2 | HIS | B | 206 | 37.842 | 39.504 | 107.058 | 1.00 | 16.78 |
| 6370 | CD2 | HIS | B | 206 | 36.609 | 39.059 | 107.462 | 1.00 | 13.69 |
| 6372 | C | HIS | B | 206 | 35.015 | 35.885 | 105.718 | 1.00 | 9.31 |
| 6373 | O | HIS | B | 206 | 35.164 | 34.675 | 105.738 | 1.00 | 9.77 |
| 6374 | N | CYS | B | 206 | 35.224 | 36.627 | 104.637 | 1.00 | 9.31 |
| 6376 | CA | CYS | B | 207 | 35.652 | 36.073 | 103.361 | 1.00 | 10.32 |
| 6378 | CB | CYS | B | 207 | 37.034 | 35.443 | 103.460 | 1.00 | 10.86 |
| 6381 | SG | CYS | B | 207 | 38.348 | 36.657 | 103.762 | 1.00 | 15.14 |
| 6382 | C | CYS | B | 207 | 34.667 | 35.088 | 102.805 | 1.00 | 8.76 |
| 6383 | O | CYS | B | 207 | 35.011 | 34.317 | 101.912 | 1.00 | 8.20 |
| 6384 | N | GLY | B | 208 | 33.433 | 35.115 | 103.297 | 1.00 | 7.91 |
| 6386 | CA | GLY | B | 208 | 32.406 | 34.217 | 102.775 | 1.00 | 7.40 |
| 6389 | C | GLY | B | 208 | 32.603 | 32.747 | 103.107 | 1.00 | 7.54 |
| 6390 | O | GLY | B | 208 | 32.037 | 31.862 | 102.490 | 1.00 | 8.17 |
| 6391 | N | ILE | B | 209 | 33.398 | 32.476 | 104.126 | 1.00 | 8.18 |
| 6393 | CA | ILE | B | 209 | 33.712 | 31.097 | 104.439 | 1.00 | 8.78 |
| 6395 | CB | ILE | B | 209 | 34.717 | 31.038 | 105.588 | 1.00 | 9.19 |
| 6397 | CG1 | ILE | B | 209 | 35.228 | 29.592 | 105.723 | 1.00 | 11.64 |
| 6400 | CD1 | ILE | B | 209 | 36.618 | 29.494 | 106.171 | 1.00 | 12.80 |
| 6404 | CG2 | ILE | B | 209 | 34.102 | 31.548 | 106.878 | 1.00 | 10.66 |
| 6408 | C | ILE | B | 209 | 32.479 | 30.221 | 104.693 | 1.00 | 8.02 |
| 6409 | O | ILE | B | 209 | 32.464 | 29.036 | 104.334 | 1.00 | 7.30 |
| 6410 | N | ALA | B | 210 | 31.429 | 30.780 | 105.285 | 1.00 | 7.38 |
| 6412 | CA | ALA | B | 210 | 30.201 | 30.046 | 105.509 | 1.00 | 7.87 |
| 6414 | CB | ALA | B | 210 | 29.674 | 30.319 | 106.921 | 1.00 | 8.78 |
| 6418 | C | ALA | B | 210 | 29.136 | 30.362 | 104.478 | 1.00 | 7.92 |
| 6419 | O | ALA | B | 210 | 27.971 | 30.007 | 104.685 | 1.00 | 9.05 |
| 6420 | N | SER | B | 211 | 29.510 | 30.982 | 103.360 | 1.00 | 6.97 |
| 6422 | CA | SER | B | 211 | 28.513 | 31.279 | 102.340 | 1.00 | 8.47 |
| 6424 | CB | SER | B | 211 | 29.114 | 32.218 | 101.316 | 1.00 | 7.74 |
| 6427 | OG | SER | B | 211 | 29.265 | 33.533 | 101.848 | 1.00 | 8.06 |
| 6429 | C | SER | B | 211 | 27.970 | 30.016 | 101.677 | 1.00 | 8.53 |
| 6430 | O | SER | B | 211 | 26.744 | 29.822 | 101.620 | 1.00 | 9.33 |
| 6431 | N | PHE | B | 212 | 28.856 | 29.148 | 101.203 | 1.00 | 8.26 |
| 6433 | CA | PHE | B | 212 | 28.425 | 27.984 | 100.461 | 1.00 | 8.97 |
| 6435 | CB | PHE | B | 212 | 28.614 | 28.246 | 98.979 | 1.00 | 9.56 |
| 6438 | CG | PHE | B | 212 | 27.776 | 29.395 | 98.473 | 1.00 | 11.11 |
| 6439 | CD1 | PHE | B | 212 | 28.340 | 30.628 | 98.234 | 1.00 | 11.91 |
| 6441 | CE1 | PHE | B | 212 | 27.553 | 31.693 | 97.786 | 1.00 | 13.66 |
| 6443 | CZ | PHE | B | 212 | 26.200 | 31.515 | 97.613 | 1.00 | 15.69 |
| 6445 | CE2 | PHE | B | 212 | 25.622 | 30.283 | 97.876 | 1.00 | 15.67 |
| 6447 | CD2 | PHE | B | 212 | 26.412 | 29.234 | 98.312 | 1.00 | 13.06 |
| 6449 | C | PHE | B | 212 | 29.162 | 26.729 | 100.890 | 1.00 | 8.20 |

FIGURE 3 (Cont.)

| A | B | C | D | E | F | G | H | I | J |
|---|---|---|---|---|---|---|---|---|---|
| 6450 | O | PHE | B | 212 | 29.967 | 26.194 | 100.157 | 1.00 | 9.55 |
| 6451 | N | PRO | B | 213 | 28.840 | 26.235 | 102.067 | 1.00 | 7.58 |
| 6452 | CA | PRO | B | 213 | 29.467 | 25.028 | 102.573 | 1.00 | 7.51 |
| 6454 | CB | PRO | B | 213 | 29.381 | 25.219 | 104.100 | 1.00 | 7.85 |
| 6457 | CG | PRO | B | 213 | 28.799 | 26.602 | 104.314 | 1.00 | 8.37 |
| 6460 | CD | PRO | B | 213 | 27.978 | 26.838 | 103.091 | 1.00 | 7.33 |
| 6463 | C | PRO | B | 213 | 28.687 | 23.803 | 102.150 | 1.00 | 7.29 |
| 6464 | O | PRO | B | 213 | 27.458 | 23.840 | 102.094 | 1.00 | 8.78 |
| 6465 | N | SER | B | 214 | 29.388 | 22.716 | 101.906 | 1.00 | 7.32 |
| 6467 | CA | SER | B | 214 | 28.730 | 21.454 | 101.622 | 1.00 | 8.06 |
| 6469 | CB | SER | B | 214 | 28.403 | 21.347 | 100.149 | 1.00 | 8.21 |
| 6472 | OG | SER | B | 214 | 29.575 | 21.438 | 99.349 | 1.00 | 9.81 |
| 6474 | C | SER | B | 214 | 29.615 | 20.302 | 102.029 | 1.00 | 7.59 |
| 6475 | O | SER | B | 214 | 30.833 | 20.443 | 102.149 | 1.00 | 7.85 |
| 6476 | N | TYR | B | 215 | 29.003 | 19.152 | 102.241 | 1.00 | 8.34 |
| 6478 | CA | TYR | B | 215 | 29.761 | 17.946 | 102.557 | 1.00 | 8.50 |
| 6480 | CB | TYR | B | 215 | 30.026 | 17.772 | 104.056 | 1.00 | 8.96 |
| 6483 | CG | TYR | B | 215 | 28.795 | 17.546 | 104.891 | 1.00 | 10.08 |
| 6484 | CD1 | TYR | B | 215 | 28.092 | 18.605 | 105.438 | 1.00 | 11.59 |
| 6486 | CE1 | TYR | B | 215 | 26.962 | 18.386 | 106.215 | 1.00 | 11.64 |
| 6488 | CZ | TYR | B | 215 | 26.533 | 17.114 | 106.447 | 1.00 | 13.10 |
| 6489 | OH | TYR | B | 215 | 25.386 | 16.889 | 107.201 | 1.00 | 16.38 |
| 6491 | CE2 | TYR | B | 215 | 27.208 | 16.054 | 105.925 | 1.00 | 12.70 |
| 6493 | CD2 | TYR | B | 215 | 28.337 | 16.268 | 105.155 | 1.00 | 11.46 |
| 6495 | C | TYR | B | 215 | 29.038 | 16.745 | 101.993 | 1.00 | 8.54 |
| 6496 | O | TYR | B | 215 | 27.802 | 16.728 | 101.924 | 1.00 | 9.15 |
| 6497 | N | PRO | B | 216 | 29.798 | 15.762 | 101.557 | 1.00 | 8.44 |
| 6498 | CA | PRO | B | 216 | 29.233 | 14.543 | 101.005 | 1.00 | 8.78 |
| 6500 | CB | PRO | B | 216 | 30.322 | 14.095 | 100.028 | 1.00 | 8.88 |
| 6503 | CG | PRO | B | 216 | 31.601 | 14.545 | 100.702 | 1.00 | 8.53 |
| 6506 | CD | PRO | B | 216 | 31.277 | 15.741 | 101.519 | 1.00 | 8.41 |
| 6509 | C | PRO | B | 216 | 29.083 | 13.482 | 102.059 | 1.00 | 10.39 |
| 6510 | O | PRO | B | 216 | 29.679 | 13.557 | 103.117 | 1.00 | 10.24 |
| 6511 | N | GLU | B | 217 | 28.299 | 12.469 | 101.743 | 1.00 | 10.96 |
| 6513 | CA | GLU | B | 217 | 28.221 | 11.317 | 102.614 | 1.00 | 13.19 |
| 6515 | CB | GLU | B | 217 | 27.005 | 11.396 | 103.549 | 1.00 | 15.26 |
| 6518 | CG | GLU | B | 217 | 27.318 | 12.274 | 104.768 | 1.00 | 18.05 |
| 6521 | CD | GLU | B | 217 | 26.124 | 12.591 | 105.663 | 1.00 | 22.53 |
| 6522 | OE1 | GLU | B | 217 | 26.097 | 12.144 | 106.848 | 1.00 | 27.25 |
| 6523 | OE2 | GLU | B | 217 | 25.227 | 13.303 | 105.189 | 1.00 | 22.86 |
| 6524 | C | GLU | B | 217 | 28.321 | 10.075 | 101.731 | 1.00 | 13.81 |
| 6525 | O | GLU | B | 217 | 28.107 | 10.120 | 100.521 | 1.00 | 13.33 |
| 6526 | N | ILE | B | 218 | 28.704 | 8.968 | 102.344 | 1.00 | 14.68 |
| 6528 | CA | ILE | B | 218 | 28.898 | 7.712 | 101.620 | 1.00 | 16.34 |
| 6530 | CB | ILE | B | 218 | 30.356 | 7.277 | 101.777 | 1.00 | 16.17 |
| 6532 | CG1 | ILE | B | 218 | 31.211 | 8.231 | 100.959 | 1.00 | 17.81 |
| 6535 | CD1 | ILE | B | 218 | 32.681 | 8.041 | 101.087 | 1.00 | 19.32 |
| 6539 | CG2 | ILE | B | 218 | 30.577 | 5.862 | 101.271 | 1.00 | 17.38 |
| 6543 | C | ILE | B | 218 | 27.899 | 6.654 | 102.079 | 1.00 | 18.67 |
| 6544 | O | ILE | B | 218 | 27.164 | 6.116 | 101.235 | 1.00 | 21.88 |
| 6545 | O5 | E64 | B | 219 | 34.121 | 30.173 | 90.104 | 1.00 | 26.67 |

FIGURE 3 (Cont.)

| A | B | C | D | E | F | G | H | I | J |
|---|---|---|---|---|---|---|---|---|---|
| 6546 | C11 | E64 | B | 219 | 33.822 | 29.072 | 90.553 | 1.00 | 24.39 |
| 6547 | C6 | E64 | B | 219 | 34.642 | 28.498 | 91.669 | 1.00 | 20.50 |
| 6549 | C7 | E64 | B | 219 | 34.118 | 29.099 | 92.976 | 1.00 | 20.45 |
| 6552 | C8 | E64 | B | 219 | 34.705 | 28.458 | 94.230 | 1.00 | 18.22 |
| 6554 | C10 | E64 | B | 219 | 34.683 | 26.931 | 94.166 | 1.00 | 17.40 |
| 6558 | C9 | E64 | B | 219 | 34.018 | 29.001 | 95.485 | 1.00 | 18.67 |
| 6562 | N1 | E64 | B | 219 | 36.071 | 28.806 | 91.559 | 1.00 | 19.79 |
| 6564 | C4 | E64 | B | 219 | 36.859 | 27.888 | 90.993 | 1.00 | 21.86 |
| 6565 | O4 | E64 | B | 219 | 36.392 | 26.846 | 90.563 | 1.00 | 21.74 |
| 6566 | C3 | E64 | B | 219 | 38.333 | 28.132 | 90.843 | 1.00 | 23.81 |
| 6568 | O3 | E64 | B | 219 | 38.539 | 29.270 | 90.033 | 1.00 | 27.96 |
| 6570 | C2 | E64 | B | 219 | 39.019 | 28.435 | 92.162 | 1.00 | 25.36 |
| 6573 | C1 | E64 | B | 219 | 40.503 | 28.169 | 92.048 | 1.00 | 26.17 |
| 6574 | O2 | E64 | B | 219 | 40.931 | 27.091 | 91.407 | 1.00 | 22.97 |
| 6576 | O1 | E64 | B | 219 | 41.313 | 28.926 | 92.555 | 1.00 | 27.62 |
| 6577 | N2 | E64 | B | 219 | 32.802 | 28.317 | 90.117 | 1.00 | 23.21 |
| 6579 | C12 | E64 | B | 219 | 31.842 | 28.668 | 89.079 | 1.00 | 25.60 |
| 6582 | C13 | E64 | B | 219 | 32.436 | 28.304 | 87.736 | 1.00 | 27.50 |
| 6585 | C14 | E64 | B | 219 | 31.439 | 27.509 | 86.905 | 1.00 | 31.00 |
| 6588 | C15 | E64 | B | 219 | 31.759 | 27.646 | 85.422 | 1.00 | 33.32 |
| 6591 | N3 | E64 | B | 219 | 30.531 | 27.322 | 84.703 | 1.00 | 37.32 |
| 6593 | C16 | E64 | B | 219 | 30.100 | 27.805 | 83.535 | 1.00 | 40.73 |
| 6594 | N5 | E64 | B | 219 | 30.762 | 28.709 | 82.812 | 1.00 | 42.37 |
| 6597 | N4 | E64 | B | 219 | 28.937 | 27.347 | 83.083 | 1.00 | 42.34 |
| 6600 | O | HOH | W | 1 | 65.010 | 24.930 | 63.116 | 1.00 | 55.52 |
| 6603 | O | HOH | W | 2 | 77.256 | 36.811 | 70.602 | 1.00 | 10.08 |
| 6606 | O | HOH | W | 3 | 47.993 | 24.927 | 100.087 | 1.00 | 8.83 |
| 6609 | O | HOH | W | 4 | 35.329 | 20.114 | 84.864 | 1.00 | 11.34 |
| 6612 | O | HOH | W | 5 | 33.947 | 15.288 | 105.007 | 1.00 | 9.78 |
| 6615 | O | HOH | W | 6 | 69.860 | 18.539 | 71.383 | 1.00 | 9.71 |
| 6618 | O | HOH | W | 7 | 51.786 | 20.083 | 103.934 | 1.00 | 12.76 |
| 6621 | O | HOH | W | 8 | 42.117 | 15.546 | 102.628 | 1.00 | 9.67 |
| 6624 | O | HOH | W | 9 | 34.089 | 34.712 | 110.116 | 1.00 | 9.09 |
| 6627 | O | HOH | W | 10 | 57.841 | 36.909 | 46.760 | 1.00 | 11.84 |
| 6630 | O | HOH | W | 11 | 84.176 | 34.864 | 53.493 | 1.00 | 11.13 |
| 6633 | O | HOH | W | 12 | 29.083 | 7.162 | 93.810 | 1.00 | 11.10 |
| 6636 | O | HOH | W | 13 | 63.992 | 42.975 | 56.093 | 1.00 | 10.67 |
| 6639 | O | HOH | W | 14 | 44.051 | 13.459 | 90.398 | 1.00 | 12.26 |
| 6642 | O | HOH | W | 15 | 47.954 | 17.469 | 105.221 | 1.00 | 9.60 |
| 6645 | O | HOH | W | 16 | 78.158 | 27.636 | 55.502 | 1.00 | 10.51 |
| 6648 | O | HOH | W | 17 | 29.801 | 9.397 | 105.035 | 1.00 | 12.95 |
| 6651 | O | HOH | W | 18 | 80.933 | 31.456 | 59.132 | 1.00 | 10.26 |
| 6654 | O | HOH | W | 19 | 66.723 | 29.785 | 75.948 | 1.00 | 11.37 |
| 6657 | O | HOH | W | 20 | 39.958 | 15.418 | 104.301 | 1.00 | 9.71 |
| 6660 | O | HOH | W | 21 | 31.652 | 29.091 | 101.619 | 1.00 | 8.26 |
| 6663 | O | HOH | W | 22 | 37.278 | 33.577 | 107.249 | 1.00 | 12.20 |
| 6666 | O | HOH | W | 23 | 68.372 | 36.610 | 82.094 | 1.00 | 11.82 |
| 6669 | O | HOH | W | 24 | 21.336 | 20.339 | 100.798 | 1.00 | 15.70 |
| 6672 | O | HOH | W | 25 | 80.910 | 33.978 | 60.177 | 1.00 | 10.81 |
| 6675 | O | HOH | W | 26 | 65.778 | 30.096 | 82.353 | 1.00 | 13.90 |
| 6678 | O | HOH | W | 27 | 40.211 | 8.325 | 102.491 | 1.00 | 11.50 |

FIGURE 3 (Cont.)

| A | B | C | D | E | F | G | H | I | J |
|---|---|---|---|---|---|---|---|---|---|
| 6681 | O | HOH | W | 28 | 50.399 | 17.771 | 103.857 | 1.00 | 11.17 |
| 6684 | O | HOH | W | 29 | 70.695 | 22.827 | 71.951 | 1.00 | 13.80 |
| 6687 | O | HOH | W | 30 | 79.230 | 26.844 | 48.350 | 1.00 | 14.14 |
| 6690 | O | HOH | W | 31 | 84.737 | 30.861 | 71.997 | 1.00 | 16.20 |
| 6693 | O | HOH | W | 32 | 66.490 | 27.793 | 58.204 | 1.00 | 15.85 |
| 6696 | O | HOH | W | 33 | 75.998 | 45.177 | 57.586 | 1.00 | 11.16 |
| 6699 | O | HOH | W | 34 | 73.674 | 35.740 | 44.133 | 1.00 | 12.84 |
| 6702 | O | HOH | W | 35 | 41.002 | 19.405 | 99.840 | 1.00 | 12.86 |
| 6705 | O | HOH | W | 36 | 31.787 | 29.189 | 114.809 | 1.00 | 13.55 |
| 6708 | O | HOH | W | 37 | 45.430 | 7.693 | 95.667 | 1.00 | 13.84 |
| 6711 | O | HOH | W | 38 | 65.608 | 22.433 | 50.774 | 1.00 | 15.92 |
| 6714 | O | HOH | W | 39 | 49.314 | 23.576 | 109.440 | 1.00 | 13.79 |
| 6717 | O | HOH | W | 40 | 41.348 | 22.075 | 99.724 | 1.00 | 11.40 |
| 6720 | O | HOH | W | 41 | 43.344 | 15.473 | 97.890 | 1.00 | 13.19 |
| 6723 | O | HOH | W | 42 | 45.289 | 20.160 | 99.204 | 1.00 | 11.07 |
| 6726 | O | HOH | W | 43 | 65.196 | 30.118 | 57.852 | 1.00 | 15.59 |
| 6729 | O | HOH | W | 44 | 77.829 | 37.272 | 65.052 | 1.00 | 12.60 |
| 6732 | O | HOH | W | 45 | 22.990 | 18.020 | 83.905 | 1.00 | 12.44 |
| 6735 | O | HOH | W | 46 | 74.531 | 15.031 | 66.409 | 1.00 | 14.01 |
| 6738 | O | HOH | W | 47 | 46.525 | -0.565 | 86.250 | 1.00 | 15.59 |
| 6741 | O | HOH | W | 48 | 44.506 | 7.677 | 108.526 | 1.00 | 18.31 |
| 6744 | O | HOH | W | 49 | 24.823 | 27.933 | 101.275 | 1.00 | 15.64 |
| 6747 | O | HOH | W | 50 | 41.551 | 23.852 | 97.703 | 1.00 | 14.28 |
| 6750 | O | HOH | W | 51 | 22.156 | 13.766 | 95.128 | 1.00 | 17.49 |
| 6753 | O | HOH | W | 52 | 46.449 | 14.820 | 108.045 | 1.00 | 14.57 |
| 6756 | O | HOH | W | 53 | 22.404 | 14.931 | 87.993 | 1.00 | 14.26 |
| 6759 | O | HOH | W | 54 | 34.934 | 27.188 | 119.486 | 1.00 | 12.62 |
| 6762 | O | HOH | W | 55 | 66.480 | 29.064 | 45.047 | 1.00 | 16.16 |
| 6765 | O | HOH | W | 56 | 74.259 | 51.169 | 56.178 | 1.00 | 15.59 |
| 6768 | O | HOH | W | 57 | 74.681 | 17.440 | 76.138 | 1.00 | 13.33 |
| 6771 | O | HOH | W | 58 | 50.624 | 36.057 | 107.470 | 1.00 | 18.21 |
| 6774 | O | HOH | W | 59 | 45.186 | 42.471 | 100.718 | 1.00 | 17.49 |
| 6777 | O | HOH | W | 60 | 83.342 | 43.442 | 54.949 | 1.00 | 14.01 |
| 6780 | O | HOH | W | 61 | 90.914 | 34.338 | 54.411 | 1.00 | 15.98 |
| 6783 | O | HOH | W | 62 | 32.419 | 25.044 | 121.776 | 1.00 | 15.63 |
| 6786 | O | HOH | W | 63 | 75.841 | 39.452 | 76.864 | 1.00 | 16.29 |
| 6789 | O | HOH | W | 64 | 76.349 | 34.598 | 61.937 | 1.00 | 14.31 |
| 6792 | O | HOH | W | 65 | 67.559 | 26.825 | 46.469 | 1.00 | 14.30 |
| 6795 | O | HOH | W | 66 | 32.799 | 9.507 | 84.280 | 1.00 | 16.71 |
| 6798 | O | HOH | W | 67 | 75.524 | 14.683 | 75.872 | 1.00 | 17.73 |
| 6801 | O | HOH | W | 68 | 72.816 | 35.384 | 65.258 | 1.00 | 15.54 |
| 6804 | O | HOH | W | 69 | 79.024 | 46.881 | 60.098 | 1.00 | 18.27 |
| 6807 | O | HOH | W | 70 | 25.300 | 36.095 | 106.795 | 1.00 | 21.84 |
| 6810 | O | HOH | W | 71 | 75.055 | 20.341 | 79.965 | 1.00 | 17.44 |
| 6813 | O | HOH | W | 72 | 74.959 | 34.188 | 64.251 | 1.00 | 12.05 |
| 6816 | O | HOH | W | 73 | 48.413 | 13.244 | 91.367 | 1.00 | 19.01 |
| 6819 | O | HOH | W | 74 | 65.680 | 25.473 | 48.156 | 1.00 | 20.00 |
| 6822 | O | HOH | W | 75 | 73.335 | 38.204 | 77.359 | 1.00 | 15.82 |
| 6825 | O | HOH | W | 76 | 67.735 | 13.736 | 65.881 | 1.00 | 20.17 |
| 6828 | O | HOH | W | 77 | 83.583 | 22.403 | 68.438 | 1.00 | 19.88 |
| 6831 | O | HOH | W | 78 | 45.617 | 11.849 | 84.593 | 1.00 | 15.50 |

FIGURE 3 (Cont.)

| A | B | C | D | E | F | G | H | I | J |
|---|---|---|---|---|---|---|---|---|---|
| 6834 | O | HOH | W | 79 | 29.835 | 24.041 | 95.835 | 1.00 | 16.54 |
| 6837 | O | HOH | W | 80 | 87.513 | 31.594 | 61.382 | 1.00 | 17.76 |
| 6840 | O | HOH | W | 81 | 60.755 | 46.719 | 60.826 | 1.00 | 19.58 |
| 6843 | O | HOH | W | 82 | 72.604 | 24.584 | 49.668 | 1.00 | 14.32 |
| 6846 | O | HOH | W | 83 | 78.831 | 38.373 | 60.052 | 1.00 | 15.59 |
| 6849 | O | HOH | W | 84 | 29.583 | 34.343 | 96.391 | 1.00 | 20.83 |
| 6852 | O | HOH | W | 85 | 29.523 | 24.066 | 98.543 | 1.00 | 15.16 |
| 6855 | O | HOH | W | 86 | 61.902 | 34.407 | 44.835 | 1.00 | 17.37 |
| 6858 | O | HOH | W | 87 | 32.100 | 29.010 | 118.657 | 1.00 | 19.96 |
| 6861 | O | HOH | W | 88 | 46.537 | 7.959 | 98.915 | 1.00 | 19.34 |
| 6864 | O | HOH | W | 89 | 38.941 | 35.784 | 114.688 | 1.00 | 17.32 |
| 6867 | O | HOH | W | 90 | 73.772 | 42.226 | 41.887 | 1.00 | 16.84 |
| 6870 | O | HOH | W | 91 | 85.009 | 35.494 | 69.481 | 1.00 | 18.61 |
| 6873 | O | HOH | W | 92 | 64.136 | 21.863 | 74.156 | 1.00 | 16.04 |
| 6876 | O | HOH | W | 93 | 54.810 | 26.652 | 104.608 | 1.00 | 18.74 |
| 6879 | O | HOH | W | 94 | 68.581 | 44.811 | 46.405 | 1.00 | 14.75 |
| 6882 | O | HOH | W | 95 | 88.170 | 40.424 | 55.085 | 1.00 | 19.76 |
| 6885 | O | HOH | W | 96 | 87.015 | 18.313 | 62.426 | 1.00 | 20.57 |
| 6888 | O | HOH | W | 97 | 21.612 | 17.501 | 97.855 | 1.00 | 18.49 |
| 6891 | O | HOH | W | 98 | 67.849 | 45.243 | 72.981 | 1.00 | 19.80 |
| 6894 | O | HOH | W | 99 | 31.277 | 3.778 | 88.274 | 1.00 | 15.81 |
| 6897 | O | HOH | W | 100 | 41.310 | 37.219 | 100.311 | 1.00 | 14.86 |
| 6900 | O | HOH | W | 101 | 25.674 | 14.947 | 103.096 | 1.00 | 13.67 |
| 6903 | O | HOH | W | 102 | 63.900 | 47.126 | 56.817 | 1.00 | 19.69 |
| 6906 | O | HOH | W | 103 | 59.512 | 26.756 | 66.061 | 1.00 | 17.75 |
| 6909 | O | HOH | W | 104 | 43.275 | 18.022 | 99.196 | 1.00 | 14.21 |
| 6912 | O | HOH | W | 105 | 53.303 | 25.372 | 97.929 | 1.00 | 20.11 |
| 6915 | O | HOH | W | 106 | 87.057 | 21.303 | 62.462 | 1.00 | 22.76 |
| 6918 | O | HOH | W | 107 | 80.224 | 13.610 | 67.646 | 1.00 | 17.11 |
| 6921 | O | HOH | W | 108 | 47.502 | 25.539 | 110.532 | 1.00 | 18.19 |
| 6924 | O | HOH | W | 109 | 34.285 | 39.410 | 104.697 | 1.00 | 16.86 |
| 6927 | O | HOH | W | 110 | 70.977 | 49.159 | 68.949 | 1.00 | 22.50 |
| 6930 | O | HOH | W | 111 | 47.100 | 35.779 | 114.411 | 1.00 | 18.95 |
| 6933 | O | HOH | W | 112 | 38.143 | 19.523 | 81.694 | 1.00 | 20.23 |
| 6936 | O | HOH | W | 113 | 43.637 | 14.656 | 95.450 | 1.00 | 21.49 |
| 6939 | O | HOH | W | 114 | 63.576 | 22.118 | 58.826 | 1.00 | 16.42 |
| 6942 | O | HOH | W | 115 | 76.104 | 35.646 | 78.518 | 1.00 | 18.28 |
| 6945 | O | HOH | W | 116 | 68.100 | 38.804 | 69.840 | 1.00 | 19.35 |
| 6948 | O | HOH | W | 117 | 73.621 | 18.644 | 78.256 | 1.00 | 18.30 |
| 6951 | O | HOH | W | 118 | 77.000 | 29.366 | 82.123 | 1.00 | 20.45 |
| 6954 | O | HOH | W | 119 | 26.270 | 27.074 | 107.272 | 1.00 | 16.28 |
| 6957 | O | HOH | W | 120 | 77.882 | 40.796 | 59.099 | 1.00 | 19.93 |
| 6960 | O | HOH | W | 121 | 36.189 | 21.235 | 124.141 | 1.00 | 21.89 |
| 6963 | O | HOH | W | 122 | 68.476 | 18.405 | 60.149 | 1.00 | 15.17 |
| 6966 | O | HOH | W | 123 | 84.779 | 36.965 | 67.175 | 1.00 | 21.09 |
| 6969 | O | HOH | W | 124 | 34.078 | 2.283 | 83.802 | 1.00 | 20.70 |
| 6972 | O | HOH | W | 125 | 79.568 | 42.502 | 73.503 | 1.00 | 20.34 |
| 6975 | O | HOH | W | 126 | 75.644 | 41.242 | 74.871 | 1.00 | 18.90 |
| 6978 | O | HOH | W | 127 | 26.850 | 32.919 | 111.666 | 1.00 | 19.44 |
| 6981 | O | HOH | W | 128 | 60.860 | 43.219 | 49.502 | 1.00 | 23.90 |
| 6984 | O | HOH | W | 129 | 42.204 | 26.107 | 119.463 | 1.00 | 19.22 |

FIGURE 3 (Cont.)

| A | B | C | D | E | F | G | H | I | J |
|---|---|---|---|---|---|---|---|---|---|
| 6987 | O | HOH | W | 130 | 49.152 | 25.722 | 93.353 | 1.00 | 19.84 |
| 6990 | O | HOH | W | 131 | 22.173 | 14.870 | 97.728 | 1.00 | 17.59 |
| 6993 | O | HOH | W | 132 | 50.529 | 24.312 | 86.650 | 1.00 | 22.79 |
| 6996 | O | HOH | W | 133 | 49.974 | 17.846 | 94.440 | 1.00 | 20.83 |
| 6999 | O | HOH | W | 134 | 64.643 | 25.879 | 84.419 | 1.00 | 25.49 |
| 7002 | O | HOH | W | 135 | 77.212 | 12.184 | 67.336 | 1.00 | 22.24 |
| 7005 | O | HOH | W | 136 | 79.094 | 44.230 | 65.373 | 1.00 | 24.45 |
| 7008 | O | HOH | W | 137 | 73.438 | 42.654 | 70.506 | 1.00 | 19.42 |
| 7011 | O | HOH | W | 138 | 78.008 | 36.620 | 62.218 | 1.00 | 18.28 |
| 7014 | O | HOH | W | 139 | 29.557 | 29.079 | 116.583 | 1.00 | 21.15 |
| 7017 | O | HOH | W | 140 | 85.483 | 41.887 | 56.116 | 1.00 | 23.48 |
| 7020 | O | HOH | W | 141 | 22.329 | 8.089 | 96.113 | 1.00 | 29.93 |
| 7023 | O | HOH | W | 142 | 44.945 | 13.032 | 108.894 | 1.00 | 21.43 |
| 7026 | O | HOH | W | 143 | 37.715 | 35.949 | 117.239 | 1.00 | 23.64 |
| 7029 | O | HOH | W | 144 | 76.704 | 31.796 | 43.140 | 1.00 | 22.03 |
| 7032 | O | HOH | W | 145 | 54.009 | 29.526 | 108.354 | 1.00 | 19.62 |
| 7035 | O | HOH | W | 146 | 62.245 | 16.869 | 70.598 | 1.00 | 22.94 |
| 7038 | O | HOH | W | 147 | 81.467 | 10.966 | 64.846 | 1.00 | 23.12 |
| 7041 | O | HOH | W | 148 | 80.439 | 34.852 | 44.985 | 1.00 | 24.62 |
| 7044 | O | HOH | W | 149 | 45.732 | 2.587 | 83.663 | 1.00 | 27.98 |
| 7047 | O | HOH | W | 150 | 72.895 | 30.385 | 82.319 | 1.00 | 21.62 |
| 7050 | O | HOH | W | 151 | 28.699 | 34.868 | 111.312 | 1.00 | 22.94 |
| 7053 | O | HOH | W | 152 | 38.207 | 27.599 | 120.117 | 1.00 | 20.73 |
| 7056 | O | HOH | W | 153 | 68.067 | 13.151 | 70.812 | 1.00 | 22.37 |
| 7059 | O | HOH | W | 154 | 63.792 | 46.700 | 67.516 | 1.00 | 18.60 |
| 7062 | O | HOH | W | 155 | 74.466 | 12.302 | 65.441 | 1.00 | 22.64 |
| 7065 | O | HOH | W | 156 | 67.453 | 14.556 | 68.385 | 1.00 | 19.53 |
| 7068 | O | HOH | W | 157 | 61.803 | 44.776 | 67.262 | 1.00 | 22.39 |
| 7071 | O | HOH | W | 158 | 92.109 | 41.530 | 46.097 | 1.00 | 33.03 |
| 7074 | O | HOH | W | 159 | 90.436 | 32.927 | 56.949 | 1.00 | 21.54 |
| 7077 | O | HOH | W | 160 | 61.212 | 46.206 | 56.924 | 1.00 | 27.34 |
| 7080 | O | HOH | W | 161 | 54.361 | 19.443 | 104.821 | 1.00 | 22.44 |
| 7083 | O | HOH | W | 162 | 84.475 | 34.504 | 65.544 | 1.00 | 22.92 |
| 7086 | O | HOH | W | 163 | 37.800 | 43.169 | 113.680 | 1.00 | 34.29 |
| 7089 | O | HOH | W | 164 | 63.766 | 20.015 | 54.070 | 1.00 | 23.13 |
| 7092 | O | HOH | W | 165 | 77.947 | 10.223 | 63.372 | 1.00 | 23.72 |
| 7095 | O | HOH | W | 166 | 84.179 | 45.697 | 43.266 | 1.00 | 21.04 |
| 7098 | O | HOH | W | 167 | 62.620 | 15.819 | 66.566 | 1.00 | 23.82 |
| 7101 | O | HOH | W | 168 | 45.015 | 4.319 | 105.225 | 1.00 | 25.52 |
| 7104 | O | HOH | W | 169 | 29.860 | 11.838 | 108.319 | 1.00 | 28.70 |
| 7107 | O | HOH | W | 170 | 29.796 | 36.520 | 113.307 | 1.00 | 23.15 |
| 7110 | O | HOH | W | 171 | 47.779 | 9.147 | 95.571 | 1.00 | 25.53 |
| 7113 | O | HOH | W | 172 | 46.305 | 19.665 | 116.018 | 1.00 | 23.98 |
| 7116 | O | HOH | W | 173 | 73.324 | 24.575 | 81.394 | 1.00 | 28.15 |
| 7119 | O | HOH | W | 174 | 81.826 | 21.373 | 81.323 | 1.00 | 25.13 |
| 7122 | O | HOH | W | 175 | 67.521 | 18.647 | 52.736 | 1.00 | 24.00 |
| 7125 | O | HOH | W | 176 | 73.964 | 13.732 | 73.954 | 1.00 | 20.97 |
| 7128 | O | HOH | W | 177 | 82.938 | 32.532 | 79.736 | 1.00 | 27.09 |
| 7131 | O | HOH | W | 178 | 41.410 | 2.201 | 93.875 | 1.00 | 31.58 |
| 7134 | O | HOH | W | 179 | 62.181 | 36.160 | 77.123 | 1.00 | 24.12 |
| 7137 | O | HOH | W | 180 | 72.377 | 16.978 | 80.033 | 1.00 | 29.09 |

FIGURE 3 (Cont.)

| A | B | C | D | E | F | G | H | I | J |
|---|---|---|---|---|---|---|---|---|---|
| 7140 | O | HOH | W | 181 | 84.704 | 18.843 | 58.758 | 1.00 | 24.37 |
| 7143 | O | HOH | W | 182 | 27.019 | 23.309 | 80.445 | 1.00 | 23.76 |
| 7146 | O | HOH | W | 183 | 23.709 | 21.602 | 94.537 | 1.00 | 26.10 |
| 7149 | O | HOH | W | 184 | 43.949 | 29.380 | 92.572 | 1.00 | 25.52 |
| 7152 | O | HOH | W | 185 | 86.008 | 36.386 | 47.697 | 1.00 | 22.06 |
| 7155 | O | HOH | W | 186 | 92.965 | 35.195 | 52.236 | 1.00 | 21.93 |
| 7158 | O | HOH | W | 187 | 38.937 | 2.842 | 98.558 | 1.00 | 25.49 |
| 7161 | O | HOH | W | 188 | 27.877 | 5.745 | 98.635 | 1.00 | 22.43 |
| 7164 | O | HOH | W | 189 | 80.001 | 20.043 | 80.063 | 1.00 | 21.35 |
| 7167 | O | HOH | W | 190 | 64.452 | 51.202 | 62.580 | 1.00 | 27.81 |
| 7170 | O | HOH | W | 191 | 32.927 | 4.134 | 98.960 | 1.00 | 26.51 |
| 7173 | O | HOH | W | 192 | 65.937 | 45.480 | 46.077 | 1.00 | 35.92 |
| 7176 | O | HOH | W | 193 | 44.788 | 23.480 | 114.645 | 1.00 | 42.84 |
| 7179 | O | HOH | W | 194 | 26.159 | 25.745 | 100.057 | 1.00 | 18.70 |
| 7182 | O | HOH | W | 195 | 63.706 | 49.096 | 54.532 | 1.00 | 37.57 |
| 7185 | O | HOH | W | 196 | 55.020 | 40.321 | 52.812 | 1.00 | 19.23 |
| 7188 | O | HOH | W | 197 | 25.315 | 21.525 | 111.034 | 1.00 | 26.85 |
| 7191 | O | HOH | W | 198 | 80.843 | 43.795 | 71.372 | 1.00 | 46.96 |
| 7194 | O | HOH | W | 199 | 67.231 | 55.152 | 55.093 | 1.00 | 29.31 |
| 7197 | O | HOH | W | 200 | 48.799 | 38.205 | 104.624 | 1.00 | 22.09 |
| 7200 | O | HOH | W | 201 | 27.683 | 11.578 | 84.511 | 1.00 | 31.40 |
| 7203 | O | HOH | W | 202 | 45.405 | 40.413 | 106.017 | 1.00 | 28.51 |
| 7206 | O | HOH | W | 203 | 76.944 | 10.958 | 69.233 | 1.00 | 25.05 |
| 7209 | O | HOH | W | 204 | 65.446 | 18.804 | 75.042 | 1.00 | 25.39 |
| 7212 | O | HOH | W | 205 | 80.016 | 23.611 | 50.987 | 1.00 | 28.81 |
| 7215 | O | HOH | W | 206 | 28.038 | 24.101 | 121.546 | 1.00 | 29.27 |
| 7218 | O | HOH | W | 207 | 59.699 | 31.319 | 71.489 | 1.00 | 32.51 |
| 7221 | O | HOH | W | 208 | 64.988 | 15.117 | 67.493 | 1.00 | 29.39 |
| 7224 | O | HOH | W | 209 | 42.084 | 34.250 | 93.828 | 1.00 | 25.67 |
| 7227 | O | HOH | W | 210 | 80.528 | 35.862 | 78.977 | 1.00 | 27.53 |
| 7230 | O | HOH | W | 211 | 45.798 | 5.027 | 96.511 | 1.00 | 36.67 |
| 7233 | O | HOH | W | 212 | 21.432 | 21.784 | 105.197 | 1.00 | 26.15 |
| 7236 | O | HOH | W | 213 | 24.121 | 14.552 | 107.313 | 1.00 | 29.18 |
| 7239 | O | HOH | W | 214 | 45.768 | 38.609 | 108.412 | 1.00 | 23.61 |
| 7242 | O | HOH | W | 215 | 74.297 | 20.562 | 49.376 | 1.00 | 29.54 |
| 7245 | O | HOH | W | 216 | 80.495 | 12.408 | 70.838 | 1.00 | 35.17 |
| 7248 | O | HOH | W | 217 | 55.359 | 27.582 | 107.030 | 1.00 | 25.03 |
| 7251 | O | HOH | W | 218 | 65.652 | 35.893 | 73.241 | 1.00 | 22.44 |
| 7254 | O | HOH | W | 219 | 30.897 | 3.007 | 85.391 | 1.00 | 29.85 |
| 7257 | O | HOH | W | 220 | 76.079 | 51.114 | 50.726 | 1.00 | 32.09 |
| 7260 | O | HOH | W | 221 | 28.278 | 39.053 | 106.654 | 1.00 | 23.09 |
| 7263 | O | HOH | W | 222 | 34.500 | -0.749 | 93.641 | 1.00 | 23.32 |
| 7266 | O | HOH | W | 224 | 54.257 | 36.708 | 102.341 | 1.00 | 24.03 |
| 7269 | O | HOH | W | 225 | 34.015 | 40.165 | 108.178 | 1.00 | 25.71 |
| 7272 | O | HOH | W | 226 | 47.282 | 8.190 | 107.971 | 1.00 | 31.71 |
| 7275 | O | HOH | W | 227 | 38.761 | 24.784 | 80.970 | 1.00 | 28.57 |
| 7278 | O | HOH | W | 228 | 35.184 | 35.469 | 116.866 | 1.00 | 25.60 |
| 7281 | O | HOH | W | 229 | 73.228 | 16.306 | 56.053 | 1.00 | 24.65 |
| 7284 | O | HOH | W | 230 | 21.873 | 9.940 | 90.372 | 1.00 | 32.75 |
| 7287 | O | HOH | W | 231 | 32.517 | 30.932 | 120.042 | 1.00 | 29.78 |
| 7290 | O | HOH | W | 232 | 48.007 | 37.148 | 107.567 | 1.00 | 29.47 |

FIGURE 3 (Cont.)

| A | B | C | D | E | F | G | H | I | J |
|---|---|---|---|---|---|---|---|---|---|
| 7293 | O | HOH | W | 233 | 27.807 | 27.331 | 117.878 | 1.00 | 24.65 |
| 7296 | O | HOH | W | 234 | 29.674 | 16.833 | 81.251 | 1.00 | 27.77 |
| 7299 | O | HOH | W | 235 | 21.026 | 24.807 | 101.986 | 1.00 | 25.08 |
| 7302 | O | HOH | W | 236 | 36.656 | 16.396 | 79.299 | 1.00 | 32.24 |
| 7305 | O | HOH | W | 237 | 36.628 | 29.483 | 121.060 | 1.00 | 26.67 |
| 7308 | O | HOH | W | 238 | 51.551 | 22.230 | 88.170 | 1.00 | 32.31 |
| 7311 | O | HOH | W | 239 | 85.577 | 40.299 | 58.882 | 1.00 | 28.85 |
| 7314 | O | HOH | W | 240 | 77.012 | 15.283 | 53.326 | 1.00 | 31.74 |
| 7317 | O | HOH | W | 241 | 85.871 | 39.231 | 60.881 | 1.00 | 29.66 |
| 7320 | O | HOH | W | 242 | 29.085 | 26.155 | 120.124 | 1.00 | 24.30 |
| 7323 | O | HOH | W | 243 | 36.049 | 21.515 | 80.599 | 1.00 | 30.01 |
| 7326 | O | HOH | W | 244 | 85.802 | 23.740 | 69.227 | 1.00 | 31.62 |
| 7329 | O | HOH | W | 245 | 45.749 | 15.045 | 93.432 | 1.00 | 23.37 |
| 7332 | O | HOH | W | 246 | 21.760 | 25.827 | 99.361 | 1.00 | 25.11 |
| 7335 | O | HOH | W | 247 | 33.430 | 16.807 | 78.475 | 1.00 | 34.83 |
| 7338 | O | HOH | W | 248 | 74.847 | 47.438 | 66.670 | 1.00 | 26.51 |
| 7341 | O | HOH | W | 249 | 40.390 | 37.884 | 113.584 | 1.00 | 26.86 |
| 7344 | O | HOH | W | 250 | 66.350 | 34.046 | 41.054 | 1.00 | 31.51 |
| 7347 | O | HOH | W | 251 | 77.314 | 43.419 | 75.052 | 1.00 | 24.14 |
| 7350 | O | HOH | W | 252 | 32.250 | 35.413 | 93.556 | 1.00 | 28.44 |
| 7353 | O | HOH | W | 253 | 62.708 | 29.230 | 57.294 | 1.00 | 41.56 |
| 7356 | O | HOH | W | 254 | 73.683 | 47.964 | 41.641 | 1.00 | 26.73 |
| 7359 | O | HOH | W | 255 | 33.513 | 21.733 | 80.763 | 1.00 | 25.82 |
| 7362 | O | HOH | W | 256 | 47.124 | 9.180 | 101.705 | 1.00 | 41.34 |
| 7365 | O | HOH | W | 257 | 63.985 | 37.367 | 69.357 | 1.00 | 36.90 |
| 7368 | O | HOH | W | 258 | 25.794 | 18.863 | 111.361 | 1.00 | 27.99 |
| 7371 | O | HOH | W | 259 | 26.148 | 4.763 | 101.980 | 1.00 | 36.19 |
| 7374 | O | HOH | W | 260 | 79.876 | 17.371 | 82.630 | 1.00 | 35.27 |
| 7377 | O | HOH | W | 261 | 86.600 | 32.704 | 68.444 | 1.00 | 28.95 |
| 7380 | O | HOH | W | 262 | 61.572 | 47.421 | 51.208 | 1.00 | 32.40 |
| 7383 | O | HOH | W | 263 | 70.972 | 42.547 | 71.224 | 1.00 | 26.25 |
| 7386 | O | HOH | W | 264 | 36.254 | 0.745 | 95.309 | 1.00 | 28.20 |
| 7389 | O | HOH | W | 265 | 80.944 | 42.590 | 68.002 | 1.00 | 31.46 |
| 7392 | O | HOH | W | 266 | 64.056 | 21.313 | 76.961 | 1.00 | 27.51 |
| 7395 | O | HOH | W | 267 | 26.928 | 35.313 | 109.096 | 1.00 | 29.67 |
| 7398 | O | HOH | W | 268 | 42.200 | 23.496 | 115.194 | 1.00 | 29.69 |
| 7401 | O | HOH | W | 269 | 29.505 | 2.051 | 92.621 | 1.00 | 31.79 |
| 7404 | O | HOH | W | 270 | 68.308 | 28.527 | 43.160 | 1.00 | 29.07 |
| 7407 | O | HOH | W | 271 | 87.017 | 11.767 | 64.698 | 1.00 | 30.32 |
| 7410 | O | HOH | W | 272 | 59.392 | 44.489 | 55.575 | 1.00 | 26.52 |
| 7413 | O | HOH | W | 273 | 74.346 | 13.024 | 79.361 | 1.00 | 34.63 |
| 7416 | O | HOH | W | 274 | 67.952 | 42.569 | 69.612 | 1.00 | 30.03 |
| 7419 | O | HOH | W | 275 | 40.192 | 41.551 | 113.516 | 1.00 | 39.84 |
| 7422 | O | HOH | W | 276 | 54.851 | 24.105 | 69.996 | 1.00 | 24.17 |
| 7425 | O | HOH | W | 277 | 70.814 | 29.834 | 41.017 | 1.00 | 29.50 |
| 7428 | O | HOH | W | 278 | 74.500 | 27.703 | 81.294 | 1.00 | 31.61 |
| 7431 | O | HOH | W | 279 | 28.217 | 34.852 | 98.846 | 1.00 | 26.88 |
| 7434 | O | HOH | W | 280 | 72.434 | 11.723 | 74.551 | 1.00 | 32.09 |
| 7437 | O | HOH | W | 281 | 47.506 | 36.216 | 109.766 | 1.00 | 30.23 |
| 7440 | O | HOH | W | 282 | 70.477 | 26.063 | 82.263 | 1.00 | 31.95 |
| 7443 | O | HOH | W | 283 | 24.274 | 18.842 | 108.749 | 1.00 | 31.37 |

FIGURE 3 (Cont.)

| A | B | C | D | E | F | G | H | I | J |
|---|---|---|---|---|---|---|---|---|---|
| 7446 | O | HOH | W | 284 | 63.798 | 50.464 | 50.479 | 1.00 | 27.86 |
| 7449 | O | HOH | W | 285 | 45.444 | 28.336 | 90.116 | 1.00 | 31.78 |
| 7452 | O | HOH | W | 286 | 44.397 | 42.008 | 109.394 | 1.00 | 36.54 |
| 7455 | O | HOH | W | 287 | 72.063 | 47.805 | 72.134 | 1.00 | 32.28 |
| 7458 | O | HOH | W | 288 | 52.093 | 17.730 | 100.428 | 1.00 | 31.19 |
| 7461 | O | HOH | W | 289 | 83.838 | 24.094 | 72.607 | 1.00 | 36.48 |
| 7464 | O | HOH | W | 290 | 48.491 | 10.401 | 98.010 | 1.00 | 41.02 |
| 7467 | O | HOH | W | 291 | 62.641 | 34.294 | 42.089 | 1.00 | 36.84 |
| 7470 | O | HOH | W | 292 | 47.476 | 12.203 | 81.918 | 1.00 | 30.86 |
| 7473 | O | HOH | W | 293 | 32.799 | 22.283 | 124.734 | 1.00 | 39.98 |
| 7476 | O | HOH | W | 294 | 81.302 | 47.861 | 58.483 | 1.00 | 33.92 |
| 7479 | O | HOH | W | 295 | 34.262 | -2.100 | 88.542 | 1.00 | 31.40 |
| 7482 | O | HOH | W | 296 | 69.917 | 44.390 | 42.273 | 1.00 | 34.06 |
| 7485 | O | HOH | W | 297 | 47.174 | 24.749 | 112.815 | 1.00 | 34.07 |
| 7488 | O | HOH | W | 298 | 87.181 | 14.997 | 65.222 | 1.00 | 28.90 |
| 7491 | O | HOH | W | 299 | 60.350 | 23.957 | 66.007 | 1.00 | 29.48 |
| 7494 | O | HOH | W | 300 | 69.932 | 47.480 | 74.488 | 1.00 | 45.24 |
| 7497 | O | HOH | W | 301 | 58.655 | 30.458 | 67.811 | 1.00 | 31.29 |
| 7500 | O | HOH | W | 302 | 35.081 | 26.060 | 127.087 | 1.00 | 30.72 |
| 7503 | O | HOH | W | 303 | 42.845 | 41.950 | 112.369 | 1.00 | 34.59 |
| 7506 | O | HOH | W | 304 | 62.484 | 42.162 | 67.666 | 1.00 | 31.32 |
| 7509 | O | HOH | W | 305 | 38.111 | 18.137 | 79.537 | 1.00 | 35.46 |
| 7512 | O | HOH | W | 306 | 59.061 | 26.409 | 78.987 | 1.00 | 30.96 |
| 7515 | O | HOH | W | 307 | 81.629 | 43.899 | 42.265 | 1.00 | 33.11 |
| 7518 | O | HOH | W | 308 | 35.055 | 14.289 | 116.028 | 1.00 | 38.80 |
| 7521 | O | HOH | W | 309 | 78.391 | 22.250 | 81.153 | 1.00 | 40.38 |
| 7524 | O | HOH | W | 310 | 60.340 | 34.775 | 66.818 | 1.00 | 33.17 |
| 7527 | O | HOH | W | 311 | 60.868 | 33.801 | 78.775 | 1.00 | 29.81 |
| 7530 | O | HOH | W | 312 | 68.971 | 35.381 | 39.999 | 1.00 | 29.30 |
| 7533 | O | HOH | W | 313 | 52.041 | 28.832 | 112.247 | 1.00 | 29.43 |
| 7536 | O | HOH | W | 314 | 50.321 | 19.458 | 90.921 | 1.00 | 35.02 |
| 7539 | O | HOH | W | 315 | 75.213 | 17.230 | 54.157 | 1.00 | 32.92 |
| 7542 | O | HOH | W | 316 | 63.962 | 11.916 | 58.541 | 1.00 | 30.95 |
| 7545 | O | HOH | W | 317 | 71.667 | 22.451 | 82.856 | 1.00 | 28.69 |
| 7548 | O | HOH | W | 318 | 62.803 | 14.065 | 70.900 | 1.00 | 37.87 |
| 7551 | O | HOH | W | 319 | 75.264 | 10.936 | 63.579 | 1.00 | 30.51 |
| 7554 | O | HOH | W | 320 | 72.663 | 44.505 | 40.441 | 1.00 | 31.56 |
| 7557 | O | HOH | W | 321 | 43.572 | 45.605 | 103.119 | 1.00 | 38.36 |
| 7560 | O | HOH | W | 322 | 87.344 | 20.235 | 66.867 | 1.00 | 30.03 |
| 7563 | O | HOH | W | 323 | 86.071 | 21.874 | 59.813 | 1.00 | 35.10 |
| 7566 | O | HOH | W | 324 | 34.473 | 2.319 | 97.473 | 1.00 | 47.08 |
| 7569 | O | HOH | W | 325 | 29.557 | 35.238 | 93.423 | 1.00 | 31.30 |
| 7572 | O | HOH | W | 326 | 80.013 | 8.993 | 61.285 | 1.00 | 37.25 |
| 7575 | O | HOH | W | 327 | 31.474 | 11.261 | 112.272 | 1.00 | 42.99 |
| 7578 | O | HOH | W | 328 | 44.237 | 22.839 | 80.184 | 1.00 | 32.80 |
| 7581 | O | HOH | W | 329 | 43.461 | 38.047 | 112.877 | 1.00 | 30.92 |
| 7584 | O | HOH | W | 330 | 45.822 | 4.507 | 101.461 | 1.00 | 35.12 |
| 7587 | O | HOH | W | 331 | 38.585 | 38.368 | 118.185 | 1.00 | 31.59 |
| 7590 | O | HOH | W | 332 | 35.378 | 41.847 | 105.419 | 1.00 | 35.24 |
| 7593 | O | HOH | W | 333 | 77.069 | 42.917 | 59.203 | 1.00 | 31.40 |
| 7596 | O | HOH | W | 334 | 41.057 | 12.912 | 116.677 | 1.00 | 33.85 |

FIGURE 3 (Cont.)

| A | B | C | D | E | F | G | H | I | J |
|---|---|---|---|---|---|---|---|---|---|
| 7599 | O | HOH | W | 335 | 69.512 | 12.067 | 65.222 | 1.00 | 35.35 |
| 7602 | O | HOH | W | 336 | 89.623 | 19.821 | 66.141 | 1.00 | 40.09 |
| 7605 | O | HOH | W | 337 | 55.680 | 21.578 | 103.927 | 1.00 | 32.12 |
| 7608 | O | HOH | W | 338 | 75.368 | 44.997 | 38.071 | 1.00 | 37.52 |
| 7611 | O | HOH | W | 339 | 68.321 | 26.723 | 84.085 | 1.00 | 31.87 |
| 7614 | O | HOH | W | 340 | 66.028 | 30.105 | 42.876 | 1.00 | 33.11 |
| 7617 | O | HOH | W | 341 | 62.002 | 43.504 | 47.319 | 1.00 | 31.59 |
| 7620 | O | HOH | W | 342 | 87.185 | 36.536 | 45.368 | 1.00 | 34.96 |
| 7623 | O | HOH | W | 343 | 75.303 | 11.955 | 61.440 | 1.00 | 37.83 |
| 7626 | O | HOH | W | 344 | 81.356 | 41.161 | 42.157 | 1.00 | 33.89 |
| 7629 | O | HOH | W | 345 | 21.410 | 11.714 | 96.191 | 1.00 | 30.18 |
| 7632 | O | HOH | W | 346 | 41.358 | 2.333 | 97.218 | 1.00 | 41.85 |
| 7635 | O | HOH | W | 347 | 43.395 | 37.459 | 116.263 | 1.00 | 42.43 |
| 7638 | O | HOH | W | 348 | 36.582 | -0.943 | 82.920 | 1.00 | 31.22 |
| 7641 | O | HOH | W | 349 | 64.367 | 12.644 | 64.796 | 1.00 | 37.95 |
| 7644 | O | HOH | W | 350 | 62.349 | 28.355 | 52.235 | 1.00 | 28.54 |
| 7647 | O | HOH | W | 351 | 45.725 | 30.098 | 88.003 | 1.00 | 34.61 |
| 7650 | O | HOH | W | 352 | 69.971 | 17.624 | 53.338 | 1.00 | 42.35 |
| 7653 | O | HOH | W | 353 | 19.842 | 19.735 | 104.611 | 1.00 | 33.98 |
| 7656 | O | HOH | W | 354 | 49.768 | 12.676 | 98.330 | 1.00 | 39.97 |
| 7659 | O | HOH | W | 355 | 84.345 | 19.356 | 54.985 | 1.00 | 38.56 |
| 7662 | O | HOH | W | 356 | 73.789 | 48.846 | 68.555 | 1.00 | 32.04 |
| 7665 | O | HOH | W | 357 | 57.829 | 40.220 | 43.059 | 1.00 | 41.52 |
| 7668 | O | HOH | W | 358 | 45.315 | 42.949 | 104.926 | 1.00 | 34.81 |
| 7671 | O | HOH | W | 359 | 52.164 | 33.072 | 101.101 | 1.00 | 35.58 |
| 7674 | O | HOH | W | 360 | 26.513 | 32.017 | 113.761 | 1.00 | 36.86 |
| 7677 | O | HOH | W | 361 | 28.670 | 26.050 | 95.404 | 1.00 | 44.40 |
| 7680 | O | HOH | W | 362 | 68.624 | 12.178 | 74.531 | 1.00 | 44.12 |
| 7683 | O | HOH | W | 363 | 63.357 | 36.988 | 74.328 | 1.00 | 35.04 |
| 7686 | O | HOH | W | 364 | 76.963 | 50.677 | 40.686 | 1.00 | 34.68 |
| 7689 | O | HOH | W | 365 | 30.904 | 7.363 | 107.191 | 1.00 | 49.14 |
| 7692 | O | HOH | W | 366 | 79.005 | 45.990 | 38.757 | 1.00 | 44.46 |
| 7695 | O | HOH | W | 367 | 66.282 | 36.689 | 70.671 | 1.00 | 31.78 |
| 7698 | O | HOH | W | 368 | 83.393 | 25.368 | 79.985 | 1.00 | 36.49 |
| 7701 | O | HOH | W | 369 | 48.269 | 15.812 | 93.362 | 1.00 | 28.66 |
| 7704 | O | HOH | W | 370 | 79.581 | 22.260 | 48.824 | 1.00 | 42.68 |
| 7707 | O | HOH | W | 371 | 79.371 | 14.503 | 82.894 | 1.00 | 44.40 |
| 7710 | O | HOH | W | 372 | 77.348 | 53.621 | 50.687 | 1.00 | 43.71 |
| 7713 | O | HOH | W | 373 | 49.851 | 29.256 | 116.702 | 1.00 | 37.95 |
| 7716 | O | HOH | W | 374 | 31.679 | 41.049 | 106.529 | 1.00 | 42.95 |
| 7719 | O | HOH | W | 375 | 37.604 | 4.999 | 110.395 | 1.00 | 35.02 |
| 7722 | O | HOH | W | 376 | 40.818 | 7.244 | 112.377 | 1.00 | 33.66 |
| 7725 | O | HOH | W | 377 | 72.235 | 34.634 | 41.688 | 1.00 | 39.53 |
| 7728 | O | HOH | W | 378 | 42.262 | 43.781 | 98.104 | 1.00 | 32.33 |
| 7731 | O | HOH | W | 379 | 80.658 | 44.682 | 61.601 | 1.00 | 36.18 |
| 7734 | O | HOH | W | 380 | 83.088 | 28.243 | 77.474 | 1.00 | 34.65 |
| 7737 | O | HOH | W | 381 | 57.660 | 29.389 | 57.797 | 1.00 | 37.39 |
| 7740 | O | HOH | W | 382 | 79.911 | 38.309 | 41.088 | 1.00 | 46.12 |
| 7743 | O | HOH | W | 383 | 24.388 | 13.964 | 83.335 | 1.00 | 43.93 |
| 7746 | O | HOH | W | 384 | 66.934 | 21.126 | 48.582 | 1.00 | 39.54 |
| 7749 | O | HOH | W | 385 | 45.581 | 5.110 | 107.583 | 1.00 | 44.67 |

FIGURE 3 (Cont.)

| A | B | C | D | E | F | G | H | I | J |
|---|---|---|---|---|---|---|---|---|---|
| 7752 | O | HOH | W | 386 | 68.788 | 32.420 | 85.158 | 1.00 | 34.02 |
| 7755 | O | HOH | W | 387 | 25.104 | 23.891 | 94.195 | 1.00 | 32.43 |
| 7758 | O | HOH | W | 388 | 68.345 | 41.020 | 40.114 | 1.00 | 34.75 |
| 7761 | O | HOH | W | 389 | 62.887 | 18.711 | 74.252 | 1.00 | 34.84 |
| 7764 | O | HOH | W | 390 | 29.838 | 31.117 | 93.514 | 1.00 | 39.99 |
| 7767 | O | HOH | W | 391 | 82.088 | 14.664 | 70.183 | 1.00 | 24.83 |
| 7770 | O | HOH | W | 392 | 48.942 | 13.656 | 94.644 | 1.00 | 37.51 |
| 7773 | O | HOH | W | 393 | 26.394 | 6.241 | 93.499 | 1.00 | 35.60 |
| 7776 | O | HOH | W | 394 | 26.509 | 5.757 | 86.209 | 1.00 | 33.17 |
| 7779 | O | HOH | W | 395 | 67.142 | 14.359 | 76.050 | 1.00 | 38.86 |
| 7782 | O | HOH | W | 396 | 81.643 | 43.583 | 75.342 | 1.00 | 38.31 |
| 7785 | O | HOH | W | 397 | 19.447 | 23.515 | 105.814 | 1.00 | 34.11 |
| 7788 | O | HOH | W | 398 | 51.805 | 34.070 | 113.447 | 1.00 | 36.32 |
| 7791 | O | HOH | W | 399 | 83.084 | 14.244 | 56.918 | 1.00 | 39.06 |
| 7794 | O | HOH | W | 400 | 83.735 | 21.442 | 52.945 | 1.00 | 46.70 |
| 7797 | O | HOH | W | 401 | 30.976 | 42.578 | 102.690 | 1.00 | 38.62 |
| 7800 | O | HOH | W | 402 | 73.593 | 20.208 | 82.459 | 1.00 | 35.51 |
| 7803 | O | HOH | W | 403 | 77.630 | 37.009 | 79.927 | 1.00 | 40.96 |
| 7806 | O | HOH | W | 404 | 82.046 | 39.380 | 44.220 | 1.00 | 43.89 |
| 7809 | O | HOH | W | 405 | 23.583 | 7.080 | 90.796 | 1.00 | 29.66 |
| 7812 | O | HOH | W | 406 | 41.632 | 5.408 | 83.615 | 1.00 | 36.08 |
| 7815 | O | HOH | W | 407 | 76.536 | 53.015 | 47.077 | 1.00 | 37.16 |
| 7818 | O | HOH | W | 408 | 86.797 | 14.752 | 69.083 | 1.00 | 33.41 |
| 7821 | O | HOH | W | 409 | 59.469 | 20.118 | 74.119 | 1.00 | 38.57 |
| 7824 | O | HOH | W | 410 | 51.694 | 28.116 | 95.871 | 1.00 | 31.61 |
| 7827 | O | HOH | W | 411 | 66.294 | 42.050 | 44.131 | 1.00 | 39.17 |
| 7830 | O | HOH | W | 412 | 43.946 | 2.770 | 96.711 | 1.00 | 43.29 |
| 7833 | O | HOH | W | 413 | 43.482 | 19.336 | 120.539 | 1.00 | 42.91 |
| 7836 | O | HOH | W | 414 | 69.486 | 49.525 | 45.498 | 1.00 | 37.65 |
| 7839 | O | HOH | W | 415 | 84.143 | 14.562 | 76.797 | 1.00 | 34.50 |
| 7842 | O | HOH | W | 416 | 68.761 | 22.499 | 47.575 | 1.00 | 31.51 |
| 7845 | O | HOH | W | 417 | 40.979 | 19.293 | 119.290 | 1.00 | 43.70 |
| 7848 | O | HOH | W | 418 | 34.426 | 29.963 | 84.029 | 1.00 | 37.22 |
| 7851 | O | HOH | W | 419 | 71.965 | 8.475 | 62.847 | 1.00 | 38.39 |
| 7854 | O | HOH | W | 420 | 57.222 | 30.883 | 60.921 | 1.00 | 19.03 |
| 7857 | O | HOH | W | 421 | 25.563 | 28.888 | 92.175 | 1.00 | 37.48 |
| 7860 | O | HOH | W | 422 | 62.393 | 40.653 | 65.870 | 1.00 | 34.28 |
| 7863 | O | HOH | W | 423 | 34.533 | 42.550 | 113.946 | 0.50 | 41.65 |
| 7866 | O | HOH | W | 424 | 39.391 | 31.970 | 91.332 | 1.00 | 43.58 |
| 7869 | O | HOH | W | 425 | 53.733 | 27.672 | 110.463 | 1.00 | 33.81 |
| 7872 | O | HOH | W | 426 | 28.962 | 14.335 | 81.311 | 1.00 | 35.33 |
| 7875 | O | HOH | W | 427 | 87.901 | 35.818 | 62.391 | 1.00 | 43.93 |
| 7878 | O | HOH | W | 428 | 52.020 | 29.992 | 97.868 | 1.00 | 39.74 |
| 7881 | O | HOH | W | 429 | 34.190 | 5.785 | 111.872 | 1.00 | 42.28 |
| 7884 | O | HOH | W | 430 | 71.587 | 12.062 | 66.527 | 1.00 | 34.10 |
| 7887 | O | HOH | W | 431 | 39.489 | 18.775 | 77.101 | 1.00 | 45.88 |
| 7890 | O | HOH | W | 432 | 35.837 | 10.980 | 116.864 | 1.00 | 43.05 |
| 7893 | O | HOH | W | 433 | 75.417 | 52.267 | 54.084 | 1.00 | 41.41 |
| 7896 | O | HOH | W | 434 | 67.615 | 18.692 | 50.057 | 1.00 | 36.86 |
| 7899 | O | HOH | W | 435 | 44.811 | 8.718 | 83.330 | 1.00 | 39.80 |
| 7902 | O | HOH | W | 436 | 70.886 | 31.145 | 84.751 | 1.00 | 28.92 |

FIGURE 3 (Cont.)

| A | B | C | D | E | F | G | H | I | J |
|---|---|---|---|---|---|---|---|---|---|
| 7905 | O | HOH | W | 437 | 51.197 | 32.306 | 97.309 | 1.00 | 36.75 |
| 7908 | O | HOH | W | 438 | 28.548 | 31.609 | 115.342 | 1.00 | 33.14 |
| 7911 | O | HOH | W | 439 | 32.126 | 39.301 | 115.079 | 1.00 | 31.75 |
| 7914 | O | HOH | W | 440 | 26.502 | 17.382 | 77.696 | 1.00 | 44.20 |
| 7917 | O | HOH | W | 441 | 81.898 | 11.730 | 55.444 | 1.00 | 44.33 |
| 7920 | O | HOH | W | 442 | 49.945 | 40.841 | 103.415 | 1.00 | 40.42 |
| 7923 | O | HOH | W | 443 | 58.304 | 37.456 | 64.461 | 1.00 | 38.51 |
| 7926 | O | HOH | W | 444 | 57.463 | 29.462 | 101.080 | 1.00 | 43.07 |
| 7929 | O | HOH | W | 445 | 36.238 | 14.017 | 77.566 | 1.00 | 35.63 |
| 7932 | O | HOH | W | 446 | 60.085 | 47.591 | 53.931 | 1.00 | 41.81 |
| 7935 | O | HOH | W | 447 | 46.068 | 40.220 | 110.575 | 1.00 | 43.86 |
| 7938 | O | HOH | W | 448 | 93.634 | 26.879 | 63.332 | 1.00 | 42.95 |
| 7941 | O | HOH | W | 449 | 81.337 | 26.373 | 43.904 | 1.00 | 41.94 |
| 7944 | O | HOH | W | 450 | 77.903 | 43.642 | 61.433 | 1.00 | 39.38 |
| 7947 | O | HOH | W | 451 | 69.005 | 50.348 | 67.279 | 1.00 | 32.78 |
| 7950 | O | HOH | W | 452 | 68.851 | 46.965 | 43.843 | 1.00 | 45.79 |
| 7953 | O | HOH | W | 453 | 60.160 | 30.024 | 62.616 | 1.00 | 40.29 |
| 7956 | O | HOH | W | 454 | 68.654 | 52.954 | 67.169 | 1.00 | 43.09 |
| 7959 | O | HOH | W | 455 | 76.029 | 26.107 | 80.714 | 1.00 | 36.96 |
| 7962 | O | HOH | W | 456 | 83.200 | 28.613 | 44.821 | 1.00 | 43.10 |
| 7965 | O | HOH | W | 457 | 85.142 | 39.882 | 76.006 | 0.50 | 36.02 |
| 7968 | O | HOH | W | 458 | 25.854 | 29.474 | 118.578 | 1.00 | 42.63 |
| 7971 | O | HOH | W | 459 | 41.830 | 42.765 | 94.946 | 1.00 | 66.37 |
| 7974 | O | HOH | W | 460 | 34.334 | 28.010 | 121.678 | 1.00 | 38.12 |
| 7977 | O | HOH | W | 461 | 75.313 | 49.263 | 64.920 | 1.00 | 36.35 |
| 7980 | O | HOH | W | 462 | 36.766 | 39.821 | 119.105 | 1.00 | 42.65 |
| 7983 | O | HOH | W | 463 | 21.484 | 10.505 | 85.861 | 1.00 | 51.47 |
| 7986 | O | HOH | W | 464 | 51.305 | 16.539 | 96.840 | 1.00 | 40.12 |
| 7989 | O | HOH | W | 465 | 49.722 | 43.738 | 99.013 | 1.00 | 37.76 |
| 7992 | O | HOH | W | 466 | 64.274 | 44.842 | 47.738 | 1.00 | 38.08 |
| 7995 | O | HOH | W | 467 | 69.756 | 11.164 | 70.065 | 1.00 | 39.31 |
| 7998 | O | HOH | W | 468 | 38.968 | 27.656 | 123.703 | 1.00 | 38.81 |
| 8001 | O | HOH | W | 469 | 82.187 | 17.294 | 51.824 | 1.00 | 40.91 |
| 8004 | O | HOH | W | 470 | 73.140 | 11.005 | 58.875 | 1.00 | 47.18 |
| 8007 | O | HOH | W | 471 | 35.280 | 19.220 | 78.470 | 1.00 | 48.42 |
| 8010 | O | HOH | W | 472 | 35.184 | 32.385 | 90.803 | 1.00 | 28.91 |
| 8013 | O | HOH | W | 473 | 79.028 | 46.766 | 67.060 | 1.00 | 42.02 |
| 8016 | O | HOH | W | 474 | 58.103 | 22.205 | 74.262 | 1.00 | 43.33 |
| 8019 | O | HOH | W | 475 | 61.416 | 37.369 | 42.799 | 1.00 | 55.35 |
| 8022 | O | HOH | W | 476 | 57.221 | 22.152 | 105.660 | 1.00 | 37.83 |
| 8025 | O | HOH | W | 477 | 51.024 | 32.286 | 94.075 | 1.00 | 54.76 |
| 8028 | O | HOH | W | 478 | 86.392 | 39.420 | 66.320 | 1.00 | 48.76 |
| 8031 | O | HOH | W | 479 | 77.588 | 43.434 | 38.590 | 1.00 | 43.29 |
| 8034 | O | HOH | W | 480 | 34.464 | 16.627 | 116.852 | 1.00 | 37.01 |
| 8037 | O | HOH | W | 481 | 31.329 | 10.974 | 82.359 | 1.00 | 31.83 |
| 8040 | O | HOH | W | 482 | 24.070 | 26.807 | 96.362 | 1.00 | 46.55 |
| 8043 | O | HOH | W | 483 | 31.824 | 40.744 | 112.604 | 1.00 | 50.95 |
| 8046 | O | HOH | W | 484 | 21.204 | 7.983 | 93.738 | 1.00 | 48.48 |
| 8049 | O | HOH | W | 485 | 72.696 | 18.336 | 52.975 | 1.00 | 40.58 |
| 8052 | O | HOH | W | 486 | 44.682 | 17.061 | 76.967 | 1.00 | 44.18 |
| 8055 | O | HOH | W | 487 | 70.663 | 15.492 | 80.703 | 1.00 | 41.84 |

FIGURE 3 (Cont.)

| A | B | C | D | E | F | G | H | I | J |
|---|---|---|---|---|---|---|---|---|---|
| 8058 | O | HOH | W | 488 | 57.064 | 25.166 | 103.588 | 1.00 | 34.81 |
| 8061 | O | HOH | W | 489 | 37.416 | 33.890 | 89.885 | 1.00 | 45.01 |
| 8064 | O | HOH | W | 490 | 48.808 | 29.874 | 93.382 | 1.00 | 39.49 |
| 8067 | O | HOH | W | 491 | 81.114 | 52.145 | 54.365 | 1.00 | 34.19 |
| 8070 | O | HOH | W | 492 | 60.916 | 40.117 | 45.014 | 1.00 | 49.27 |
| 8073 | O | HOH | W | 493 | 87.580 | 36.700 | 64.605 | 1.00 | 45.03 |
| 8076 | O | HOH | W | 494 | 28.751 | 23.686 | 76.633 | 1.00 | 40.84 |
| 8079 | O | HOH | W | 495 | 38.862 | 7.486 | 115.832 | 1.00 | 36.14 |
| 8082 | O | HOH | W | 496 | 26.388 | 25.331 | 116.574 | 1.00 | 39.14 |
| 8085 | O | HOH | W | 497 | 67.656 | 24.470 | 45.331 | 1.00 | 40.99 |
| 8088 | O | HOH | W | 498 | 69.747 | 28.320 | 85.491 | 1.00 | 34.10 |
| 8091 | O | HOH | W | 499 | 79.157 | 19.648 | 48.848 | 1.00 | 50.77 |
| 8094 | O | HOH | W | 500 | 35.410 | 30.470 | 87.201 | 1.00 | 41.41 |
| 8097 | O | HOH | W | 501 | 32.492 | 0.664 | 96.413 | 1.00 | 39.20 |
| 8100 | O | HOH | W | 502 | 30.740 | 0.439 | 94.308 | 1.00 | 39.62 |
| 8103 | O | HOH | W | 503 | 51.414 | 9.199 | 99.427 | 1.00 | 51.33 |
| 8106 | O | HOH | W | 504 | 73.875 | 15.376 | 84.082 | 1.00 | 39.15 |
| 8109 | O | HOH | W | 505 | 55.890 | 29.533 | 67.341 | 1.00 | 43.19 |
| 8112 | O | HOH | W | 506 | 30.063 | 5.482 | 84.894 | 1.00 | 39.03 |
| 8115 | O | HOH | W | 507 | 82.232 | 50.586 | 56.992 | 1.00 | 40.90 |
| 8118 | O | HOH | W | 508 | 20.037 | 18.392 | 102.027 | 1.00 | 43.88 |
| 8121 | O | HOH | W | 509 | 49.965 | 30.105 | 89.488 | 1.00 | 46.51 |
| 8124 | O | HOH | W | 510 | 81.428 | 30.380 | 84.090 | 1.00 | 33.88 |
| 8127 | O | HOH | W | 511 | 29.987 | 17.190 | 119.110 | 1.00 | 41.07 |
| 8130 | O | HOH | W | 512 | 66.147 | 49.202 | 65.871 | 1.00 | 37.48 |
| 8133 | O | HOH | W | 513 | 32.697 | 13.462 | 114.610 | 1.00 | 47.34 |
| 8136 | O | HOH | W | 514 | 75.976 | 23.931 | 82.144 | 1.00 | 39.03 |
| 8139 | O | HOH | W | 515 | 74.330 | 38.046 | 81.018 | 1.00 | 31.43 |
| 8142 | O | HOH | W | 516 | 28.219 | 0.316 | 91.245 | 1.00 | 40.92 |
| 8145 | O | HOH | W | 517 | 74.757 | 10.587 | 71.386 | 1.00 | 38.69 |
| 8148 | O | HOH | W | 518 | 77.907 | 51.057 | 61.453 | 1.00 | 41.18 |
| 8151 | O | HOH | W | 519 | 65.667 | 11.738 | 72.078 | 1.00 | 51.87 |
| 8154 | O | HOH | W | 520 | 76.156 | 38.427 | 40.321 | 1.00 | 37.32 |
| 8157 | O | HOH | W | 521 | 22.154 | 16.737 | 110.149 | 1.00 | 47.30 |
| 8160 | O | HOH | W | 522 | 24.981 | 17.351 | 113.232 | 1.00 | 38.33 |
| 8163 | O | HOH | W | 523 | 82.375 | 26.374 | 76.413 | 1.00 | 36.63 |
| 8166 | O | HOH | W | 524 | 79.076 | 46.568 | 71.199 | 1.00 | 40.64 |
| 8169 | O | HOH | W | 525 | 58.986 | 32.286 | 64.289 | 1.00 | 44.77 |
| 8172 | O | HOH | W | 526 | 25.625 | -0.091 | 89.906 | 1.00 | 47.87 |
| 8175 | O | HOH | W | 527 | 20.675 | 18.226 | 107.890 | 1.00 | 43.15 |
| 8178 | O | HOH | W | 528 | 53.719 | 21.535 | 97.399 | 1.00 | 38.34 |
| 8181 | O | HOH | W | 529 | 70.091 | 49.852 | 71.363 | 1.00 | 46.43 |
| 8184 | O | HOH | W | 530 | 65.710 | 10.722 | 68.316 | 1.00 | 46.58 |
| 8187 | O | HOH | W | 531 | 58.523 | 29.264 | 77.931 | 1.00 | 50.19 |
| 8190 | O | HOH | W | 532 | 75.007 | 21.150 | 45.963 | 1.00 | 42.71 |
| 8193 | O | HOH | W | 533 | 90.100 | 34.890 | 61.134 | 1.00 | 43.21 |
| 8196 | O | HOH | W | 534 | 76.029 | 16.233 | 84.972 | 1.00 | 50.95 |
| 8199 | O | HOH | W | 535 | 57.290 | 45.395 | 56.572 | 1.00 | 41.53 |
| 8202 | O | HOH | W | 536 | 79.034 | 53.482 | 53.953 | 1.00 | 45.83 |
| 8205 | O | HOH | W | 537 | 31.414 | -0.965 | 85.300 | 1.00 | 42.04 |
| 8208 | O | HOH | W | 538 | 86.663 | 27.162 | 44.492 | 1.00 | 38.65 |

FIGURE 3 (Cont.)

| A | B | C | D | E | F | G | H | I | J |
|---|---|---|---|---|---|---|---|---|---|
| 8211 | O | HOH | W | 539 | 22.241 | 21.804 | 107.644 | 1.00 | 42.55 |
| 8214 | O | HOH | W | 540 | 19.522 | 12.661 | 98.527 | 1.00 | 42.80 |
| 8217 | O | HOH | W | 541 | 50.321 | 8.270 | 93.513 | 1.00 | 41.46 |
| 8220 | O | HOH | W | 542 | 85.443 | 9.963 | 63.939 | 1.00 | 43.91 |
| 8223 | O | HOH | W | 543 | 28.634 | 9.593 | 84.503 | 1.00 | 37.85 |
| 8226 | O | HOH | W | 544 | 22.689 | 11.016 | 105.997 | 1.00 | 47.21 |
| 8229 | O | HOH | W | 545 | 26.887 | 12.624 | 113.084 | 1.00 | 47.15 |
| 8232 | O | HOH | W | 546 | 27.117 | 2.873 | 94.393 | 1.00 | 41.31 |
| 8235 | O | HOH | W | 547 | 57.067 | 25.983 | 108.052 | 1.00 | 37.53 |
| 8238 | O | HOH | W | 548 | 24.956 | 23.645 | 117.873 | 1.00 | 51.24 |
| 8241 | O | HOH | W | 549 | 64.164 | 30.352 | 59.866 | 1.00 | 43.38 |
| 8244 | O | HOH | W | 550 | 72.971 | 27.190 | 85.347 | 1.00 | 48.35 |
| 8247 | O | HOH | W | 551 | 51.710 | 31.912 | 117.232 | 1.00 | 45.34 |
| 8250 | O | HOH | W | 552 | 55.097 | 33.482 | 110.146 | 1.00 | 41.77 |
| 8253 | O | HOH | W | 553 | 59.768 | 22.449 | 78.026 | 1.00 | 39.66 |
| 8256 | O | HOH | W | 554 | 66.097 | 16.589 | 52.830 | 1.00 | 36.95 |
| 8259 | O | HOH | W | 555 | 59.316 | 22.334 | 101.691 | 1.00 | 44.95 |
| 8262 | O | HOH | W | 556 | 35.383 | 43.855 | 107.407 | 1.00 | 50.46 |
| 8265 | O | HOH | W | 557 | 91.966 | 30.332 | 61.640 | 1.00 | 47.63 |
| 8268 | O | HOH | W | 558 | 35.665 | 0.387 | 109.138 | 1.00 | 45.78 |
| 8271 | O | HOH | W | 559 | 65.894 | 16.532 | 76.954 | 1.00 | 46.35 |
| 8274 | O | HOH | W | 560 | 84.011 | 47.321 | 58.712 | 1.00 | 43.55 |
| 8277 | O | HOH | W | 561 | 51.036 | 32.874 | 119.829 | 1.00 | 51.48 |
| 8280 | O | HOH | W | 562 | 45.439 | 39.575 | 94.936 | 0.50 | 39.83 |
| 8283 | O | HOH | W | 563 | 20.295 | 28.361 | 110.544 | 1.00 | 41.32 |
| 8286 | O | HOH | W | 564 | 31.867 | 1.884 | 108.575 | 1.00 | 43.27 |
| 8289 | O | HOH | W | 565 | 24.260 | 2.211 | 93.353 | 1.00 | 45.14 |
| 8292 | O | HOH | W | 566 | 85.121 | 15.813 | 57.409 | 1.00 | 50.14 |
| 8295 | O | HOH | W | 567 | 25.273 | 19.060 | 118.076 | 1.00 | 38.20 |
| 8298 | O | HOH | W | 568 | 81.597 | 13.045 | 83.500 | 1.00 | 43.69 |
| 8301 | O | HOH | W | 569 | 70.217 | 42.042 | 38.925 | 1.00 | 49.82 |
| 8304 | O | HOH | W | 570 | 81.413 | 26.380 | 83.755 | 1.00 | 48.43 |
| 8307 | O | HOH | W | 571 | 57.458 | 28.415 | 74.089 | 1.00 | 39.95 |
| 8310 | O | HOH | W | 572 | 26.395 | 1.843 | 103.480 | 1.00 | 44.49 |
| 8313 | O | HOH | W | 573 | 40.464 | 0.126 | 78.979 | 1.00 | 50.46 |
| 8316 | O | HOH | W | 574 | 81.934 | 33.436 | 43.613 | 1.00 | 45.48 |
| 8319 | O | HOH | W | 575 | 51.496 | 26.972 | 114.029 | 1.00 | 46.03 |
| 8322 | O | HOH | W | 576 | 33.843 | -0.164 | 83.253 | 1.00 | 39.24 |
| 8325 | O | HOH | W | 577 | 33.910 | 30.938 | 81.060 | 1.00 | 41.93 |
| 8328 | O | HOH | W | 578 | 48.531 | 28.037 | 92.092 | 1.00 | 46.69 |
| 8331 | O | HOH | W | 579 | 52.642 | 43.598 | 100.051 | 1.00 | 48.51 |
| 8334 | O | HOH | W | 580 | 89.609 | 27.940 | 51.458 | 1.00 | 46.53 |
| 8337 | O | HOH | W | 581 | 27.953 | 41.151 | 96.275 | 1.00 | 26.17 |
| 8340 | O | HOH | W | 582 | 19.736 | 25.690 | 110.594 | 1.00 | 37.59 |
| 8343 | O | HOH | W | 583 | 42.010 | 40.196 | 113.497 | 1.00 | 48.49 |
| 8346 | O | HOH | W | 584 | 80.043 | 32.326 | 41.329 | 1.00 | 46.08 |
| 8349 | O | HOH | W | 585 | 49.529 | 35.398 | 118.296 | 1.00 | 41.95 |
| 8352 | O | HOH | W | 586 | 53.112 | 19.466 | 91.417 | 1.00 | 38.65 |
| 8355 | O | HOH | W | 587 | 75.825 | 12.813 | 77.520 | 1.00 | 34.91 |
| 8358 | O | HOH | W | 588 | 64.794 | 13.016 | 73.920 | 1.00 | 49.49 |
| 8361 | O | HOH | W | 589 | 62.166 | 18.668 | 77.736 | 1.00 | 53.44 |

FIGURE 3 (Cont.)

| A | B | C | D | E | F | G | H | I | J |
|---|---|---|---|---|---|---|---|---|---|
| 8364 | O | HOH | W | 590 | 51.227 | 30.521 | 121.427 | 1.00 | 48.93 |
| 8367 | O | HOH | W | 591 | 40.921 | 2.633 | 81.606 | 1.00 | 36.89 |
| 8370 | O | HOH | W | 592 | 36.264 | 44.963 | 99.507 | 1.00 | 40.02 |
| 8373 | O | HOH | W | 593 | 49.419 | 23.263 | 83.999 | 1.00 | 44.62 |
| 8376 | O | HOH | W | 594 | 70.339 | 11.588 | 76.510 | 1.00 | 43.54 |
| 8379 | O | HOH | W | 595 | 54.232 | 30.312 | 104.467 | 1.00 | 28.80 |
| 8382 | O | HOH | W | 596 | 40.103 | 32.300 | 120.462 | 1.00 | 43.57 |
| 8385 | O | HOH | W | 597 | 32.893 | -2.613 | 90.203 | 1.00 | 41.26 |
| 8388 | O | HOH | W | 598 | 63.944 | 26.741 | 57.379 | 1.00 | 44.16 |
| 8391 | O | HOH | W | 599 | 89.725 | 21.936 | 62.970 | 1.00 | 41.95 |
| 8394 | O | HOH | W | 600 | 31.081 | 25.860 | 94.873 | 1.00 | 42.83 |
| 8397 | O | HOH | W | 601 | 20.303 | 23.707 | 109.013 | 1.00 | 45.74 |
| 8400 | O | HOH | W | 602 | 51.744 | 37.892 | 105.337 | 1.00 | 44.52 |
| 8403 | O | HOH | W | 603 | 57.183 | 33.427 | 61.957 | 1.00 | 45.67 |
| 8406 | O | HOH | W | 604 | 36.956 | -1.520 | 105.464 | 1.00 | 43.07 |
| 8409 | O | HOH | W | 605 | 35.479 | 7.117 | 80.813 | 1.00 | 41.26 |
| 8412 | O | HOH | W | 606 | 87.601 | 24.790 | 49.846 | 1.00 | 45.05 |
| 8415 | O | HOH | W | 607 | 21.885 | 15.786 | 105.987 | 1.00 | 43.29 |
| 8418 | O | HOH | W | 608 | 65.204 | 17.630 | 81.522 | 1.00 | 43.09 |
| 8421 | O | HOH | W | 609 | 55.089 | 21.859 | 95.530 | 1.00 | 50.41 |
| 8424 | O | HOH | W | 610 | 45.486 | 27.431 | 118.393 | 1.00 | 42.46 |
| 8427 | O | HOH | W | 611 | 39.925 | 4.123 | 110.987 | 1.00 | 45.56 |
| 8430 | O | HOH | W | 612 | 26.615 | 24.169 | 98.955 | 1.00 | 29.48 |
| 8433 | O | HOH | W | 613 | 29.316 | 17.540 | 77.998 | 1.00 | 46.79 |
| 8436 | O | HOH | W | 614 | 85.582 | 22.805 | 50.023 | 1.00 | 47.03 |
| 8439 | O | HOH | W | 615 | 66.748 | 37.902 | 39.527 | 1.00 | 38.14 |
| 8442 | O | HOH | W | 616 | 82.067 | 25.724 | 47.938 | 1.00 | 51.42 |
| 8445 | O | HOH | W | 617 | 52.993 | 25.214 | 109.562 | 1.00 | 32.02 |
| 8448 | O | HOH | W | 618 | 76.927 | 24.322 | 54.990 | 1.00 | 43.99 |
| 8451 | O | HOH | W | 619 | 31.800 | 40.598 | 96.007 | 1.00 | 46.88 |
| 8454 | O | HOH | W | 620 | 24.266 | 10.521 | 104.060 | 1.00 | 49.92 |
| 8457 | O | HOH | W | 621 | 63.129 | 25.870 | 54.940 | 1.00 | 53.80 |
| 8460 | O | HOH | W | 622 | 41.556 | 43.942 | 112.076 | 1.00 | 45.67 |
| 8463 | O | HOH | W | 623 | 58.655 | 42.429 | 66.051 | 1.00 | 39.64 |
| 8466 | O | HOH | W | 624 | 38.479 | 21.736 | 77.473 | 1.00 | 56.01 |
| 8469 | O | HOH | W | 625 | 39.434 | 13.757 | 115.073 | 1.00 | 53.57 |
| 8472 | O | HOH | W | 626 | 32.466 | 23.353 | 78.452 | 1.00 | 55.44 |
| 8475 | O | HOH | W | 627 | 89.067 | 26.528 | 54.655 | 1.00 | 36.58 |

SEQUENCE LISTING

```
<160> NUMBER OF SEQ ID NOS: 4

<210> SEQ ID NO 1
<211> LENGTH: 331
<212> TYPE: PRT
<213> ORGANISM: Homo sapiens
<220> FEATURE:
<221> NAME/KEY: MISC_FEATURE
<222> LOCATION: (1)..(331)
<223> OTHER INFORMATION: Amino acid sequence for full-length human wild
      type Cathepsin S
<300> PUBLICATION INFORMATION:
<308> DATABASE ACCESSION NUMBER: AF230097
<309> DATABASE ENTRY DATE: 2002-04-08
<313> RELEVANT RESIDUES: (1)..(331)

<400> SEQUENCE: 1

Met Lys Arg Leu Val Cys Val Leu Leu Val Cys Ser Ser Ala Val Ala
1               5                   10                  15

Gln Leu His Lys Asp Pro Thr Leu Asp His His Trp His Leu Trp Lys
            20                  25                  30

Lys Thr Tyr Gly Lys Gln Tyr Lys Glu Lys Asn Glu Glu Ala Val Arg
        35                  40                  45

Arg Leu Ile Trp Glu Lys Asn Leu Lys Phe Val Met Leu His Asn Leu
    50                  55                  60

Glu His Ser Met Gly Met His Ser Tyr Asp Leu Gly Met Asn His Leu
65                  70                  75                  80

Gly Asp Met Thr Ser Glu Glu Val Met Ser Leu Met Ser Ser Leu Arg
                85                  90                  95

Val Pro Ser Gln Trp Gln Arg Asn Ile Thr Tyr Lys Ser Asn Pro Asn
            100                 105                 110

Arg Ile Leu Pro Asp Ser Val Asp Trp Arg Glu Lys Gly Cys Val Thr
        115                 120                 125

Glu Val Lys Tyr Gln Gly Ser Cys Gly Ala Cys Trp Ala Phe Ser Ala
    130                 135                 140

Val Gly Ala Leu Glu Ala Gln Leu Lys Leu Lys Thr Gly Lys Leu Val
145                 150                 155                 160

Ser Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
            180                 185                 190

Ile Asp Asn Lys Gly Ile Asp Ser Asp Ala Ser Tyr Pro Tyr Lys Ala
        195                 200                 205
```

```
Met Asp Leu Lys Cys Gln Tyr Asp Ser Lys Tyr Arg Ala Ala Thr Cys
    210                 215                 220

Ser Lys Tyr Thr Glu Leu Pro Tyr Gly Arg Glu Asp Val Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
            260                 265                 270

Thr Gln Asn Val Asn His Gly Val Leu Val Val Gly Tyr Gly Asp Leu
        275                 280                 285

Asn Gly Lys Glu Tyr Trp Leu Val Lys Asn Ser Trp Gly His Asn Phe
    290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
                325                 330
```

<210> SEQ ID NO 2
<211> LENGTH: 996
<212> TYPE: DNA
<213> ORGANISM: Homo sapiens
<220> FEATURE:
<221> NAME/KEY: misc_feature
<222> LOCATION: (1)..(996)
<223> OTHER INFORMATION: Human cDNA sequence for Cathepsin S

<400> SEQUENCE: 2

```
atgaaacggc tggtttgtgt gctcttggtg tgctcctctg cagtggcaca gttgcataaa      60
gatcctaccc tggatcacca ctggcatctc tggaagaaaa cctatggcaa acaatacaag     120
gaaaagaatg aagaagcagt acgacgtctc atctgggaaa agaatctaaa gtttgtgatg     180
cttcacaacc tggagcattc aatgggaatg cactctatacg atctgggcat gaaccacctg     240
ggagacatga ccagtgaaga agtgatgtct ttgatgagtt ccctgagagt tcccagccag     300 tgcagagaa atatcacata taagtcaaac cctaatcgga tattgcctga ttctgtggac     360
tggagagaga aagggtgtgt tactgaagtg aaatatcaag gttcttgtgg tgcttgctgg     420
gctttcagtg ctgtggggc cctggaagca cagctgaagc tgaaaacagg aaagctggtg     480
tctctcagtg cccagaacct ggtggattgc tcaactgaaa aatatggaaa caaaggctgc     540
aatggtggct tcatgacaac ggctttccag tacatcattg ataacaaggg catcgactca     600
gacgcttcct atccctacaa agccatggat ctgaaatgtc aatatgactc aaaatatcgt     660
gctgccacat gttcaaagta cactgaactt ccttatggca gagaagatgt cctgaaagaa     720
gctgtggcca ataaaggccc agtgtctgtt ggtgtagatg cgcgtcatcc ttctttcttc     780
ctctacagaa gtggtgtcta ctatgaacca tcctgtactc agaatgtgaa tcatggtgta     840
cttgtggttg gctatggtga tcttaatggg aagaatact ggcttgtgaa aacagctgg     900 ggccacaact ttggtgaaga aggatatatt cggatggcaa gaaataaagg aaatcattgt     960
gggattgcta gctttccctc ttacccagaa atctag                               996
```

<210> SEQ ID NO 3
<211> LENGTH: 225
<212> TYPE: PRT
<213> ORGANISM: Artificial
<220> FEATURE:
<223> OTHER INFORMATION: Amino acid sequence for resdues 114-331 of
      Cathepsin S with a C-terminal Glycine-6x-histidine tag
<220> FEATURE:

```
<221> NAME/KEY: MISC_FEATURE
<222> LOCATION: (1)..(218)
<223> OTHER INFORMATION: Amino acid sequence for residues 114-331 of
      Cathepsin S
<220> FEATURE:
<221> NAME/KEY: MISC_FEATURE
<222> LOCATION: (219)..(225)
<223> OTHER INFORMATION: Amino acid sequence for C-terminal
      Glycine-6x-histidine tag

<400> SEQUENCE: 3

Ile Leu Pro Asp Ser Val Asp Trp Arg Glu Lys Gly Cys Val Thr Glu
1               5                   10                  15

Val Lys Tyr Gln Gly Ser Cys Gly Ala Cys Trp Ala Phe Ser Ala Val
            20                  25                  30

Gly Ala Leu Glu Ala Gln Leu Lys Leu Lys Thr Gly Lys Leu Val Ser
        35                  40                  45

Leu Ser Ala Gln Asn Leu Val Asp Cys Ser Thr Glu Lys Tyr Gly Asn
50                  55                  60

Lys Gly Cys Asn Gly Gly Phe Met Thr Thr Ala Phe Gln Tyr Ile Ile
65                  70                  75                  80

Asp Asn Lys Gly Ile Asp Ser Asp Ala Ser Tyr Pro Tyr Lys Ala Met
                85                  90                  95

Asp Gln Lys Cys Gln Tyr Asp Ser Lys Tyr Arg Ala Ala Thr Cys Ser
            100                 105                 110

Lys Tyr Thr Glu Leu Pro Tyr Gly Arg Glu Asp Val Leu Lys Glu Ala
        115                 120                 125

Val Ala Asn Lys Gly Pro Val Ser Val Gly Val Asp Ala Arg His Pro
    130                 135                 140

Ser Phe Phe Leu Tyr Arg Ser Gly Val Tyr Tyr Glu Pro Ser Cys Thr
145                 150                 155                 160

Gln Asn Val Asn His Gly Val Leu Val Val Gly Tyr Gly Asp Leu Asn
                165                 170                 175

Gly Lys Glu Tyr Trp Leu Val Lys Asn Ser Trp Gly His Asn Phe Gly
            180                 185                 190

Glu Glu Gly Tyr Ile Arg Met Ala Arg Asn Lys Gly Asn His Cys Gly
        195                 200                 205

Ile Ala Ser Phe Pro Ser Tyr Pro Glu Ile Gly His His His His His
    210                 215                 220

His
225

<210> SEQ ID NO 4
<211> LENGTH: 340
<212> TYPE: PRT
<213> ORGANISM: Artificial
<220> FEATURE:
<223> OTHER INFORMATION: Amino acid sequence for Cathepsin S with an
      N-terminal Methionine-Proline and a C-terminal
      Glycine-6x-histidine tag
<220> FEATURE:
<221> NAME/KEY: MISC_FEATURE
<222> LOCATION: (1)..(2)
<223> OTHER INFORMATION: Amino acid sequence for an N-terminal
      Methionine-Proline tag
<220> FEATURE:
<221> NAME/KEY: MISC_FEATURE
<222> LOCATION: (3)..(333)
<223> OTHER INFORMATION: Amino acid sequence for Cathepsin S
<220> FEATURE:
<221> NAME/KEY: MISC_FEATURE
<222> LOCATION: (334)..(340)
<223> OTHER INFORMATION: Amino acid sequence for a C-terminal
```

-continued

Glycine-6x-histidine tag

<400> SEQUENCE: 4

```
Met Pro Met Lys Arg Leu Val Cys Val Leu Val Cys Ser Ser Ala
 1               5                  10                  15

Val Ala Gln Leu His Lys Asp Pro Thr Leu Asp His Trp His Leu
             20                  25                  30

Trp Lys Lys Thr Tyr Gly Lys Gln Tyr Lys Glu Lys Asn Glu Ala
             35                  40                  45

Val Arg Arg Leu Ile Trp Glu Lys Asn Leu Lys Phe Val Met Leu His
         50                  55                  60

Asn Leu Glu His Ser Met Gly Met His Ser Tyr Asp Leu Gly Met Asn
 65                  70                  75                  80

His Leu Gly Asp Met Thr Ser Glu Glu Val Met Ser Leu Met Ser Ser
                 85                  90                  95

Leu Arg Val Pro Ser Gln Trp Gln Arg Asn Ile Thr Tyr Lys Ser Asn
                100                 105                 110

Pro Asn Arg Ile Leu Pro Asp Ser Val Asp Trp Arg Glu Lys Gly Cys
             115                 120                 125

Val Thr Glu Val Lys Tyr Gln Gly Ser Cys Gly Ala Cys Trp Ala Phe
130                 135                 140

Ser Ala Val Gly Ala Leu Glu Ala Gln Leu Lys Leu Lys Thr Gly Lys
145                 150                 155                 160

Leu Val Ser Leu Ser Ala Gln Asn Leu Val Asp Cys Ser Thr Glu Lys
                165                 170                 175

Tyr Gly Asn Lys Gly Cys Asn Gly Gly Phe Met Thr Thr Ala Phe Gln
                180                 185                 190

Tyr Ile Ile Asp Asn Lys Gly Ile Asp Ser Asp Ala Ser Tyr Pro Tyr
            195                 200                 205

Lys Ala Met Asp Gln Lys Cys Gln Tyr Asp Ser Lys Tyr Arg Ala Ala
210                 215                 220

Thr Cys Ser Lys Tyr Thr Glu Leu Pro Tyr Gly Arg Glu Asp Val Leu
225                 230                 235                 240

Lys Glu Ala Val Ala Asn Lys Gly Pro Val Ser Val Gly Val Asp Ala
                245                 250                 255

Arg His Pro Ser Phe Phe Leu Tyr Arg Ser Gly Val Tyr Tyr Glu Pro
            260                 265                 270

Ser Cys Thr Gln Asn Val Asn His Gly Val Leu Val Val Gly Tyr Gly
            275                 280                 285

Asp Leu Asn Gly Lys Glu Tyr Trp Leu Val Lys Asn Ser Trp Gly His
            290                 295                 300

Asn Phe Gly Glu Glu Gly Tyr Ile Arg Met Ala Arg Asn Lys Gly Asn
305                 310                 315                 320

His Cys Gly Ile Ala Ser Phe Pro Ser Tyr Pro Glu Ile Gly His His
                325                 330                 335

His His His His
            340
```

…

CRYSTALLIZATION OF CATHEPSIN S

RELATED APPLICATION

This application claims the benefit of U.S. Provisional Application No. 60/405,423, filed Aug. 23, 2002, which is incorporated herein by reference.

FIELD OF THE INVENTION

The present invention relates to the cysteine protease "cathepsins" of the papain superfamily and more specifically to a particular cathepsin known as Cathepsin S ("CatS"). Provided is CatS in crystalline form, methods of forming crystals comprising CatS, methods of using crystals comprising CatS, a crystal structure of CatS, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein.

SUMMARY OF THE INVENTION

The present invention is directed to crystals comprising CatS and particularly crystals comprising CatS that have sufficient size and quality to obtain useful information about the structural properties of CatS and molecules or complexes that may associate with CatS.

In one embodiment, a composition is provided that comprises a protein in crystalline form wherein at least a portion of the protein has 55%, 65%, 75%, 85%, 90%, 95%, 97%, 99% or greater identity with residues SEQ. ID No. 1.

In one variation, the protein has activity characteristic of CatS. For example, the protein may optionally be inhibited by inhibitors of wild type CatS. The protein crystal may also diffract X-rays for a determination of structure coordinates to a resolution of 4 Å, 3.5 Å, 3.0 Å or less.

In one variation, the protein crystal has a crystal lattice in a P4122 space group. The protein crystal may also have a crystal lattice having unit cell dimensions, +/−5%, of a—b=85.159 Å and c=152.18 Å.

The present invention is also directed to crystallizing CatS. The present invention is also directed to the conditions useful for crystallizing CatS. It should be recognized that a wide variety of crystallization methods can be used in combination with the crystallization conditions to form crystals comprising CatS including, but not limited to, vapor diffusion, batch, dialysis, and other methods of contacting the protein solution for the purpose of crystallization.

The present invention is also directed to crystallizing CatS. The present invention is also directed to the conditions useful for crystallizing CatS. It should be recognized that a wide variety of crystallization methods can be used in combination with the crystallization conditions to form crystals comprising CatS including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues SEQ. ID No. 1; and storing the crystallization volume under conditions suitable for crystal formation.

In one variation, the crystallization volume comprises the protein in a concentration between 1 mg/ml and 50 mg/ml, and 5-50% w/v of precipitant wherein the precipitant comprises one or more members of the group comprising PEG having a molecular weight range between 200-20000, 2-methyl-2,4-pentanediol (MPD) and isopropanol, and wherein the crystallization volume has a pH between pH 4 and pH 10.

The method may optionally further comprise forming a protein crystal that has a crystal lattice in a P4122 space group. The method also optionally further comprises forming a protein crystal that has a crystal lattice having unit cell dimensions, +/−5%, of a=b=85.159 Å and c=152.18 Å. The invention also relates to protein crystals formed by these methods.

The present invention is also directed to a composition comprising an isolated protein that comprises or consists of one or more of the protein sequence(s) of CatS taught herein for crystallizing CatS. The present invention is also directed to a composition comprising an isolated nucleic acid molecule that comprises or consists of the nucleotides for expressing the protein sequence of CatS taught herein for crystallizing CatS.

The present invention is also directed to an expression vector that may be used to express the isolated proteins taught herein for crystallizing CatS.

The present invention is also directed to an expression vector that may be used to express the isolated proteins taught herein for crystallizing CatS. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for CatS as well as structure coordinates that are comparatively similar to these structure coordinates. It is noted that these comparatively similar structure coordinates may encompass proteins with similar sequences and/or structures, such as other cathepsins. For example, machine-readable data storage media is provided having data storage material encoded with machine-readable data that comprises structure coordinates that are comparatively similar to the structure coordinates of CatS. The present invention is also directed to a machine readable data storage medium having data storage material encoded with machine readable data, which, when read by an appropriate machine, can display a three dimensional representation of all or a portion of a structure of CatS or a model that is comparatively similar to the structure of all or a portion of CatS.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1. The amino acids being overlayed and compared need not to be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.65, 0.43, or 0.33 when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 | alpha-carbon atoms[1] | 0.65 | 0.43 | 0.33 |
| (4 Angstrom set) | main-chain atoms[1] | 0.63 | 0.42 | 0.32 |
| (relative to E64) | all non-hydrogen[2] | 0.67 | 0.44 | 0.33 |
| Table 3 | alpha-carbon atoms[1] | 0.41 | 0.27 | 0.20 |
| (7 Angstrom set) | main-chain atoms[1] | 0.40 | 0.26 | 0.20 |
| (relative to E64) | all non-hydrogen[2] | 0.35 | 0.24 | 0.18 |
| Table 4 | alpha-carbon atoms[1] | 0.36 | 0.24 | 0.18 |
| (10 Angstrom set) | main-chain atoms[1] | 0.37 | 0.25 | 0.19 |
| (relative to E64) | all non-hydrogen[2] | 0.25 | 0.17 | 0.13 |
| Table 5 | alpha-carbon atoms[1] | 0.19 | 0.13 | 0.10 |
| (4 Angstrom set) | main-chain atoms[1] | 0.19 | 0.13 | 0.10 |
| (relative to Trp186) | all non-hydrogen[2] | 0.15 | 0.10 | 0.07 |
| Table 6 | alpha-carbon atoms[1] | 0.56 | 0.38 | 0.28 |
| (7 Angstrom set) | main-chain atoms[1] | 0.55 | 0.37 | 0.27 |
| (relative to Trp186) | all non-hydrogen[2] | 0.62 | 0.41 | 0.30 |
| Table 7 | alpha-carbon atoms[1] | 0.30 | 0.20 | 0.15 |
| (10 Angstrom set) | main-chain atoms[1] | 0.30 | 0.20 | 0.15 |
| (relative to Trp186) | all non-hydrogen[2] | 0.39 | 0.26 | 0.19 |
| SEQ. ID No. 1 | alpha-carbon atoms[1] | 0.29 | 0.19 | 0.14 |
| | main-chain atoms[1] | 0.29 | 0.19 | 0.14 |
| | all non-hydrogen[2] | 0.35 | 0.23 | 0.17 |

[1] the RMSD computed between the atoms of all amino acids that are common to both the target and the reference in the aligned and superposed structure. The amino acids need not to be identical.
[2] the RMSD computed only between identical amino acids, which are common to both the target and the reference in the aligned and superposed structure.

The present invention is also directed to a three-dimensional structure of all or a portion of CatS. This three-dimensional structure may be used to identify binding sites, to provide mutants having desirable binding properties, and ultimately, to design, characterize, or identify ligands capable of interacting with CatS. Ligands that interact with CatS may be any type of atom, compound, protein or chemical group that binds to or otherwise associates with the protein. Examples of types of ligands include natural substrates for CatS, inhibitors of CatS, and heavy atoms. The inhibitors of CatS may optionally be used as drugs to treat therapeutic indications by modifying the in vivo activity of CatS.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing a three dimensional representation of a structure based on the structure coordinates; and displaying the three dimensional representation.

The present invention is also directed to a method for solving a three-dimensional crystal structure of a target protein using the structure of CatS.

In various embodiments, computational methods are provided comprising: taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

These methods may optionally further comprise determining a three-dimensional crystal structure based upon the computed three-dimensional electron density map.

The present invention is also directed to using a crystal structure of CatS, in particular the structure coordinates of CatS and the surface contour defined by them, in methods for screening, designing, or optimizing molecules or other chemical entities that interact with and preferably inhibit CatS.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of CatS and/or its structure coordinates to evaluate the ability of entities to associate with CatS. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein; and contacting the entity with a protein wherein at least a portion of the protein has 55%, 65%, 75%, 85%, 90%, 95%, 97%, 99% or greater identity with residues SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for CatS, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for CatS, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of CatS. For example, the protein may optionally be inhibited by inhibitors of wild type CatS.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues SEQ. ID No. 1; and performing rational drug design using a three dimensional structure that is based on the obtained structure coordinates.

The protein crystals may optionally have a crystal lattice with a P4122 space group and unit cell dimensions, +/−5%, of a=b=85.159 Å and c=152.18 Å.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2, 3 and 4 referred to in this application.

FIG. 3 lists a set of atomic structure coordinates for the catalytic domain of CatS (residues 115-331 of SEQ. ID No. 1) as derived by X-ray crystallography from a crystal that comprises the protein. The reference numbers in column E of FIG. 3 correspond to residue numbers of SEQ. ID No. 3. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2:
FIG. 2 illustrates a crystal of the complex of the catalytic domain of CatS (residues 115-331 of SEQ. ID No. 1)—with E64.

The present invention relates to the cysteine protease "cathepsins" of the papain superfamily and more specifically to a particular cathepsin known as Cathepsin S ("CatS"). More specifically, the present invention relates to CatS in crystalline form, methods of forming crystals comprising CatS, methods of using crystals comprising CatS, a crystal structure of CatS, and methods of using the crystal structure.

In describing protein structure and function herein, reference is made to amino acids comprising the protein. The amino acids may also be referred to by their conventional abbreviations; A=Ala Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. CatS

Cathepsin S (CatS) is a cysteine protease of the papain superfamily. It plays a key role in the generation of a major histocompatibility complex (MHC) class II restricted T-cell response by antigen-presenting cells. Therefore, selective inhibition of this enzyme may be useful in modulating class II restricted T-cell responses in immune related disorders such as rheumatoid arthritis, multiple sclerosis and extrinsic asthma.

Cathepsin S is located primarily in lymphatic tissues, the spleen, and in lung macrophages. CatS is a monomeric, 331 amino acids, 37.5 kDa protein. When activated by proteolytic cleavage at low pH, the first 114 residues of the protein are removed, yielding the active, monomeric protein comprising residues 115-331.

It should be understood that the methods and compositions provided relating to CatS are not intended to be limited to the wild type, full length form of CatS (GenBank Accession Number NP 004070; Wiederanders, B et al "Phylogenetic conservation of cysteine proteases: Cloning and expression of a cDNA coding for human cathepsin S." J. Biol. Chem. 267, 13708-13713). Instead, the present invention also relates to fragments and variants of CatS as described herein.

In one embodiment, CatS comprises the wild-type form of full length CatS, set forth herein as SEQ. ID No. 1.

It should be recognized that the invention may be readily extended to various variants of wild-type CatS and variants of fragments thereof. In another embodiment, CatS comprises a sequence that has at least 65% identity, preferably at least 70%, 80%, 90%, 95% or higher identity with SEQ. ID No. 1.

It is also noted that the above sequences of CatS is also intended to encompass isoforms, mutants and fusion proteins of these sequences. An example of a fusion protein is provided by SEQ. ID No. 3, which includes a 7 residue C-terminal tag (GHHHHHH) that may be used to facilitate purification of the protein. The extended construct is represented in the two sets of structure coordinates shown in FIG. 3, represented by chains "A" and "B".

With the crystal structure provided herein, where amino acid residues are positioned in the structure are now known. As a result, the impact of different substitutions can be more easily predicted and understood.

Figure 5A:
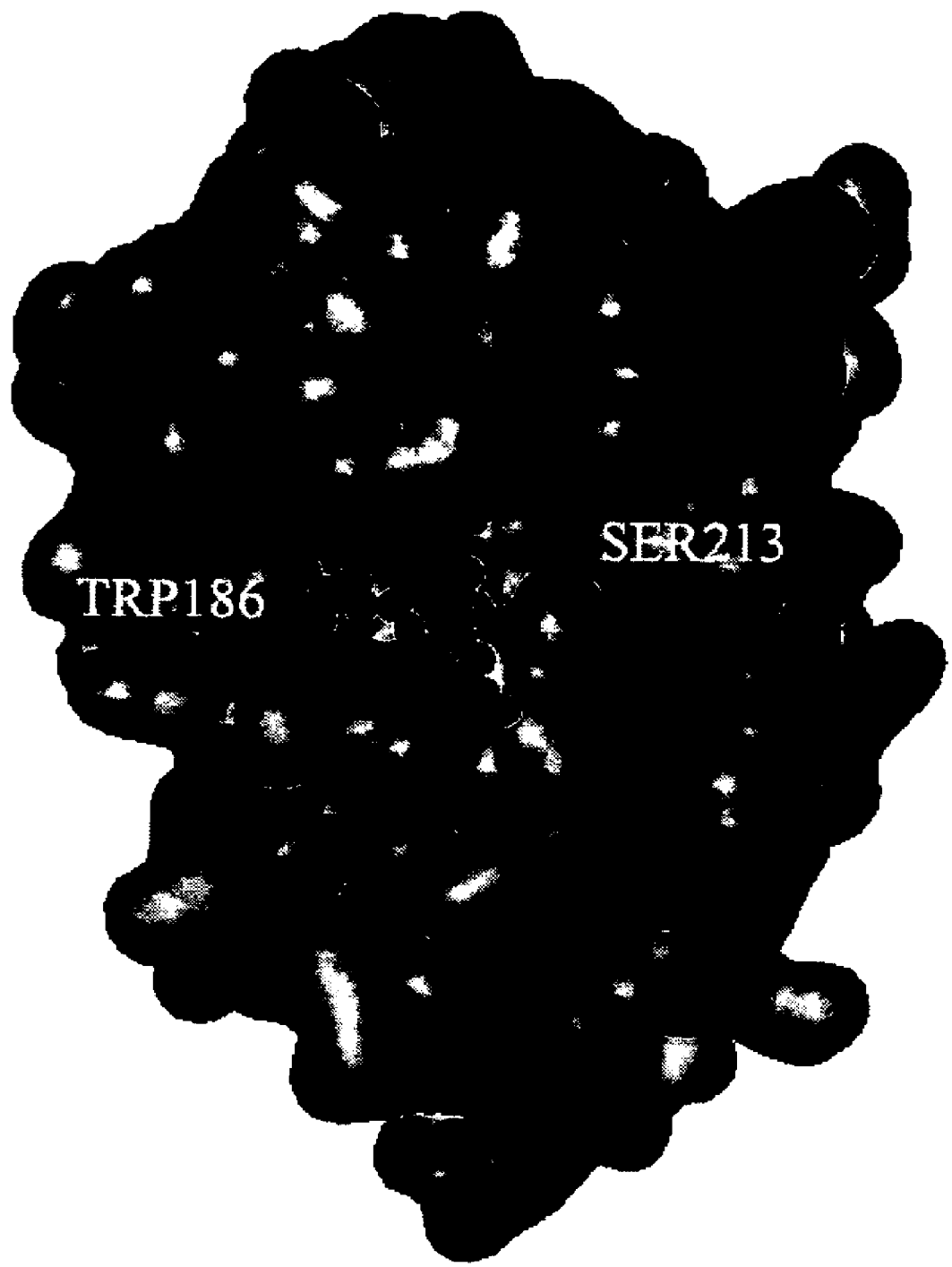
FIG. 5A illustrates a surface accessible representation of the molecular surface of the catalytic domain of CatS (residues 115-331 of SEQ. ID No. 1) showing the long binding pocket with E64 bound in the active site, based on the structure coordinates shown in FIG. 3, chain A.
Figure 5B:
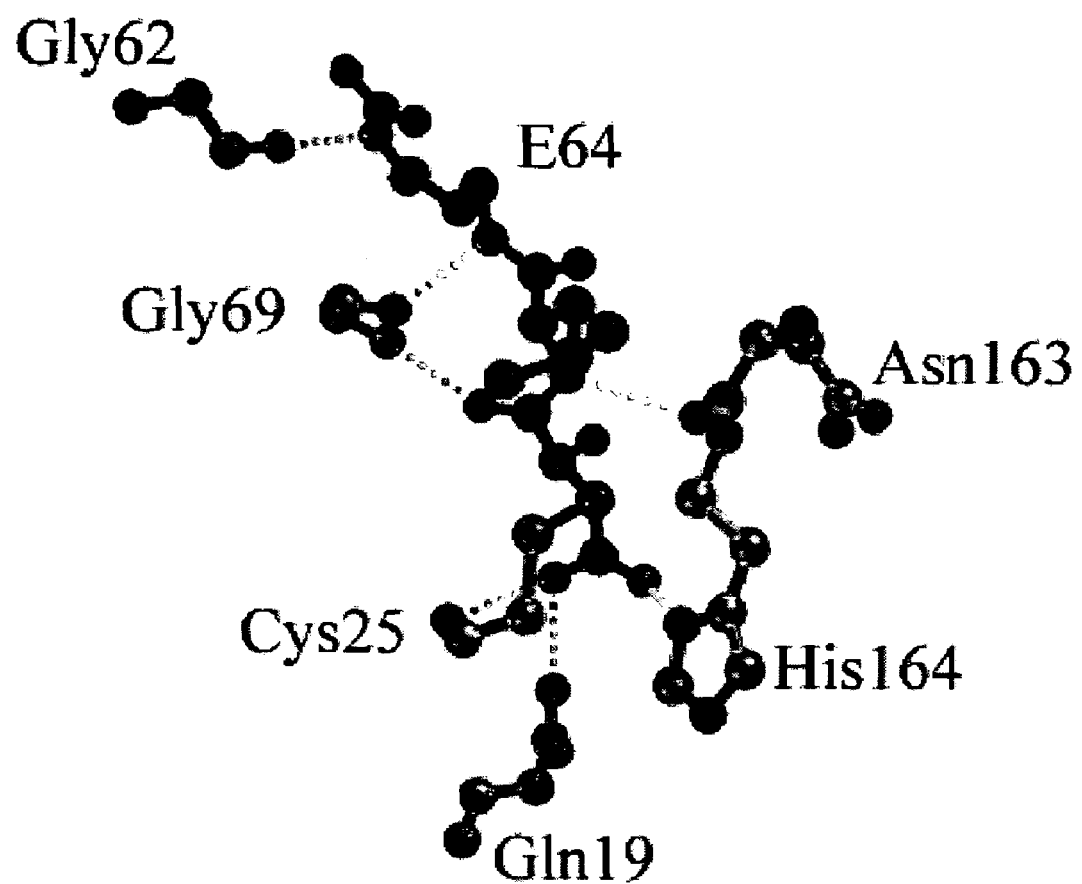
FIG. 5B illustrates key interactions between groups in the binding pockets and the E64 molecule.

For example, based on the crystal structure, applicants have determined that CatS has an elongated binding pocket capable of binding to an E64 molecule (L-trans-epoxysuccinyl-leucylamido(4-guanidino)butane). FIGS. 5A and 5B illustrate an E64 molecule bound in the CatS binding pocket.

The amino acids shown in Table 2 were found to be within 4 Angstroms of and therefore close enough to interact with E64. Applicants have also determined that the amino acids of Table 3 are within 7 Angstroms of E64 and therefore are also close enough to interact with that substrate or analogs thereof. Further it has been determined that the amino acids of Table 4 are within 10 Angstroms of the bound E64.

The extent of the CatS binding pocket is shown in Table 5 were the listed amino acids are found to be within 4 Angstroms of the CatS binding pocket residue, Trp186. Applicants have also determined that the amino acids of Table 6 are within 7 Angstroms of Trp 186 and therefore are also close enough to interact with CatS substrates or analogs thereof. The extent of the CatS binding pocket is further shown in Table 7 were the listed amino acids are found to be within 4 Angstroms of the CatS binding pocket residue, Ser213. Applicants have also determined that the amino acids of Table 8 are within 7 Angstroms of Ser213 and therefore are also close enough to interact with CatS substrates or analogs thereof.

One or more of these sets of amino acids is preferably conserved in a variant of CatS. Hence, CatS may optionally comprise a sequence that has at least 65% identity, preferably at least 70%, 80%, 90%, 95% or higher identity with SEQ. ID No. 1 where at least the residues shown in Tables 1, 2, 3, 4, 5, 6 and/or 7 are conserved with the exception of 0, 1, 2, 3, or 4 residues. It should be recognized that one might optionally vary some of the binding site residues in order to determine the effect such changes have on structure or activity.

TABLE 2

The catalytic domain of CatS (residues 115-331 of SEQ. ID No. 1) binding site residues within 4 Angstroms of E64.

| | | | | | |
|---|---|---|---|---|---|
| GLN | 19 | GLY | 23 | ALA | 24 |
| CYS | 25 | TRP | 26 | GLY | 62 |
| ALA | 64 | ASN | 67 | GLY | 68 |
| GLY | 69 | PHE | 70 | MET | 71 |
| GLY | 137 | VAL | 162 | ASN | 163 |
| HIS | 164 | GLY | 165 | | |

TABLE 3

The catalytic domain of CatS (residues 115-331 of SEQ. ID No. 1) binding site residues within 7 Angstroms of E64.

| | | | | | |
|---|---|---|---|---|---|
| GLN | 19 | GLY | 20 | CYS | 22 |
| GLY | 23 | ALA | 24 | CYS | 25 |
| TRP | 26 | ALA | 27 | PHE | 28 |
| SER | 29 | TYR | 61 | GLY | 62 |
| ASN | 63 | ALA | 64 | GLY | 65 |
| CYS | 66 | ASN | 67 | GLY | 68 |
| GLY | 69 | PHE | 70 | MET | 71 |
| VAL | 136 | GLY | 137 | VAL | 138 |
| ALA | 140 | VAL | 162 | ASN | 163 |
| HUS | 164 | GLY | 165 | VAL | 166 |
| ASN | 184 | SER | 185 | TRP | 186 |
| PHE | 211 | | | | |

TABLE 4

The catalytic domain of CatS (residues 115-331 of SEQ. ID No. 1) binding site residues within 10 Angstroms of E64.

| | | | | | |
|---|---|---|---|---|---|
| TYR | 18 | GLN | 19 | GLY | 20 |
| SER | 21 | CYS | 22 | GLY | 23 |
| ALA | 24 | CYS | 25 | TRP | 26 |
| ALA | 27 | PHE | 28 | SER | 29 |
| ALA | 30 | VAL | 54 | SER | 57 |
| THR | 58 | GLU | 59 | LYS | 60 |
| TYR | 61 | GLY | 62 | ASN | 63 |
| ALA | 64 | GLY | 65 | CYS | 66 |
| ASN | 67 | GLY | 68 | GLY | 69 |
| PHE | 70 | MET | 71 | THR | 72 |
| THR | 73 | ALA | 74 | TYR | 92 |
| ASP | 96 | GLU | 115 | SER | 135 |
| VAL | 136 | GLY | 137 | VAL | 138 |
| ASP | 139 | ALA | 140 | ALA | 141 |
| PHE | 145 | PHE | 146 | GLN | 160 |
| ASN | 161 | VAL | 162 | ASN | 163 |
| HIS | 164 | GLY | 165 | VAL | 166 |
| LEU | 167 | ASN | 184 | SER | 185 |
| TRP | 186 | CYS | 206 | GLY | 207 |
| ILE | 208 | SER | 209 | PHE | 210 |
| PRO | 212 | SER | 213 | | |

TABLE 5

The catalytic domain of CatS (residues 115-331 of SEQ. ID No. 1) binding site residues within 4 Angstroms of Trp186.

| | | | | | |
|---|---|---|---|---|---|
| LYS | 17 | TYR | 18 | GLN | 19 |
| PHE | 28 | ASN | 184 | SER | 185 |
| TRP | 186 | GLY | 187 | | |

TABLE 6

The catalytic domain of CatS (residues 115-331 of SEQ. ID No. 1) binding site residues within 7 Angstroms of Trp186.

| | | | | | |
|---|---|---|---|---|---|
| VAL | 16 | LYS | 17 | TYR | 18 |
| GLN | 19 | GLY | 20 | ALA | 24 |
| CYS | 25 | TRP | 26 | PHE | 28 |
| SER | 29 | HIS | 164 | GLY | 165 |
| VAL | 166 | LYS | 183 | ASN | 184 |
| SER | 185 | TRP | 186 | GLY | 187 |
| HIS | 188 | PHE | 190 | GLY | 194 |

TABLE 7

The catalytic domain of CatS (residues 115-331 of SEQ. ID No. 1) binding site residues within 4 Angstroms of Ser213.

| | | | | | |
|---|---|---|---|---|---|
| GLU | 115 | LEU | 116 | VAL | 134 |
| SER | 135 | VAL | 136 | ALA | 209 |
| SER | 210 | PHE | 211 | PRO | 212 |
| SER | 213 | | | | |

TABLE 8

The catalytic domain of CatS (residues 115-331 of SEQ. ID No. 1) binding site residues within 7 Angstroms of Ser213.

| | | | | | |
|---|---|---|---|---|---|
| MET | 71 | THR | 72 | PHE | 75 |
| THR | 114 | GLU | 115 | LEU | 116 |
| PRO | 117 | TYR | 118 | GLY | 119 |
| ARG | 120 | LEU | 124 | ALA | 127 |
| VAL | 134 | SER | 135 | VAL | 136 |
| GLY | 137 | GLY | 207 | ILE | 208 |
| ALA | 209 | SER | 210 | PHE | 211 |
| PRO | 212 | SER | 213 | TYR | 214 |

With the benefit of the crystal structure and guidance provided by Tables 1, 2, 3, 4, 5, 6 and 7, a wide variety of CatS variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of CatS.

Variants of CatS may be insertional variants in which one or more amino acid residues are introduced into a predetermined site in the CatS sequence. For instance, insertional variants can be fusions of heterologous proteins or polypeptides to the amino or carboxyl terminus of the subunits.

Variants of CatS also may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as the Glu→Asp, Ser→Cys, Cys→Ser, and His→Ala for example.

Another class of variants is deletional variants, which are characterized by the removal of one or more amino acid residues from the CatS sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; 0-methylisourea, 2,4-pentanedione; and transaminaseN: talyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$, of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, Proteins: Structure and Molecular Properties, W.H. Freeman & Co., San Francisco, pp. 79-86, 1983), acetylation of the N-terminal amine and amidation of any C-terminal carboxyl group.

As can be seen, modifications of the nucleic sequence encoding CatS may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type CatS is functional in the sense that the resulting protein is capable of associating with at least one same chemical entity that is also capable of selectively associating with a protein comprising SEQ. ID No. 1 since this common associative ability evidences that at least a portion of the native structure has been conserved. That chemical entity may optionally be E64.

It is noted the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of CatS, and the atomic structure coordinates obtained there from, can be used to identify compounds that bind to the native domain. These compounds may affect the activity or the native domain.

Amino acid substitutions, deletions and additions that do not significantly interfere with the three-dimensional structure of CatS will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of CatS will be apparent to those having skills in the art, particularly in view of the three dimensional structure of CatS provided herein.

2. Cloning, Expression and Purification of CatS

The gene encoding CatS can be isolated from RNA, cDNA or cDNA libraries. In this case, the portion of the gene encoding amino acid residues 1-331 of SEQ ID No. 1 was isolated and is shown as SEQ. I.D. No. 2.

Construction of expression vectors and recombinant proteins from the DNA sequence encoding CatS may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of CatS. Example 1 provides one such expression system.

Once expressed, purification steps are employed to produce CatS in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

CatS may optionally be affinity labeled during cloning, preferably with a Glycine-poly-histidine (Gly-His$_6$) region, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization & Crystals Comprising CatS

One aspect of the present invention relates to methods for forming crystals comprising CatS as well as crystals comprising CatS.

In one embodiment, a method for forming crystals comprising CatS is provided comprising forming a crystallization volume comprising CatS, one or more precipitants, optionally a buffer, optionally an additive and optionally an organic solvent; and storing the crystallization volume under conditions suitable for crystal formation.

In yet another embodiment, a method for forming crystals comprising CatS is provided comprising forming a crystallization volume comprising CatS in solution comprising the components shown in Table 9; and storing the crystallization volume under conditions suitable for crystal formation.

TABLE 9

| Precipitant |
| --- |
| 5-50% w/v comprising one or more of any of the PEGs from the 200-20000 molecular weight range, 2-methyl-2,4-pentanediol (MPD) or isopropanol |
| pH |
| pH 4-10. Buffers that may be used include, but are not limited to imidazole, acetate, hepes, citrate, tris, CHES, MES and combinations thereof. |
| Additives |
| 0.1 mM-3 M comprising one or more of benzamidine or 1,2,3-heptanetriol. |
| Protein Concentration |
| 1 mg/ml-50 mg/ml |
| Temperature |
| 1° C.-25° C. |

In yet another embodiment, a method for forming crystals comprising CatS is provided comprising forming a crystallization volume comprising CatS; introducing crystals comprising CatS as nucleation sites, and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro and/or macro seeding of crystals may also be performed to facilitate crystallization.

It should be understood that forming crystals comprising CatS and crystals comprising CatS according to the invention are not intended to be limited to the wild-type, full length CatS shown in SEQ. ID No. 1. Rather, it should be recognized that the invention may be extended to various other fragments and variants of wild-type CatS as described above.

It should also be understood that forming crystals comprising CatS and crystals comprising CatS according to the invention may be such that CatS is complexed with one or more ligands and one or more copies of the same ligand. The ligand used to form the complex may be any ligand capable of binding to CatS. In one variation, the ligand is a natural substrate. In another variation, the ligand is an inhibitor, such as E64.

In one particular variation, the ligand binds to the first and/or second binding pocket of the protein. Examples of such ligands include, but are not limited to, small molecule inhibitors of CatS such as E64.

Optionally, the CatS complex may further comprise organics, especially benzamidine which may be introduced in any suitable manner. For example, the organics may be introduced by incubating the desired ligand with a suitable organic such as benzamidine prior to incubation with the CatS protein.

In one particular embodiment, CatS crystals have a crystal lattice in the $P4_1 22$ space group. CatS crystals may also optionally have unit cell dimensions, +/−5%, of a=b=85.159 Å and c=152.18 Å.

CatS crystals also preferably are capable of diffracting X-rays for determination of atomic coordinates to a resolution of greater than 2.2 Å.

Crystals comprising CatS may be formed by a variety of different methods known in the art. For example, crystallizations may be performed by batch, dialysis, and vapor diffusion (sitting drop and hanging drop) methods. A detailed description of basic protein crystallization setups may be found in McRee, D. and David. P., *Practical Protein Crystallography*, $2^{nd}$ Ed. (1999), Academic Press Inc. Further descriptions regarding performing crystallization experiments are provided in Stevens, et al. (2000) *Curr. Opin. Struct. Biol.*: 10(5):558-63, and U.S. Pat. Nos. 6,296, 673, 5,419,278, and 5,096,676.

In one variation, crystals comprising CatS are formed by mixing substantially pure CatS with an aqueous buffer containing a precipitant at a concentration just below a concentration necessary to precipitate the protein. One suitable precipitant for crystallizing CatS is polyethylene glycol (PEG), which combines some of the characteristics of the salts and other organic precipitants (see, for example, Ward et al., *J. Mol. Biol.* 98:161, 1975, and McPherson, *J. Biol. Chem.* 251:6300, 1976.

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a CatS-E64 complex were obtained. In order to accomplish this, systematic broad screen crystallization trials were performed on a CatS-E64 complex using the sitting drop technique. Over 1000 individual trials were performed in which pH, temperature and precipitants were varied. In each experiment, a 100 nL mixture of CatS-E64 complex and precipitant was placed on a platform positioned over a well containing 100 µL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect CatS crystallization was obtained. Based on this understanding, a series of crystallization conditions were identified that may be used to form crystals comprising CatS. These conditions are summarized in Table 9. A particular example of crystallization conditions that may be used to form crystals diffraction quality crystals of the CatS-E64 complex is detailed in Example 2. FIG. 2 illustrates crystals of the CatS-E64 complex formed using the crystallization conditions provided in Table 9.

One skilled in the art will recognize that the crystallization conditions provided in Table 9 and Example 2 can be varied and still yield protein crystals comprising CatS. For example, it is noted that variations on the crystallization conditions described herein can be readily determined by taking the conditions provided in Table 9 and performing fine screens around those conditions by varying the type and concentration of the components in order to determine additional suitable conditions for crystallizing CatS, variants of CatS, and ligand complexes thereof.

Crystals comprising CatS have a wide range of uses. For example, now that crystals comprising CatS have been produced, it is noted that crystallizations may be performed using such crystals as a nucleation site within a concentrated protein solution. According to this variation, a concentrated protein solution is prepared and a crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising CatS according to the present invention, the crystals so formed can be used by this crystallization technique to initiate crystal growth of other CatS comprising crystals, including CatS complexed to other ligands.

As will be described herein in greater detail, crystals may also be used to perform X-ray or neutron diffraction analysis in order to determine the three-dimensional structure of CatS and, in particular, to assist in the identification of its active site. Knowledge of the binding site region allows rational design and construction of ligands including inhibitors. Crystallization and structural determination of CatS mutants having altered bioactivity allows the evaluation of whether such changes are caused by general structure deformation or by side chain alterations at the substitution site.

4. X-Ray Data Collection and Structure Determination

Crystals comprising CatS may be obtained as described above in Section 3. As described herein, these crystals may then be used to perform x-ray data collection and for structure determination.

In one embodiment, described in Example 2, crystals of a CatS-E64 complex were obtained where CatS has the sequence of residues shown in SEQ. ID No. 3. These particular crystals were used to determine the three dimensional structure of CatS. However, it is noted that other crystals comprising CatS including different CatS variants, fragments, and complexes thereof may also be used.

Diffraction data was collected from cryocooled crystals (100K) of the CatS-E64 complex at the Advanced Light Source beam line 5.0.3 using an ADSC CCD detector. The diffraction pattern of the CatS-E64 complex displayed symmetry consistent with space group $P4_122$ with unit cell dimensions a=b=85.159 Å and c=152.18 Å. Data were collected and integrated to 1.5 Å with HKL2000 (Z. Ostwinowski and W. Minor "Processing of X-ray Diffraction Data Collected in Oscillation Mode", Methods in Enzymology, Volume 276: Macromolecular Crystallography, Part A, pages 307-326, 1997, C. W. Carter, Jr. & R. M. Sweet, Eds. Academic Press.).

All crystallographic calculations were performed using the CCP4 program package (Collaborative Computational Project, N. The CCP4 Suite: Programs for Protein Crystallography. *Acta Cryst.* D50, 760-763 (1994)). The initial phases for the CatS-E64 complex were obtained by the molecular replacement method using the program MOLREP (CCP4). The coordinates of Cathepsin K (PDB code 1AYU) were used as a search model for the solution of the CatS-E64 structure. The highest solution from the translation function was subjected to a rigid body refinement against the maximum likelihood target function as implemented in REFMAC (CCP4). Rigid body refinement was followed by 50 cycles of iterative map/model/phase improvement using ARP_WARP map (Perrakis, A., Morris, R. J. & Lamzin, V. S.) This was followed by alternating cycles of manual rebuilding of the model with Xfit (McRee, D. E. XtalView/Xfit—A versatile program for manipulating atomic coordinates and electron density *J. Struct. Biol.* 125, 156-65 (1999)), ARP_WARP map improvement (Perrakis, A., Morris, R. J. & Lamzin, V. S. Automated protein model building combined with iterative structure refinement) and geometrically restrained refinement against a maximum likelihood target function as implemented in REFMAC (CCP4) until the refinement reached convergence. All stages of model refinement were carried with bulk solvent correction and anisotropic scaling. The data collection and data refinement statistics are given in Table 10.

TABLE 10

| Crystal data | | |
|---|---|---|
| Ligands | | E64, water |
| Space group | | $P4_122$ |
| Unit cell dimensions | | a = b = 85.159Å and c = 152.18Å CatS-E64 |
| Data collection | | |
| X-ray source | | ALS 5.0.3 |
| Wavelength [Å] | | 1.0 |
| Resolution [Å] | | 50-1.5 |
| Observations (unique) | | 86434 |
| Redundancy | | 10 |
| Completeness | overall (outer shell) | 96% (87%) |
| I/σ(I) | overall (outer shell) | 23 (2) |
| $R_{symm}$[1] | overall (outer shell) | 0.066 (0.57) |
| Refinement | | |
| Reflections used | | 80501 |
| R-factor | | 17.1% |
| $R_{free}$ | | 19.1% |
| r.m.s bonds | | 0.013 |
| r.m.s angles | | 1.53 |

[1]$R_{symm} = \Sigma_{hkl}\Sigma_i \mid I(hkl)_i - <I(hkl)> \mid / \Sigma_{hkl}\Sigma_i <I(hkl)_i>$ over I observations of a reflection hkl During structure determination, it was realized that each unit cell comprised two CatS-E64 complexes. Structure coordinates were determined for each of the two complexes in the unit cell. The resultant two sets of structural coordinates from the refinement are presented in FIG. 3, as chains A and B. The active site binding pocket is shown in FIGS. 5A and 5B with a bound E64 molecule. Key interactions between groups in the binding pocket and the E64 molecule are depicted in and described in FIG. 5B.

It is noted that the sequence of the structure coordinates presented in FIG. 3 differ in some regards from the sequence shown in SEQ. ID No. 1.

For some residues, the electron density obtained was insufficient to identify the side chain. As a result, the side chains of these residues were truncated such that a different amino acid is reported. Tables 10 and 11 summarize the differences between SEQ. ID No. 3 and the truncated residues appearing in FIG. 3 as chains 'A' and 'B' respectively.

TABLE 11

Truncated Residues in The Structure Coordinates of FIG. 3 chain A.

| GLU15-ALA | LYS41-ALA | LYS64-ALA |
|---|---|---|
| LYS104-ALA | LYS141-ALA | GLU193-ALA |

TABLE 12

Truncated Residues in The Structure Coordinates of FIG. 3 chain B.

| LYS41-ALA | LYS44-ALA | LYS60-ALA |
|---|---|---|
| LYS64-ALA | LYS98-ALA | LYS177-ALA |

It is also noted that structure coordinates are not reported for some residues because the electron density obtained was insufficient to identify the position of these residues. For FIG. 3, chain A, structure coordinates for residues 220-225 (using numbering from SEQ. No. 3) are not reported. For FIG. 3, chain B, structure coordinates for residues 219-225 are not reported.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand These variations in coordinates may be generated because of mathematical manipulations of the CatS structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of CatS would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3, as described in the accompanying User's Manual. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1, Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a reference protein from the atomic coordinates of a reference protein or portions of thereof. The structure coordinates for CatS, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1AYU was identified as having the smallest RMSD values relative to the structure coordinates provided herein. Table 13 below provides a series of RMSD values that were calculated by the above described process using the structure coordinates in FIG. 3 as the reference protein and the structure coordinates from PDB code: 1AYU (Human Cathepsin K) as the target protein.

TABLE 13

| AA RESIDUES USED TO PERFORM RMSD COMPARISON WITH PDB:1AYU | PORTION OF EACH AA RESIDUE USED TO PERFORM RMSD COMPARISON WITH PDB:1AYU | RMSD [Å] |
|---|---|---|
| Table 2 | alpha-carbon atoms[1] | 1.30 |
| (4 Angstrom set) | main-chain atoms[1] | 1.27 |
| (relative to E64) | all non-hydrogen[2] | 1.34 |
| Table 3 | alpha-carbon atoms[1] | 0.82 |
| (7 Angstrom set) | main-chain atoms[1] | 0.79 |
| (relative to E64) | all non-hydrogen[2] | 0.71 |
| Table 4 | alpha-carbon atoms[1] | 0.73 |
| (10 Angstrom set) | main-chain atoms[1] | 0.75 |
| (relative to E64) | all non-hydrogen[2] | 0.51 |
| Table 5 | alpha-carbon atoms[1] | 0.38 |
| (4 Angstrom set) | main-chain atoms[1] | 0.38 |
| (relative to Trp186) | all non-hydrogen[2] | 0.30 |
| Table 6 | alpha-carbon atoms[1] | 1.13 |
| (7 Angstrom set) | main-chain atoms[1] | 1.09 |
| (relative to Trp186) | all non-hydrogen[2] | 1.23 |
| Table 7 | alpha-carbon atoms[1] | 0.61 |
| (10 Angstrom set) | main-chain atoms[1] | 0.60 |
| (relative to Trp186) | all non-hydrogen[2] | 0.78 |
| SEQ. ID No. 1 | alpha-carbon atoms[1] | 0.58 |
| | main-chain atoms[1] | 0.58 |
| | all non-hydrogen[2] | 0.70 |

[1] the RMSD computed between the atoms of all amino acids that are common to both the target and the reference in the aligned and superposed structure. The amino acids need not to be identical.
[2] the RMSD computed only between identical amino acids, which are common to both the target and the reference in the aligned and superposed structure.

It is noted that mutants and variants of CatS as well as other cathepsins are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted, there are many different ways to express the surface contours of the CatS structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. CatS-E64 Structure

The present invention is also directed to a three-dimensional crystal structure of CatS. This crystal structure may be used to identify binding sites, to provide mutants having desirable binding properties, and ultimately, to design, characterize, or identify ligands that interact with CatS.

The three-dimensional crystal structure of CatS may be generated, as is known in the art, from the structure coordinates shown in FIG. 3 and similar such coordinates.

The refined crystal structure of CatS-E64, determined according to the present invention, contains amino acids residues 114-331 as numbered according to SEQ. ID No. 1 (based on the coordinates of FIG. 3) and a bound E64 molecule. A total of 627 water molecules were included.

Figure 4:
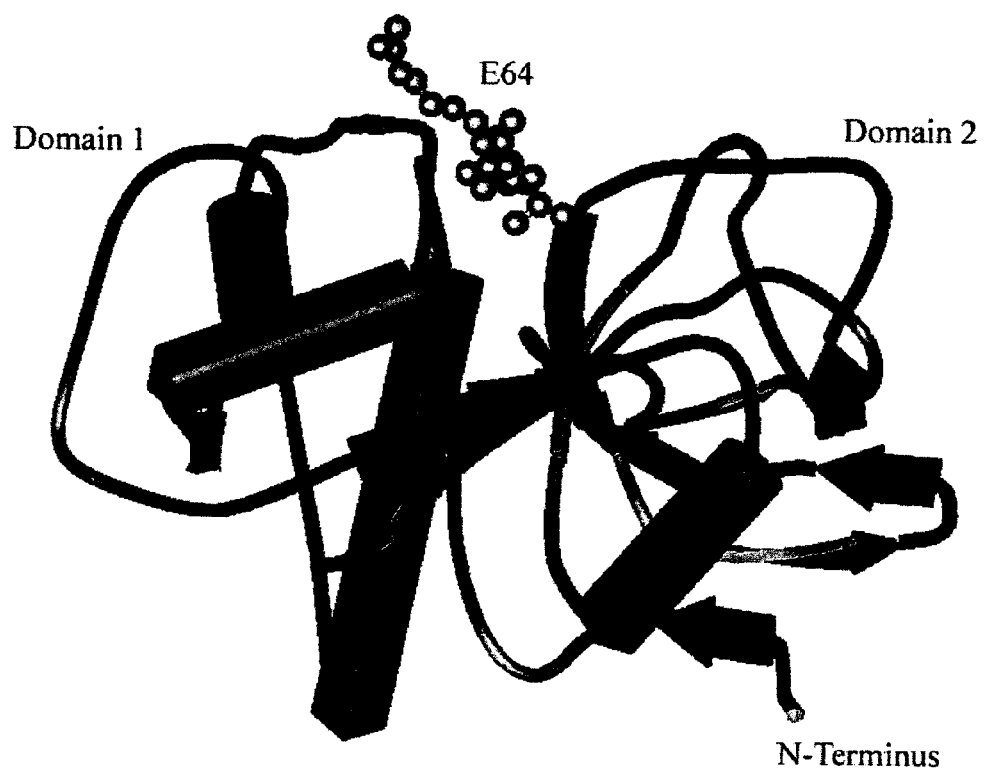
FIG. 4 is a schematic diagram highlighting the secondary structural elements of the catalytic domain of CatS (residues 115-331 of SEQ. ID No. 1) and the binding region of E64.

FIG. 4 illustrates a schematic diagram overview of the structure of CatS, highlighting the secondary structural elements of the protein. CatS forms a monomeric structure consisting of two domains. Domain 1 contains three helices and a hydrophobic core, while domain 2 consists of an anti-parallel β-barrel enclosing a hydrophobic core flanked by α-helices on either side of the barrel surface. Three disulfides, two in domain 1 and one in domain 2, play a role in stabilizing the overall structure of the protein. The structure of CatS is very similar to the structures of the plant protein papain (PDB code 9PAP), cathepsin K (PDB code 1MEM), cathepsin H (PDB code 8PCH), and cathepsin L (PDB code 1CS8). Superposition of 200 aligned residues in these structures with the CatS structure results in a root mean square deviation of less than 0.8 Angstroms in the positions of the main chain atoms in all cases.

FIG. 5B shows the detailed interactions between E64 bound in the active site of CatS based on the structure coordinates shown in FIG. 3, chain A. The binding pocket of CatS is long and deep, as shown in FIG. 5A, and is lined mainly by polar residues. A covalent link is formed between a carbon atom on E64 and the sulfur atom of C25.

6. CatS Binding Pocket and Ligand Interaction

The term "binding site" or "binding pocket", as the terms are used herein, refers to a region of a protein that, as a result of its shape and surface properties (charge, hydrophobicity, etc.), favorably associates with a ligand or substrate. The term "CatS-like binding pocket" refers to a portion of a molecule or molecular complex whose shape is sufficiently similar to the CatS binding pockets as to bind common ligands. This commonality of shape may be quantitatively defined based on a comparison to a reference point, that reference point being the structure coordinates provided herein. For example, the commonality of shape may be quantitatively defined based on a root mean square deviation (rmsd) from the structure coordinates of the backbone atoms of the amino acids that make up the binding pockets in CatS (as set forth in FIG. 3).

The "active site binding pocket" (FIG. 5A) or "active site" of CatS refers to the area on the surface of CatS where the substrate (and an E64 inhibitor molecule) binds. Figures 5A and 5B illustrate E64 bound in the active site of CatS based on the crystal structure of the present invention.

To date, the active site binding pockets of cathepsins have been actively pursued as targets for the design of small molecule inhibitors. The crystal structure described in the present invention represents the highest resolution, and thus most accurate structure of a member of the cathepsin class (compared to available structures in the public domain), which could be used for the design of more potent inhibitors. A number of key substrate binding and catalytic residues observed in the active site binding pocket of CatS are conserved among all cathepsins. However, sequence variability exists between CatS and other members of the cathepsin protein family, so that the subtle differences in shape and chemical content may be explored to confer specificity of inhibition.

In resolving the crystal structure of CatS in complex with E64, applicants determined that CatS amino acids in Table 2 (above) are within 4 Angstroms of and therefore close enough to interact with the E64 molecule. Applicants have determined that the amino acids of Table 3 (above) are within 7 Angstroms of bound E64 and therefore are also close enough to interact with that inhibitor or analogs thereof. Applicants have also determined that the amino acids of Table 4 (above) are within 10 Angstroms of bound E64 and therefore are also close enough to interact with that inhibitor or analogs thereof. Applicants have also determined that the amino acids of Table 5 (above) are within 4 Angstroms of Trp186 and therefore are also close enough to interact with substrates/potential inhibitors. Applicants have also determined that the amino acids of Table 6 (above) are within 7 Angstroms of Trp186 and therefore are also close enough to interact with substrates/potential inhibitors. Applicants have also determined that the amino acids of Table 7 (above) are within 4 Angstroms of Ser213 and therefore are also close enough to interact with substrates/potential inhibitors. Applicants have also determined that the amino acids of Table 8 (above) are within 7 Angstroms of Ser213 and therefore are also close enough to interact with substrates/potential inhibitors. The sets of amino acids described in Tables 3 through 7 are preferably conserved in variants of CatS. While it is desirable to largely conserve these residues, it should be recognized however that variants may also involve varying 1, 2, 3, 4 or more of the residues set forth in Tables 1, 2, 3, 4, 5, 6 and 7 in order to evaluate the roles these amino acids play in the binding pocket.

With the knowledge of the CatS crystal structure provided herein, Applicants define the CatS binding pocket where the relative positioning of the 4, 7, and/or 10 Angstroms sets of amino acids are substantially conserved. Again, it is noted that it may be desirable to form variants where 1, 2, 3, 4 or more of the residues set forth in Tables 1, 2, 3, 4, 5, 6 and 7 are varied in order to evaluate the roles these amino acids play in the binding pockets. Accordingly, any set of structure coordinates for a protein from any source having a root mean square deviation of main-chain atoms of less than 0.3 Å when superimposed on the main-chain atom positions of the corresponding atomic coordinates of either FIG. 3, chain A or chain B, for the 4, 7, and/or 10 Angstroms sets of amino acids shall be considered identical. As noted previously, the root mean square deviation is intended to be limited to only those main-chain atoms of amino acid residues that are common to both the protein fragments represented in FIG. 3 chain, A or B, and the protein whose structure coordinates are being compared to the coordinates shown in FIG. 3 chain, A or B, since the sequence of the protein may be varied somewhat.

In one embodiment, the invention relates to data, computer readable media comprising data, and uses of the data where the data comprises the structure coordinates shown in FIG. 3, chain A or B, or structure coordinates having a root mean square deviation of non-hydrogen atoms of less than 0.8 Å when superimposed on the non-hydrogen atom positions of the corresponding atomic coordinates of FIG. 3, chains A or chain B, for the 4, 7, and/or 10 Angstroms sets of amino acids detailed in tables 1, 2, 3, 4, 5, 6 and/or 7. Optionally, the root mean square deviation of non-hydrogen atoms is less than 0.8 Å, 0.7 Å, 0.6 Å, 0.5 Å, 0.4 Å, 0.3 Å, or less.

It will be readily apparent to those of skill in the art that the numbering of amino acids in other isoforms of CatS may be different than that set forth for CatS. Corresponding amino acids in other isoforms of CatS are easily identified by visual inspection of the amino acid sequences or by using commercially available homology software programs, as further described below.

7. System For Displaying the Three Dimensional Structure of CatS

The present invention is also directed to machine-readable data storage media having data storage material encoded with machine-readable data that comprises structure coordinates for CatS. The present invention is also directed to a machine readable data storage media having data storage material encoded with machine readable data, which, when read by an appropriate machine, can display a three dimensional representation of a structure of CatS.

All or a portion of the CatS coordinate data shown in FIG. 3, when used in conjunction with a computer programmed with software to translate those coordinates into the three-dimensional structure of CatS may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of CatS and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an CatS-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising CatS or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other CatS-like enzymes, and isoforms of CatS.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
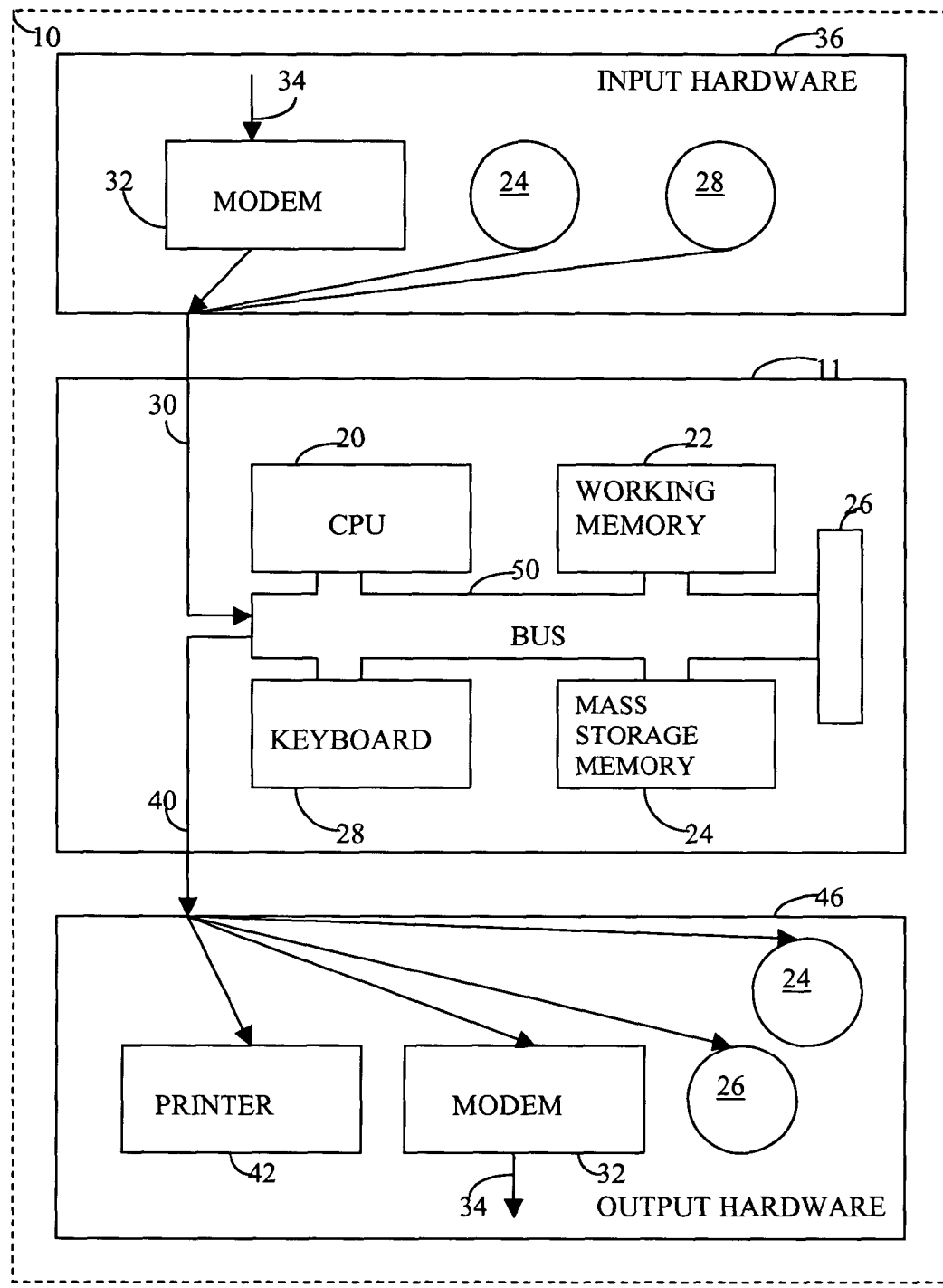
FIG. 6 illustrates a system that may be used to carry out instructions for displaying a crystal structure of the catalytic domain of CatS (residues 115-331 of SEQ. ID No. 1) encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices may, similarly implement output hardware 46, coupled to computer 11 by output lines 40. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to using the three dimensional structure of CatS described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of CatS

The three-dimensional crystal structure of the present invention may be used to identify CatS binding sites, be used as a molecular replacement model to solve the structure of unknown crystallized proteins, to design mutants having desirable binding properties, and ultimately, to design, characterize, identify entities capable of interacting with CatS and other structurally similar proteins as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The CatS structure coordinates provided herein are useful for screening and identifying drugs that inhibit CatS and other structurally similar proteins. For example, the structure encoded by the data may be computationally evaluated for its ability to associate with putative substrates or ligands. Such compounds that associate with CatS may inhibit CatS, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with CatS or a fragment or variant thereof by using all or a portion of the structure coordinates provided in FIG. 3 or functional equivalents thereof. A method is also provided for evaluating the potential of an entity to associate with CatS or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3 and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an CatS-like binding pocket. One embodiment of the method comprises: using all or a portion of the structure coordinates provided herein to generate a three-dimensional structure of an CatS-like binding pocket; employing the three-dimensional structure to design or select a potential ligand; synthesizing the potential ligand; and contacting the synthesized potential ligand with a protein comprising an CatS-like binding pocket to determine the ability of the potential ligand to interact with protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 2, 3, and/or 4 that are present.

As noted previously, the three-dimensional structure of an CatS-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an CatS-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for CatS, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity; and contacting a protein having an CatS-like binding pocket with the synthesized entity.

With the structure provided herein, the present invention for the first time permits the use of molecular design techniques to identify, select or design potential inhibitors of CatS, based on the structure of an CatS-like binding pocket. Such a predictive model is valuable in light of the high costs associated with the preparation and testing of the many diverse compounds that may possibly bind to the CatS protein.

According to this invention, a potential CatS inhibitor may now be evaluated for its ability to bind an CatS-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an CatS-like binding pocket may be computationally evaluated using a series of steps in which chemical entities or fragments are screened and selected for their ability to associate with the CatS-like binding pockets.

One skilled in the art may use one of several methods to screen entities (whether chemical or protein) for their ability to associate with an CatS-like binding pocket. This process may begin by visual inspection of, for example, an CatS-like binding pocket on a computer screen based on the CatS structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of CatS. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif). This area is reviewed in Y. C. Martin, "3D Database Searching in Drug Design", J. Med. Chem., 35, pp. 2145-2154 (1992); HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif Instead of proceeding to build an inhibitor of an CatS-like binding pocket in a step-wise fashion one fragment or entity at a time as described above, inhibitory or other CatS binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation)", J. Comput. Aided Mol. Design, 7, pp. 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an CatS binding pocket may be tested and optimized by computational evaluation. For example, an effective CatS binding pocket inhibitor preferably demonstrates a relatively small difference in energy between its bound and free states (i.e., a small deformation energy of binding). Thus, the most efficient CatS binding pocket inhibitors should preferably be designed with deformation energy of binding of not greater than about 10 kcal/mole, more preferably, not greater than 7 kcal/mole. CatS binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an CatS binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT.1995); AMBER, version 4.1 (P. A. Kollman, University of California at San Francisco, COPYRGT 1995); QUANTA/CHARMM (Molecular Simulations, Inc., San Diego, Calif. COPYRGT.1995); Insight II/Discover (Molecular Simulations, Inc., San Diego, Calif. COPYRGT.1995); DelPhi (Molecular Simulations, Inc., San Diego, Calif. COPYRGT.1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an CatS binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an CatS-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the CatS provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of CatS according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of CatS can be resolved by this method.

In one embodiment, the method of molecular replacement is utilized to obtain structural information about the present invention and any other CatS-like molecule. The structure coordinates of CatS, as provided by this invention, are particularly useful in solving the structure of other isoforms of CatS or CatS complexes.

The structure coordinates of CatS as provided by this invention are useful in solving the structure of CatS variants that have amino acid substitutions, additions and/or deletions (referred to collectively as "CatS mutants", as compared to naturally occurring CatS). These CatS mutants may optionally be crystallized in co-complex with a ligand, such as an inhibitor, substrate analogue or a suicide substrate. The crystal structures of a series of such complexes may then be solved by molecular replacement and compared with that of CatS. Potential sites for modification within the various binding sites of the enzyme may thus be identified. This information provides an additional tool for determining the most efficient binding interactions such as, for example, increased hydrophobic interactions, between CatS and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRIGHT.1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known CatS inhibitors, and more importantly, to design new CatS inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of CatS

Crystals, crystallization conditions and the diffraction pattern of CatS that can be generated from the crystals also have a range of uses. One particular use relates to screening entities that are not known ligands of CatS for their ability to bind to CatS. For example, with the availability of crystallization conditions, crystals and diffraction patterns of CatS provided according to the present invention, it is possible to take a crystal of CatS; expose the crystal to one or more entities that may be a ligand of CatS; and determine whether a ligand/CatS complex is formed. The crystals of CatS may be exposed to potential ligands by various methods, including but not limited to, soaking a crystal in a solution of one or more potential ligands or co-crystallizing CatS in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligandl CatS complex(es) may be used to design new ligands that bind tighter, bind more specifically, have better biological activity or have better safety profile than known ligands.

In one embodiment, a method is provided for identifying a ligand that binds to CatS comprising: (a) attempting to crystallize a protein that comprises a sequence wherein at least a portion of the sequence has 55%, 65%, 75%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to CatS comprising: soaking a crystal of a protein wherein at least a portion of the protein has 55%, 65%, 75%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-CatS complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of CatS

This example describes the expression of CatS. It should be noted that a variety of other expression systems and hosts are also suitable for the expression of CatS, as would be readily appreciated by one of skill in the art.

The portion of the gene encoding residues 114-331 (from SEQ. ID No. 1) was amplified by PCR and cloned into a modified pFastbac vector (Invitrogen) with a Glycine-6x-histidine tag at the C-terminus.

Expression in this vector generated a fusion of CatS residues 114-331 of SEQ. ID No. 1 with a C-terminal Glycine-6x-histidine tag, the amino acid sequence of which is shown in FIG. 1 as SEQ. ID. No. 3. Recombinant baculoviruses incorporating the CatS constructs were generated by transposition using the Bac-to-Bac system (Invitrogen). High-titer viral stocks were generated by infection of *Spodoptera frugiperda* Sf9 cells and the expression of recombinant protein was carried out by infection of *Trichoplusia ni* Hi5 cells (Invitrogen) in 10 L Wave Bioreactors (Wave Biotech).

Most of the protein was secreted into the media. The cell supernatant was concentrated, and diafiltered by cross flow ultrafiltration. The protein in the supernatant was purified by passage over ProBond (InVitrogen) resin. After activation was achieved by altering the pH to low pH, E64 was added and cation exchange chromatography was used to isolate the CatS-E64 complex. The CatS (SEQ. ID No.3) protein purity as determined on denaturing SDS-PAGE gel was 90-95%. CatS (SEQ. ID No. 3) was concentrated to a final concentration of 8.5 mg/ml and stored at 4° C. in a buffer containing 25 mM Sodium Acetate, pH 5.5, 150 mM NaCl, 1.5 mM benzamidine and a five-fold molar excess of E64.

Example 2

Crystallization of CatS-E64 Complex

This example describes the crystallization of the complex of CatS (SEQ. ID No. 3)—with E64. It is noted that the precise crystallization conditions used may be further varied, for example by performing a fine screen based on these crystallization conditions.

Residues 114-331 of CatS with a C-terminal Glycine-6x-histidine tag (SEQ. ID No. 3) protein samples were incubated with 1.5 mM benzamidine and a fivefold molar excess of E64 before setting crystallization trials. Crystals were obtained after an extensive and broad screen of conditions, followed by optimization. Diffraction quality crystals were grown as in 100 nL sitting droplets using the vapor diffusion method. 50 nL comprising the CatS-E64 complex (8.5 mg/ml) was mixed with 50 nL from a reservoir solution (100 µL) comprising 0.2M citrate/citric acid pH=5.0, 16% (w/v) PEG 4000 and 5% (w/v) PEG 200. The resulting solution was incubated over a period of one week at 4° C.

Crystals typically appeared after 48 hours and grew to a maximum size within 72 hours. Single crystals were transferred, briefly, into a cryoprotecting solution containing the reservoir solution supplemented with 30% v/v glycerol. Crystals were then flash frozen by immersion in liquid nitrogen and then stored under liquid nitrogen. A crystal of CatS-E64 complex produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

We claim:

1. A composition comprising a protein in crystalline form wherein the protein consists of SEQ ID NO:3, and wherein the protein crystal has a crystal lattice in a $P4_122$ space group and unit cell dimensions, +/−5%, of a=b=85.159 Å and c=152.18 Å.

2. A composition according to claim 1 wherein the protein crystal diffracts X-rays for a determination of structure coordinates to a resolution having a value that is less than or equal to 3.0 Angstroms.

3. A method comprising:
   forming a crystallization volume comprising a precipitant solution and a protein that consists of SEQ ID NO:3, and wherein a protein crystal is formed that has a crystal lattice in a $P4_122$ space group and unit cell dimensions, +/−5%, of a=b=85.159 Å and c=152.18 Å; and
   storing the crystallization volume under conditions suitable for formation of a protein crystal.

4. A method according to claim 3 wherein a protein crystal is formed that diffracts X-rays for a determination of structure coordinates to a resolution having a value that is less than or equal to 3.0 Angstroms.

5. A non-crystalline protein consisting of SEQ ID NO:3.

6. A non-crystalline protein consisting of residues 114-331 of SEQ ID NO:1.

7. An isolated non-crystalline protein consisting of SEQ ID NO:3.

8. An isolated non-crystalline protein consisting of residues 114-331 of SEQ ID NO:1.

9. A method for obtaining a three dimensional structure of a protein comprising the steps of:
   (a) obtaining a crystal of a protein whose sequence consists of SEQ ID NO:3, wherein the protein crystal has a crystal lattice in a $P4_122$ space group and unit cell dimensions, +/−5%, of a=b=85.159 Å and c=152.18 Å;
   (b) using the crystal obtained in step (a) to obtain an x-ray diffraction pattern; and
   (c) solving the three dimensional structure of the protein from the diffraction pattern obtained in step (b), thereby obtaining the three dimensional structure of the protein.

10. A method for identifying a compound that binds to a protein comprising the steps of:
    (a) obtaining a crystal of a protein whose sequence consists of SEQ ID NO:3, wherein the protein crystal has a crystal lattice in a $P4_122$ space group and unit cell dimensions, +/−5%, of a=b=85.159 Å and c=152.18 Å;
    (b) using the crystal obtained in step (a) to obtain an x-ray diffraction pattern;
    (c) solving the three dimensional structure of the protein from the diffraction pattern obtained in step (b), thereby obtaining the three dimensional structure of the protein; and
    (d) identifying one or more compounds that binds to the protein based on the three dimensional structure.

11. The method according to claim 10, further comprising the step of:
    contacting one or more compounds identified in step (d) with the protein whose sequence consists of SEQ ID NO:3.

12. The method according to claim 11, further comprising the step of:
    measuring an activity of the protein whose sequence consists of SEQ ID NO:3, when the protein is contacted with the one or more compounds.

13. The method according to claim 12, further comprising the step of:
    comparing activities of the protein whose sequence consists of SEQ ID NO:3, when the protein is in the presence of and in the absence of the one or more compounds.

14. The method according to claim 10, further comprising the steps of:
    contacting one or more compounds identified in step (d) with a cell that expresses a protein whose sequence consists of SEQ ID NO:3; and
    detecting whether a phenotype of the cell changes when the one or more compounds are present.

* * * * *